(12) United States Patent
Sato et al.

(10) Patent No.: US 10,399,868 B2
(45) Date of Patent: *Sep. 3, 2019

(54) OIL-WATER SEPARATION APPARATUS AND DRAINAGE SYSTEM

(71) Applicants: MITSUBISHI MATERIALS CORPORATION, Tokyo (JP); Mitsubishi Materials Electronic Chemicals Co., Ltd., Akita-shi (JP)

(72) Inventors: Kosei Sato, Akita (JP); Masato Fujita, Akita (JP); Masakazu Uotani, Akita (JP); Hiroshi Koshiyama, Akita (JP); Takeshi Kamiya, Akita (JP); Tsunetoshi Honda, Akita (JP); Hiroyuki Imai, Akita (JP); Daisuke Takano, Saitama (JP)

(73) Assignees: MITSUBISHI MATERIALS CORPORATION, Tokyo (JP); Mitsubishi Materials Electronic Chemicals Co., Ltd., Akita-shi (JP)

(*) Notice: Subject to any disclaimer, the term of this patent is extended or adjusted under 35 U.S.C. 154(b) by 280 days.

This patent is subject to a terminal disclaimer.

(21) Appl. No.: 15/329,393

(22) PCT Filed: Jul. 29, 2015

(86) PCT No.: PCT/JP2015/071544
§ 371 (c)(1),
(2) Date: Jan. 26, 2017

(87) PCT Pub. No.: WO2016/017713
PCT Pub. Date: Feb. 4, 2016

(65) Prior Publication Data
US 2017/0210643 A1   Jul. 27, 2017

(30) Foreign Application Priority Data

Jul. 30, 2014 (JP) ................................ 2014-155553
Jul. 30, 2014 (JP) ................................ 2014-155554
(Continued)

(51) Int. Cl.
*C02F 1/40* (2006.01)
*B01D 17/04* (2006.01)
(Continued)

(52) U.S. Cl.
CPC .............. *C02F 1/40* (2013.01); *B01D 17/045* (2013.01); *B01D 17/10* (2013.01); *C07C 229/06* (2013.01);
(Continued)

(58) Field of Classification Search
CPC .... C02F 1/40; C02F 2101/32; C02F 2103/32; C07C 229/06; C07C 237/06;
(Continued)

(56) References Cited

U.S. PATENT DOCUMENTS 2,266,350 A   12/1941   Womack
3,471,484 A   10/1969   Guenthner
(Continued)

FOREIGN PATENT DOCUMENTS

CN   1805774 A   7/2006
GB   1512348 A   6/1978
(Continued)

OTHER PUBLICATIONS

English translation Japanese Patent Application No. 2007-326836 A (dated Dec. 2007).*
(Continued)

*Primary Examiner* — John Kim
(74) *Attorney, Agent, or Firm* — Locke Lord LLP; James E. Armstrong, IV; Nicholas J. DiCeglie, Jr.

(57) ABSTRACT

An oil-water separation apparatus is provided which can easily separate and collect oil from a liquid mixture containing water and oil at low cost.

The oil-water separation apparatus includes an oil-water-separating member configured to separate a liquid mixture containing water and oil into moisture and oil, and a liquid reservoir subdivided into an upper region and a lower region by the oil-water-separating member. The oil-water separation apparatus filters the liquid mixture by gravity. The oil-water-separating member includes a base which includes a channel for the liquid mixture. The oil-water-separating member is formed in the base, and the oil-water-separating member contains a fluorine compound which has an oil-repellency-imparting group and a hydrophilicity-imparting group. A drain port for discharging the moisture is formed in the lower region of the liquid reservoir.

21 Claims, 28 Drawing Sheets

(30)    Foreign Application Priority Data

| Oct. 7, 2014 | (JP) | 2014-206782 |
|---|---|---|
| Nov. 25, 2014 | (JP) | 2014-238242 |
| Dec. 18, 2014 | (JP) | 2014-256646 |
| Jan. 16, 2015 | (JP) | 2015-007194 |
| Jan. 21, 2015 | (JP) | 2015-009440 |
| Jan. 21, 2015 | (JP) | 2015-009441 |
| Jan. 27, 2015 | (JP) | 2015-013505 |
| Jan. 27, 2015 | (JP) | 2015-013695 |
| Jan. 27, 2015 | (JP) | 2015-013696 |
| Jan. 27, 2015 | (JP) | 2015-013699 |
| Apr. 16, 2015 | (JP) | 2015-084239 |
| Apr. 20, 2015 | (JP) | 2015-086020 |
| May 25, 2015 | (JP) | 2015-105865 |
| Jul. 24, 2015 | (JP) | 2015-147198 |

(51) Int. Cl.

| C07C 229/06 | (2006.01) |
|---|---|
| C07C 237/06 | (2006.01) |
| C07D 211/06 | (2006.01) |
| C07D 265/30 | (2006.01) |
| C09D 7/40 | (2018.01) |
| C09D 5/16 | (2006.01) |
| C09D 201/00 | (2006.01) |
| C08L 101/00 | (2006.01) |
| B01D 17/00 | (2006.01) |
| C02F 101/32 | (2006.01) |
| C02F 103/32 | (2006.01) |

(52) U.S. Cl.
CPC .......... *C07C 237/06* (2013.01); *C07D 211/06* (2013.01); *C07D 265/30* (2013.01); *C08L 101/00* (2013.01); *C09D 5/16* (2013.01); *C09D 7/40* (2018.01); *C09D 201/00* (2013.01); *B01D 2239/0421* (2013.01); *B01D 2239/0613* (2013.01); *B01D 2239/0618* (2013.01); *B01D 2239/086* (2013.01); *C02F 2101/32* (2013.01); *C02F 2103/32* (2013.01)

(58) Field of Classification Search
CPC .......... C09D 201/00; C09D 5/16; C09D 7/40; B01D 17/045; B01D 17/10; B01D 2239/0421; B01D 2239/086; B01D 2239/0613; B01D 2239/0618; C07D 265/30; C07D 211/06
See application file for complete search history.

(56)    References Cited

U.S. PATENT DOCUMENTS

| 4,859,754 A | 8/1989 | Maekawa et al. |
|---|---|---|
| 5,443,724 A | 8/1995 | Williamson et al. |
| 6,207,777 B1 | 3/2001 | Shimada et al. |
| 2002/0004107 A1 | 1/2002 | Rogers |
| 2009/0317621 A1 | 12/2009 | Youngblood et al. |

FOREIGN PATENT DOCUMENTS

| GB | 2354458 A | 3/2001 |
|---|---|---|
| JP | 45-002299 B | 1/1970 |
| JP | 45-006006 B1 | 2/1970 |
| JP | 46-031802 Y | 11/1971 |
| JP | 49-040734 B1 | 11/1974 |
| JP | 51-012462 A | 1/1976 |
| JP | 51-012463 A | 1/1976 |
| JP | 51-059133 U | 5/1976 |
| JP | 52-021130 U | 2/1977 |
| JP | 52-052182 A | 4/1977 |
| JP | 52-074960 A | 6/1977 |
| JP | 52-090861 A | 7/1977 |
| JP | 53-109266 A | 9/1978 |
| JP | 53-111569 A | 9/1978 |
| JP | 54-061362 A | 5/1979 |
| JP | 60-139306 A | 7/1985 |
| JP | 61-257211 A | 11/1986 |
| JP | 62-035738 Y | 9/1987 |
| JP | 63-037187 U | 3/1988 |
| JP | 03-060791 A | 3/1991 |
| JP | 03-144006 A | 6/1991 |
| JP | 05-058970 A | 3/1993 |
| JP | 05-137903 A | 6/1993 |
| JP | 05-177766 A | 7/1993 |
| JP | 05-272027 A | 10/1993 |
| JP | 05-285305 A | 11/1993 |
| JP | 05-329476 A | 12/1993 |
| JP | 05-331455 A | 12/1993 |
| JP | 06-134300 A | 5/1994 |
| JP | 07-004535 U | 1/1995 |
| JP | 07-024212 A | 1/1995 |
| JP | 07-048464 A | 2/1995 |
| JP | H07-204505 A | 8/1995 |
| JP | 07-265605 A | 10/1995 |
| JP | 07-284606 A | 10/1995 |
| JP | 07-289801 A | 11/1995 |
| JP | 08-243558 A | 9/1996 |
| JP | 09-094401 A | 4/1997 |
| JP | 09-227160 A | 9/1997 |
| JP | 10-006973 A | 1/1998 |
| JP | 10-007742 A | 1/1998 |
| JP | 10-103816 A | 4/1998 |
| JP | 10-204860 A | 8/1998 |
| JP | 11-021866 A | 1/1999 |
| JP | 11-114304 A | 4/1999 |
| JP | 11-156104 A | 6/1999 |
| JP | 11-244671 A | 9/1999 |
| JP | 11-323812 A | 11/1999 |
| JP | 2000-024656 A | 1/2000 |
| JP | 2000-096082 A | 4/2000 |
| JP | 2000-126505 A | 5/2000 |
| JP | 2000-189954 A | 7/2000 |
| JP | 2000-288303 A | 10/2000 |
| JP | 2000-342359 A | 12/2000 |
| JP | 2001-000960 A | 1/2001 |
| JP | 2001-004125 A | 1/2001 |
| JP | 2001-164450 A | 6/2001 |
| JP | 2001-220374 A | 8/2001 |
| JP | 2002-105433 A | 4/2002 |
| JP | 2002-113301 A | 4/2002 |
| JP | 2002-266329 A | 9/2002 |
| JP | 2003-166173 A | 6/2003 |

(56) References Cited

FOREIGN PATENT DOCUMENTS

| | | |
|---|---|---|
| JP | 2003-227117 A | 8/2003 |
| JP | 2003-267900 A | 9/2003 |
| JP | 2004-098047 A | 4/2004 |
| JP | 2004-230278 A | 8/2004 |
| JP | 2004-298711 A | 10/2004 |
| JP | 2005-074316 A | 3/2005 |
| JP | 2005-144436 A | 6/2005 |
| JP | 2005-330354 A | 12/2005 |
| JP | 2006-110452 A | 4/2006 |
| JP | 2006-130743 A | 5/2006 |
| JP | 2006-198483 A | 8/2006 |
| JP | 2006-200269 A | 8/2006 |
| JP | 2006-292326 A | 10/2006 |
| JP | 2007-144239 A | 6/2007 |
| JP | 2007-216184 A | 8/2007 |
| JP | 2007-326821 A | 12/2007 |
| JP | 2007-326836 A | 12/2007 |
| JP | 2008-031511 A | 2/2008 |
| JP | 2008-062127 A | 3/2008 |
| JP | 2009-061376 A | 3/2009 |
| JP | 2009-127015 A | 6/2009 |
| JP | 2009-133173 A | 6/2009 |
| JP | 4406700 B2 | 2/2010 |
| JP | 2010-159563 A | 7/2010 |
| JP | 2010-201321 A | 9/2010 |
| JP | 2011-011172 A | 1/2011 |
| JP | 2013-188680 A | 9/2013 |
| JP | 2013-202569 A | 10/2013 |
| JP | 2014-036931 A | 2/2014 |
| JP | 2014-057920 A | 4/2014 |
| JP | 2014-148504 A | 8/2014 |
| JP | 2014-148670 A | 8/2014 |
| JP | 2014-158996 A | 9/2014 |
| KR | 10-2015-0001082 A | 1/2015 |
| WO | 97/036951 A1 | 10/1997 |
| WO | 2013/111372 A1 | 8/2013 |
| WO | 2013/145372 A1 | 10/2013 |

OTHER PUBLICATIONS

English translation Japanese Patent Application No. 53-109266 A (dated Sep. 1978).*
English translation Japanese Patent No. 4406700 B2 (dated Feb. 2010).*
Office Action dated Sep. 25, 2018, issued for the Japanese patent application No. 2015-007194 and English translation thereof.
Office Action dated Sep. 25, 2018, issued for the Japanese patent application No. 2015-009440 and English translation thereof.
Office Action dated Aug. 21, 2018, issued for the Japanese patent application No. 2014-238242 and English translation thereof.
Office Action dated Aug. 21, 2018, issued for the Japanese patent application No. 2014-256646 and English translation thereof.
Office Action dated Jul. 24, 2018, issued for the Japanese patent application No. 2015-013505 and English translation thereof.
Office Action dated Jul. 24, 2018, issued for the Japanese patent application No. 2015-013696 and English translation thereof.
Office Action dated Nov. 20, 2018, issued for the Japanese patent application No. 2015-013695 and English translation thereof.
Office Action dated May 15, 2018, issued for the Chinese patent application No. 201580041432.X and a partial English translation of the Search Report.
International Search Report dated Oct. 20, 2015, issued for PCT/JP2015/071489 and English translation thereof.
International Search Report dated Oct. 20, 2015, issued for PCT/JP2015/071635 and English translation thereof.
International Search Report dated Oct. 20, 2015, issued for PCT/JP2015/071680 and English translation thereof.
International Search Report dated Oct. 27, 2015, issued for PCT/JP2015/071684 and English translation thereof.
International Search Report dated Oct. 20, 2015, issued for PCT/JP2015/071544 and English translation thereof.
International Search Report dated Oct. 27, 2015, issued for PCT/JP2015/071661 and English translation thereof.
Search Report dated Jan. 4, 2018, issued for the European Patent Application No. 15827683.2.
Search Report dated Jan. 8, 2018, issued for the European Patent Application No. 15827639.4.
Search Report dated Jan. 15, 2018, issued for the European Patent Application No. 15827185.8.
Office Action dated Sep. 11, 2018, issued for the Japanese patent application No. 2015-009441 and English translation thereof.
Office Action dated Sep. 11, 2018, issued for the Japanese patent application No. 2015-013699 and English translation thereof.
Office Action dated Feb. 26, 2019, issued for the Japanese patent application No. 2015-084239 and English translation thereof.
Office Action dated Feb. 26, 2019, issued for the Japanese patent application No. 2015-086020 and English translation thereof.
Office Action dated Feb. 26, 2019, issued for the Japanese patent application No. 2015-105865 and English translation thereof.
Notice of Allowance dated Mar. 5, 2019, issued for the Japanese patent application No. 2015-147198 and English translation thereof.

* cited by examiner

OIL-WATER SEPARATION APPARATUS AND DRAINAGE SYSTEM

CROSS REFERENCE TO RELATED APPLICATIONS

This application is related to three co-pending applications: " HYDROPHILIC OIL REPELLENT AND PRODUCTION METHOD OF SAME, SURFACE COATING MATERIAL, COATING FILM, RESIN COMPOSITION, OIL-WATER SEPARATION FILTER MATERIAL, AND POROUS BODY" filed even date herewith in the names of Masato FUJITA; Masakazu UOTANI; Takeshi KAMIYA; Tsunetoshi HONDA and Daisuke TAKANO as a national phase entry of PCT/JP2015/071489; and "SURFACE COATING MATERIAL, COATING FILM, AND HYDROPHILIC OIL REPELLENT MEMBER" filed even date herewith in the names of Masakazu UOTANI; Hiroshi KOSHIYAMA; Takeshi KAMIYA; Tsunetoshi HONDA; Kosei SATO; Masato FUJITA and Daisuke TAKANO as a national phase entry of PCT/JP2015/071661; which applications are assigned to the assignee of the present application and all three incorporated by reference herein.

TECHNICAL FIELD

The present invention relates to an oil-water separation apparatus which includes an oil-water-separating member configured to separate a liquid mixture containing water and oil, into moisture and oil, and a drainage system.

BACKGROUND ART

Conventionally, oils or lards are mixed and contained in water discharged from a general house, a commercial cooking place, or a building, or water discharged from a conduit for a sewage or waste liquid treatment facility of a public establishment. Discharged water which is such a liquid mixture in which water and oil are mixed with each other is the cause of clogging of a sewerage pipe by fixation of the oil, or the cause of an odor occurring by oxidation of the oil. In addition, there are also problems in that the function of the public sewerage facility is hindered or an oil clot (white solid matter) from a sewerage facility is spilled to a harbor after heavy rain, for example. Thus, in each district, measures in which restaurant companies have to install a gathering machine which separates and collects oils, fats, and the like in a liquid mixture, and thus oils or lards are not spilled to the sewerage are also taken.

Treatment of separating an oil-water mixed liquid into oil and water is performed as waste liquid treatment in, for example, food manufacturing, fiber treatment, mechanical processing, and petroleum refining, and as an oil collection work performed in a case where an oil is spilled into a river, the sea, and the like due to, for example, an accident.

In addition, for example, when crude oil is drilled for, a method in which the seawater is injected to an oil layer of a stratum, and pressure of non-aqueous oil is increased, and thus an output is ensured is generally performed. "Water accompanying drilling in the oil field" which is water used in such drilling for crude oil contains a large amount of non-aqueous oil. Thus, treatment of removing the non-aqueous oil is performed, and then the non-aqueous oil is scrapped. However, because the non-aqueous oil is the cause of contaminating the ocean, lakes and marshes, and the like, recently, restrictions over the content of the non-aqueous oil in discharged water is reinforced. In a country or a district in which the restrictions are strongest, the content of the non-aqueous oil is required to be less than 5 mg/L.

As the conventional oil-water separation method, for example, the following methods are known: separation by using a flocculant; adhering and separation; centrifugation; pressure floatation separation; an electrolysis floatation method; coarse granulation and separation by using a coalescer (for example, see Patent Document 1); and separation by microbial degradation.

In a case of a separation method using a flocculant, there is a problem in that expenses are continuously required, and treatment of filtered agglutinates also takes much labor and cost. A case by a machine such as a centrifuge and a case by pressure floatation separation are effective for treating a large amount or for large-size utilities. However, the above cases have a problem in that it is difficult to perform in a limited space. In the electrolysis floatation method, there is a problem in that complex control, for example, changing an applied power in accordance with electrical conductivity and the treated amount of a treatment liquid is required for stably performing oil-water separation. In the coalescer method, a filter having a network structure of ultrafine fiber is used. Thus, there is a problem in that clogging normally occurs in maintenance management. In a separation method using a microorganism, there is a problem in that it takes time, and maintenance is intricate.

Water treatment by using a separation membrane which uses a porous film is performed in the related art. As oil-water separation, a reverse osmosis method, an ultrafiltration method, a precise filtration method (for example, see Patent Document L2), and the like are also known.

However, because oil and water are separated by using a hole diameter of the separation membrane in the reverse osmosis method, the ultrafiltration method, and the precise filtration method, there is a problem in that a membrane permeation flux is small. Further, in the process of performing water treatment, a separation target substance such as oil, which is provided in raw water adheres to the separation membrane, and thus fouling (clogging) occurs. A problem in that it is necessary that physical washing such as back pressure washing and air scrubbing be periodically performed occurs due to the fouling. Thus, there is a situation in which improvement of difficulty in adhering oil (antifouling property) or ease of removing adhered oil (easy washing property) is desired for the separation membrane using a porous film in order to continuously use the separation membrane for a long term.

PRIOR ART LITERATURE

Patent Documents

[Patent Document 1] Japanese Unexamined Patent Application, First Publication No. 2006-198483 (A)
[Patent Document 2] Japanese Unexamined Patent Application, First Publication No. H5-137903 (A)

DISCLOSURE OF INVENTION

Problems to be Solved by the Invention

Considering the above circumstances, an object of the present invention is to provide an oil-water separation apparatus which can separate a liquid mixture containing water and oil into moisture and oil so as to perform filtration, with a simple configuration and low cost and a drainage system.

Means for Solving the Problems

That is, according to the present invention, an oil-water separation apparatus is provided which has the following configurations.

[1] An oil-water separation apparatus is provided including an oil-water separation filter medium. The oil-water separation filter medium includes a base and an oil-water-separating member which is formed on the base and is configured to separate a liquid mixture containing water and oil into moisture and oil. The oil-water-separating member contains a fluorine compound which has an oil-repellency-imparting group and a hydrophilicity-imparting group.

[2] The fluorine compound contains one or more compounds having a structure represented by the following formulas (1) to (4).

[Chemical Formula 1]

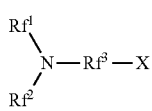

(1)

[Chemical Formula 2]

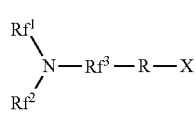

(2)

[Chemical Formula 3]

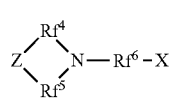

(3)

[Chemical Formula 4]

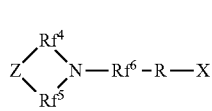

(4)

Each of $Rf^1$ and $Rf^2$ in the formulas (1) and (2) is a straight-chain or branched perfluoroalkyl group which is the same as or different from each other, and has 1 to 6 carbon atoms, and $Rf^3$ is a straight-chain or branched perfluoroalkylene group which has 1 to 6 carbon atoms.

Each of $Rf^4$, $Rf^5$, and $Rf^6$ in the formulas (3) and (4) is a straight-chain or branched perfluoroalkylene group which is the same as or different from each other, and has 1 to 6 carbon atoms. Z includes any of an oxygen atom, a nitrogen atom, a $CF_2$ group, and a CF group.

In the formulas (2) and (4), R is a linking group which is a bivalent organic group In the formulas (1) to (4), X is any one hydrophilicity-imparting group selected from the group consisting of an anion type, a cation type, and an amphoteric type.

[3] The oil-water-separating member is bound to the base by an organic binder or an inorganic binder.

[4] The oil-water separation apparatus further includes a liquid reservoir which is subdivided into an upper region and a lower region by the oil-water-separating member. A water drain port for discharging the moisture is formed in the lower region of the liquid reservoir, and filtering the liquid mixture is performed by gravity.

[5] An oil drain port for discharging the oil is formed in the upper region of the liquid reservoir.

[6] The base has a bag shape of which one end side is opened, and is formed from a porous medium which includes at least a channel through which the moisture is allowed to pass.

[7] A support member through which at least the moisture is allowed to pass is disposed on an outer surface side of the oil-water separation filter medium so as to overlap the outer surface side of the oil-water separation filter medium. The support member supports the oil-water separation filter medium from the outer surface side.

[8] The oil-water separation apparatus further includes a holding portion for holding the oil-water separation filter medium. The base is formed from a material including a channel through which at least the moisture passes.

[9] An edge of the base is attachable and detachable to and from the holding portion.

[10] The base is a bag body. The bag body is formed from a material including a channel through which at least the moisture is allowed to pass, and the bag body is filled with weights.

[11] The oil-water separation apparatus further includes a drainage net which is extended from one end portion of the bag body, and includes the oil-water-separating member. The drainage net is formed from a material including a channel through which at least moisture is allowed to pass.

[12] The base forms a curtain, and has a float for floating the base on a surface of water. The curtain is attached to a lower portion of the float. The curtain is formed from a material including a channel through which at least the moisture is allowed to pass.

[13] The base is formed from a porous base including multiple pores which penetrate a space between one surface into which the liquid mixture flows, and another surface which faces the one surface. An opening diameter of the pore is from 0.1 μm to 180 μm, and the oil-water-separating member is formed on a surface of the pore.

[14] The pore is directed from the one surface toward the other surface, and the opening diameter of the pores is reduced by stages or continuously.

[15] The oil-water separation apparatus constitutes a gathering machine. At least a preceding-stage reservoir and a subsequent-stage reservoir are arranged in series from an inflow side into which the liquid mixture flows, toward an outflow side by which the moisture obtained by oil-water separation flows out. The oil-water separation filter medium is provided so as to be attachable and detachable to and from at least one of the preceding-stage reservoir or the subsequent-stage reservoir.

[16] The base is formed from a fiber assembly. The oil-water-separating member is formed in the fiber assembly. The oil-water separation filter medium is brought into contact with the liquid mixture, so as to cause water droplets to form a liquid film and to flip oil.

[17] The oil-water separation apparatus further includes a coarsening filter which includes a coarsening member configured to be brought into contact with the liquid mixture and to coarsen a water droplet or an oil droplet. The oil-water separation filter medium is disposed on the subsequent stage side of the coarsening filter.

[18] The oil-water separation apparatus further includes an intake unit configured to take the liquid mixture in, an oil-water separation unit which includes the oil-water separation filter medium and is configured to separate the liquid mixture into moisture and oil, and a joint unit configured to connect the intake unit and the oil-water separation unit.

[19] The oil-water separation apparatus further includes a demulsification unit configured to coarsen minute oil droplets dispersed in an oil-water mixed liquid obtained by mixing moisture and oil, and to cause the oil to float on a higher layer of the moisture, an oil-water separation unit configured to perform oil-water separation of a solution mixture containing oil which is coarsened by the demulsification unit, by using the oil-water separation filter medium, and a transportation unit configured to transport the solution mixture from the demulsification unit toward the oil-water separation unit.

[20] The oil-water separation filter medium is formed on a surface of the base. The base is formed from a baglike exterior medium through which the moisture passes, and the oil does not pass. A water-absorbent material is accommodated in the exterior medium.

[21] The oil-water separation apparatus further includes a filter layer in which a filtering medium is formed, the oil-water separation filter medium formed so as to overlap the filter layer, and a liquid reservoir which accommodates the filter layer and the oil-water separation filter medium. The oil-water separation filter medium is formed in a manner such that multiple layers of an oil-water separation medium formed from the base and the oil-water-separating member which is formed around the base are disposed. The oil-water separation filter medium filters the liquid mixture by gravity.

A drainage system according to the present invention has the following configuration.

[22] A drainage system is provided which includes the oil-water separation apparatus according to any one of [1] to [3]. The drainage system includes an oil leakage detector configured to detect leakage of oil into a drainage, an oil-water separation mechanism configured to separate oil from a liquid mixture in which the oil is contained in the drainage, and a control unit configured to operate the oil-water separation mechanism, when the oil leakage detector detects leakage of oil into the drainage. The oil-water separation mechanism includes the oil-water separation apparatus.

Effects of the Invention

According to the oil-water separation apparatus and the drainage system of the present invention, it is possible to separate a liquid mixture containing water and oil into moisture and oil so as to perform filtration, with a simple configuration and low cost.

BEST MODE FOR CARRYING OUT THE INVENTION

Figure 1:
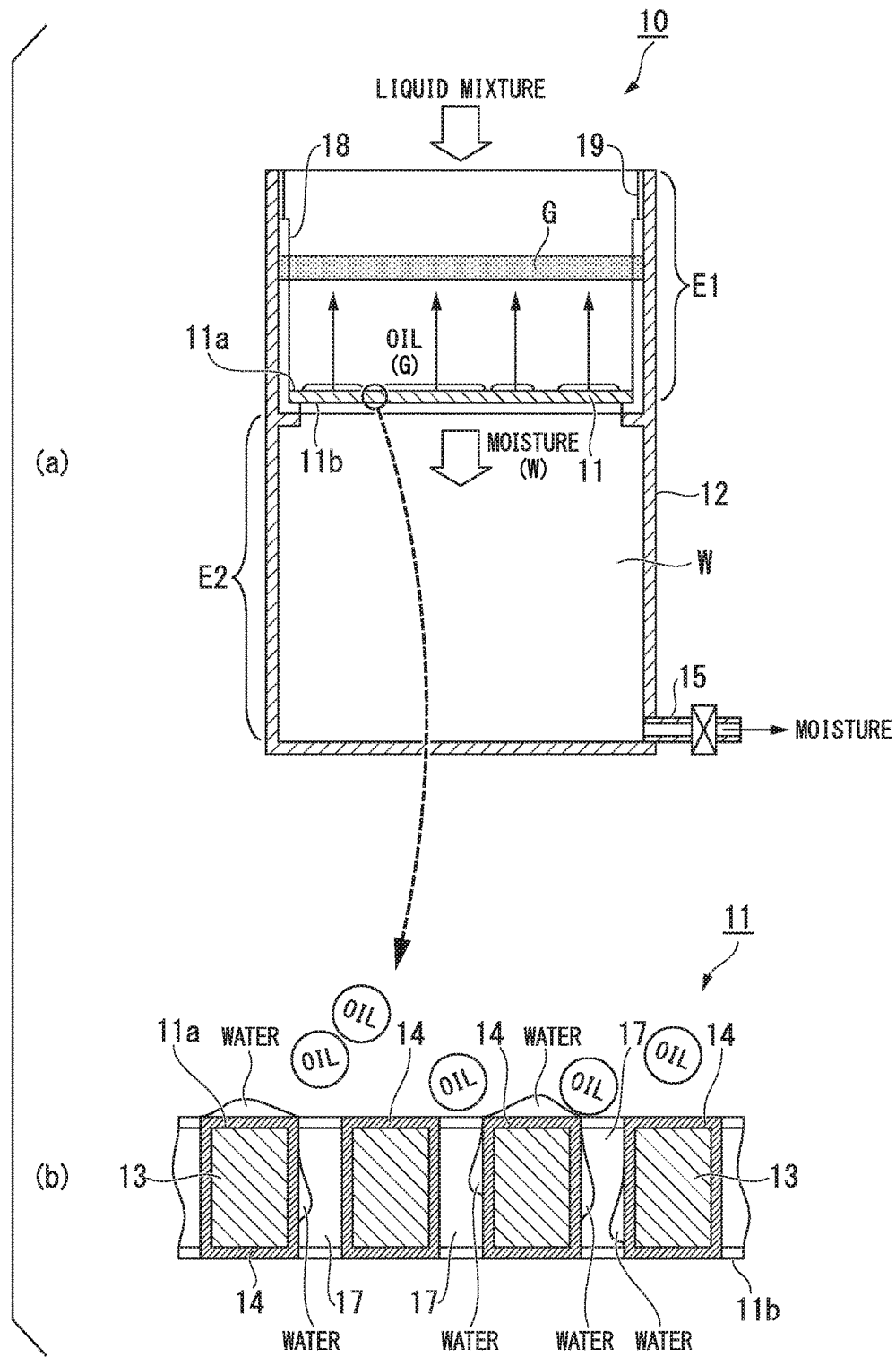
FIG. 1 is a sectional view illustrating a first embodiment of an oil-water separation apparatus according to the present invention.

Hereinafter, embodiments of an oil-water separation apparatus and a drainage system will be described with reference to the drawings. The following embodiments will be specifically described for better understandings of the gist of the invention. As long as particular designation is not performed, the following embodiments are not limited to the present invention. In the drawings used in the following descriptions, for convenience, portions as the main parts may be enlarged and illustrated for easy understandings of features of the present invention. Dimension ratios and the like of components are not limited to be the same as those in practice.

<First Embodiment>

FIG. 1(a) is a sectional view illustrating an example of an oil-water separation apparatus according to a first embodiment. FIG. 1(b) is a sectional view of an enlarged main portion illustrating an oil-water separation filter medium which constitutes the oil-water separation apparatus.

An oil-water separation apparatus 10 according to this embodiment includes an oil-water separation filter medium 11 and a liquid reservoir 12. The oil-water separation apparatus 10 includes a support member 18 which supports the oil-water separation filter medium 11 so as to be attachable and detachable to and from the liquid reservoir 12. The oil-water separation filter medium 11 includes a base 13 and an oil-water-separating member 14 formed on, for example, a surface of the base 13.

The entirety of the oil-water separation filter medium 11 is formed to have a sheet shape in this embodiment. Regarding the oil-water separation filter medium 11, the oil-water separation filter medium 11 may be formed by using filtering media having various shapes, such as a flat-film filter, a bag filter having a bag shape, and an amorphous fiber filter. Examples of the flat-film filter include a paper filter and a fiber filter sheet.

The oil-water separation filter medium 11 is provided in the liquid reservoir 12 by the support member 18, so as to, for example, be attachable and detachable. The liquid reservoir 12 is a liquid storage tank of which, for example, an upper surface is an opened surface. The liquid reservoir 12 is subdivided into an upper region and a lower region by the oil-water separation filter medium 11. That is, in the inner space of the liquid reservoir 12, a portion on a side upper than one surface 11a of the oil-water separation filter medium 11 is set to be an upper region E1, and a portion on a side lower than another surface 11b of the oil-water separation filter medium 11 is set to be a lower region E2.

The oil-water separation filter medium 11 passes moisture therethrough, from a liquid mixture containing water and oil by hydrophilicity and oil-repellent properties (below referred to as hydrophilic and oil-repellent properties). For example, if a liquid mixture is supplied to the upper region E1 of the liquid reservoir 12, the hydrophilic and oil-repellent properties of the oil-water separation filter medium 11 cause the liquid mixture to be separated into moisture and oil. The moisture (W in FIG. 1(a)) passes through the oil-water separation filter medium 11 by gravity, and is accumulated in the lower region E2 of the liquid reservoir 12. The oil (G in FIG. 1(a)) separated by the oil-water separation filter medium 11 floats in the vicinity of a liquid surface of the liquid mixture by a specific gravity difference.

A water drain port 15 is formed in the lower region E2 of the liquid reservoir 12. The water drain port 15 is used for discharging moisture which is filtered and accumulated in the lower region E2, to the outside of the liquid reservoir 12. Such a water drain port 15 may be configured from, for example, a valve and a liquid tube which penetrates a wall surface of the liquid reservoir 12.

The support member 18 is, for example, a basket-like member which includes a knob 19. The oil-water separation filter medium 11 is disposed at the bottom portion of the support member 18.

An exhaust port (not illustrated) is formed in the lower region E2 of the liquid reservoir 12. The exhaust port is used for exhausting air in the liquid reservoir 12 with storing moisture.

As illustrated in FIG. 1(b), the oil-water separation filter medium 11 includes the base 13 in which a channel 17 for a liquid is formed. The oil-water-separating member 14 is formed in the base 13. In this embodiment, the oil-water-separating member 14 is formed so as to cover the entire surface of the base 13, which includes an inner wall surface of the channel 17. The channel 17 causes the one surface 11a and the other surface 11b of the oil-water separation filter medium 11 to communicate with each other. The channel 17 mainly passes moisture therethrough, for example.

The oil-water-separating member 14 is configured of a material containing a fluorine compound which has an oil-repellency-imparting group and a hydrophilicity-imparting group. The oil-repellency-imparting group is a functional group for forming an oil droplet at a contact angle of, for example, 40° or more to the surface of the oil-water-separating member 14. The hydrophilicity-imparting group is a functional group for imparting wettability to moisture at a contact angle of, for example, 20° or less to the surface of the oil-water-separating member 14.

Such a contact angle may be measured, for example, by an automatic contact angle meter (manufactured by Kyowa Interface Science Co., Ltd, "Drop Master 701").

The oil-water-separating member 14 has hydrophilic and oil-repellent properties due to the existence of such an oil-repellency-imparting group and a hydrophilicity-imparting group. If a liquid mixture (simply may be referred to as a liquid below) containing water and oil is brought into contact with the oil-water-separating member 14, oil is aggregated as an oil droplet having a large contact angle, and moisture holds wettability in which the contact angle is small. Accordingly, oil which is aggregated and forms a large oil droplet remains on the surface of the oil-water-separating member 14, in a state where passing through the channel 17 is not allowed. The moisture which holds the wettability can pass through the channel 17 without being aggregated. With such an action, the oil-water-separating member 14 can selectively separate only oil from a liquid.

Examples of the fluorine compound forming the oil-water-separating member 14 include at least one or more among fluorine compounds represented by the following formulas (1) to (4).

[Chemical Formula 5]

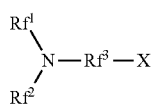
(1)

[Chemical Formula 6]

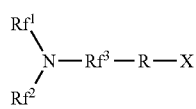
(2)

[Chemical Formula 7]

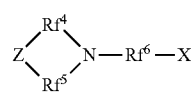
(3)

[Chemical Formula 8]

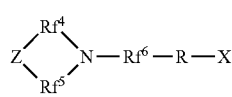
(4)

Here, each of $Rf^1$ and $Rf^2$ in the formulas (1) and (2) is a perfluoroalkyl group which is the same as or different from each other, and has 1 to 6 carbon atoms. $Rf^3$ is a perfluoroalkylene group which has 1 to 6 carbon atoms, and may be straight-chained or branched.

Each of $Rf^4$ and $Rf^5$ in the formulas (3) and (4) is a straight-chain or branched perfluoroalkylene group which is the same as or different from each other, and has 1 to 6 carbon atoms. $Rf^6$ is a perfluoroalkylene group having 1 to 6 carbon atoms, and may be straight-chained or branched. Z is an oxygen atom, a nitrogen atom, a $CF_2$ group, or a CF group. In a case where Z is a nitrogen atom or a carbon atom, a perfluoroalkyl group branched from Z may be bonded to the Z.

R in the formulas (2) and (4) is a linking group which is a bivalent organic group. Here, R may be a straight-chain or branched linking group. R may or may not include one type or more selected from an ether bond, an ester bond, an amide bond, and a urethane bond in a molecular chain.

X in the formulas (1) to (4) is any one hydrophilicity-imparting group selected from the group consisting of an anion type, a cation type, and an amphoteric type in the above formulas.

As described above, fluorine compounds represented by the formulas (1) to (4) are oil-repellent hydrophilic agents which include an oil-repellency-imparting group and a hydrophilicity-imparting group in a molecule. In other words, in the oil-water separation filter medium 11 constituting the oil-water separation apparatus 10 in this embodiment, the channel 17 is formed by the base 13, and the oil-water-separating member 14 having hydrophilic and oil-repellent properties is provided on the surface of the channel 17. A mixture which contains one more of fluorine compounds which are selected from the group consisting of the fluorine compounds represented by the formulas (1) to (4) may be used as the oil-water-separating member 14.

The oil-repellent hydrophilic agent constituting the oil-water-separating member 14 will be described below in detail, for each fluorine compound.

(Oil-Repellent Hydrophilic Agent)

"Straight-Chain Nitrogen-Containing Fluorine Compound

In a straight-chain (or branched) nitrogen-containing fluorine compound represented by the formula (1) or the formula (2), a nitrogen-containing perfluoroalkyl group formed from $Rf^1$ and $Rf^2$ and a nitrogen-containing perfluoroalkylene group formed from $Rf^3$ constitute the oil-repellency-imparting group.

In the nitrogen-containing fluorine compound represented by the formula (1) or the formula (2), the total number of carbon atoms to which fluorine is bonded in $Rf^1$ to $Rf^3$ which are the oil-repellency-imparting groups is preferably in a range of 4 to 18. If the number of carbon atoms to which fluorine is bonded is less than 4, an oil-repellent effect is insufficient, and thus this case is not preferable.

Here, R in the formula (2) is a linking group which links an oil-repellency-imparting group and a hydrophilicity-imparting group to each other in a molecular chain. The structure of the linking group R is not particularly limited as long as the linking group R is a bivalent organic group. Specific examples of the linking group R may include an oxygen atom [—O—], a carbonyl group [—C(=O)—], an imino group [—NH—], a sulphonyl group [—S(=O)$_2$—], a —OP(=O)(O—)O— group, a hydrocarbon group having 1 to 20 carbon atoms, and combinations thereof. The linking group R may include one type or more selected from a polyoxyalkylene group and an epoxy group. The hydrocarbon group may be a saturated hydrocarbon group or an unsaturated hydrocarbon group. The hydrocarbon group may be a chain hydrocarbon group or a cyclic hydrocarbon group. The chain hydrocarbon group may be a straight-chain or be branched. Examples of the hydrocarbon group may include an alkylene group, an alkenylene group, and an arylene group. The imino group and the hydrocarbon group may have a substituent.

The linking group R may or may not include one or more types of bonds selected from an ether bond, an ester bond, an amide bond, and a urethane bond in the molecular chain. The amide bond includes a carboxylic acid amide bond and a sulfonamide bond. The ester bond includes a carboxylic acid ester bond, a sulfonic acid ester bond, and a phosphate ester bond.

It is preferable that the linking group R be appropriately selected and applied in accordance with characteristics which are desired to be applied to the oil-repellent hydrophilic agent. Specific examples include a case where adjusting solubility to water or an organic solvent is desired, a case where adhesion between a surface-coating material (coating agent) containing the oil-repellent hydrophilic agent, and the base is improved so as to improve durability, and a case where compatibility between the oil-repellent hydrophilic agent, and a resin component or a paint component is desired to be improved. As the method, for example, the following methods are provided: a method in which presence or absence and the type of a polar group which influences interaction between molecules is adjusted; a method in which the length of a chain in a hydrocarbon group having a straight-chain or branched structure is adjusted; and a method in which a structure similar to a portion of a chemical structure provided in the base, or a resin component or a paint component is applied.

In the formula (1) or the formula (2), X is any one hydrophilicity-imparting group selected from the group consisting of an anion type, a cation type, and an amphoteric type.

The structure of the oil-repellent hydrophilic agent will be described below by using a case of a hydrophilicity-imparting group X.

[Anion Type]

In a case where the hydrophilicity-imparting group X is an anion type, the X has "—$CO_2M^1$", "—$SO_3M^1$", "—$OSO_2M^1$", "—$OP(OH)O_2M^1$", "—$OPO_3M^1{}_2$", "=$O_2PO_2M^1$", or "—$PO(OH)_y(OM1)_{2-y}$" at the termination ($M^1$ indicates alkali metal, alkaline-earth metal, Mg, and Al, and $R^1R^2R^3R^4N^+$; $R^1$ to $R^4$ indicate straight chain or branched alkyl groups which are independent from each other, and have hydrogen atoms or 1 to 20 carbon atoms (preferably, 1 to 10 carbon atoms)). In a case where $M^1$ is bivalent metal (alkaline-earth metal, Mg), two same anions may be bonded to $M^1$, or two different types of anions may be bonded to $M^1$. In a case where M1 is aluminium, three same anions may be bonded to M1, or two or three different types of anions may be bonded to $M^1$.

As the alkali metal, lithium (Li), sodium (Na), potassium (K), and cesium (Cs) are exemplified. As the alkaline-earth metal, calcium (Ca), strontium (Sr), and barium (Ba) are exemplified.

A quaternary ammonium salt ($R^1R^2R^3R^4N^+$) is not particularly limited as long as $R^1$ to $R^4$ indicate straight chain or branched alkyl groups which are independent from each other, and have hydrogen atoms or 1 to 20 carbon atoms (preferably, 1 to 10 carbon atoms. Here, if the number of carbon atoms of the alkyl group is equal to or less than 20, the hydrophilic and oil-repellent properties are not affected. Thus, this case is preferable. More specifically, as a case where all of $R^1$, $R^2$, $R^3$, and $R^4$ are the same compounds, for example, $(CH_3)_4N^+$, $(C_2H_5)_4N^+$, $(C_3H_7)_4N^+$, $(C_4H_9)_4N^+$, $(C_5H_{11})_4N^+$, $(C_6H_{13})_4N^+$, $(C_7H_{15})_4N^+$, $(C_8H_{17})_4N^+$, $(C_9H_{19})_4N^+$, and $(C_{10}H_{21})_4N^+$ are exemplified. As a case where all of $R^1$, $R^2$, and $R^3$ are methyl groups, for example, compounds in which $R^4$ is $(C_2H_5)$, $(C_6H_{13})$, $(C_8H_{17})$, $(C_9H_{19})$, $(C_{10}H_{21})$, $(C_{12}H_{25})$, $(C_{14}H_{29})$, $(C_{16}H_{33})$, $(C_{18}H_{37})$, or the like are exemplified. Further, as a case where all of $R^1$ and $R^2$ are methyl groups, for example, compounds in which all of $R^3$ and $R^4$ are $(C_8H_{17})$, $(C_{10}H_{21})$, $(C_{12}H_{25})$, $(C_{14}H_{29})$, $(C_{16}H_{33})$, $(C_{18}H_{37})$, or the like are exemplified. As a case where $R^1$ is a methyl group, for example, compounds in which all of $R^2$, $R^3$, and $R^4$ are $(C_4H_9)$, $(C_8H_{17})$, or the like are exemplified.

Regarding a material, for example, which is used by being brought into contact with water, such as a filter medium for oil-water separation, it is desirable that the material have durability against water, or persistence of a hydrophilic and oil-repellent effect for water. From this viewpoint, the oil-repellent hydrophilic agent constituting the oil-water-separating member 14 in this embodiment is desirably a poorly water-soluble compound having low solubility to water. That is, regarding the oil-repellent hydrophilic agent constituting the oil-water-separating member 14 in this embodiment, in a case where the hydrophilicity-imparting group X is an anion type, $M^1$ which is a counterpart ion is preferably alkaline-earth metal, Mg, or Al. Because Ca, Ba, and Mg have excellent hydrophilic and oil-repellent properties and low solubility to water, Ca, Ba, and Mg are particularly preferable.

[Cation Type]

In a case where the hydrophilicity-imparting group X is a cation type, the X has "—$N^+R^5R^6R^7.Cl^-$", "—$N^+R^5R^6R^7.Br^-$", "—$N^+R^5R^6R^7.I^-$", "—$N^+R^5R^6R^7.CH_3SO_3^-$", "—$N^+R^5R^6R^7.R^7SO_4^-$", "—$N^+R^5R^6R^7.NO_3^-$", "$(—N^+R^5R^6R^7)_2CO_3{}^{2-}$", or "$(—N^+R^5R^6R^7)_2SO_4{}^{2-}$" at the termination ($R^5$ to $R^7$ are straight chain or branched alkyl groups which are independent from each other, and have hydrogen atoms or 1 to 20 carbon atoms (preferably, 1 to 10 carbon atoms)). Here, if the number of carbon atoms of the alkyl group is equal to or less than 20, the hydrophilic and oil-repellent properties are not affected. Thus, this case is preferable.

[Amphoteric Type]

In a case where the hydrophilicity-imparting group X is an amphoteric type, the X has a carboxy betaine type of "—$N^+R^8R^9(CH_2)_nCO_2{}^-$", a sulfobetaine type of "—$N^+R^8R^9(CH_2)_nSO_3{}^-$", an amine oxide type of "—$N^+R^8R^9O^-$", or a phosphobetaine type of "—$OPO_3{}^-(CH_2)_nN^+R^8R^9R^{10}$" at the termination (n is an integer of 1 to 5, $R^8$ and $R^9$ indicates an alkyl group having a hydrogen atom or 1 to 10 carbon atoms, and $R^{10}$ indicates an alkyl group having a hydrogen atom or 1 to 10 carbon atoms or an alkylene group having 1 to 10 carbon atoms). Here, if the number of carbon atoms of the alkyl group is equal to or less than 10, the hydrophilic and oil-repellent properties are not affected. Thus, this case is preferable.

The oil-repellent hydrophilic agent constituting the oil-water-separating member 14 in this embodiment may be variously modified in a range without departing from the gist of the invention. For example, in a specific example of a structure of the above-described nitrogen-containing fluorine compound, a case where $Rf^1$ and $Rf^2$ represented by the formula (1) and the formula (2) are symmetrical as the oil-repellency-imparting group formed from a nitrogen-containing perfluoroalkyl group is described. However, the example is not limited thereto, and $Rf^1$ and $Rf^2$ may be asymmetrical.

"Cyclic Nitrogen-Containing Fluorine Compound"

In a cyclic nitrogen-containing fluorine compound represented by the formula (3) or the formula (4), a nitrogen-containing perfluoroalkylene group formed from $Rf^4$, $Rf^5$, and $Rf^6$, further, Z constitutes the oil-repellency-imparting group.

In the cyclic nitrogen-containing fluorine compound represented by the formula (3) or the formula (4), the total number of carbon atoms to which fluorine is bonded in $Rf^4$ to $Rf^6$ and Z which are the oil-repellency-imparting groups is preferably in a range of 4 to 18, and is further preferably in a range of 5 to 12. If the number of carbon atoms to which fluorine is bonded is less than 4, an oil-repellent effect is insufficient, and thus this case is not preferable.

Here, R in the formula (4) is a linking group which links an oil-repellency-imparting group and a hydrophilicity-imparting group to each other in a molecular chain. The structure of the linking group R is not particularly limited as long as the linking group R is a bivalent organic group. Specific examples of the linking group R may include an oxygen atom [—O—], a carbonyl group [—C(=O)—], an imino group [—NH—], a sulphonyl group [—S(=O)$_2$—], a —OP(=O)(O—)O— group, a hydrocarbon group having 1 to 20 carbon atoms, and combinations thereof. The linking group R may include one type or more selected from a polyoxyalkylene group and an epoxy group. The hydrocarbon group may be a saturated hydrocarbon group or an unsaturated hydrocarbon group. The hydrocarbon group may be a chain hydrocarbon group or a cyclic hydrocarbon group. The chain hydrocarbon group may be a straight-chain or be branched. Examples of the hydrocarbon group may include an alkylene group, an alkenylene group, and an arylene group. The imino group and the hydrocarbon group may have a substituent.

The linking group R may or may not include one or more types of bonds selected from an ether bond, an ester bond, an amide bond, and a urethane bond in the molecular chain. The amide bond includes a carboxylic acid amide bond and a sulfonamide bond. The ester bond includes a carboxylic acid ester bond, a sulfonic acid ester bond, and a phosphate ester bond.

In the formula (3) or the formula (4), X is any one hydrophilicity-imparting group selected from the group consisting of an anion type, a cation type, and an amphoteric type.

The structure of the oil-repellent hydrophilic agent will be described below by using a case of a hydrophilicity-imparting group X.

[Anion Type]

In a case where the hydrophilicity-imparting group X is an anion type, the X has "—$CO_2M^1$", "—$SO_3M^1$", "—$OSO_2M^1$", "—$OP(OH)O_2M^1$", "—$OPO_3M^1{}_2$", "=$O_2PO_2M^1$", or "—$PO(OH)_y(OM^1)_{2-y}$" (M1 indicates alkali metal, alkaline-earth metal, Mg, and Al, and $R^1R^2R^3R^4N^+$; $R^1$ to $R^4$ indicate straight chain or branched alkyl groups which are independent from each other, and have hydrogen atoms or 1 to 20 carbon atoms (preferably, 1 to 10 carbon atoms)). In a case where $M^1$ is bivalent metal (alkaline-earth metal, Mg), two same anions may be bonded to $M^1$, or two different types of anions may be bonded to M1. In a case where M1 is aluminium, three same anions may be bonded to M1, or two or three different types of anions may be bonded to $M^1$.

As the alkali metal, lithium (Li), sodium (Na), potassium (K), and cesium (Cs) are exemplified. As the alkaline-earth metal, calcium (Ca), strontium (Sr), and barium (Ba) are exemplified.

A quaternary ammonium salt ($R^1R^2R^3R^4N^+$) is not particularly limited as long as $R^1$ to $R^4$ indicate straight chain or branched alkyl groups which are independent from each other, and have hydrogen atoms or 1 to 20 carbon atoms (preferably, 1 to 10 carbon atoms. Here, if the number of carbon atoms of the alkyl group is equal to or less than 20, the hydrophilic and oil-repellent properties are not affected. Thus, this case is preferable. More specifically, as a case where all of $R^1$, $R^2$, $R^3$, and $R^4$ are the same compounds, for example, $(CH_3)_4N^+$, $(C_2H_5)_4N^+$, $(C_3H_7)_4N^+$, $(C_4H_9)_4N^+$, $(C_5H_{11})_4N^+$, $(C_6H_{13})_4N^+$, $(C_7H_{15})_4N^+$, $(C_8H_{17})_4N^+$, $(C_9H_{19})_4N^+$, and $(C_{10}H_{21})_4N^+$ are exemplified. As a case where all of $R^1$, $R^2$, and $R^3$ are methyl groups, for example, compounds in which $R^4$ is $(C_2H_5)$, $(C_6H_{13})$, $(C_8H_{17})$, $(C_9H_{19})$, $(C_{10}H_{21})$, $(C_{12}H_{25})$, $(C_{14}H_{29})$, $(C_{16}H_{33})$, $(C_{18}H_{37})$, or the like are exemplified. Further, as a case where all of $R^1$ and $R^2$ are methyl groups, for example, compounds in which all of $R^3$ and $R^4$ are $(C_8H_{17})$, $(C_{10}H_{21})$, $(C_{12}H_{25})$, $(C_{14}H_{29})$, $(C_{16}H_{33})$, $(C_{18}H_{37})$, or the like are exemplified. As a case where $R^1$ is a methyl group, for example, compounds in which all of $R^2$, $R^3$, and $R^4$ are $(C_4H_9)$, $(C_8H_{17})$, or the like are exemplified.

In this embodiment, when the oil-water-separating member 14 is used to, for example, be normally in contact with water, it is desirable that the oil-water-separating member 14 have durability against water, or persistence of a hydrophilic and oil-repellent effect for water. From this viewpoint, the oil-repellent hydrophilic agent used in the oil-water-separating member 14 in this embodiment is desirably a poorly water-soluble compound having low solubility to water. That is, regarding the oil-repellent hydrophilic agent used in the oil-water-separating member 14 in this embodiment, in a case where the hydrophilicity-imparting group X is an anion type, $M^1$ which is a counterpart ion is preferably alkaline-earth metal, Mg, or Al. Because Ca, Ba, and Mg have excellent hydrophilic and oil-repellent properties and low solubility to water, Ca, Ba, and Mg are particularly preferable.

[Cation Type]

In a case where the hydrophilicity-imparting group X is a cation type, the X has "—$N^+R^5R^6R^7.Cl—$", "$N^+R^5R^6R^7.Br—$", "—$N^+R^5R^6R^7.I—$", "—$N^+R^5R^6R^7.CH_3SO_3{}^-$", "—$N^+R^5R^6R^7.R^7SO_4{}^-$", "—$N^+R^5R^6R^7.NO_3{}^-$", "(—$N^+R^5R^6R^7)_2CO_3{}^{2-}$", or "(—$N^+R^5R^6R^7)_2SO_4{}^{2-}$" at the termination ($R^5$ to $R^7$ are straight chain or branched alkyl groups which are independent from each other, and have hydrogen atoms or 1 to 20 carbon atoms (preferably, 1 to 10 carbon atoms)). Here, if the number of carbon atoms of the alkyl group is equal to or less than 20, the hydrophilic and oil-repellent properties are not affected. Thus, this case is preferable.

[Amphoteric Type]

In a case where the hydrophilicity-imparting group X is an amphoteric type, the X has a carboxy betaine type of "—$N^+R^8R^9(CH_2)_nCO_2{}^-$", a sulfobetaine type of "—$N^+R^8R9(CH_2)_nSO_3{}^-$", an amine oxide type of "—$N^+R^8R^9O^-$", or a phosphobetaine type of "—$OPO_3{}^-(CH_2)_nN^+R^8R^9R^{10}$" at the termination (n is an integer of 1 to 5, $R^8$ and $R^9$ indicates an alkyl group having a hydrogen atom or 1 to 10 carbon atoms, and $R^{10}$ indicates an alkyl group having a hydrogen atom or 1 to 10 carbon atoms or an alkylene group having 1 to 10 carbon atoms). Here, if the number of carbon atoms of the alkyl group is equal to or less than 10, the hydrophilic and oil-repellent properties are not affected. Thus, this case is preferable.

The oil-repellent hydrophilic agent used in the oil-water-separating member 14 constituting the oil-water separation apparatus 10 in this embodiment may be variously modified in a range without departing from the gist of the invention. For example, in a specific example of a structure of the above-described nitrogen-containing fluorine compound, a case where $Rf^4$ and $Rf^5$ represented by the formula (3) and the formula (4) as the oil-repellency-imparting group formed from a nitrogen-containing perfluoroalkyl group are symmetrical with Z interposed between $Rf^4$ and $Rf^5$ is described. However, the example is not limited thereto, and $Rf^4$ and $Rf^5$ may be asymmetrical.

(Binder)

In the oil-water-separating member 14 in this embodiment, the nitrogen-containing fluorine compound (oil-repellent hydrophilic agent) represented by the formulas (1) to (4) is singly provided or is combined with a binder on at least a portion of the surface of the channel 17 formed by the base 13. In other words, the fluorine compound (oil-repellent hydrophilic agent) constituting the oil-water-separating member 14 exists on the surface of the base 13. In the oil-water separation apparatus 10 in this embodiment, because spillage of the fluorine compound due to a liquid to be separated does not occur, the fluorine compound is fixed to the surface of the base 13, as the oil-water-separating member 14.

Specifically, in the oil-water separation apparatus 10 in this embodiment, a portion or the entirety of the base 13 may be coated by a coating film which contains a nitrogen-containing fluorine compound (oil-repellent hydrophilic agent) represented by the formulas (1) to (4) or may be coated by a coating film which contains a binder and the nitrogen-containing fluorine compound (oil-repellent hydrophilic agent) represented by the formulas (1) to (4).

The coating film can be formed from only the above-described fluorine compound (oil-repellent hydrophilic agent) or can include the binder. In a case of including the binder, the mass composition ratio of the oil-repellent hydrophilic agent to the binder is preferably in a range of 0.2-99.9 to 99.8-0.1, more preferably in a range of 2-98 to 98-2, and further preferably in a range of 10-90 to 90-10. Here, if the mass composition ratio of the oil-repellent hydrophilic agent is equal to or less than 0.2, the hydrophilic and oil-repellent properties are sufficiently obtained. Thus, this range is preferable. If adhesion to the base 13 or durability of a coating film is to be added, the mass composition ratio is particularly preferably in a range of 10-90 to 90-10.

Specific examples of the binder include an organic binder (resin) and an inorganic binder (inorganic glass). As the organic binder (resin), for example, a thermoplastic resin, a thermoplastic elastomer, a thermosetting resin, an UV-curable resin, and the like are provided. Specific examples include a thermoplastic resin such as polyvinyl chloride, polyethylene, polypropylene, polycarbonate, polyester, polystyrene, a silicone resin, polyvinyl acetal, polyvinyl alcohol, an acrylic polyol resin, a polyester polyol resin, a urethane resin, a fluororesin, and a thermoplastic acrylic resin; and a thermosetting resin such as an epoxy resin, a phenol resin, and a thermosetting acrylic resin.

The binder is desirably used for exhibiting characteristics of the hydrophilic and oil-repellent properties provided in the oil-water-separating member 14 up to the maximum. As the binder, a hydrophilic polymer is preferably used. As the hydrophilic polymer, a polymer containing a hydroxy group is preferable.

As the hydrophilic polymer, specifically, for example, polysaccharide such as polyvinyl alcohol, polyvinyl butyral, and cellulose, and derivatives thereof are exemplified. These substances may be singly used or be used in combination of two types or more. The hydrophilic polymer may be crosslinked by a crosslinking agent. Such crosslinking causes durability of a coating film to be improved.

The crosslinking agent is not particularly limited, and may be appropriately selected in accordance with the purpose. Specific examples of the crosslinking agent include an epoxy compound, an isocyanate compound, an aldehyde compound, an ultraviolet crosslinking type compound, a leaving group-containing compound, a carboxylic acid compound, and a urea compound.

Specific examples of the inorganic binder (inorganic glass) include a silane compound such as trialkoxysilane represented by a chemical formula $[R^{14}Si(OR^{15})_3]$, tetraalkoxysilane represented by a chemical formula $[Si(OR^{16})_4]$ ($R^{14}$ to $R^{16}$ each independently is alkyl group having 1 to 6 carbon atoms); and water glass. Among these substances, water glass is preferable because an effect of improving durability is high.

(Base)

In the oil-water separation apparatus 10 in this embodiment, the channel 17 for a liquid, which mainly passes the separated water therethrough, is formed by the base 13. Specifically, in a case where the oil-water separation filter medium 11 in this embodiment is formed to have a film shape by the fibrous base 13, a space between fibers functions as the channel 17 for a liquid. In a case where the oil-water separation filter medium 11 is formed by stacking (or filling with) the particulate base 13, a gap between particles functions as the channel 17 for a liquid. In a case where the base 13 is a porous medium, an inner space of the pore in the porous medium also functions as the channel 17 for a liquid. In a case where the base 13 is formed to be a net-like member, for example, to be a net which is formed of metal and has a small hole diameter, vacancy of the net functions as the channel 17 for a liquid.

The material of the base 17 is not particularly limited as long as the material can form a channel for a liquid to be separated. The material of the base 17 may be organic matter or inorganic matter. In addition, the material of the base 17 may be a composite of organic matter and inorganic matter. Thus, as a form of the base in the filter medium in this embodiment, fibrous organic matter, particulate organic matter, fibrous inorganic matter, and particulate inorganic matter, a porous medium of organic matter, a porous medium of inorganic matter, and the like are exemplified.

Here, the organic matter usable as the base is not particularly limited. Specific examples of the organic matter include various resins such as a thermoplastic resin, a thermoplastic elastomer, a thermosetting resin, and an UV-curable resin, a natural polymer such as cellulose, and derivatives thereof. Specific examples include a thermoplastic resin such as polyvinyl chloride, polyethylene, polypropylene, polycarbonate, polyester, polystyrene, a silicone resin, polyvinyl acetal, polyvinyl alcohol, polyamide, polyimide, an acrylic polyol resin, a polyester polyol resin, a urethane resin, a fluororesin, and a thermoplastic acrylic resin, or a thermosetting resin such as an epoxy resin, a phenol resin, and a thermosetting acrylic resin. Pulp, cotton, or the like is exemplified.

A material usable as the base is not particularly limited. Specific examples of the material include a carbon-based substance such as active carbon, and an inorganic substance such as anthracite, sand, gravel, garnet, glass, ceramics, and metal.

Examples of fiber useable as the base may include an organic fiber such as synthetic fiber, natural fiber, and cellulosic fiber, or an inorganic fiber such as metallic fiber, carbon fiber, glass fiber, and ceramics fiber. These fibers may be singly used or be used by mixing or mixed-spinning two types or more thereof. As a fiber assembly usable as the base, for example, a film-like or sheet-like aggregate such as filter paper, woven fabric, knitted fabric, nonwoven fabric, a net, and mesh may be exemplified. As the fiber assembly, an object obtained by winding fiber (winding to be columnar) to form a filter may be used. In the fiber assembly, fibers may be stuck to each other or be fused in a range without closing a channel for a liquid between fibers.

As particles usable as the base, for example, inorganic particles such as anthracite, and, gravel, garnet, glass, ceramics, and metal may be exemplified. These particles may be singly used or be used as a mixture of two types or more thereof. As an example of an aggregate of particles usable as the base, an object (for example, sand filter) in which a plurality of particles are stacked on a porous substrate, and an object in which a porous bag or a porous container is filled with a plurality of particles may be exemplified. In the aggregate of particles, particles may be stuck to each other or be sintered in a range without closing a channel for a liquid between particles.

Examples of the porous medium which is usable as the base, and has a continuous pore may include an organic porous medium such as porous fluororesin, porous polypropylene, porous polyethylene, porous polyester, porous polystyrene, porous polysulfone, porous polyethersulfone, porous vinylon, porous nylon, and porous cellulose; or an inorganic porous medium such as active carbon, ceramics, sintered metal, silica, alumina, zeolite, calcium carbonate, and clay mineral. These porous media may be singly used or be used as a mixture of two types or more thereof. The shape of the porous medium is, for example, a film shape, a sheet shape, and a particle shape. As the film-like and a sheet-like porous medium, for example, a membrane filter, and a hollow filter membrane may be exemplified. The particulate porous medium may be used as the base, in a form of an aggregate, for example. In an aggregate of the particulate porous medium, particulate porous media may be stuck to each other or be sintered in a range without closing a continuous pore.

The pore diameter (that is, channel diameter) of the continuous pore in the porous medium is preferably in a range of 0.1 to 180 µm, more preferably in a range of 0.1 to 150 µm, further preferably in a range of 0.5 to 75 µm, and particularly preferably in a range of 1 to 50 µm. If the pore diameter of the porous medium is in the above range, oil is not permeated, and a water-passing rate in a practically-appropriate range is obtained. Thus, such a porous medium is preferable as the base for oil-water separation.

The base which may be used in the filter medium in this embodiment is not particularly limited. Specific examples of such a base include filter paper which is mainly formed of cellulose, a filter cloth (polyester, polyethylene, polypropylene, polytetrafluoroethylene, nylon, polyimide, polyacrylonitrile, polysulfone, polyethersulfone, polyphenylene sulfide, and the like), a nonwoven filter (polyester, polyethylene, polypropylene, rayon, nylon, polyphenylene sulfide, and the like), a fibrous filter (resin, glass, ceramics, and metal), a sintered filter (object obtained by directly bonding powder or fiber of metal, ceramics, plastics, and the like by heat and pressure), a metal net, a metal mesh, a filter plate (an object obtained by performing compression molding of cellulose, glass fiber, and the like), and an object in which silica, alumina, zeolite, calcium carbonate, talc, a clay mineral such as montmorillonite, and the like are stacked (or filled).

The filter medium in this embodiment, which is configured by the base having hydrophilicity is preferable because of having high holding properties to the base in which a coating film containing an oil-repellent hydrophilic agent is provided. Here, organic matter usable as the base having hydrophilicity is not particularly limited. As such organic matter, organic matter which itself can be subjected to hydrophilic and oil-repellent treatment, and organic matter which is subjected to hydrophilization treatment and then is subjected to hydrophilic and oil-repellent treatment are provided. As the organic matter which itself can be subjected to hydrophilic and oil-repellent treatment, organic matter having a polar group is appropriate. Examples of such organic matter include various resins such as a thermoplastic resin, a thermoplastic elastomer, a thermosetting resin, and an UV-curable resin, a natural polymer such as cellulose, and derivatives thereof. Specific examples include a thermoplastic resin such as polyvinyl chloride, polycarbonate, polyester, polyvinyl acetal, polyvinyl alcohol, an acrylic polyol resin, a polyester polyol resin, a urethane resin, and a thermoplastic acrylic resin, or a thermosetting resin such as an epoxy resin, a phenol resin, and a thermosetting acrylic resin. Pulp, cotton, or the like is exemplified.

As the base having hydrophilicity, a polymeric material may be provided in which a functional group having hydrophilicity, such as a hydroxyl group, a carboxyl group, an amino group, a ketone group, and a sulfone group is introduced by a chemical reaction with acid, alkali, a sulfurous gas, or a fluorine gas.

As the base having hydrophilicity, organic matter may be provided in which the surface of polymer is subjected to hydrophilization by a finishing agent having hydrophilicity. Examples of the finishing agent having hydrophilicity include polyalkylene oxide containing polyethylene glycol, polycarboxylic acid, polyisocyanate, a vinyl group, a glycidyl ether group, polyamine, N-methoxymethylol, and the like; a polymeric electrolyte; and a cellulose-based substance having hydrophilicity.

As the base having hydrophilicity, a fluororesin, polypropylene, polyethylene, and polystyrene of which the surface is subjected to hydrophilization by any one or more of plasma treatment, corona treatment, and ozone treatment may be provided.

Chemical treatment, plasma treatment, corona treatment, or the like may be performed on various resins having a polar group, natural polymer such as cellulose, and derivatives thereof, and the like, which are described above.

It is preferable that porous vinylon, porous nylon, porous polyvinyl alcohol, a vinyl copolymer containing a porous polyalkylene oxide chain, porous cellulose, and composites thereof be used as a porous medium which is the base having a polar group.

It is preferable that porous fluororesin, porous polypropylene, porous polyethylene, porous polystyrene, porous polyester, porous polysulfone, porous polyethersulfone (which are subjected to hydrophilization treatment), and composites thereof be used as the porous medium which is the base having a polar group.

The channel width of the base (that is, width of a channel configured by the base) is preferably in a range of 0.1 to 180 µm, more preferably in a range of 0.1 to 150 µm, further preferably in a range of 0.5 to 75 µm, and particularly preferably in a range of 1 to 50 µm. If the channel width of the filter medium is in the above range, oil is not permeated, and a water-passing rate in a practically-appropriate range is obtained. Thus, such a filter medium is preferable.

In a case where the base is a porous medium, the porous medium may hold a nitrogen-containing fluorine compound (oil-repellent hydrophilic agent) represented by the formulas (1) to (4).

As a holding method, for example, a method in which a porous medium to be held is added to a dissolving liquid or a dispersion liquid of the nitrogen-containing fluorine compound (oil-repellent hydrophilic agent), and is dried so as to remove a solvent may be appropriately applied. As a proportion for holding, selection to cause the mass composition ratio of an oil-repellent hydrophilic agent and a porous medium to be held to be in a range of a pair of 1 to 50 and 99 to 50 is preferable from the viewpoint of characteristics of the hydrophilic and oil-repellent properties.

In a case where the obtained porous medium is a particulate porous medium, the surface of the base such as filter paper, nonwoven fabric, or a cartridge filter is subjected to fixing treatment, and thus more excellent oil-water separation performance is obtained. Thus, this case is more preferable. In order to perform fixation to the base, the above described resins or glassiness may be used.

The base of the filter medium in this embodiment may have a form in a manner such that formation is performed to be fibrous or particulate, by a resin composition which contains the above-described organic matter (resin) and one or more nitrogen-containing fluorine compounds (oil-repellent hydrophilic agents) represented by the formulas (1) to (4). That is, the above-described oil-repellent hydrophilic agent may be used as an additive for imparting the function of the hydrophilic and oil-repellent properties to various resins.

The resin composition may further contain an additive as an arbitrary component, in addition to the oil-repellent hydrophilic agent and a resin. The additive is used for applying function such as a fluidity-improving agent, a surfactant, a flame retardant, a conductivity-imparting agent, and an antifungal agent, which is different from hydrophilicity and oil repellency.

A method of forming the resin composition is not particularly limited as long as the method is a method in which an oil-repellent hydrophilic agent which is appropriately selected in accordance with the type of a resin can be dispersed or dissolved. Specifically, for example, as a method of mixing an oil-repellent hydrophilic agent to a thermoplastic resin, there is a method of mixing by kneading and the like by an extrusion method or a rolling method.

In the resin composition, the mass composition ratio of the oil-repellent hydrophilic agent and the resin is preferably in a range of a pair of 0.2 to 99.9 and 99.8 to 0.1, more preferably in a range of a pair of 2 to 98 and 98 to 2, and further preferably in a range of a pair of 10 to 90 and 90 to 10. If the mass composition ratio of the oil-repellent hydrophilic agent is equal to or more than 0.2, it is possible to sufficiently exhibit the hydrophilic and oil-repellent function. Thus, this ratio is preferable. If the mass composition ratio of the oil-repellent hydrophilic agent is equal to or more than 90, moldability is easily held without damaging resin physical properties. Thus, this range is preferable.

Further, in a case where the base of the filter medium in this embodiment is a porous medium, one or more nitrogen-containing fluorine compounds (oil-repellent hydrophilic agents) represented by the formulas (1) to (4) may be used in a form of the porous medium. Thus, excellent oil-water separation performance is obtained, and accordingly, such a use is preferable.

As a method of obtaining a porous medium, a generally-known method may be applied. Specifically, for example, a method in which a dissolving liquid or a dispersion liquid of the oil-repellent hydrophilic agent is dried by a spray-dry method is exemplified. Regarding particles obtained by the spray-dry method, a porous medium may be formed and a particle diameter may be controlled. In addition, the particles themselves may be applied as a filtering medium. Thus, the particles are particularly preferable.

When an aggregate of particulate porous media is manufactured, a binder such as a resin or glassiness is added to a dissolving liquid or a dispersion liquid of the oil-repellent hydrophilic agent, and thus a particulate porous medium is bound. Thus, physical strength of an aggregate of the porous media may be improved, or solubility to water may be controlled and reduced.

The above-described thermoplastic resin or thermosetting resin may be used as the resin. The above-described silane compound or water glass may be used as the glassiness. The amount of used binder for the oil-repellent hydrophilic agent is not particularly limited, and the binder may be appropriately added in a range which allows particles to be bound to each other. Typically, the mass composition ratio of the oil-repellent hydrophilic agent and the binder is preferably used in a range of a pair of 0.2 to 99.9 and 99.8 to 0.1, more preferably used in a range of a pair of 2 to 98 and 98 to 2, and further preferably used in a range of a pair of 10 to 90 and 90 to 10.

<Inorganic Compound>

As the filter medium in this embodiment, a medium in which a channel is formed by a base having hydrophilicity, and a composite of one or more nitrogen-containing fluorine compounds represented by the formulas (1) to (4), and an inorganic compound having charges or an ionic group is fixed onto at least a portion of the surface of the channel may be provided.

As the inorganic compound having charges or an ionic group, specifically, for example, an inorganic particle, a clay mineral, a flocculant is exemplified.

The inorganic particle is not particularly limited as long as the inorganic particle has charges. Specifically, for example, fumed silica, colloidal silica, mullite, alumina, and zeolite are exemplified. As the inorganic particle, any of these substances may be singly used or be used as a mixture of two types or more.

The inorganic particle may be an aggregate of primary particles.

In a case where an inorganic particle is used as the inorganic compound, a composite in which at least a portion of the nitrogen-containing fluorine compound is combined with the surface of the inorganic particle by noncovalent bond is obtained.

The clay mineral is not particularly limited as long as the clay mineral has charges. Specifically, for example, bentonite, organic bentonite, smectite, and kaolinite are exemplified. As the clay mineral, any of these substances may be singly used or be used as a mixture of two types or more.

In a case where the clay mineral is used as the inorganic compound, a composite in which the nitrogen-containing fluorine compound is taken between layers of the clay mineral and thus the layers are combined is obtained.

The flocculant is not particularly limited as long as the flocculant has an ionic group. Specifically, for example, polyaluminum chloride, ferric polysulfate, and aluminum sulfate are exemplified. As the flocculant, any of these substances may be singly used or be used as a mixture of two types or more. In addition, the flocculant may be dissolved in water, and may be used in a liquid phase. In a case where the flocculant is used as the inorganic compound, a composite in which at least a portion of the nitrogen-containing fluorine compound and the flocculant are combined by noncovalent bond is obtained.

In the oil-repellent hydrophilic agent in this embodiment, the mass composition ratio of the nitrogen-containing fluorine compound and the inorganic compound is not particularly limited, and may be appropriately selected in accordance with characteristic values of the hydrophilic and oil-repellent properties or persistence of the characteristics. Specifically, the mass composition ratio of the nitrogen-containing fluorine compound and the inorganic compound may be selected in a range of a pair of 1 to 99 and 99 to 1.

As the filter medium in this embodiment, a medium in which a channel is configured by a base having hydrophilicity, and a composite of one or more nitrogen-containing fluorine compounds represented by the formulas (1) to (4), and a fluorine resin particle is fixed onto the surface of the channel may be provided.

The mass composition ratio of the nitrogen-containing fluorine compound and the fluorine resin particle is not particularly limited, and may be appropriately selected in accordance with characteristic values of the hydrophilic and oil-repellent properties or persistence of the characteristics. Specifically, the mass composition ratio of the nitrogen-containing fluorine compound and the fluorine resin particle may be selected in a range of a pair of 1 to 99 and 99 to 1.

A composite formed from one or more nitrogen-containing fluorine compounds represented by the formulas (1) to (4), and the inorganic compound or the fluorine resin particle may be formed. The obtained composite may be fixed to a channel formed by the base which has hydrophilicity. Thus, it is possible to further improve persistence of various capabilities such as the oil-water separation function and the like.

The above-described organic binder or inorganic binder may be used for forming a composite of the nitrogen-containing fluorine compound, and the inorganic compound or the fluorine resin particle, and for fixing the composite to the channel.

As described above, according to the oil-water separation apparatus 10 in this embodiment, the oil-water-separating member 14 is formed in the base 13, and thus one or more fluorine compounds in which an oil-repellency-imparting group and a hydrophilicity-imparting group are contained in a molecule is provided in the surface of the channel 17, for example. Thus, in a case where a liquid mixture of water and oil is introduced into the oil-water separation apparatus 10 in this embodiment, moisture passes through the channel 17 of the base 13, but oil can hardly pass through the channel 17. Accordingly, the oil-water separation apparatus 10 in this embodiment can perform separation into water and oil only by gravity, and can perform separation into moisture and oil at low cost with a simple configuration.

The water drain port 15 for discharging moisture is formed in the lower region E2 of the liquid reservoir 12, in which moisture W separated by the oil-water separation filter medium 11 is accumulated. Thus, it is possible to easily discharge moisture separated by gravity, to the outside of the liquid reservoir 12 by opening the water drain port 15, without labor of, for example, drawing moisture accumulated in the lower region E2 up by using a pump. Oil G separated by the oil-water separation filter medium 11 floats on the surface layer of the liquid mixture by a specific gravity difference from that of the moisture W. Thus, the knob 19 is gripped so as to extract the oil-water separation filter medium 11 from the liquid reservoir 12 along with the support member 18, thereby it is possible to easily collect the oil G. The oil G which floats on the surface layer of the liquid mixture may be scooped and collected by a ladle.

Further, in the oil-water separation apparatus 10 in this embodiment, the hydrophilic and oil-repellent properties are applied to the channel 17 formed by the base 13. Thus, adhering of an organic molecule, or soil and mud is difficult, and accordingly, excellent anti-fouling properties are obtained. Attached dirt is easily removed by physical treatment of, for example, back pressure washing, and ease of washability is also excellent.

In the oil-water separation apparatus 10 in this embodiment, in a case of containing only the fluorine compounds represented by the formulas (1) to (4), it is possible to apply excellent hydrophilic and oil-repellent properties while a perfluoroalkyl group having 8 or more carbon atoms which are continuously bonded to each other is not contained, and a chemical structure which does not have a concern of generating PFOS or PFOA, which becomes a problem from the viewpoint of bioaccumulation or environmental adaptability, is provided.

<Modification Example of First Embodiment>

Figure 2:
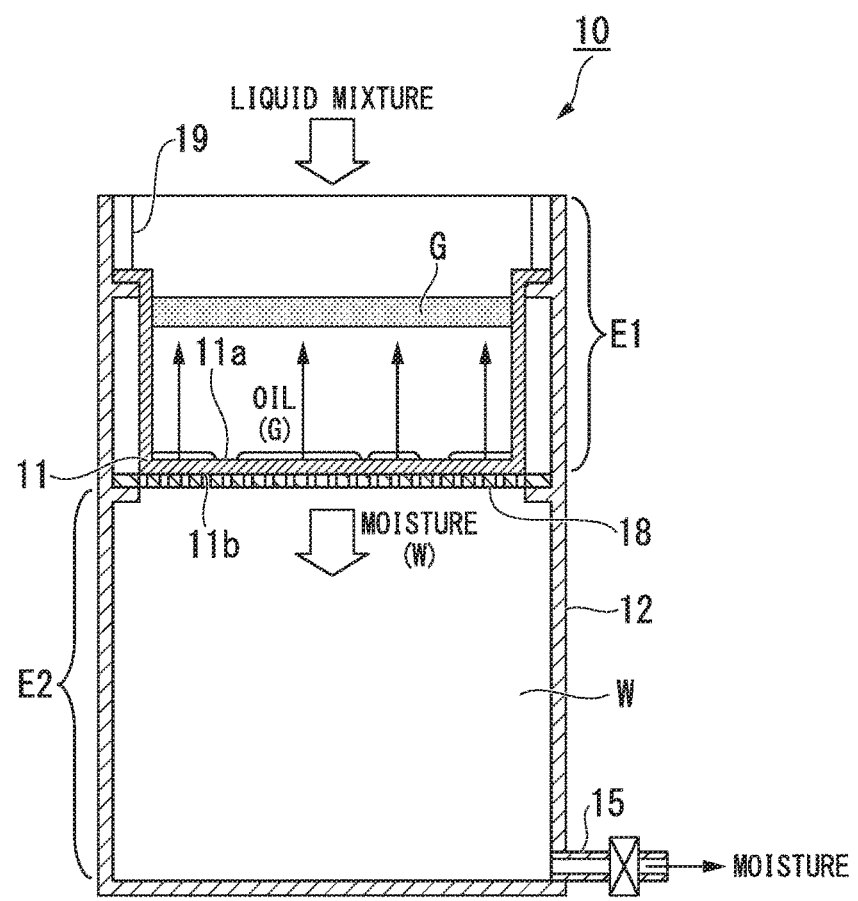
FIG. 2 is a sectional view illustrating a modification example of the first embodiment of the oil-water separation apparatus according to the present invention.

FIG. 2 illustrates an example in which a bag type filter is applied as the oil-water separation filter medium 11 which is used in the oil-water separation apparatus 10 of the embodiment illustrated in FIG. 1. In the oil-water separation apparatus 10 of this embodiment, an oil-water separation filter medium 11 formed to have a bag type which allows a liquid to be permeated from the bottom surface and the side surface (circumferential surface) is used. Such an oil-water separation filter medium 11 has, for example, a knob 19 for extraction attached thereto. The entirety of the oil-water separation filter medium 11 is attachable and detachable to and from the liquid reservoir 12.

A support member 18 is attached to the liquid reservoir 12. The support member 18 supports the bottom surface of such a bag type oil-water separation filter medium 11. As a plate medium in which multiple holes are formed through which a liquid can pass, for example, a punching metal plate is used as the support member 18 in this embodiment.

In such an oil-water separation apparatus 10 of the embodiment, oil-water separation may be also performed on the side surface (circumferential surface) in addition to the bottom surface of the oil-water separation filter medium 11. Thus, it is possible to separate and collect oil from a liquid with much more efficiency.

<Second Embodiment>

Figure 3:
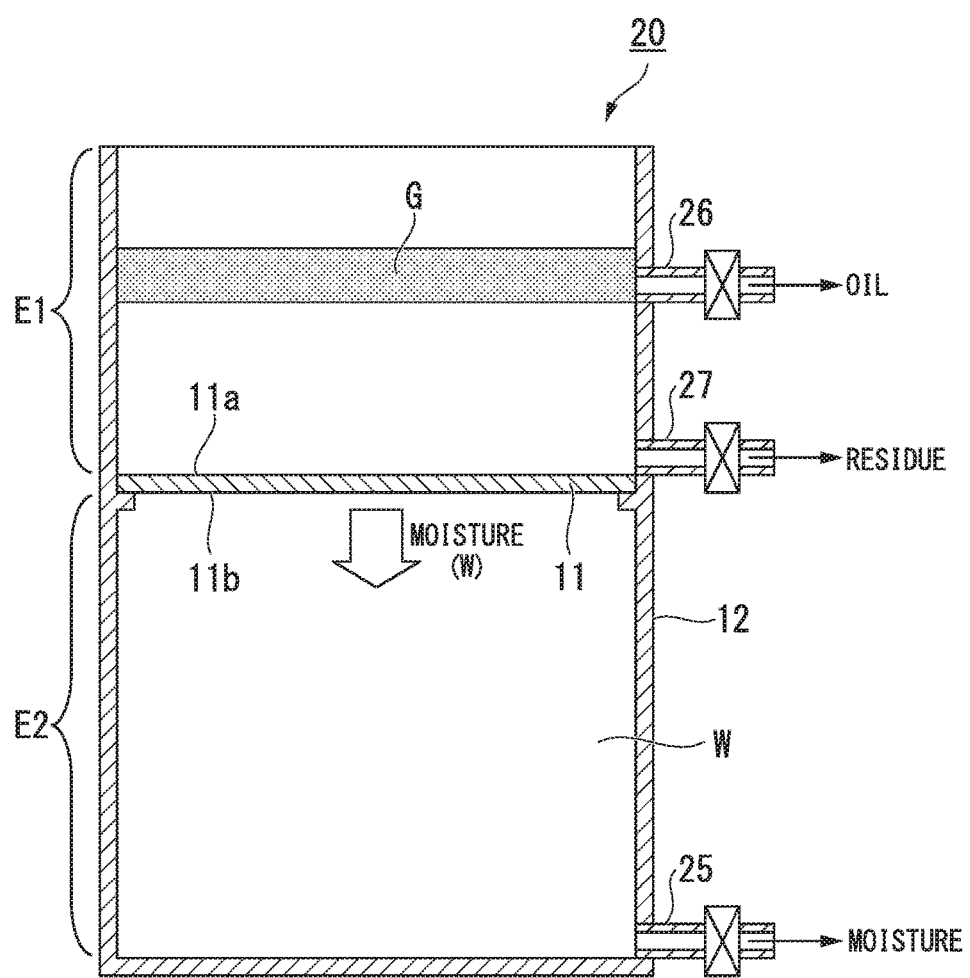
FIG. 3 is a sectional view illustrating a second embodiment of the oil-water separation apparatus according to the present invention.

FIG. 3 is a sectional view illustrating an oil-water separation apparatus according to a second embodiment of the present invention.

An oil-water separation apparatus 20 in this embodiment includes an oil-water separation filter medium 11 and a liquid reservoir 12, similarly to those in the first embodiment. The oil-water separation filter medium 11 separates a liquid mixture which is introduced into the liquid reservoir 12 and contains water and oil into moisture and oil by using hydrophilic and oil-repellent properties, and causes the moisture to pass therethrough. For example, if a liquid mixture is supplied to the upper region E1 of the liquid reservoir 12, the hydrophilic and oil-repellent properties of the oil-water separation filter medium 11 cause the liquid mixture to be separated into moisture and oil. The moisture (W in FIG. 3) passes through the oil-water separation filter medium 11 by gravity, and is accumulated in the lower region E2 of the liquid reservoir 12. The oil (G in FIG. 3) separated by the oil-water separation filter medium 11 floats in the vicinity of a liquid surface of the liquid mixture by a specific gravity difference.

A water drain port 25 is formed in the lower region E2 of the liquid reservoir 12. The water drain port 15 is used for discharging moisture which is filtered and accumulated in the lower region E2 to the outside of the liquid reservoir 12. Such a water drain port 25 may be configured from, for example, a valve and a liquid tube which penetrates a wall surface of the liquid reservoir 12.

In the upper region E1 of the liquid reservoir 12, an oil drain port 26 is formed in the vicinity of a position corresponding to a liquid level of the introduced liquid mixture. The oil drain port 26 is used for discharging oil which is separated by the oil-water separation filter medium 11 and floats in the vicinity of the liquid level, to the outside of the liquid reservoir 12. Such an oil drain port 26 may be configured from, for example, a valve and a liquid tube which penetrates the wall surface of the liquid reservoir 12.

Further, in the upper region E1 of the liquid reservoir 12, a liquid-discharging port 27 is formed in the vicinity of a position at which the oil-water separation filter medium 11 is formed. The liquid-discharging port 27 is used for causing a solid body which is deposited on one surface 11a side of the oil-water separation filter medium 11 to flow out of the liquid reservoir 12 along with a solution mixture. The solid body is, for example, a solid contained in the liquid mixture, or impurities obtained by oil-water separation. Such a liquid-discharging port 27 may be configured from, for example, a valve and a liquid tube which penetrates the wall surface of the liquid reservoir 12.

In this embodiment, the oil drain port 26 and the water drain port 25 are provided in the liquid reservoir 12, and thus it is possible to easily discharge, for example, oil which floats in the vicinity of the liquid level of the liquid mixture separated by the oil-water separation filter medium 11 to the outside of the liquid reservoir 12, by opening the oil drain port 26. Thus, it is possible to easily extract only oil from the liquid reservoir 12 without a labor of scooping and collecting the oil which floats in the vicinity of the liquid level, by using a ladle.

Liquid level detection means is preferably provided in the upper region E1 of the liquid reservoir 12. The liquid level detection means detects a liquid level position of a liquid mixture separated by the oil-water separation filter medium 11. As the liquid level detection means, a liquid level meter which communicates with an inside of the liquid reservoir 12, a liquid level detection device using an optical sensor, and the like are exemplified. Such liquid level detection means is provided, and thus it is possible to precisely know a timing for operating the oil drain port 26 so as to discharge the floating oil, and to appropriately discharge only oil from the oil drain port 26, even in a structure in which directly and visually recognizing the inside of the liquid reservoir 12 is not possible.

In this embodiment, the liquid-discharging port 27 is provided in the vicinity of the oil-water separation filter medium 11, and thus it is possible to cause a solid body which is deposited on the one surface 11a side of the oil-water separation filter medium 11 to flow out of the liquid reservoir 12 along with a solution mixture. Thus, only the liquid-discharging port 27 is opened, and a waste liquid containing the deposited solid body is caused to flow out without performing, for example, a clogging prevention operation in which the oil-water separation filter medium 11 is extracted from the liquid reservoir 12 and thus the deposited solid body is removed, and which takes labor, and accordingly, it is possible to prevent clogging of the oil-water separation filter medium 11. Accordingly, it is possible to significantly reduce labor relating to maintenance of the oil-water separation filter medium 11.

<Third Embodiment>

Figure 4:
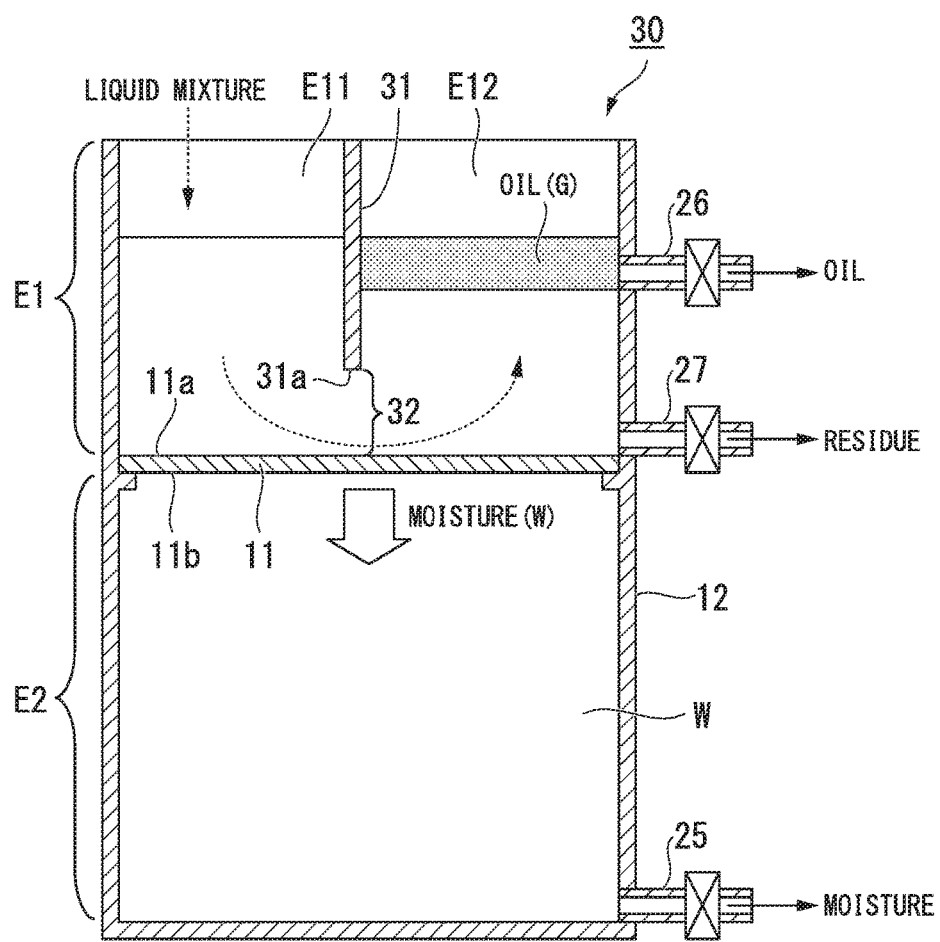
FIG. 4 is a sectional view illustrating a third embodiment of the oil-water separation apparatus according to the present invention.

FIG. 4 is a sectional view illustrating an oil-water separation apparatus according to a third embodiment of the present invention.

An oil-water separation apparatus 30 in this embodiment includes an oil-water separation filter medium 11 and a liquid reservoir 12. The oil-water separation filter medium 11 has a configuration similar to that in the first embodiment. The oil-water separation filter medium 11 separates a liquid mixture which is introduced into the liquid reservoir 12 and contains water and oil into moisture and oil by using hydrophilic and oil-repellent properties, and causes the moisture to pass therethrough. For example, if a liquid mixture is supplied to the upper region E1 of the liquid reservoir 12, the hydrophilic and oil-repellent properties of the oil-water separation filter medium 11 cause the liquid mixture to be separated into moisture and oil. The moisture (W in FIG. 4) passes through the oil-water separation filter medium 11 by gravity, and is accumulated in the lower region E2 of the liquid reservoir 12. The oil (G in FIG. 4) separated by the oil-water separation filter medium 11 floats in the vicinity of a liquid surface of the liquid mixture by a specific gravity difference.

A distributing plate 31 is formed in the oil-water separation apparatus 30 of this embodiment. The distributing plate 31 subdivides the upper region E1 of the liquid reservoir 12 into a plurality of small regions E11 and E12. The distributing plate 31 is a plate-like member which is extended in the upper region E1 of the liquid reservoir 12 in a vertical direction. Such a distributing plate 31 causes the upper region E1 of the liquid reservoir 12 to be subdivided into the small region E11 and the small region E12 which are arranged along a horizontal direction.

A gap 32 which is separate from the oil-water separation filter medium 11 and functions to link the small region E11 and the small region E12 to each other is formed at a lower end 31a of the distributing plate 31. The liquid mixture may flow between the small region E11 and the small region E12 through the gap 32.

A water drain port 25 for discharging moisture to the outside of the liquid reservoir 12 is formed in the lower region E2 of the liquid reservoir 12. An oil drain port 26 for discharging oil to the outside of the liquid reservoir 12 is formed in the small region 12 of the upper region E1 in the liquid reservoir 12. A liquid-discharging port 27 is formed in the vicinity of the oil-water separation filter medium 11 in the upper region E1 of the liquid reservoir 12. The liquid-discharging port 27 discharges a solid body deposited on the one surface 11a side of the oil-water separation filter medium 11.

In the oil-water separation apparatus 30 of this embodiment, a liquid mixture before oil-water separation is introduced into, for example, the small region E11. The liquid mixture introduced into the small region E11 flows along the one surface 11a of the oil-water separation filter medium 11 by the distributing plate 31, and flows into the small region E12 through the gap 32. Such a distributing plate 31 is provided in the upper region E1 of the liquid reservoir 12, and thus it is possible to bring the liquid mixture into contact with the oil-water separation filter medium 11 without irregularity, and to separate the liquid mixture into oil G and moisture W by the oil-water separation filter medium 11, with high efficiency. Further, turbulence of a liquid occurs in the small region E11 with introduction of the liquid mixture. However, in the small region E12 partitioned by the distributing plate 31, an occurrence of turbulence of a liquid can be suppressed, and an interface between an oil phase (oil) and a water phase (moisture) can be stably formed.

The moisture separated by the oil-water separation filter medium 11 passes through the oil-water separation filter medium 11 by gravity, and is accumulated in the lower region E2 of the liquid reservoir 12. The oil G and the moisture W which are separated in this manner can be easily discharged from the liquid reservoir 12 to the outside thereof by opening the oil drain port 26 and the water drain port 25, respectively.

<Fourth Embodiment>

Figure 5:
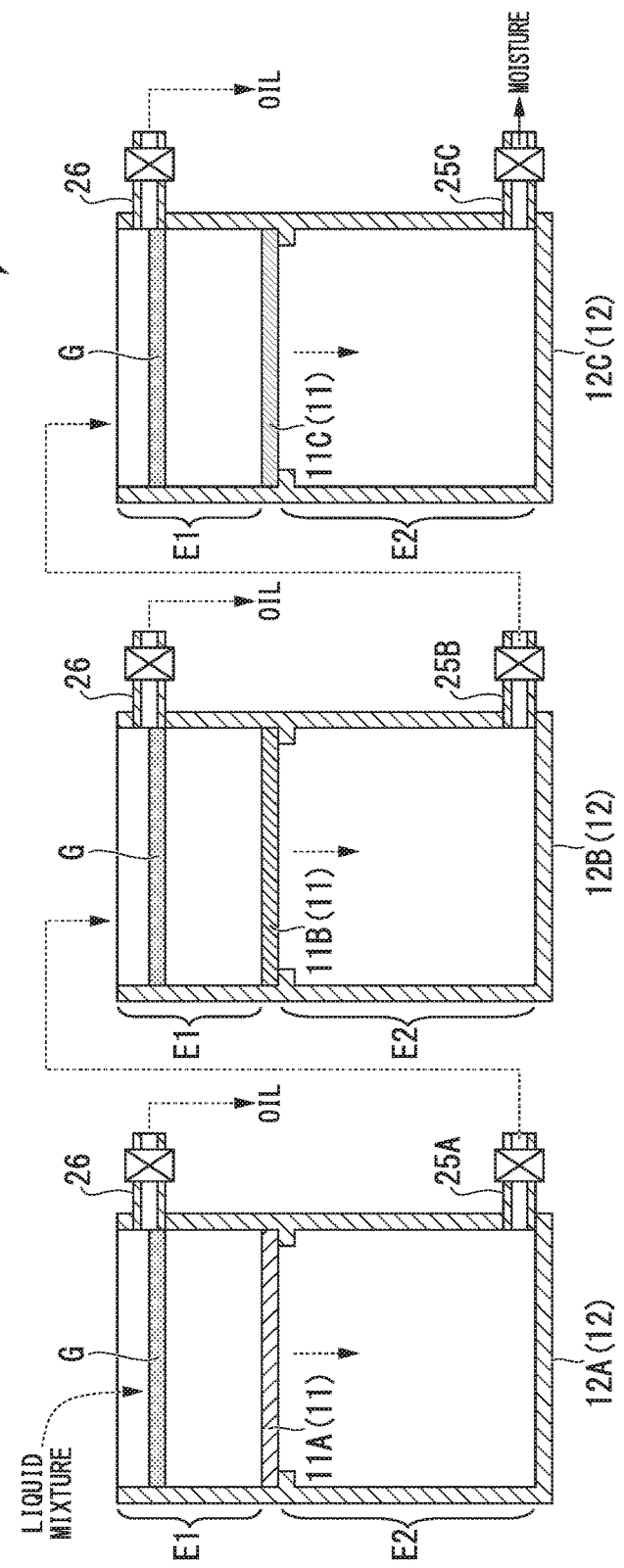
FIG. 5 is a sectional view illustrating a fourth embodiment of the oil-water separation apparatus according to the present invention.

FIG. 5 is a sectional view illustrating an oil-water separation apparatus according to a fourth embodiment of the present invention.

In an oil-water separation apparatus 40 of this embodiment, for example, three liquid reservoirs 12 in which an oil-water separation filter medium 11 having a configuration similar to that in the first embodiment is provided are arranged in series. That is, a liquid reservoir 12A, a liquid reservoir 12B, and a liquid reservoir 12C are arranged in order from the preceding stage side to the subsequent stage side. A liquid tube is provided so as to cause a liquid discharged from a water drain port 25A to flow into the upper region E1 of the liquid reservoir 12B. The water drain port 25A is provided in the lower region E2 of the liquid reservoir 12A. Similarly, a liquid tube is provided so as to cause a liquid discharged from a water drain port 25B to flow into the upper region E1 of the liquid reservoir 12C. The water drain port 25B is provided in the lower region E2 of the liquid reservoir 12B.

Oil-water separation filter media 11 provided in the liquid reservoirs 12A, 12B, and 12C of the oil-water separation apparatus 40 in this embodiment have a width (average opening diameter) of a channel 17 (see FIG. 1(b)) which is different from each other. That is, the width of the channel 17 of the oil-water separation filter medium 11B provided in the liquid reservoir 12B is narrower than the width of the channel 17 of the oil-water separation filter medium 11A provided in the liquid reservoir 12A. The width of the channel 17 of the oil-water separation filter medium 11C provided in the liquid reservoir 12C is further narrower than the width of the channel 17 of the oil-water separation filter medium 11B provided in the liquid reservoir 12B. That is, the width (average opening diameter) of the channel 17 gradually becomes narrower (smaller) in order of the oil-water separation filter medium 11A, the oil-water separation filter medium 11B, and the oil-water separation filter medium 11C.

Such a width (average opening diameter) of the channel 17 may be changed in accordance with a material for forming the base 13 (see FIG. 1(b)). For example, in a case where the base 13 is a porous base, the oil-water separation filter medium 11A, the oil-water separation filter medium 11B, and the oil-water separation filter medium 11C may be formed by using porous bases which have a pore diameter different from each other. For example, in a case where the base 13 is a fibrous base or a particulate base, the oil-water separation filter medium 11A, the oil-water separation filter medium 11B, and the oil-water separation filter medium 11C may be formed by using fibrous bases having a space between fibers which is different from each other, or by using particulate bases having a gap between particles which is different from each other.

In this embodiment, the liquid reservoir 12A, the liquid reservoir 12B, and the liquid reservoir 12C which respectively include the oil-water separation filter medium 11A, the oil-water separation filter medium 11B, and the oil-water separation filter medium 11C having a width of the channel 17 which is different from each other are arranged in series so as to constitute the oil-water separation apparatus 40. Thus, it is possible to reduce pressure loss with filtration by the oil-water separation filter medium.

That is, in a case where a liquid mixture is subjected to oil-water separation by using only one oil-water separation filter medium, and only moisture is filtered, the channel of the oil-water separation filter medium is required to have a width fine enough such that oil aggregated in the oil-water-separating member is never permeated. In addition, pressure loss largely occurs by blockage and the like of the channel due to the oil.

In this embodiment, oil contained in a liquid mixture is roughly separated and collected in the oil-water separation filter medium 11A at the preceding stage side, which has a large channel width. Then, oil which has not been collected in the oil-water separation filter medium 11A at the preceding stage side is reliably captured and collected in the oil-water separation filter medium 11B or the oil-water separation filter medium 11C at the subsequent stage side, which has a small channel width. Thus, in this embodiment, the channel 17 formed in the base 13 constituting the oil-water separation filter medium 11A or the oil-water separation filter medium 11B mainly passes moisture, and also allows oil of a certain degree to be passed.

Oil is roughly collected in the oil-water separation filter medium 11A at the preceding stage side, and thus the proportion of the oil in the liquid mixture flowing into the oil-water separation filter medium 11B or the oil-water separation filter medium 11C having a small channel width is reduced. Thus, blockage of the channel 17 occurring by oil in the oil-water separation filter medium 11B or the oil-water separation filter medium 11C which has a small channel width causing pressure loss to easily occur is reduced. Accordingly, it is possible to realize the oil-water separation apparatus 40 in which pressure loss is reduced in the entirety, and efficient oil-water separation is possible only by gravity.

According to the oil-water separation apparatus 40 in this embodiment, in which the channel width gradually becomes narrower, oil having relatively high viscosity which causes clogging to easily occur, for example, lard solidified at a normal temperature is separated and collected in the oil-water separation filter medium 11A having a large channel width. Thus, it is possible to easily perform oil-water separation at the subsequent stage side, and to efficiently perform oil-water separation treatment of an oil-water mixed liquid containing suspended matter.

In this embodiment, the liquid reservoirs 12A, 12B, and 12C may be arranged on the same one surface. For example, an upper end of the liquid reservoir 12B is disposed at a position lower than the water drain port 25A of the liquid reservoir 12A, an upper end of the liquid reservoir 12C is disposed at a position lower than the water drain port 25B of the liquid reservoir 12B, that is, the liquid reservoirs 12A, 12B, and 12C may be arranged so as to be step-like. Thus, it is possible to perform oil-water separation of a solution mixture in stages only by gravity, without using external motivity of a pump and the like.

<Fifth Embodiment>

Figure 6:
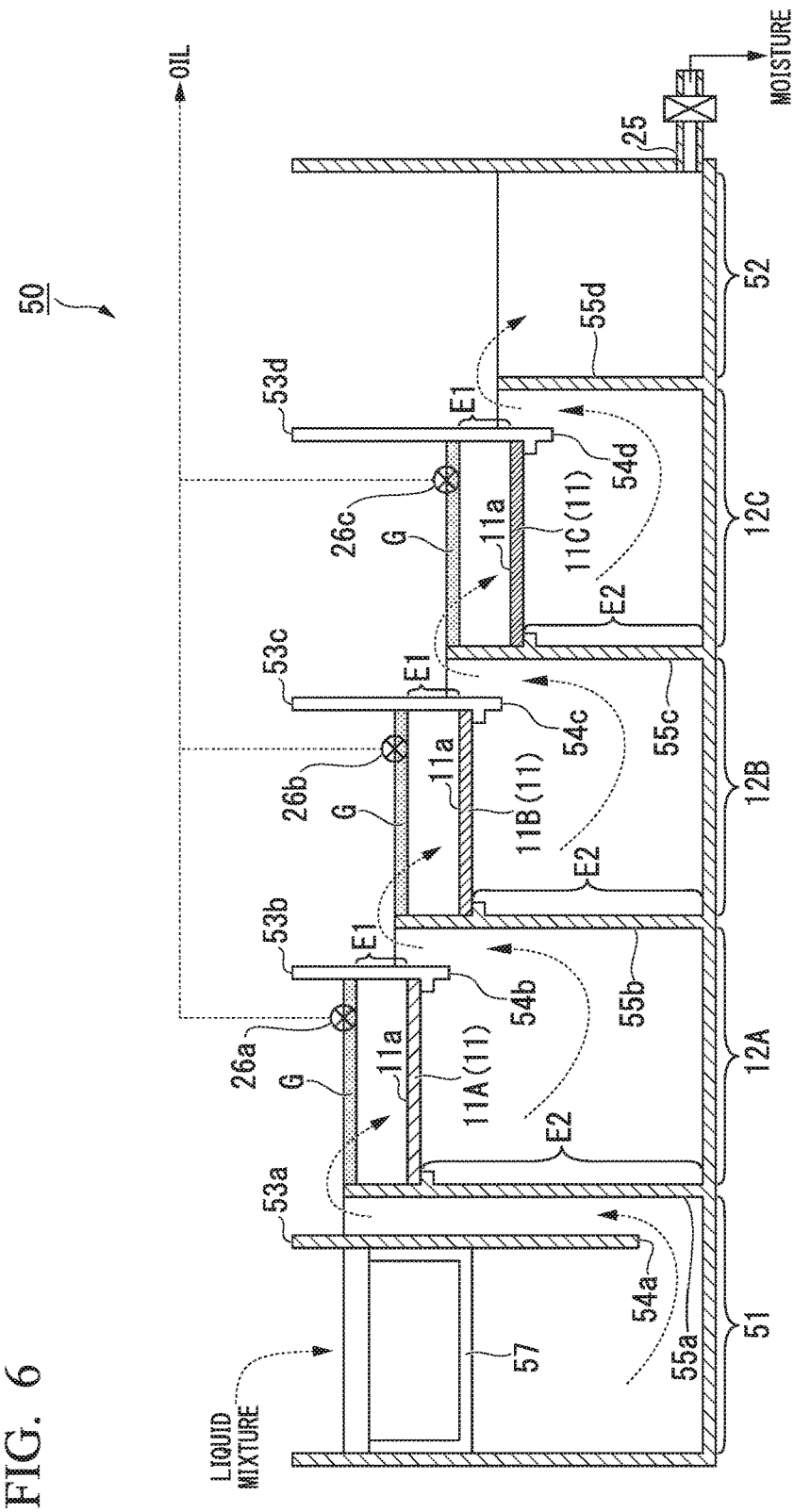
FIG. 6 is a sectional view illustrating a fifth embodiment of the oil-water separation apparatus according to the present invention.

FIG. 6 is a sectional view illustrating an oil-water separation apparatus according to a fifth embodiment of the present invention.

In an oil-water separation apparatus 50 of this embodiment, for example, three liquid reservoirs 12 in which an oil-water separation filter medium 11 having a configuration similar to that in the first embodiment is provided are arranged in series. That is, a liquid reservoir 12A, a liquid reservoir 12B, and a liquid reservoir 12C are arranged in order from the preceding stage side to the subsequent stage side. An introduction reservoir (liquid reservoir) 51 is disposed on the preceding stage side of the liquid reservoir 12A, and a discharge reservoir (liquid reservoir) 52 is disposed on the subsequent stage side of the liquid reservoir 12C.

Surfaces on which the reservoirs 12A, 12B, 12C, 51, and 52 are adjacent to each other are subdivided by partition walls 53a to 53d, respectively. Openings 54a to 54d corresponding to water drain ports of the reservoirs 12A, 12B, 12C, and 51 are formed at lower portions of the partition walls 53a to 53d, respectively. Guiding plates 55a to 55d are formed in the reservoirs 12A, 12B, 12C, and 51, respectively. Each of the guiding plates 55a to 55d guides a discharged liquid from the liquid reservoir at the preceding stage into the upper region E1 of the liquid reservoir.

A mesh basket 57 for removing, for example, solid matter (trash and the like) contained in a liquid mixture is formed in the introduction reservoir (liquid reservoir) 51, so as to be attachable and detachable. The oil-water separation filter medium 11 may be also formed on the upper surface, the lower surface, or the side surface of such a mesh basket 57. The discharge reservoir (liquid reservoir) 52 is, for example, a buffer tank, and has a water drain port 25 formed therein.

In this embodiment, similarly to the fourth embodiment, the oil-water separation filter media 11 provided in the liquid reservoirs 12A, 12B, and 12C of the oil-water separation apparatus 40 have a width (average opening diameter) of a channel 17 (see FIG. 1(b)) which is different from each other. That is, the width of the channel 17 of the oil-water separation filter medium 11B provided in the liquid reservoir 12B is narrower than the width of the channel 17 of the oil-water separation filter medium 11A provided in the liquid reservoir 12A. The width of the channel 17 of the oil-water separation filter medium 11C provided in the liquid reservoir 12C is further narrower than the width of the channel 17 of the oil-water separation filter medium 11B provided in the liquid reservoir 12B. That is, the width (average opening diameter) of the channel 17 gradually becomes narrower (smaller) in order of the oil-water separation filter medium 11A, the oil-water separation filter medium 11B, and the oil-water separation filter medium 11C.

The guiding plates 55a to 55d are formed so as to cause a height position of the upper end of the guiding plate to become lower than that of the liquid reservoir at the just preceding stage toward the liquid reservoir on the subsequent stage side. That is, regarding the height of the upper ends of the guiding plates 55a to 55d, the guiding plate 55a is highest, and the height gradually becomes smaller toward the guiding plate 55d. The liquid reservoirs 12A, 12B, 12C, and 52 cause the upper ends of the guiding plates 55a to 55d to become overflowed respectively, and thus a liquid from the reservoir at the previous stage flows in. Thus, a water level when each of the liquid reservoirs 12A, 12B, 12C, and 52 is in a standstill state is the same as the height of the upper ends of the guiding plates 55a to 55d. The water level of each of the liquid reservoirs 12A, 12B, 12C, and 52 gradually becomes lower from the liquid reservoir 12A to the discharge reservoir (liquid reservoir) 52.

When oil-water separation of a solution mixture is performed by using the oil-water separation apparatus 50 which has such a configuration, firstly, the solution mixture is introduced into the introduction reservoir (liquid reservoir) 51. Firstly, solid matter (trash and the like) which may block the oil-water separation filter medium 11A at the subsequent stage is removed in the solution mixture which has flowed into the introduction reservoir (liquid reservoir) 51 by the mesh basket 57. A solution mixture obtained by removing the solid matter flows out from the opening 54a, overflows the guiding plate 55a, and then flows into the upper region E1 of the liquid reservoir 12A. The in-flowed solution mixture is brought into contact with the oil-water separation filter medium 11A, and thus most of oil is separated and collected through the oil drain port 26a.

Moisture and a small amount of oil which has passed through the oil-water separation filter medium 11A having a large width of the channel 17 flows out from the opening 54b, overflows the guiding plate 55b, and then flows into the upper region E1 of the liquid reservoir 12B. The in-flowed solution mixture having a small amount of oil is brought into contact with the oil-water separation filter medium 11B having a small width of the channel 17, and thus most of the remaining oil is separated and collected through the oil drain port 26b.

Moisture and a fine amount of oil which has passed through the oil-water separation filter medium 11B having a small width of the channel 17 flows out from the opening 54c, overflows the guiding plate 55c, and then flows into the upper region E1 of the liquid reservoir 12C. The in-flowed solution mixture containing the fine amount of oil is brought into contact with the oil-water separation filter medium 11C having a further small width of the channel 17, and thus most of the remaining oil is totally separated and collected through the oil drain port 26c.

Moisture which has passed through the oil-water separation filter medium 11C having a further small width of the channel 17 flows out from the opening 54d, overflows the guiding plate 55d, and then flows into the discharge reservoir (liquid reservoir) 52. Thus, only filtered moisture is discharged from the water drain port 25 provided in the discharge reservoir (liquid reservoir) 52.

According to the oil-water separation apparatus 50 having such a configuration, the height of the upper ends of the guiding plates 55a to 55d is reduced toward the liquid reservoir at the subsequent stage side, and thus it is possible to gradually lower the liquid level positions of the reservoirs, and to perform multi-stage filtration only by gravity. The width of the channel 17 of the base 13 constituting the oil-water separation filter media 11A to 11C is gradually reduced, and thus it is possible to realize the oil-water separation apparatus 50 in which pressure loss is reduced in the entirety, and efficient oil-water separation is possible only by gravity.

<Sixth Embodiment>

Figure 7:
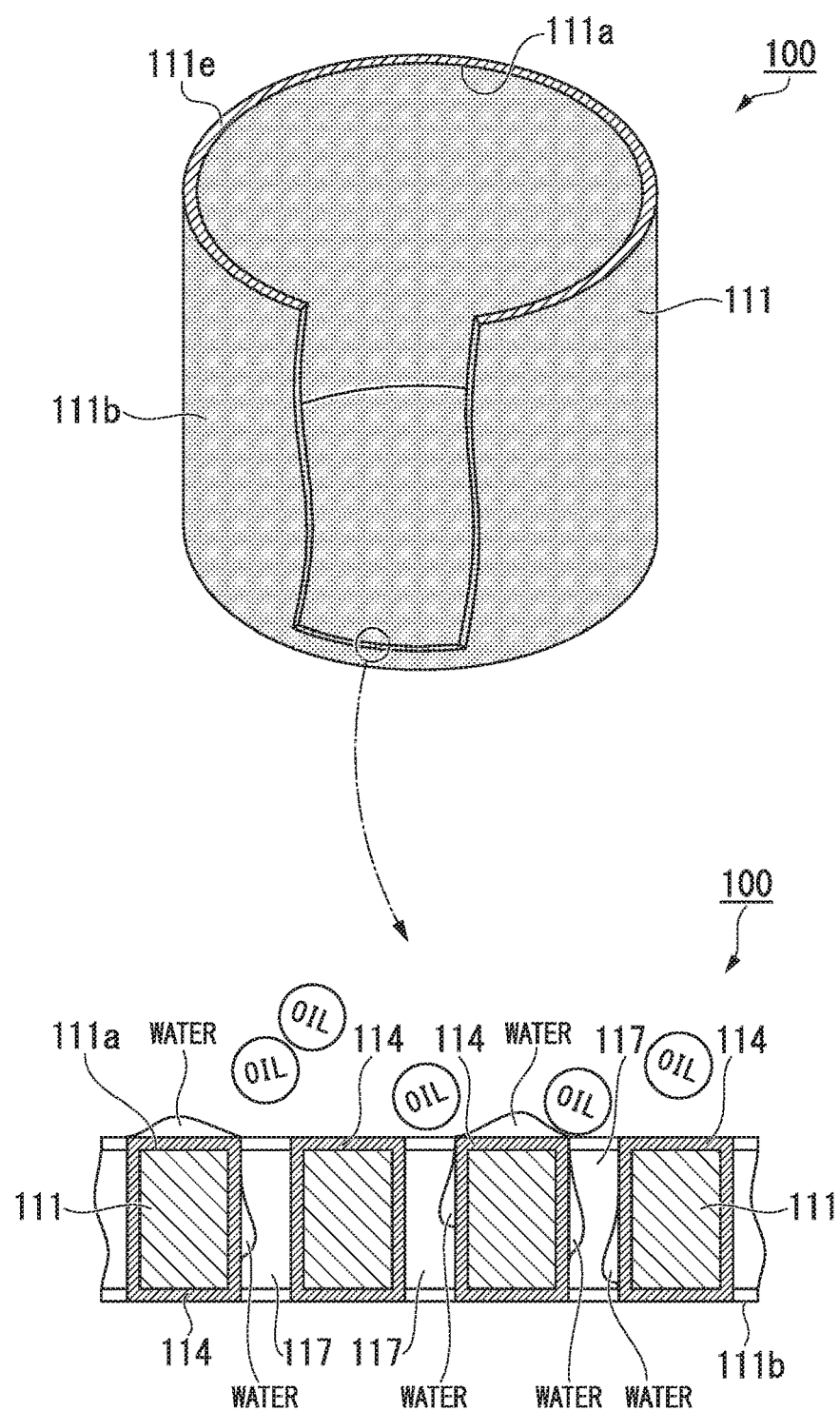
FIG. 7 is a partial perspective view and a diagram of an enlarged main portion illustrating a sixth embodiment of the oil-water separation apparatus according to the present invention.

FIG. 7 is a partial perspective view and a diagram of an enlarged main portion illustrating an embodiment of the oil-water separation filter medium.

An oil-water separation filter medium 100 in this embodiment includes a base 111 and an oil-water-separating member 114 formed in the base 111.

As the base 111, a baglike object having an upper portion which forms an open end 111e, for example, in this embodiment, an object formed to be a bottomed columnar shape, is appropriately used. In this embodiment, such a base 111 is configured from a flexible porous fiber. The porous fiber is a fiber assembly, and has a gap between fibers or between pieces of twist yarn. Woven fabric, knitted fabric, nonwoven fabric, or the like is appropriate.

As illustrated at the lower portion of the figure in FIG. 7, a channel 117 for a liquid is formed in the base 111. Such a channel 117 is formed from pores (fine hole, hollow, and communication hole) of the porous fiber forming the base 111. The channel 117 causes the inner surface 111a and an outer surface 111b of the baglike base 111 to communicate with each other, and passes moisture therethrough.

An oil-water-separating member 114 is formed on a surface (surface layer) of at least the inner surface 111a of the base 111. In this embodiment, the oil-water-separating member 114 is formed in the entirety of the inner surface 111a and the outer surface 111b of the base 111, which includes the surface of the inner wall of the channel 117.

In the oil-water-separating member 114, particles of the oil-water-separating member 114 may be dispersed (diffused) on the surface of the base 111 so as to form a film shape. Further, the particles of the oil-water-separating member 114 may be dispersed to an inner side in a thickness direction of the base 111.

The oil-water-separating member 114 is configured from a material containing a fluorine compound which has an oil-repellency-imparting group and a hydrophilicity-imparting group. The oil-repellency-imparting group is a functional group for forming an oil droplet on the surface of the oil-water-separating member 114 at a contact angle of, for example, 40° or more. The hydrophilicity-imparting group is a functional group for imparting wettability to moisture at a contact angle of, for example, 20° or less to the surface of the oil-water-separating member 114.

Such a contact angle may be measured, for example, by an automatic contact angle meter (manufactured by Kyowa Interface Science Co., Ltd, "Drop Master 701").

The oil-water-separating member 114 imparts the hydrophilic and oil-repellent properties to the base 111 by the existence of such an oil-repellency-imparting group and a hydrophilicity-imparting group. If a liquid mixture (may be simply referred to as a liquid below) containing water and oil is brought into contact with the base 111 in which the oil-water-separating member 114 is formed, the oil is aggregated as an oil droplet having a large contact angle, and moisture holds wettability in which the contact angle is small. Accordingly, oil which is aggregated and forms a large oil droplet passing through the channel 117 is not allowed. The moisture which holds the wettability can pass through the channel 117 without being aggregated. With such an action, the oil-water-separating member 114 can selectively separate only oil from a liquid.

<Seventh Embodiment>

Figure 8:
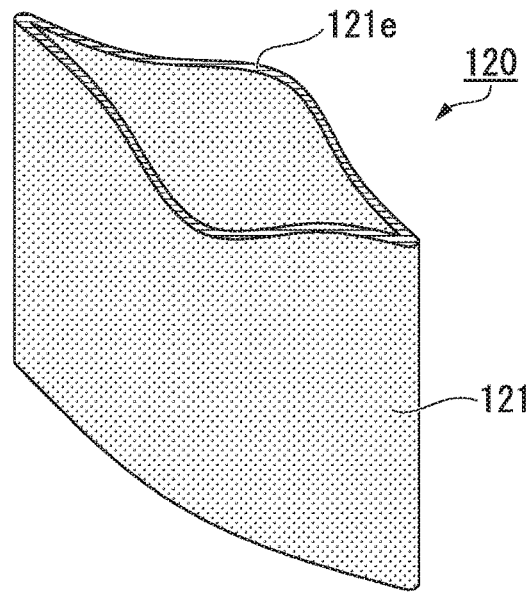
FIG. 8 is a perspective view illustrating a seventh embodiment of the oil-water separation apparatus according to the present invention.

FIG. 8 is a perspective view illustrating another embodiment of the oil-water separation filter medium.

An oil-water separation filter medium 120 of this embodiment is formed to have a bag shape in which two sheet-like bases 121 overlap each other, and peripheral edges other than an open end 121e at an upper portion are bonded to each other. Similarly to an example illustrated at the lower portion of the figure in FIG. 7, an oil-water-separating member 114 is formed in the base 121. The oil-water-separating member 114 is formed from a material containing a fluorine compound which has an oil-repellency-imparting group and a hydrophilicity-imparting group.

In manufacturing the oil-water separation filter medium 120 having such a form, the oil-water separation filter medium 120 may be formed in only a manner such that a sheet-like base 21 in which the oil-water-separating member 114 is formed is folded up, and peripheral edges are bonded to each other. Thus, it is possible to easily manufacture the baglike oil-water separation filter medium 20 at low cost.

<Eighth Embodiment>

Figure 9:
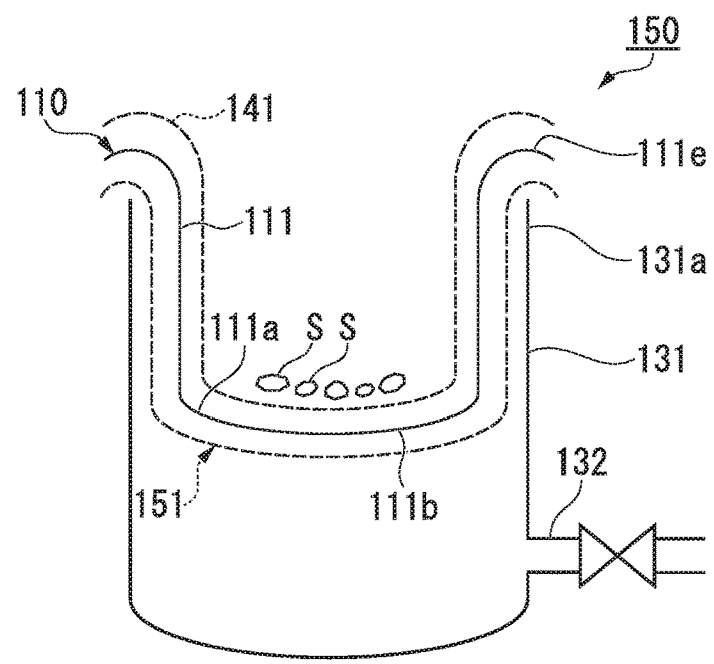
FIG. 9 is a diagram illustrating an eighth embodiment of the oil-water separation apparatus according to the present invention.

FIG. 9 is a diagram illustrating an oil-water separation apparatus according to an eighth embodiment.

In an oil-water separation apparatus 150 of this embodiment, a dispersion plate 141 is provided on an inner surface 111a side of an oil-water separation filter medium 110, and a support member 151 is disposed on an outer surface 111b side of the oil-water separation filter medium 110, so as to be overlapped. The support member 151 has, for example, a bottomed columnar shape. An upper edge of the support member 151 is bent outwardly, and thus the upper edge of the support member 151 overlaps the oil-water separation filter medium 110, and the support member 151 is hooked and engaged on an edge on an open surface 131a side of the liquid reservoir 131. The support member 151 is configured from a hard member through which at least moisture is allowed to pass, for example, from a metal material (a punching plate) in which multiple openings are formed. Such a support member 151 supports the flexible oil-water separation filter medium 110 from the outer surface 111b side.

Such a support member 151 is formed to overlap the outer surface 111b side of the oil-water separation filter medium 110. Thus, for example, even though a large amount of liquid flows into the oil-water separation filter medium 110 at one time, it is possible to prevent modification of the oil-water separation filter medium 110 or breaking of the bottom portion occurring by the weight of a liquid, and to efficiently perform oil-water separation filtration of a liquid. Such a support member 151 may use a ceramics material which has a relatively large pore, a hard plastic material in which an opening is formed, and the like.

<Ninth Embodiment>

Figure 10:
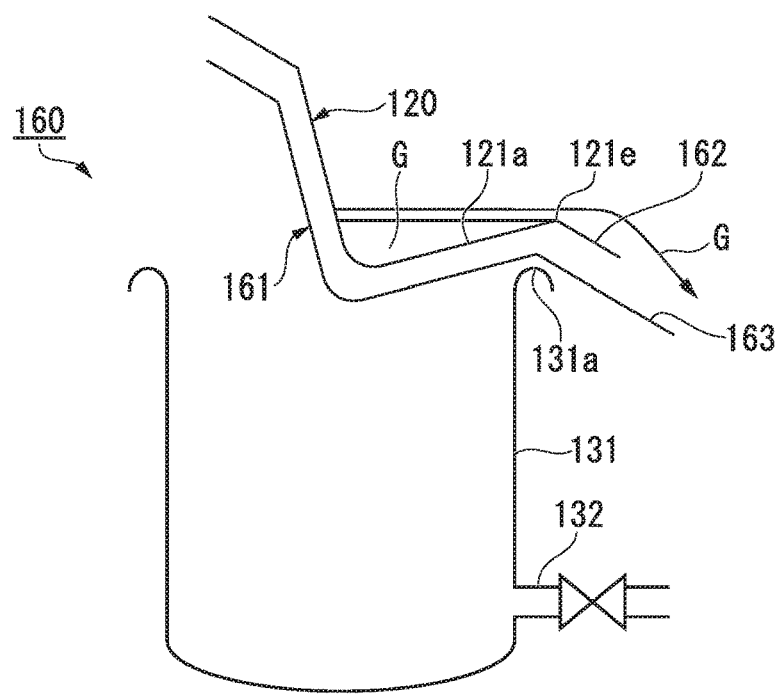
FIG. 10 is a diagram illustrating a ninth embodiment of the oil-water separation apparatus according to the present invention.

As in the oil-water separation apparatus 160 illustrated in FIG. 10, if the support member 161 is inclined in a state where oil remains on an inner side 121a of the oil-water separation filter medium 120, oil G can selectively flow out from the oil drain port 162 toward an oil discharge groove. Thus, it is possible to efficiently collect the oil G which is separated by the oil-water separation filter medium 120, and to increase a life cycle of the oil-water separation filter medium 120.

<Tenth Embodiment>

Figure 11:
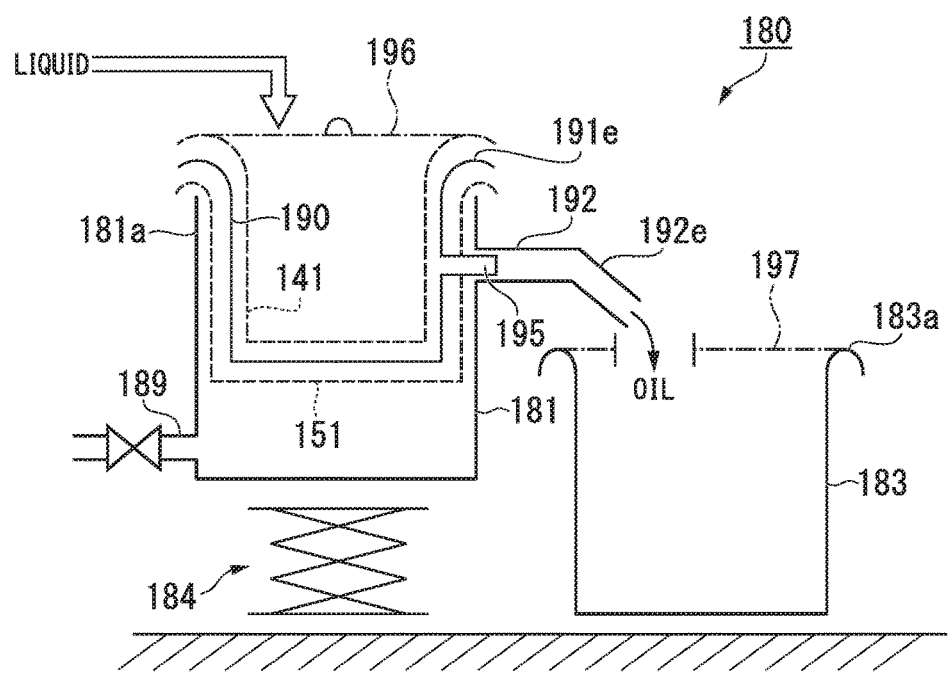
FIG. 11 is a diagram illustrating a tenth embodiment of the oil-water separation apparatus according to the present invention.

FIG. 11 is a diagram illustrating an oil-water separation apparatus according to a tenth embodiment.

An oil-water separation apparatus 180 in this embodiment includes a liquid reservoir 181 which holds the oil-water separation filter medium 190 on the inside of the liquid reservoir 181. A liquid-discharging port 189 is formed at a lower portion of the liquid reservoir 181. In the liquid reservoir 181, an upper portion forms an open surface, and an oil discharge channel 192 which is extended to the outside of the liquid reservoir 181 is formed in the vicinity of the open surface, so as to be integrated with the liquid reservoir 181.

The oil discharge channel 192 guides oil separated by the oil-water separation filter medium 190 to the outside of the liquid reservoir 181. The oil discharge channel 192 may be formed, for example, in a manner such that a portion of the liquid reservoir 181, which corresponds to an upper edge thereof, is cut out and is developed outwardly.

An oil drain port 195 is formed in the vicinity of the open end 191e of the oil-water separation filter medium 190, that is, at a portion being in contact with the oil discharge channel 192. The oil drain port 195 causes the separated oil to flow toward the oil discharge channel 192. Such an oil drain port 195 is formed from, for example, an opening which is formed on a circumferential surface of the oil-water separation filter medium 190, and a cylindrical member which is connected to the opening. The cylindrical member may be bonded to the circumferential surface of the oil-water separation filter medium 190, for example, by sewing the member and the circumferential surface together or by heat welding.

A dispersion plate 141 like, for example, a mesh member is further provided on the inner surface side of the oil-water separation filter 190. The dispersion plate 141 has, for example, a bottomed columnar shape. An upper edge of the dispersion plate 141 is bent outwardly, and thus the upper edge of the dispersion plate 141 is separated over the oil-water separation filter 190, and the dispersion plate 141 is hooked and engaged on an edge on an open surface 181a side of the liquid reservoir 181.

Regarding such a dispersion plate 141, when a liquid mixture containing water and oil is input to the liquid reservoir 181, the dispersion plate 141 receives the liquid mixture temporarily. Thus, the liquid mixture has a passing rate which is significantly lowered when the liquid mixture passes through the dispersion plate 141, and it is possible to largely relieve collision of the liquid mixture added to the oil-water separation filter 190. It is possible to suppress trapping of air. In addition, even though solid matter such as a trash, which has a relatively large size, is put and mixed in a liquid mixture flowing into the oil-water separation apparatus 180, it is possible to remove this solid matter in advance, and thus to prevent blockage of the oil-water separation filter 190 occurring by the trash.

A support member 151 is disposed on the outer surface side of the oil-water separation filter 190 so as to be overlapped. The support member 151 has, for example, a bottomed columnar shape. An upper edge of the support member 151 is bent outwardly, and thus the upper edge of the support member 151 overlaps the oil-water separation filter 190, and the support member 151 is hooked and engaged on an edge on an open surface 181a side of the liquid reservoir 181. The support member 151 is configured from a hard member through which at least moisture is allowed to pass, for example, from a metal material (a punching plate) in which multiple openings are formed. Such a support member 151 supports the flexible oil-water separation filter 190 from the outer surface side thereof.

Such a support member 151 is formed to overlap the outer surface side of the oil-water separation filter 190. Thus, for example, even though a large amount of liquid flows into the oil-water separation filter 190 at one time, it is possible to prevent modification of the oil-water separation filter 190 or breaking of the bottom portion occurring by the weight of a liquid, and to efficiently perform oil-water separation filtration of a liquid. Such a support member 151 may use a ceramics material which has a relatively large pore, a hard plastic material in which an opening is formed, and the like.

An oil tank 183 is disposed at an outflow end 192e of the oil discharge channel 192. The oil tank 183 is used for receiving oil which flows out through the oil discharge channel 192. Further, the oil-water separation apparatus 180 includes a liquid reservoir-moving means 184 for moving the liquid reservoir 181 up and down. It is preferable that a lid member 196 for covering an open surface 181a of the liquid reservoir 181 or a lid member 197 for covering an open surface 183a of the oil tank 183 be further provided.

If the oil-water separation apparatus 180 having such a configuration is used, it is possible to continuously separate and collect oil from a liquid with a simple configuration. For example, if a liquid containing water and oil is continuously caused to flow into the oil-water separation filter medium 190 of the oil-water separation apparatus 180, oil separated by the oil-water separation filter medium 190 floats in the vicinity of a liquid level of the oil-water separation filter medium 190 by the specific gravity difference. The oil flows out from an oil drain port 195 formed in the vicinity of an upper edge of the oil-water separation filter medium 190, through the oil discharge channel 192. The outflowing oil is stored in the oil tank 183. Moisture obtained by removing oil in the oil-water separation filter medium 190 so as to perform filtration is stored at the lower portion of the liquid reservoir 181. The moisture obtained in this manner can be easily discharged to the outside of the liquid reservoir 181 from the liquid-discharging port 189. In addition, it is possible to set the height of the liquid reservoir 181 to be at an optimum position in accordance with the height of the oil tank 183 by using the liquid reservoir-moving means 184.

As described above, if the oil-water separation apparatus 180 in this embodiment is used, oil-water separation of a liquid may be continuously performed until the oil tank 183 is filled with the separated oil. In the liquid reservoir 181 used in such an oil-water separation apparatus 180, the oil discharge channel 192 is formed only by cutting the upper edge out and bending the cut upper edge outwardly. Thus, even though an oil discharge groove and the like as another member is not bonded, it is possible to continuously discharge oil to the outside of the liquid reservoir 181 at low cost. The open surface 181a of the liquid reservoir 181 or the open surface 183a of the oil tank 183 is covered by the lid members 196 and 197, respectively. Thus, it is possible to prevent dropping of trash or dust into the liquid reservoir 181 or the oil tank 183, and to prevent diffusion of odor or a volatile component of a liquid or waste oil.

<11th Embodiment>

Figure 12:
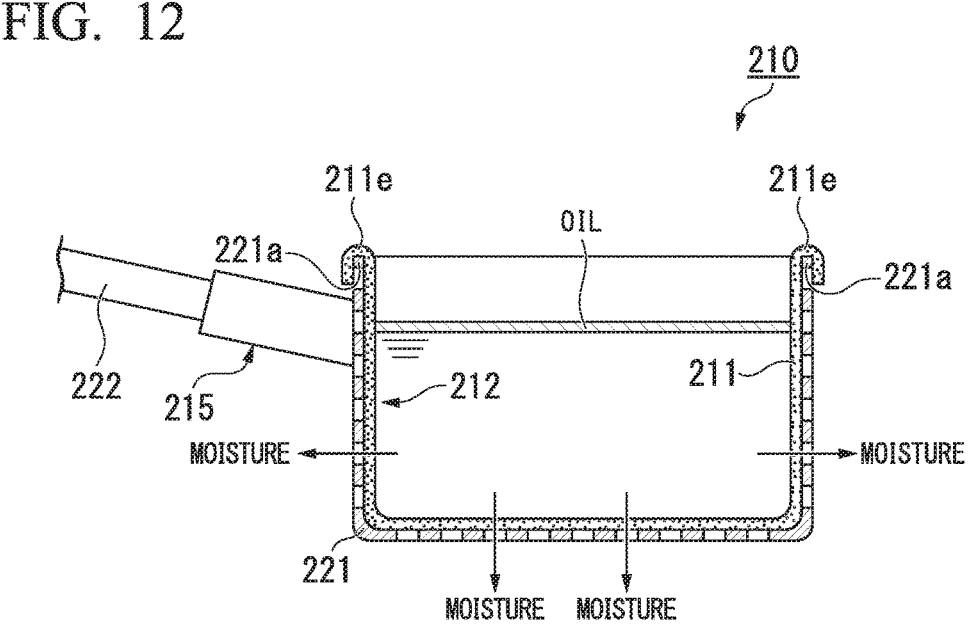
FIG. 12 is a sectional view illustrating an 11th embodiment of the oil-water separation apparatus according to the present invention.

FIG. 12 is a sectional view illustrating an oil-water separation and collection tool (oil-water separation apparatus) according to an 11th embodiment. An oil-water separation and collection tool (oil-water separation apparatus) 210 in this embodiment includes an oil-water separation filter medium 212 and an operation member 215. The oil-water separation filter medium 212 includes an oil-water-separating member 14 (see FIG. 1(b)) formed in a baglike base 211. The operation member 215 is used for operating the oil-water separation filter medium 212.

As the base 211, a baglike object which has an upper portion which forms an open end 211e, for example, in this embodiment, an object formed to have a cylindrical shape having a bottom, is appropriately used. Such a base 211 is configured from, for example, a flexible porous fiber such as woven fabric or nonwoven fabric.

The operation member 215 includes a holding portion 221 for holding the oil-water separation filter medium 212, and a rodlike gripping portion 222 extended outwardly from the holding portion 221. The operation member 215 is formed to be a ladle type in the entirety. The holding portion 221 is, for example, a bottomed cylindrical member in which multiple openings are formed. The holding portion 221 is formed from metal, hard resin, and the like. The gripping portion 222 is a rodlike member which has one end which is fixed to the circumferential surface of the holding portion 221, and is extended outwardly from the holding portion 221. The gripping portion 222 is formed from a metal rod, a resin rod, a wooden rod, and the like. Such a holding portion 221 and a gripping portion 222 may be joined and fixed, for example, by using a screw or by fusion.

The oil-water separation filter medium 212 formed to have a bottomed cylindrical shape is provided in the holding portion 221 constituting the operation member 215. The open end 211e side of the base 211 constituting the oil-water separation filter medium 212 is folded back so as to interpose an opening edge 221a of the holding portion 221. Thus, the oil-water separation filter medium 212 is engaged with the holding portion 221.

According to the oil-water separation and collection tool (oil-water separation apparatus) 210 of this embodiment, for example, it is possible to easily perform separation into moisture and oil and collect the oil in only a manner such that a user grips the gripping portion 222 of the operation member 215, scoops up a liquid in which water and oil are mixed, and puts the scooped liquid into the baglike oil-water separation filter medium 212 held by the holding portion 221.

That is, the oil-water-separating member 14 formed in the base 211 contains one or more fluorine compounds in which an oil-repellency-imparting group and a hydrophilicity-imparting group are included in a molecule. Thus, if a liquid mixture of water and oil is input to the oil-water separation filter medium 212, moisture passes through the channel of the base 211, but the oil is aggregated, and passing through the channel of the base 211 is not possible. If the moisture completely permeates the base 211, only the separated oil remains on the surface of the inner side of the oil-water separation filter medium 212.

Thus, the oil-water separation and collection tool (oil-water separation apparatus) 210 in this embodiment can separate a liquid into water and oil only by gripping the gripping portion 222 and scooping up the liquid containing oil. In addition, the oil-water separation and collection tool 210 can perform separation into moisture and oil at low cost with a simple configuration and collect the oil. As an example, if the vicinity of a water surface from which oil is oozed is scooped by using the oil-water separation and collection tool 210 in this embodiment, it is possible to easily separate only oil. In, for example, a place in which oil is spilled out, the spilled oil can be rapidly and easily collected. As an example, when oil is spilled to a drainage channel having an oil trap, only the oil-water separation and collection tool 210 in this embodiment is input to the oil trap so as to perform scooping, and thus it is possible to easily separate moisture and oil and collect the oil.

The oil remaining on the surface of the inner side of the oil-water separation filter medium 212 is removed, and thus it is possible to repeatedly use the oil-water separation filter medium 212. A method in which replacement with a new oil-water separation filter medium 212 is performed without removing the separated oil whenever the oil-water separation filter medium 212 is used once or several times, and the oil-water separation filter medium 212 used for collecting oil is discarded may be performed.

In the oil-water separation filter medium 212 constituting the oil-water separation and collection tool 210 in this embodiment, the hydrophilic and oil-repellent properties are applied to the base 211. Thus, adhering of an organic molecule, or soil and mud is difficult, and accordingly, excellent anti-fouling properties are obtained. Attached dirt is easily removed by physical treatment of, for example, turning over and washing, and ease of washability is also excellent.

In the oil-water separation filter medium 212 constituting the oil-water separation and collection tool 210 in this embodiment, in a case of containing only the fluorine compounds represented by the formulas (1) to (4), it is possible to apply excellent hydrophilic and oil-repellent properties while a perfluoroalkyl group having 8 or more carbon atoms which are continuously bonded to each other is not contained, and a chemical structure which does not have a concern of generating PFOS or PFOA, which becomes a problem from the viewpoint of bioaccumulation or environmental adaptability, is provided.

<12th Embodiment>

Figure 13:
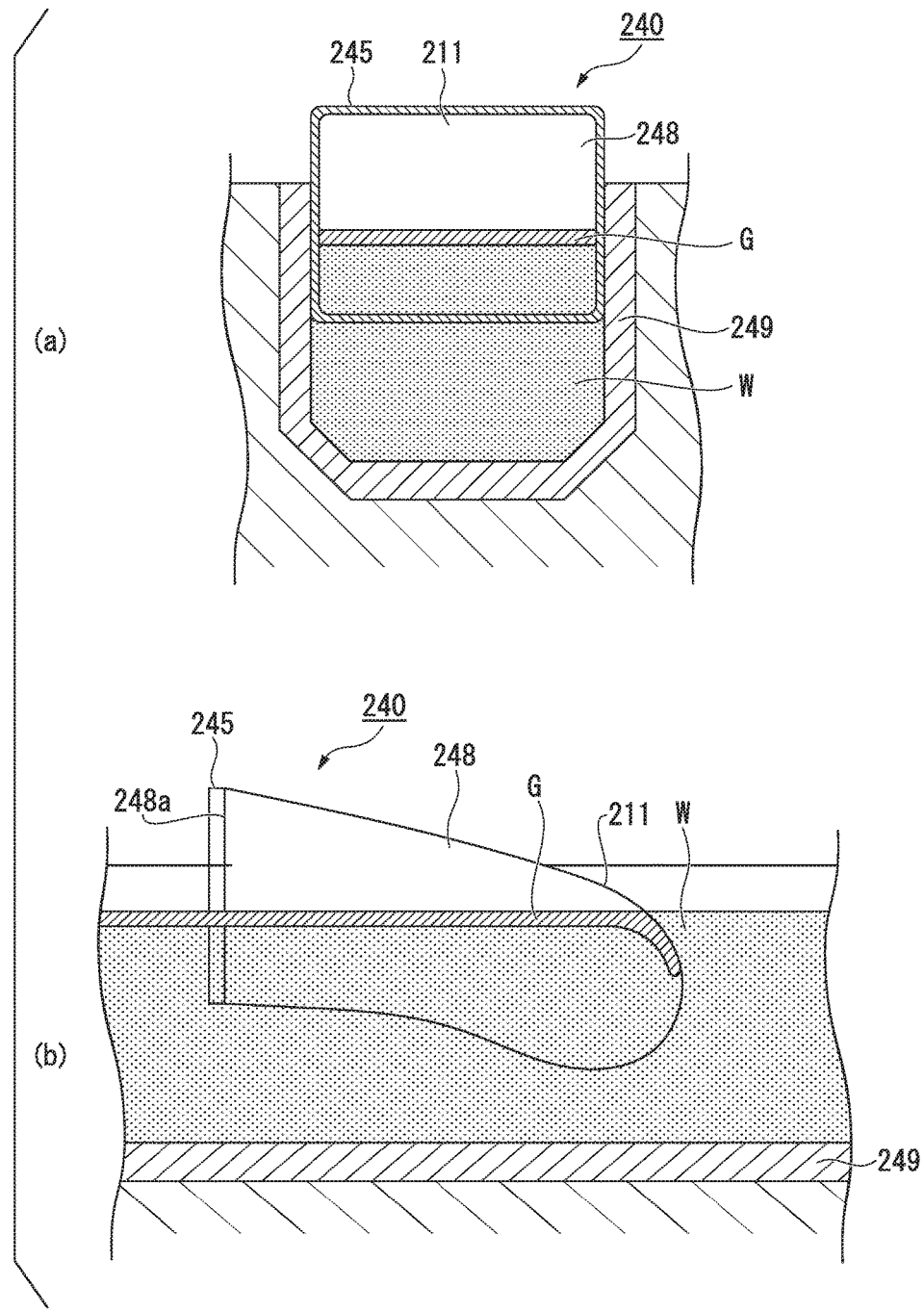
FIG. 13 is a sectional view illustrating a 12th embodiment of the oil-water separation apparatus according to the present invention.

FIG. 13(a) is a front sectional view illustrating another embodiment of the oil-water separation and collection tool (oil-water separation apparatus). FIG. 13(b) is a side sectional view.

An oil-water separation and collection tool (oil-water separation apparatus) 240 in this embodiment includes an oil-water separation filter medium 248 and a holding portion 245. The oil-water separation filter medium 248 includes an oil-water-separating member 14 (see FIG. 1(b)) formed in the base 211. The holding portion 245 is used for holding the oil-water separation filter medium 248. The holding portion 245 is configured from a wire material which has a polygonal shape and has elasticity. An edge 248a on an open end side of the oil-water separation filter medium 248 is attached to be attachable and detachable to and from such a holding portion 245 having a polygonal frame shape.

The holding portion 245 may have a configuration in which the edge 248a on the open end side of the oil-water separation filter medium 248 is held by being wound or a configuration in which a clip and the like is formed and the edge 248a is interposed between clips. The holding portion 245 may be formed from a frame body which is formed from metal such as SUS and aluminium, which has sufficient elasticity, or may be formed from a frame body which is formed from resin such as vinyl chloride and polyethylene, which has sufficient elasticity.

The base 211 constituting the oil-water separation filter medium 248 may be formed from a baglike flexible fiber, for example.

The oil-water separation and collection tool 240 having such a configuration may be inserted into a drainage ditch 249 and be used for collecting oil. For example, when oil G is spilled to the drainage ditch 249 in which an oil trap and the like are not installed, the holding portion 245 is compressed and deformed and is inserted to an upper portion of the drainage ditch 249 such that the holding portion 245 is positioned to be parallel to the cross-section of the drainage ditch 249. The oil G flowing in the drainage channel is lighter than moisture W. Thus, an oil film is formed on a water surface, and flows by a water stream.

If the oil-water separation and collection tool 240 as a simple oil trap is installed on a path of such a drainage ditch 249, the hydrophilic and oil-repellent properties of the oil-water separation filter medium 248 cause only the oil G to remain in the oil-water separation filter medium 248, and cause the moisture W to pass therethrough. Accordingly, it is possible to efficiently and reliably collect oil G spilled to the drainage ditch 249 in which an oil trap and the like are not installed.

The oil-water separation and collection tool 240 may be installed in a form of being installed at an upper portion in which the oil G flows, and not being installed at a lower portion in a depth direction of the drainage ditch 249. Thus, it is possible to suppress a load on a water stream. Accordingly, in a case where the oil-water separation and collection tool 240 is installed over the entirety thereof in the depth direction of the drainage ditch 249, the base 211 may employ a filter having an aperture relatively smaller than an aperture of a lower limit which causes a flow rate of water flowing in the drainage ditch 249 not to be reduced. Accordingly, it is possible to reduce the risk of the oil G being permeated through the oil-water separation and collection tool 240.

The holding portion 245 for holding the oil-water separation filter medium 248 is configured from a wire material having elasticity. Thus, it is possible to perform compression and deformation so as to match with the width size of the drainage ditch 249, and it is possible to engage the oil-water separation and collection tool 240 with the inner side of the drainage ditch 249 by an elastic force. For example, the width of the holding portion 245 is formed to be wider than the width of the drainage ditch 249, and when the oil-water separation and collection tool 240 is used, the holding portion 245 is compressed and deformed, and is inserted into the upper portion of the drainage ditch 249. Thus, at the upper portion of the drainage ditch 249 in which oil flows, there is no gap between the wall surface of the drainage ditch 249 and the holding portion 245. Thus, it is possible to reliably capture oil and to independently hold the oil-water separation filter medium 248 in the drainage ditch 249 even by using an engagement tool and the like.

<13th Embodiment>

Figure 14:
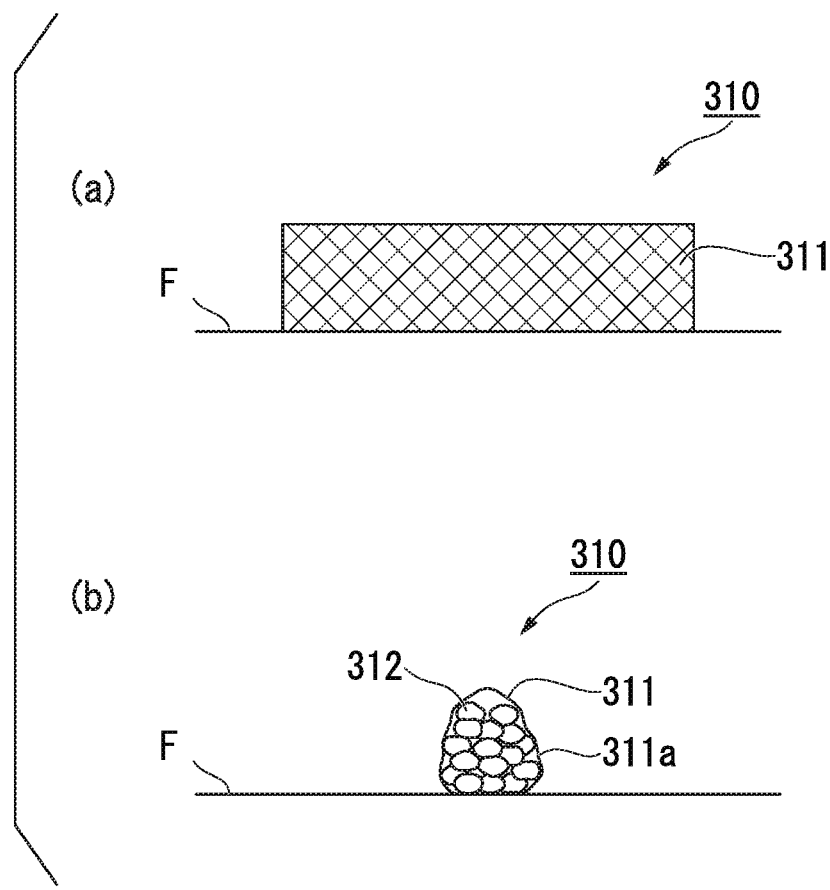
FIG. 14 is a front view and a sectional view illustrating a 13th embodiment of the oil-water separation apparatus according to the present invention.

FIG. 14(a) is a front view schematically illustrating a configuration of a sandbag (oil-water separation apparatus) according to a 13th embodiment. FIG. 14(b) is a sectional view of the sandbag illustrating in FIG. 15(a).

A sandbag (oil-water separation apparatus) 310 in this embodiment includes an oil-water separation filter medium and a weight 312. The oil-water separation filter medium is formed from a bag body (base) 311 including the oil-water-separating member 14 (see FIG. 1(b)) which has hydrophilic and oil-repellent properties. The bag body is filled with weights 312. The oil-water-separating member 14 (see FIG. 1(b)) is formed on at least an outer surface 311a of the bag body 311.

The bag body (base) 311 is formed from a material including a channel through which at least moisture is allowed to pass. For example, the bag body (base) 311 is formed from a sheet-like fibrous base such as woven fabric, knitted fabric, or nonwoven fabric, or from a polymeric porous base. As a specific example, a natural fiber, organic polymer, a glass fiber, and the like are exemplified. In this embodiment, a nonwoven fabric sheet formed from a polypropylene porous medium is used as the bag body 311. A more-detailed specific example of the bag body 311 will be described later.

The weight 312 may be a material having sufficient weight to prevent a sandbag laid on the ground (or a floor) F from moving. For example, in addition to sediment which is normally used, a water-absorptive material which can absorb and hold moisture may be used. As the water-absorptive material, various water-absorbing materials such as water-absorptive polymer or a physical water-absorbing material having properties such that a porous surface easily absorbs water molecules may be used. The shape of the weight 312 may be a particulate body, powder, a gel-like substance, and the like which have a particle diameter to an extent of not being left outwardly from the bag body 311. A more-detailed specific example of the weight 312 will be described later.

For example, a channel through which moisture is allowed to pass is formed in the bag body 311. Such a channel is formed from pores (fine hole, hollow, and communication hole) of a sheet-like fibrous base or a polymeric porous base constituting the bag body 311. In a case of using a weight which is formed from a water-absorptive material, it is preferable that, when the weight 312 is used, the weight 312 be caused to absorb the predetermined amount of moisture in advance, so as to increase the weight. The channel causes the outer surface and the inner surface of the baglike bag body 311 to communicate with each other, and passes moisture therethrough. Moisture which reaches the inner surface side of the bag body 311 is absorbed by the weight 312 in a case where the amount of absorbed water in the weight 312 has margin in a water-absorbing capacity of the e weight 312. When the weight 312 reaches an upper limit of the amount of absorbed water, moisture itself is discharged.

An oil-water-separating member 14 (see FIG. 1(b)) is formed on the surface (surface layer) of at least the outer surface of the bag body 311. In this embodiment, the oil-water-separating member 14 is formed in the entirety of the outer surface and the inner surface of the bag body 311 which includes an inner wall surface of the channel.

The oil-water-separating member 14 may be formed such that at least the oil-water-separating member 14 forms a film on the surface of the bag body 311. Further, the oil-water-separating member 14 may be impregnated to the inner side in a depth direction of the bag body 311.

(Bag Body)

In the bag body 311 constituting the sandbag 310 in this embodiment, the channel for a liquid, which passes the separated water therethrough, is formed in the bag body 311. Specifically, regarding the channel of the bag body 311, a space between fibers in the fibers constituting the bag body 311 or pores of a porous medium constituting the bag body 311 functions as the channel for moisture.

The peripheral edge of the bag body 311 is preferably closed, for example, by sewing using a string-shaped medium such as a thread, by adhering with an adhesive having oil resistance, or by heat welding. The string-shaped medium is preferably a substance having oil-repellent properties or a substance subjected to oil-repellent treatment. The binding place is preferably sealed by an oil-repellent member.

The material of the bag body 311 is not particularly limited as long as the material is a fiber or a porous medium which can form a channel for a liquid to be separated. The material of the bag body 311 may be organic matter or inorganic matter. In addition, the material of the base 17 may be a composite of organic matter and inorganic matter. Thus, as a form of the bag body 311 in the sandbag 310 of this embodiment, fibrous or porous organic matter and fibrous or porous inorganic matter are exemplified.

A member such as a polypropylene porous medium (for example, nonwoven fabric) or a fluororesin porous medium, which passes oil therethrough but flips water, is subjected to hydrophilic and oil-repellent treatment, and thus water is allowed to pass. Thus, the member can be used for damming oil. In particular, a fluororesin porous film having excellent chemical resistance is subjected to hydrophilic treatment, and thus water passes through the film and oil is flipped. Accordingly, the fluororesin porous film may be used for preventing diffusion of oil.

Here, organic matter usable as the bag body 311 is not particularly limited. Specifically, for example, an object obtained by forming a sheet body as follows to be baglike is exemplified: a cellulose filter paper, a filter cloth (polyester, polyethylene, polypropylene, polytetrafluoroethylene, nylon, polyimide, polyacrylonitrile, polysulfone, polyethersulfone, polyphenylene sulfide, and the like), a nonwoven fabric filter (polyester, polyethylene, polypropylene, rayon, nylon, polyphenylene sulfide, and the like), and a fibrous filter (resin, glass, ceramics, metal).

In the bag body 311, the width of the channel (that is, an average interval of fibers or an average width of a hollow of a porous material) is, for example, preferably 0.1 to 180 μm, more preferably 0.5 to 75 μm, and further preferably 1 to 50 μm. Here, if the width of the channel is less than 0.1 μm, permeation resistance of water (moisture) is increased, and it may take time to perform permeation. Thus, the above range is not preferable. If the width of the channel is more than 180 μm, oil starts to pass through the channel. Thus, the above range is not preferable. On the contrary, if the channel width of the filter medium is in the above range, oil is not permeated, and a water-passing rate in a practically-appropriate range is obtained. Thus, such a filter medium is preferable. The channel formed in the bag body 311 is not necessarily limited to a configuration in which oil is never caused to pass through the channel. A case of a width which mainly allows moisture to pass and allows oil to pass at a predetermined proportion is also provided.

The oil-water-separating member 14 (see FIG. 1(b)) holds the fluorine compound (oil-repellent hydrophilic agent) represented by the formulas (1) to (4), in the above-described bag body (base) 311.

As a method of holding the fluorine compound in the bag body 311 such as a porous medium, the following method and the like may be applied. That is, the bag body 311 which is to hold the compound is immersed in a dissolving liquid or a dispersion liquid of the fluorine compound (oil-repellent hydrophilic agent), or the bag body 311 is subjected to spray coating with the dissolving liquid or the dispersion liquid. Then, a solvent is removed by drying. As a proportion for holding, selection to cause the mass composition ratio of an oil-repellent hydrophilic agent and a porous medium to be held to be in a range of a pair of 1 to 50 and 99 to 50 is preferable from the viewpoint of characteristics of the hydrophilic and oil-repellent properties.

As the bag body 311 in the sandbag (oil-water separation apparatus) 310 of this embodiment, a form of a bag body 311 formed to have a fibrous shape by a resin composition of one or more of the above-described organic matter (resin) and the fluorine compounds (oil-repellent hydrophilic agents) represented by the formulas (1) to (4) may be used. That is, the above-described oil-repellent hydrophilic agent may be used as an additive for imparting the function of the hydrophilic and oil-repellent properties to various resins.

As the bag body 311 in the sandbag 310 of this embodiment, a form obtained by being formed to have a fibrous shape by a resin composition of one or more of the above-described organic matter (resin) and the fluorine compounds (oil-repellent hydrophilic agents) represented by the formulas (1) to (4) may be used. That is, the above-described oil-repellent hydrophilic agent may be used as an additive for imparting the function of the hydrophilic and oil-repellent properties to various resins.

(Weight)

The weight 312 constituting the sandbag 310 in this embodiment may use water-absorptive polymer or an inorganic water-absorbent material in addition to sediment which is normally used. A substance having specific gravity larger than that of water may be appropriately used. In a case where a substance having specific gravity larger than that of water is used and thus the substance is disposed on the ground or a floor, it is possible to stably install the sandbag. A combination of different types of materials may be used as the weight. For example, sand and water-absorptive polymer may be used as the weight.

As the substance having specific gravity larger than that of water, a substance having density of 1.2 or more, and particularly, a substance having density of 2 or more is preferable. Specifically, manganese sand (density 2.5 to 2.7 $g/cm^3$), garnet (density 3.8 to 4.1 $g/cm^3$), and ferric oxide content (density 5.2 $g/cm^3$) are exemplified.

As the water-absorptive polymer, for example, a polyacrylate salt, a crosslinking type of isobutylene-maleic anhydride, a polysulfonate salt, a maleic anhydride salt, polyacrylamide, polyvinyl alcohol, polyethylene oxide, and polysaccharides such as starch or cellulose may be used.

In particular, from a viewpoint of water-absorptive properties, crosslinked sodium polyacrylate is preferable. As a preferable specific example of the water-absorptive polymer, "AQUALIC CA" (product name: manufactured by NIPPON SHOKUBAI CO., LTD.), "AQUALIC CS" (product name: manufactured by NIPPON SHOKUBAI CO., LTD.), and the like are exemplified.

As the inorganic water-absorbent material, silica gel, a molecular sieve, and the like are exemplified.

The shape of the weight 312 is not particularly limited. For example, the weight 312 may have a particulate shape forming a spherical shape or a polygonal shape, or have a fibrous shape. The diameter may be about 50 to 1500 µm, and more preferably about 100 to 850 µm.

As the water-absorbent material, a material in which specific gravity of the entirety in a state of absorbing water is set to be equal to or more than 1.0 is preferably used. Thus, for example, it is possible to prevent floating of the sandbag 310 on an oil surface when the sandbag 310 is disposed in oil having specific gravity of 1 or less.

<14th Embodiment>

Figure 15:
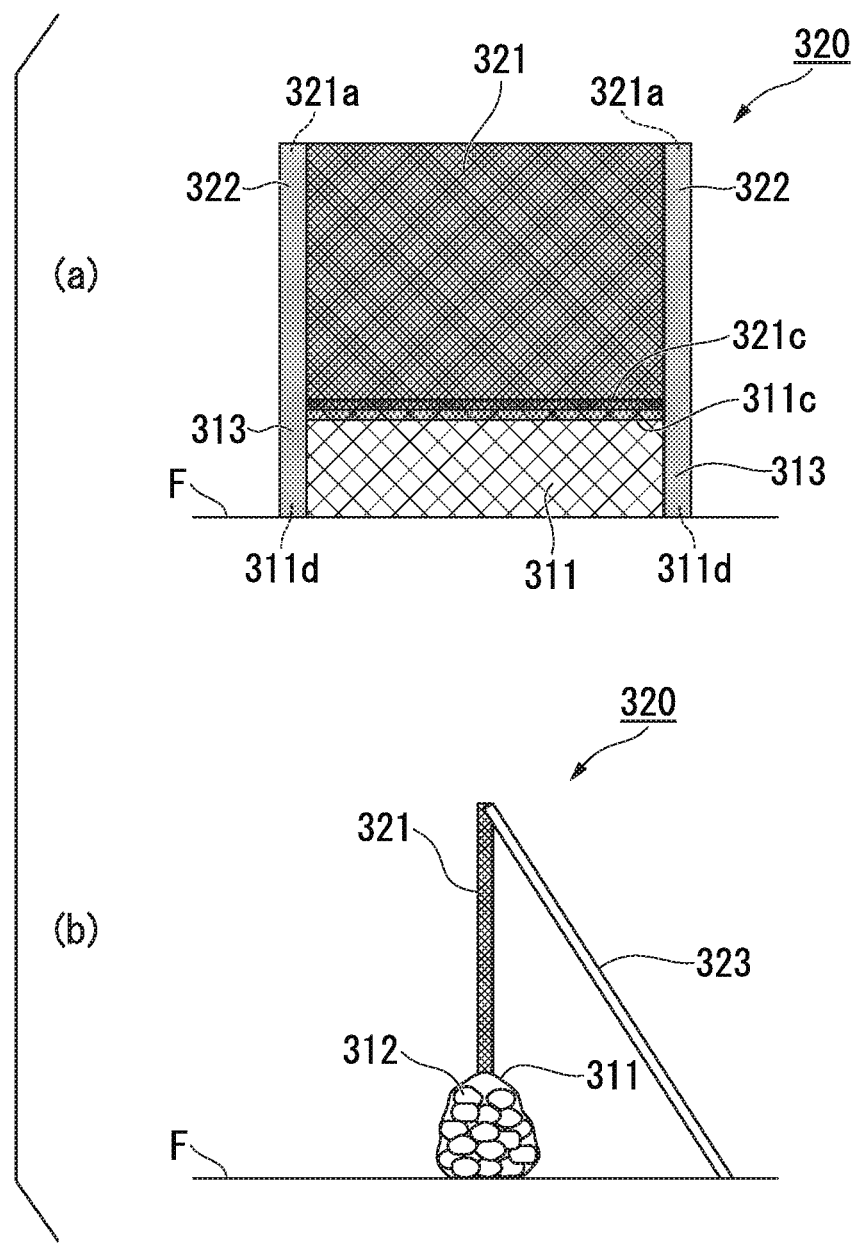
FIG. 15 is a front view and a sectional view illustrating a 14th embodiment of the oil-water separation apparatus according to the present invention.

FIG. 15(a) is a front view schematically illustrating a configuration of a sandbag (oil-water separation apparatus) according to a 14th embodiment. FIG. 15(b) is a sectional view of the sandbag illustrated in FIG. 15(a).

A sandbag (oil-water separation apparatus) 320 in this embodiment includes an oil-water separation filter medium, a weight 312, a drainage net 321, and a supporting rod 323. The oil-water separation filter medium is formed from a bag body (base) 311 including the oil-water-separating member 14 (see FIG. 1(b)) which has hydrophilic and oil-repellent properties. The bag body is filled with weights 312. The drainage net 321 is extended from one end portion 311c of the bag body and includes an oil-water-separating member having hydrophilic and oil-repellent properties. The supporting rod 323 is attached to the drainage net 321 in order to prevent turnover. An oil-water-separating member 14 (see FIG. 1(b)) is formed on at least the outer surface of the drainage net 321, similarly to the bag body 311.

The drainage net 321 is formed from a material including a channel through which at least moisture is allowed to pass. The drainage net 321 may use a material similar to that of the bag body 311.

The drainage net 321 in this embodiment has a configuration in which an end portion 321c is attached to the end portion 311c of the bag body 311 on an opposite side of the ground or a floor. The drainage net 321 may be formed from a material which is the same as that of the bag body 311 or is different from that of the bag body 311. The drainage net 321 in this embodiment has a configuration in which the drainage net and the bag are separately provided, but may have a configuration in which the drainage net and the bag are integrally provided.

The drainage net 321 may be attached to the bag body 311, for example, by sewing using a string-shaped medium such as a thread, by adhering with an adhesive having oil resistance, or by heat welding. The binding place of the drainage net 321 and the bag body 311 is preferably sealed by an oil-repellent member.

A channel through which moisture is allowed to pass is formed in the drainage net 321, similarly to the bag body 311. Such a channel is formed from pores (fine hole, hollow, and communication hole) of a sheet-like fibrous base or a polymeric porous base constituting the drainage net 321. The channel causes the outer surface and the inner surface of the baglike drainage net 321 to communicate with each other, and passes moisture therethrough. Moisture itself which reaches a counterpart side of the drainage net 321 may be left out.

An oil-water-separating member 14 (see FIG. 1(b)) is formed on the surface (surface layer) of at least the outer surface of the drainage net 321, similarly to the bag body 311.

A rigid member is embedded to the drainage net 321 in this embodiment, so as to be disposed in a direction from the bag body to the drainage net, that is, to be disposed upwardly from the ground or a floor. One or a plurality of rigid members may be used.

The rigid member is provided, and thus it is possible to maintain the drainage net in a state of being developed.

The rigid member has, for example, a configuration in which both ends of the drainage net are formed to be cylindrical, and thus the rodlike rigid member is inserted into the cylinder when the rigid member is used, and the rodlike rigid member is pulled out when the rigid member is not used. This configuration can cause the drainage net to be folded or cause the drainage net to be wound to the sandbag and thus cause the drainage net to be compact. Thus, this configuration is excellent in storing properties.

As the rigid member, a member formed from, for example, metal or resin may be used.

The drainage net 321 may include a joint unit 322 at the side end portion 321a thereof. The joint unit 322 is used for joining side end portions of the bag body of another sandbag and the drainage net to each other.

The drainage net 321 has a configuration including the joint unit 322, and thus joining to another sandbag without a gap is possible. This is effective for preventing leakage of oil. A plurality of sandbags which are joined to each other are laid to surround a leakage place, and thus it is possible to use the sandbags as a simple oil-retaining wall, for preventing diffusion of oil.

In the sandbag 320 of this embodiment, the bag body 311 also includes a joint unit 313 at the side end portion 311d thereof. The joint unit 313 is formed to be continuous from the joint unit 322 of the drainage net 321.

Regarding the configuration in which the bag body 311 includes the joint unit 313, a sheet material constituting the bag body may be bent and folded by the side end portion, and the folded portions may be bonded to each other, and thus a region for providing the joint unit may be provided.

As the joint unit 322 and the joint unit 313, a fastener or a hook-and-loop fastener may be used. A fastener type bonding method is used, and thus hydrophilic and oil-repellent sandbags which are appended to the drainage net are easily joined and separated to and from each other. As the hook-and-loop fastener, for example, Magic Tape (registered trademark: manufactured by KURARAY CO., LTD) may be exemplified.

A male fastener or hook-and-loop fastener is attached to one of both ends 321a and 321a of the drainage net 321, and a female fastener or hook-and-loop fastener is attached to another thereof, and thus fastening with a pair of male and female fasteners may be performed between sandbags to be joined to each other.

The member of the joint unit 322 and the joint unit 313 (for example, fastener or hook-and-loop fastener) is preferably a substance having oil-repellent properties or a substance subjected to oil-repellent treatment.

The hook-and-loop fastener is a fastening tool which is highly convenient. Because joining can be easily performed and laying time can be reduced, the hook-and-loop fastener is preferable. In a case of using the hook-and-loop fastener, a side end portion of the drainage net (having hydrophilic and oil-repellent properties) of a sandbag to be joined and a side end portion of the bag body are double overlapped with each other. Thus, a high oil-shielding effect is obtained.

The sandbag (oil-water separation apparatus) 320 in this embodiment further includes a supporting rod 323 attached to the drainage net 321 in order to prevent turnover.

One end of the supporting rod 323 is installed at a position separated from the bag body 311 on the ground (or floor) F, and thus the function of developing the drainage net or of supporting the drainage net is improved.

The supporting rod 323 in this embodiment is round rodlike, but the shape of the supporting rod 323 is not particularly limited.

The supporting rod 323 may be combined to a rigid body, for example, by using a hinge or screwing, in a state of being movable.

With this configuration, it is possible to ensure the function of developing the drainage net or of supporting the drainage net, and to also obtain compact properties while being stored.

One or a plurality of supporting rods may be provided. For example, supporting rods are provided on both sides of the drainage net, and thus it is possible to achieve more improvement of installation stability.

<15th Embodiment>

Figure 16:
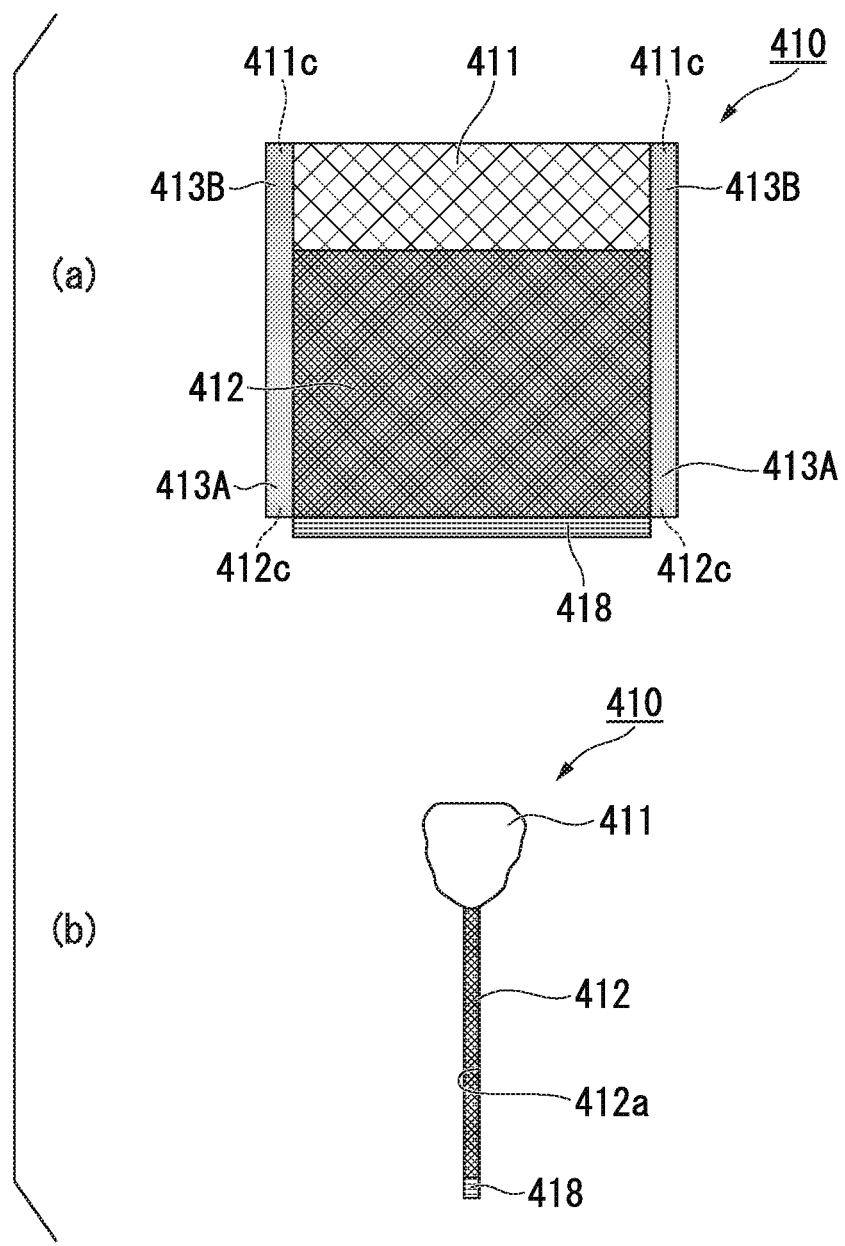
FIG. 16 is a front view and a sectional view illustrating a 15th embodiment of the oil-water separation apparatus according to the present invention.

FIG. 16(a) is a front view schematically illustrating a configuration of an oil fence (oil-water separation apparatus) according to a 15th embodiment. FIG. 16(b) is a sectional view of the oil fence illustrated in FIG. 16(a).

An oil fence (oil-water separation apparatus) 410 in this embodiment includes a float 411 and an oil-water separation filter medium. The float 411 is used to float on a water surface. The oil-water separation filter medium is attached to a lower portion of the float and is formed from a curtain (base) 412 including an oil-water-separating member which has hydrophilic and oil-repellent properties. An oil-water-separating member 14 (see FIG. 1(b)) is formed on at least an inner surface 412a of the curtain 412.

As the float 411, a well-known object may be used. For example, a foamed resin float or a float and sink type float may be used. As the foamed resin, for example, foamed styrene, foamed polyethylene, foamed urethane, and the like are used. However, the foamed styrene is preferable. As the float and sink type float, for example, a rubber air float in which air can flow out and flow in is provided. An oil-repellent layer may be formed on the outer surface of the float 411.

A more-detailed specific example of the float 411 will be described later.

The curtain (base) 412 is formed from a material including a channel through which at least moisture is allowed to pass.

For example, the curtain (base) 412 is formed from a sheet-like fibrous base such as woven fabric, knitted fabric, or nonwoven fabric, or from a polymeric porous base. As a specific example, a natural fiber, organic polymer, a glass fiber, and the like are exemplified. In this embodiment, as the curtain 412, a nonwoven fabric sheet formed from a polypropylene porous medium is used. A more-detailed specific example of the curtain 412 will be described later.

For example, a channel through which moisture is allowed to pass is formed in the curtain 412. Such a channel is formed from pores (fine hole, hollow, and communication hole) of a sheet-like fibrous base or a polymeric porous base constituting the curtain 412. The channel causes the inner surface 412a and an outer surface (not illustrated) of the curtain 412 to communicate with each other, and thus passes moisture therethrough. Moisture which reaches the outer surface side of the curtain 412 is permeated itself.

An oil-water-separating member 14 (see FIG. 1(b)) is formed on the surface (surface layer) of at least the inner surface 412a of the curtain 412. In this embodiment, the oil-water-separating member 14 is formed in the entirety of the inner surface 412a and the outer surface of the curtain 412 which includes an inner wall surface of the channel.

The oil-water-separating member 14 may be formed such that the oil-water-separating member 14 forms a film on the surface of the curtain 412. Further, the oil-water-separating member 14 may be impregnated to the inner side in a depth direction of the curtain 412.

The oil-water-separating member 14 imparts the hydrophilic and oil-repellent properties to the curtain 412 by the existence of an oil-repellency-imparting group and a hydrophilicity-imparting group. If oil containing moisture is brought into contact with the curtain 412 in which the oil-water-separating member 14 is formed, the oil is aggregated as an oil droplet having a large contact angle, and moisture holds wettability in which the contact angle is small. Thus, the moisture which holds the wettability can pass through the channel in a state of being in contact with the oil-water-separating member 14. With such an action, the oil-water-separating member 14 can selectively separate and pass only moisture in oil, and can increase a water-permeating rate.

(Float)

As the float, a well-known object may be used, and another configuration may be used.

The float may be configured from a float main body which floats on a water surface, and a cover for covering the float main body. As the float main body, an object which is the same as the above-described float 411 may be used. As the cover, for example, texture (for example, synthetic fiber canvas and sheet), a polyvinyl chloride resin coating sheet, and the like may be used. The cover is subjected to hydrophilic and oil-repellent treatment, and thus it is possible to reduce the risk of oil passing over the oil fence.

The float may be also configured from a bag body which allows oil to pass therethrough, and an oil absorbent material which is accommodated in the bag body. As the oil absorbent material, floating active carbon which absorbs oil, flips water, and floats on water is preferable.

As a preferable commercial product, "SUMIREI" (product name: manufactured by TANIGUCHI SHOKAI CO., LTD.) is exemplified.

The peripheral edge of the bag body is preferably closed, for example, by sewing using a string-shaped medium such as a thread, by adhering with an adhesive having oil resistance, or by heat welding. The string-shaped medium is preferably a material having lipophilicity or a material subjected to lipophilic treatment. The binding place is preferably sealed by a lipophilic member.

The bag body and the curtain are preferably bonded to each other, for example, by sewing using a string-shaped medium such as a thread, by adhering with an adhesive having oil resistance, or by heat welding. The string-shaped medium is preferably a substance having oil-repellent properties or a substance subjected to oil-repellent treatment. The binding place is preferably sealed by an oil-repellent member.

(Curtain)

In the curtain constituting the oil fence (oil-water separation apparatus) in this embodiment, the channel for a liquid through which the separated water passes is formed in the curtain. Specifically, regarding the channel of the curtain, a space between fibers in the fibers constituting the curtain or pores of a porous medium constituting the curtain functions as the channel for moisture.

In this manner, the curtain is attached to the float, for example, by sewing using a string-shaped medium such as a thread, by adhering with an adhesive having oil resistance, or by heat welding. The binding place of the curtain and the float is preferably sealed by an oil-repellent member.

The material of the curtain is not particularly limited as long as the material is a fiber or a porous medium which can form a channel of a liquid to be separated. The material of the curtain may be organic matter or inorganic matter. In addition, the material of the base 17 may be a composite of organic matter and inorganic matter. Thus, as a form of the curtain in the oil fence, fibrous or porous organic matter and fibrous or porous inorganic matter are exemplified.

A member such as a polypropylene porous medium (for example, nonwoven fabric) or a fluororesin porous medium, which passes oil therethrough but flips water, is subjected to hydrophilic and oil-repellent treatment, and thus water is allowed to pass. Thus, the member can be used for damming oil. In particular, a fluororesin porous film having excellent chemical resistance is subjected to hydrophilic treatment, and thus water passes through the film and oil is flipped. Accordingly, the fluororesin porous film may be used for preventing diffusion of oil.

Here, organic matter usable as the curtain is not particularly limited. Specifically, for example, a sheet body as follows is exemplified: a cellulose filter paper, a filter cloth (polyester, polyethylene, polypropylene, polytetrafluoroethylene, nylon, polyimide, polyacrylonitrile, polysulfone, polyethersulfone, polyphenylene sulfide, and the like), a nonwoven fabric filter (polyester, polyethylene, polypropylene, rayon, nylon, polyphenylene sulfide, and the like), and a fibrous filter (resin, glass, ceramics, metal).

In the curtain, the width of the channel (that is, an average interval of fibers or an average width of a hollow of a porous material) is, for example, preferably 0.1 to 180 more preferably 0.5 to 75 µm, and further preferably 1 to 50 µm. Here, if the width of the channel is less than 0.1 µm, permeation resistance of water (moisture) is increased, and it may take time to perform permeation. Thus, the above range is not preferable. If the width of the channel is more than 180 µm, oil starts to pass through the channel. Thus, the above range is not preferable. On the contrary, if the channel width of the filter medium is in the above range, oil is not permeated, and a water-passing rate in a practically-appropriate range is obtained. Thus, such a filter medium is preferable.

The channel formed in the curtain is not necessarily limited to a configuration in which oil is never caused to pass through the channel. A case of a width which mainly allows moisture to pass and allows oil to pass at a predetermined proportion is also provided.

The oil-water-separating member 14 (see FIG. 1(*b*)) holds the fluorine compound (oil-repellent hydrophilic agent) represented by the formulas (1) to (4) in the above-described curtain.

As a method of holding the fluorine compound in the curtain such as a porous medium, the following method and the like may be applied. That is, the curtain which is to hold the compound is immersed in a dissolving liquid or a dispersion liquid of the fluorine compound (oil-repellent hydrophilic agent), or the curtain is subjected to spray coating with the dissolving liquid or the dispersion liquid. Then, a solvent is removed by drying. As a proportion for holding, selection to cause the mass composition ratio of an oil-repellent hydrophilic agent and a porous medium to be held to be in a range of a pair of 1 to 50 and 99 to 50 is preferable from the viewpoint of characteristics of the hydrophilic and oil-repellent properties.

As the curtain in the oil fence, a form of a curtain obtained by being formed to have a fibrous shape by a resin composition of one or more of the above-described organic matter (resin) and the fluorine compounds (oil-repellent hydrophilic agents) represented by the formulas (1) to (4) may be used. That is, the above-described oil-repellent hydrophilic agent may be used as an additive for imparting the function of the hydrophilic and oil-repellent properties to various resins.

As the curtain in the oil fence, a form obtained by being formed to have a fibrous shape by a resin composition of one or more of the above-described organic matter (resin) and the fluorine compounds (oil-repellent hydrophilic agents) represented by the formulas (1) to (4) may be used.

That is, the above-described oil-repellent hydrophilic agent may be used as an additive for imparting the function of the hydrophilic and oil-repellent properties to various resins.

The curtain in the oil fence further includes a joint unit at the side end portion thereof. The joint unit is used for joining the side end portion of the curtain to a side end portion of the curtain of another oil fence. The configuration of including the joint unit is provided, and thus joining to another oil fence is possible. Thus, the number of a plurality of oil fences joined to each other can be adjusted in accordance with the size of a range of leaked oil.

In the oil fence, the float also includes a joint unit at the side end portion thereof. This joint unit is formed to be continuous from the joint unit of the curtain.

A fastener or a hook-and-loop fastener is attached to both ends of the curtain, and thus it is possible to join curtains to each other without a gap. Accordingly, this is effective for preventing leakage of oil.

As the configuration in which the float includes a joint unit, for example, a case where the float is formed from a float main body and a cover of the float main body and the joint unit is attached to the cover may be used.

As the joint unit and the joint unit, a fastener or a hook-and-loop fastener may be used. A fastener type bonding method is used, and thus curtains are easily joined and separated to and from each other. As the hook-and-loop fastener, for example, Magic Tape (registered trademark: manufactured by KURARAY CO., LTD) may be exemplified.

A male fastener or hook-and-loop fastener is attached to one of both ends 411c and 412c of the curtain, and a female fastener or hook-and-loop fastener is attached to another thereof, and thus fastening with a pair of male and female fasteners may be performed between sandbags to be joined to each other.

As a member of the joint unit and the joint unit (for example, fastener or hook-and-loop fastener), a member of a material having oil-repellent properties, or a member subjected to oil-repellent treatment is preferably used.

The hook-and-loop fastener is a fastening tool which is highly convenient. Because joining can be easily performed and grounding time can be reduced, the hook-and-loop fastener is preferable. In a case using the hook-and-loop fastener, a joint unit of the curtain (having hydrophilic and oil-repellent properties) of an oil fence to be joined and a joint unit of the float are double overlapped with each other. Thus, a high oil-shielding effect is obtained.

The oil fence may further include a weight which is attached to a lower end portion of the curtain. The weight is preferable because of maintaining the curtain to be hung in a direction of a river bottom or a sea bottom and to be developed. As the weight, for example, a metal wire, an iron chain, an iron weight, or the like may be used.

As the weight, an object having a different configuration may be used.

The weight may be attached to a portion lower than the float in a form of a weight bag accommodated in the bag body including an oil-water-separating member which has hydrophilic and oil-repellent properties.

The portion lower than the float may be positioned under the float. For example, the weight may be attached between the float and the curtain, and be attached to a lower end portion of the curtain.

The number of weight bags included in the oil fence may be one or plural.

The weight may use water-absorptive polymer or an inorganic water-absorbent material in addition to sediment which is normally used. A substance having specific gravity larger than that of water may be appropriately used. A combination of different types of materials may be used as the weight. For example, sand and water-absorptive polymer may be used as the weight. As the weight, a metal wire, an iron chain, an iron weight, or the like which are described as the example of the weight may be used.

As the substance having specific gravity larger than that of water, a substance having density of 1.2 or more, and particularly, a substance having density of 2 or more is preferable. Specifically, manganese sand (density 2.5 to 2.7 g/cm$^3$), garnet (density 3.8 to 4.1 g/cm$^3$), and ferric oxide content (density 5.2 g/cm$^3$) are exemplified.

As the weight, sand or a chain may be used. However, if a water-absorptive material such as water-absorptive polymer is used, the weight bag has a light weight, and thus the work of transportation or installation is easily performed. The water-absorptive material with which the bag body is filled absorbs water in water or the sea, and thus the water-absorptive material can perform a function as the weight.

As the water-absorptive polymer, for example, a polyacrylate salt, a crosslinking type of isobutylene-maleic anhydride, a polysulfonate salt, a maleic anhydride salt, polyacrylamide, polyvinyl alcohol, polyethylene oxide, and polysaccharides such as starch or cellulose may be used.

In particular, from a viewpoint of water-absorptive properties, crosslinked sodium polyacrylate is preferable. As a preferable specific example of the water-absorptive polymer, "AQUALIC CA" (product name: manufactured by NIPPON SHOKUBAI CO., LTD.), "AQUALIC CS" (product name: manufactured by NIPPON SHOKUBAI CO., LTD.), and the like are exemplified. In a case of being used in the sea, "AQUALIC CS" which is water-absorptive polymer for salt resistance is more preferable.

The peripheral edge of the bag body is preferably closed, for example, by sewing using a string-shaped medium such as a thread, by adhering with an adhesive having oil resistance, or by heat welding. In a case of using a string-shaped medium, as the string-shaped medium, a substance having oil-repellent properties or a substance subjected to oil-repellent treatment.

In such a weight bag, in a case where the bag body is filled with the water-absorptive material such as water-absorptive polymer, the weight bag has a light weight and thus handling in transportation or installation is easily performed. Thus, this bag body is particularly effective, for example, when fast installation in emergencies is required.

<16th Embodiment>

Figure 17:
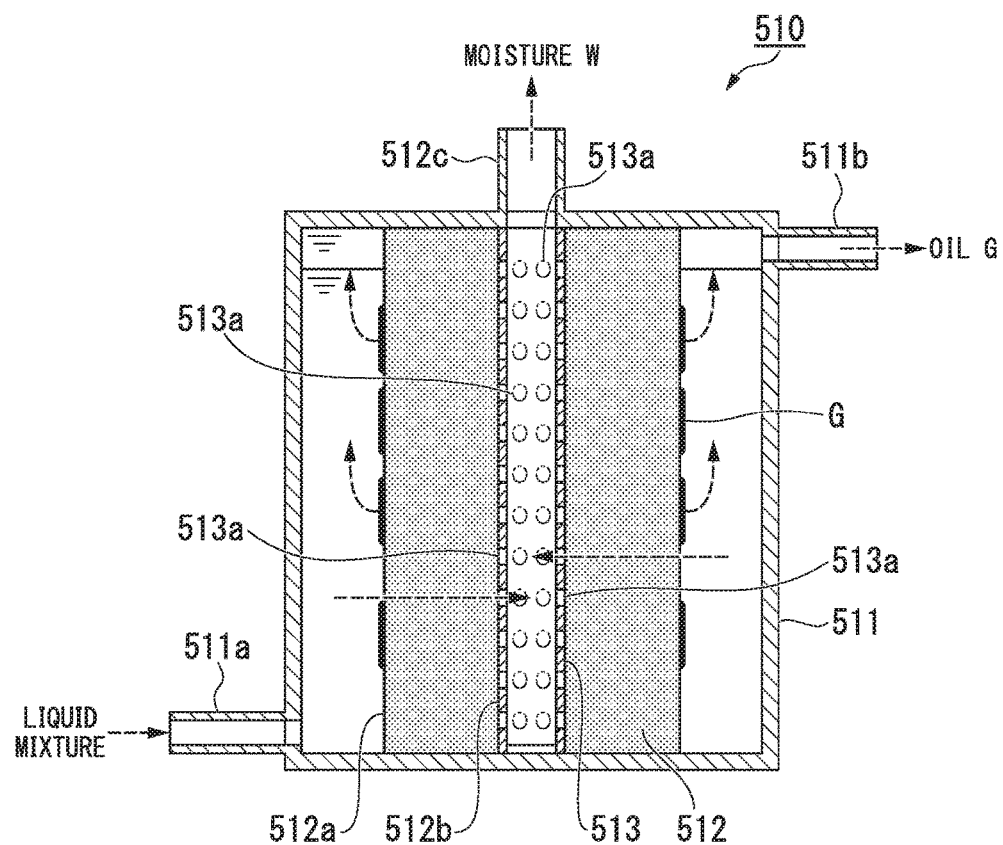
FIG. 17 is a sectional view illustrating a 16th embodiment of the oil-water separation apparatus according to the present invention.

FIG. 17 is a sectional view illustrating an example of an oil-water separation apparatus including an oil-water separation porous medium according to the present invention.

An oil-water separation apparatus 510 in this embodiment includes a filter case 511 and an oil-water separation porous medium (oil-water separation filter medium) 512 accommodated in the filter case 511.

The oil-water separation porous medium (oil-water separation filter medium) 512 is formed to have, for example, a hollow columnar shape. In this embodiment, a liquid mixture containing water and oil is caused to flow from one surface 512a side which functions as an outer circumferential surface of the oil-water separation porous medium 512 having a hollow columnar shape. Water after oil-water separation is caused to flow out from another surface 512b side which functions as an inner circumferential surface of the oil-water separation porous medium 512.

A hollow tube 513 is formed so as to be in contact with a hollow part, that is, the other side 512b of the oil-water separation porous medium 512. Multiple openings 513a are formed in the hollow tube 513. The openings 513a are used for guiding moisture which flows out from the other surface 512b side of the oil-water separation porous medium 512 into the hollow tube 513.

An inflow port 511a, an oil drain port 511b, and a water drain port 512c are formed in the filter case 511. The inflow port 511a causes a liquid mixture to flow into the inside thereof. The oil drain port 511b causes oil separated by the oil-water separation porous medium 512 to flow out by overflow. The water drain port 512c is connected to the hollow tube 513 and causes moisture separated by the oil-water separation porous medium 512 to flow out.

Figure 18:
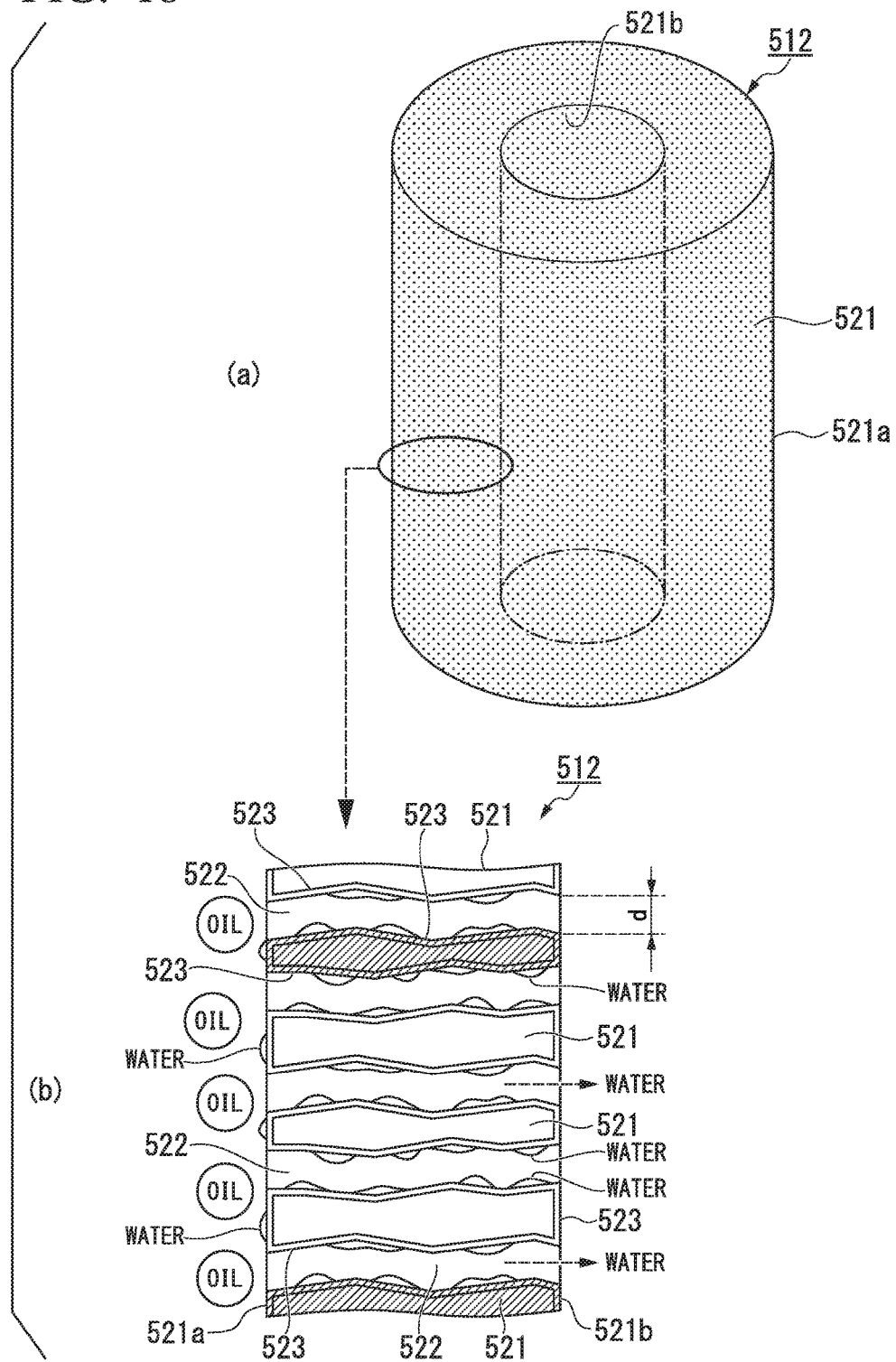
FIG. 18 is a perspective view of an enlarged main portion- and a sectional view of the enlarged main portion of the figure in FIG. 17.

FIG. 18(a) is an exterior perspective view illustrating the oil-water separation porous medium according to the present invention. FIG. 18(b) is a diagram of an enlarged main portion illustrating the oil-water separation porous medium according to the present invention.

The oil-water separation porous medium (oil-water separation filter medium) 512 includes a porous base (base) 521 formed to have a hollow columnar shape by using a porous material of which the entirety has water permeation. In the porous base 521, multiple pores (channels) 522 which penetrate a space between the outer circumferential surface 521a and the inner circumferential surface 521b are formed. An oil-water-separating member 523 is formed on the outer circumferential surface 521a, the inner circumferential surface 521b, and the surface (inner side surface) of the pore 522.

In the oil-water separation porous medium (oil-water separation filter medium) 512, multiple oil-water-separating members 523 are distributed in the porous base 521 in a predetermined thickness range. That is, in the oil-water separation porous medium (oil-water separation filter medium) 512 of this embodiment, the oil-water-separating members 523 are distributed and disposed in the porous base 521. In practice, a clear interface between a portion for forming the oil-water-separating member 523, and the porous base 521 on the inner side of the portion is not provided.

The porous base (base) 521 is formed from a material including multiple pores (channels) 522. For example, the porous base (base) 521 is formed from a fiber, a porous resin, ceramics, and the like. The pore 522 functions as a channel for moisture. As such a porous base 521, a base in which an opening diameter d of each pore 522 is 0.1μm to 180 μm is used. The opening diameter d is more preferably 0.5 to 75 μm, and further preferably 1 to 50 vim. Here, if the opening diameter d of the pore 22 is less than 0.1 μm, permeation resistance of water is large, and pressing may be required or time to perform permeation may be required. Thus, the above range is not preferable. If the opening diameter d of the pore 522 is more than 180 μm, oil starts to pass through the channel. Thus, the above range is not preferable. On the contrary, if the opening diameter d of the pore 522 is in the above range, oil is not permeated, and a water-passing rate in a practically-appropriate range is obtained. Thus, the above range is preferable.

The oil-water separation porous medium 512 having such a configuration separates a liquid mixture containing water and oil into moisture W and oil G by hydrophilicity and oil-repellent properties (below referred to as hydrophilic and oil-repellent properties) of the oil-water-separating member 523 formed in the porous base 521.

For example, if the oil-water separation filter 510 is disposed on a discharging path on which a liquid mixture is discharged, and the liquid mixture from an inflow port 511a is caused to flow into the one surface 512a of the oil-water separation porous medium 512, the liquid mixture is separated into moisture and oil by the hydrophilic and oil-repellent properties of the oil-water-separating member 523. The moisture W passes from the one surface 512a of the oil-water separation porous medium 512 through the other surface 512b by, for example, liquid pressure. It is not possible for the oil G after oil-water separation is performed by the oil-water-separating member 523 to pass through the pore 522 of the porous base 521. Thus, the oil G remains on the outer circumferential surface 512a of the oil-water separation porous medium 512, and floats on an upper portion of the filter case 511 by the specific gravity difference from the moisture W.

In this embodiment, a plurality of oil-water separation filters 510 are arranged in series, and can be used as a multi-stage type oil-water separation filter.

The oil-water-separating member 523 is configured from a material containing a fluorine compound which has an oil-repellency-imparting group and a hydrophilicity-imparting group. The oil-repellency-imparting group is a functional group for forming an oil droplet on the surface of the oil-water-separating member 523 at a contact angle of, for example, 40° or more. The hydrophilicity-imparting group is a functional group for imparting wettability to moisture at a contact angle of, for example, 20° or less to the surface of the oil-water-separating member 523.

The oil-water-separating member 523 has hydrophilic and oil-repellent properties due to the existence of such an oil-repellency-imparting group and a hydrophilicity-imparting group. If a liquid mixture containing water and oil is brought into contact with the oil-water-separating member 523, oil is aggregated as an oil droplet having a large contact angle, and moisture holds wettability in which the contact angle is small. Accordingly, oil which is aggregated and forms a large oil droplet remains on the surface of the oil-water separation porous medium 512 or floats on the surface layer of the liquid mixture by a specific gravity difference from that of the water. The moisture which holds the wettability can pass through the pores 522 of the oil-water separation porous medium 512 without being aggregated. With such an action, the oil-water separation porous medium 512 can separate oil from a liquid mixture.

An action of the oil-water separation filter 510 including the oil-water separation porous medium 512 which has a configuration as described above will be described. If a liquid mixture containing water and oil is caused to flow in from the inflow port 511a of the oil-water separation filter 510 in this embodiment, the liquid mixture is separated into moisture and oil by hydrophilic and oil-repellent properties of the oil-water-separating member 523 formed in the porous base 521 which constitutes the oil-water separation porous medium 512.

It is not possible for the separated oil to pass through the pore 522 having an opening diameter which is in a range of 0.1 μm to 180 μm. Thus, the separated oil floats on the upper portion of the filter case 511 by the specific gravity difference from the moisture. The moisture is trapped by the hydrophilicity of the oil-water-separating member 523, and is formed to be a liquid film. Then, the moisture passes through the pore 522 and reaches the inside of the hollow tube 513.

The separated oil is discharged from the oil drain port 511b by overflow. The moisture is discharged from the water drain port 512c at the upper portion of the filter case 511.

As described above, a solution mixture by mixing water and oil is only caused to flow into the oil-water separation filter 510 in this embodiment, and thus it is possible to efficiently and reliably separate the solution mixture into oil and moisture.

In the oil-water separation porous medium 512, the hydrophilic and oil-repellent properties are applied to the porous base 521. Thus, adhering of an organic molecule, or soil and mud is difficult, and accordingly, excellent antifouling properties are obtained. Attached dirt is easily removed by physical treatment of, for example, turning over and washing, and ease of washability is also excellent.

In the oil-water separation porous medium 512, in a case of containing only the fluorine compounds represented by the formulas (1) to (4), it is possible to apply excellent hydrophilic and oil-repellent properties while a perfluoroalkyl group having 8 or more carbon atoms which are continuously bonded to each other is not contained, and a chemical structure which does not have a concern of generating PFOS or PFOA, which becomes a problem from the viewpoint of bioaccumulation or environmental adaptability, is provided.

Figure 26:
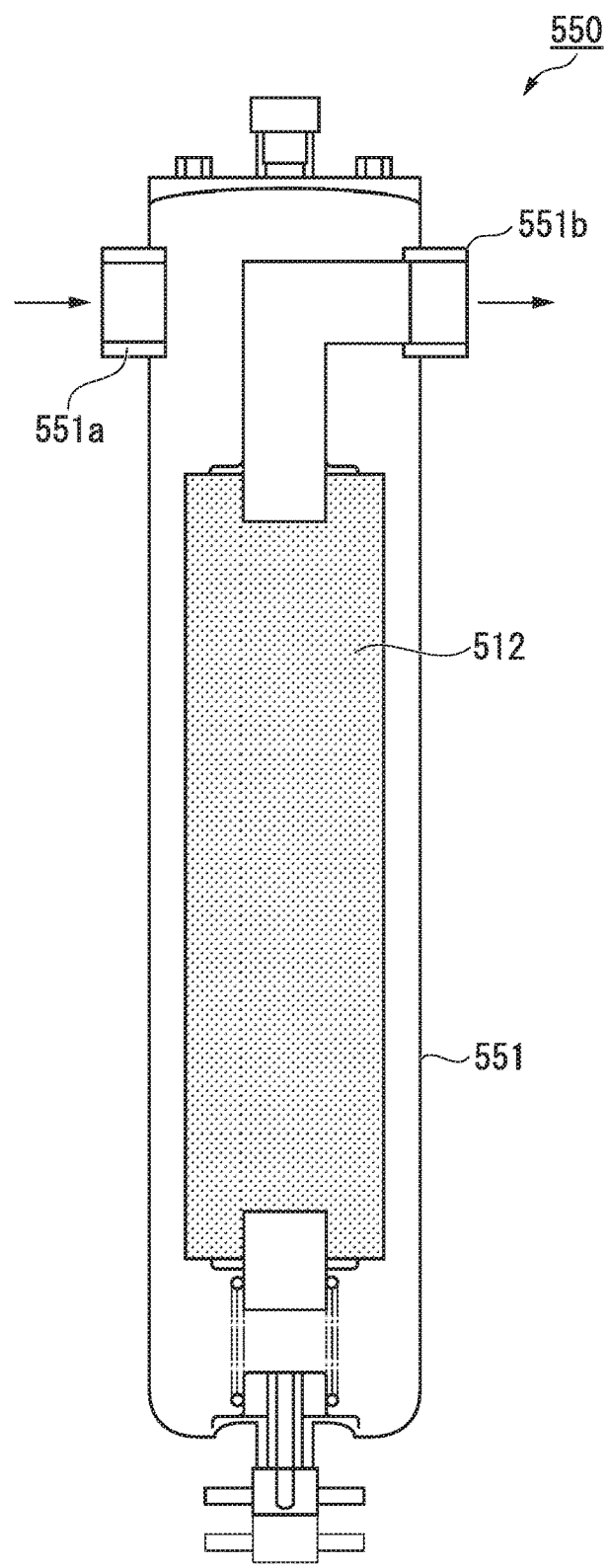
FIG. 26 is a sectional view illustrating a modification example of the 16th embodiment of the oil-water separation apparatus according to the present invention.

FIG. 26 is a sectional view illustrating a modification example of an oil-water separation filter according to a 16th embodiment.

The oil-water separation filter 550 includes a filter case 551 and an oil-water separation porous medium (oil-water separation filter medium) 512 accommodated in the filter case 551. The oil-water separation porous medium 512 is formed to have, for example, a columnar shape, similarly to the 16th embodiment.

An inflow port 551a and a water drain port 551b are formed in the filter case 551 in this embodiment. The inflow port 551a causes a liquid mixture to flow into the inside of the filter. The water drain port 551b causes moisture after oil is separated by the oil-water separation porous medium 512 to flow out of the filter.

In this embodiment, the oil-water separation porous medium 512 is applied to a general filter case 551 in which a liquid mixture is introduced from an upper portion into the filter case 551, and moisture is caused to flow out from the upper portion. In this case, the oil separated by the oil-water separation porous medium 512 is accumulated in the filter case 551. Thus, a batch type use form as follows is employed. After oil-water separation for the predetermined amount is performed, for example, oil-water separation performance is decreased, and a supply of the liquid mixture is stopped. Accumulated oil is discharged from the inflow port 551a, and then oil-water separation is performed again. Thus, for example, a plurality of oil-water separation filters 550 are prepared and are appropriately switched and used, and thus it is possible to efficiently perform oil-water separation. Even though a filter case 551 which does not include an oil drain port is provided, it is possible to efficiently perform oil-water separation by using the oil-water separation porous medium 512.

Regarding the filter case of the oil-water separation filter as in the above-described embodiment, a filter case which further includes a valve for an air vent at the top may be used. Oil which is separated by oil-water separation and floats in the filter case is extracted from such a valve for an air vent to the outside of the filter case. Thus, it is possible to continuously perform oil-water separation with efficiency.

If one filter case has a configuration in which a plurality of oil-water separation porous media are stored and oil-water separation is performed by using the plurality of oil-water separation porous media, it is possible to improve oil-water separation capability per unit time, and to perform oil-water separation of a liquid mixture with further efficiency.

In the filter case of the oil-water separation apparatus as in the above-described embodiment, a position of forming the inflow port or the water drain port is not particularly limited. The inflow port or the water drain port may be formed at a certain position, for example, the upper portion or the lower portion of the filter case, in accordance with the configuration of the apparatus. The shape of the filter case may be any shape, for example, a cuboid shape or a spherical shape in addition to the above-described columnar shape.

Further, as another embodiment, an oil-water separation porous medium (oil-water separation filter medium) may include a porous base (base) and an oil-water-separating member. The porous base (base) includes multiple pores (channels). The oil-water-separating member is formed on the entirety of the surface of the porous base, which includes the surface of the pore. The pore which penetrates a space between one surface and the other surface of the porous base may also have a configuration in which the opening diameter continuously becomes narrower from the one surface toward the other surface.

As a method in which the opening diameter of the pore in such a porous base continuously becomes narrower, for example, a method in which formation density of fibers constituting the porous base 521 is continuously changed from the one surface toward the other surface, a method in which chemicals are dipped from the one surface side of the porous base 521, and thus the opening diameter of air is continuously increased, and the like are exemplified. A method in which winding density is slowly changed from the center toward the outside in a bobbin cartridge and the like may be provided simulatively as a form in which the opening diameter of the pore is continuously increased.

As described above, the configuration in which the opening diameter of the pore continuously becomes narrower from the one surface of the porous base toward the other surface is provided, and thus it is possible to prevent oil from passing through the pore 522, to increase a passing rate of moisture, and to perform oil-water separation of a solution mixture with more efficiency.

As still another embodiment, the pore (channel) which penetrates a space between the one surface and the other surface of the porous base (base) may have a configuration in which the opening diameter becomes narrower from the one surface toward the other surface in stages. For example, the opening diameter of the pore may be changed at three stages.

As a method in which the opening diameter of the pore of such a porous base becomes narrower in stages, for example, a case where a porous base having a pore of a first opening diameter, a porous base having a pore of a second opening diameter which is narrower than the first opening diameter, and a porous base having a pore of a third opening diameter which is narrower than the second opening diameter are layered and stuck to each other is exemplified.

As described above, the configuration in which the opening diameter of the pore continuously becomes narrower from the one surface of the porous base toward the other surface thereof is provided, and thus it is possible to prevent oil from passing through the pore, to increase a passing rate of moisture, and to perform oil-water separation of a solution mixture with more efficiency.

<17th Embodiment>

FIG. 19(a) is a perspective view illustrating an example of an oil-water separation and collection tool (oil-water separation apparatus). FIG. 19(b) is a diagram illustrating the main portion of the oil-water separation and collection tool (oil-water separation apparatus).

An oil-water separation and collection tool (oil-water separation apparatus) 610 in this embodiment includes an oil-water separation filter medium formed from a base 611 and an oil-water-separating member 612. The oil-water-separating member 612 is formed on, for example, the surface of the base 611. The entirety of such an oil-water separation and collection tool 610 is formed to have, for example, a sheet shape. The oil-water separation and collection tool 610 is disposed, for example, on the bottom surface of the inner side of a basket-like support member 615 formed to be rectangular parallelepiped, and constitutes an oil-water separation and collection unit 616. Such an oil-water separation and collection unit 616 may be applied to a gathering machine which will be described later. The oil-water separation and collection unit 616 may include a knob for easily performing extraction from the gathering machine.

It is preferable that the oil-water separation and collection tool 610 be disposed on the bottom surface of the inner side of the support member 615, and be also disposed on the bottom surface of the outer side of the support member 615.

The oil-water separation and collection tool 610 in this embodiment separates oil from a liquid mixture containing water and oil and collects the separated oil. A channel 617 for a liquid is formed in the base 611. Such a channel 617 causes the one surface 611a side and the other surface 611b side of the base 611 to be linked to each other. The oil-water-separating member 612 is formed to cover the entirety of the surface of the base 611, which includes an inner wall surface of the channel 617.

For example, if a liquid mixture flows in from the one surface 611a side of the base 611, in such an oil-water separation and collection tool (oil-water separation apparatus) 610, oil which is separated from the liquid mixture remains on the one surface 611a side of the base 611, and moisture flows down from the other surface 611b side of the base 611 through the channel 617, by the hydrophilicity and oil-repellent properties (below referred to as hydrophilic and oil-repellent properties) of the oil-water-separating member 612.

The oil-water-separating member 612 is configured from a material containing a fluorine compound which has an oil-repellency-imparting group and a hydrophilicity-imparting group. The oil-repellency-imparting group is a functional group for forming an oil droplet on the surface of the oil-water-separating member 612 at a contact angle of, for example, 40° or more. The hydrophilicity-imparting group is a functional group for imparting wettability to moisture at a contact angle of, for example, 20° or less to the surface of the oil-water-separating member 612.

The oil-water-separating member 612 has hydrophilic and oil-repellent properties due to the existence of such an oil-repellency-imparting group and a hydrophilicity-imparting group. As illustrated in the diagram of FIG. 19(b), if a liquid mixture (may be simply referred to as a liquid below) containing water and oil is brought into contact with the oil-water-separating member 612, oil is aggregated as an oil droplet having a large contact angle, and moisture holds wettability in which the contact angle is small. Accordingly, oil which is aggregated and forms a large oil droplet remains on the surface of the oil-water-separating member 612 in a state where passing through the channel 617 is not allowed. The moisture which holds the wettability can pass through the channel 617 without being aggregated. With such an action, the oil-water-separating member 612 can selectively separate only oil from a liquid.

According to the oil-water separation and collection tool 610 of this embodiment, one or more fluorine compounds in which an oil-repellency-imparting group and a hydrophilicity-imparting group are included in a molecule are provided on the surface of the channel 617 formed by the base 611. Thus, in a case where a liquid mixture of water and oil flows into the oil-water separation and collection tool 610 in this embodiment, moisture passes through the channel 617 of the base 611, but passing of oil is not possible. Accordingly, the oil-water separation and collection tool 610 in this embodiment can perform separation into water and oil only by gravity, and can be appropriately used as an oil-water separation membrane of the gathering machine which will be described later.

In the oil-water separation and collection tool 610 of this embodiment, the hydrophilic and oil-repellent properties are applied to the surface of the channel 617 formed by the base 611. Thus, adhering of an organic molecule, or soil and mud is difficult, and accordingly, excellent anti-fouling properties are obtained. Attached dirt is easily removed by physical treatment of, for example, back pressure washing, and ease of washability is also excellent.

In the oil-water separation and collection tool 610 of this embodiment, in a case of containing only the fluorine compounds represented by the formulas (1) to (4), it is possible to apply excellent hydrophilic and oil-repellent properties while a perfluoroalkyl group having 8 or more carbon atoms which are continuously bonded to each other is not contained, and a chemical structure which does not have a concern of generating PFOS or PFOA, which becomes a problem from the viewpoint of bioaccumulation or environmental adaptability, is provided.

The oil-water separation and collection tool 610 in this embodiment may be used as the oil-water separation membrane of the gathering machine which will be described later, and the oil-water separation and collection tool 610 formed from the base 611 and the oil-water-separating member 612 formed on the surface of the base 611 may have a dip-net shape supported by a patterned support member. For example, the surface of a drainage tank storing a liquid mixture (discharged water) in which oil and water are mixed is dredged by using such a patterned oil-water separation and collection tool (oil-water separation apparatus) 610. Thus, it is possible to selectively separate only oil floating on the surface of the discharged water, from a discharged liquid, and to easily collect the separated oil.

<18th Embodiment>

A configuration of the gathering machine to which the oil-water separation apparatus having the present invention applied thereto is applied will be described.

Figure 20:
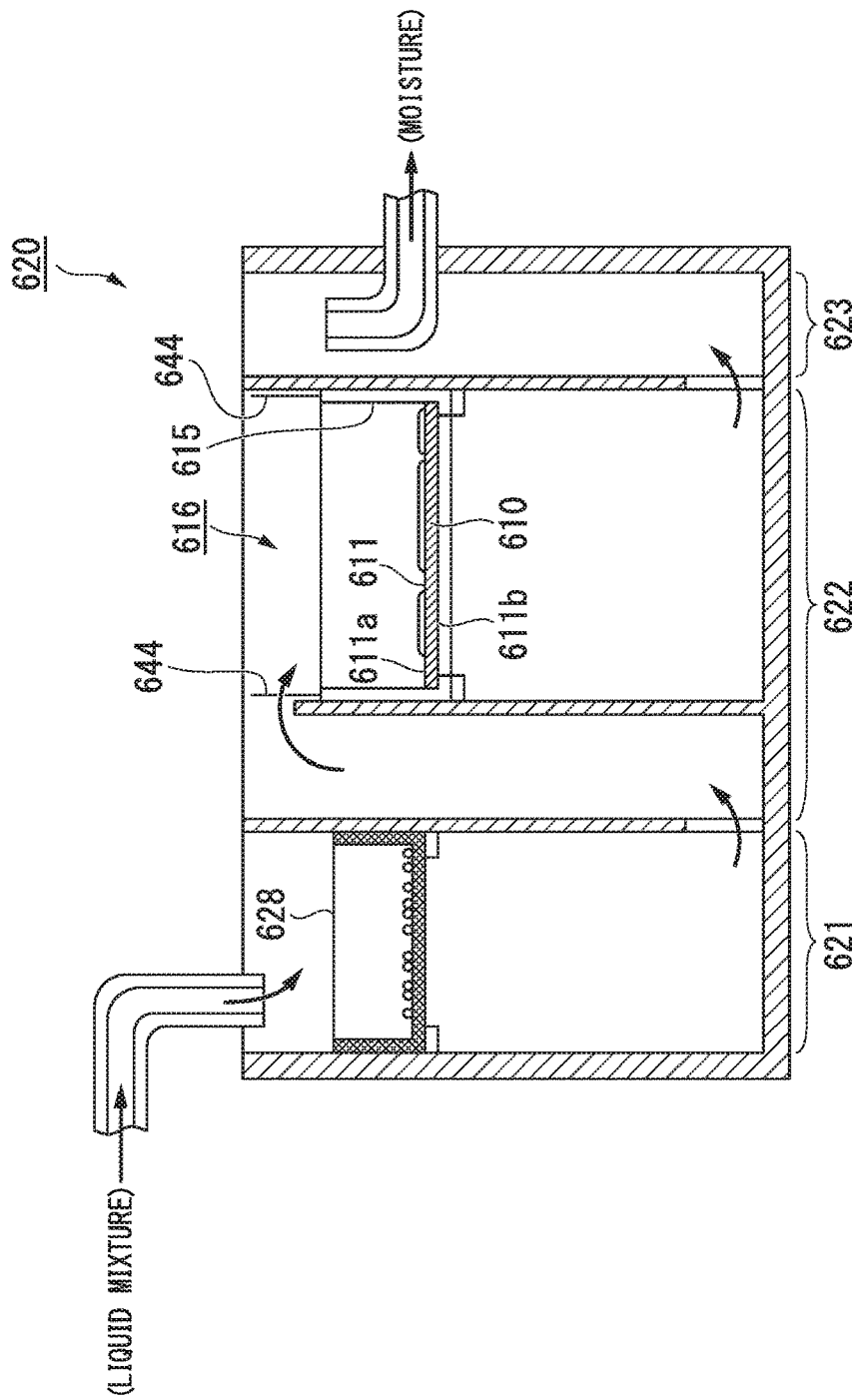
FIG. 20 is a sectional view illustrating an 18th embodiment of the oil-water separation apparatus according to the present invention.

FIG. 20 is a sectional view illustrating an embodiment of a gathering machine including the oil-water separation and collection tool (oil-water separation apparatus) according to the present invention.

A gathering machine (grease trap) 620 in this embodiment is installed at a location such as a commercial cooking place in which a liquid mixture (may be referred to as a waste liquid below) in which water, oil, solid matter, and the like are mixed is discharged. The gathering machine is a device that collects oil or solid matter, and discharges only moisture to sewerage and the like.

In the gathering machine 620 of this embodiment, a first reservoir (preceding-stage reservoir) 621, a second reservoir (subsequent-stage reservoir) 622, and a third reservoir 623 are arranged in series from an upstream side on which a waste liquid flows, toward a downstream side, in this order. The reservoirs 621 to 623 are divided by partitions including openings, respectively.

The first reservoir (preceding-stage reservoir) 621 is, for example, a liquid reservoir in which a waste liquid directly flows from an upper portion. In the first reservoir 621, a discharged liquid flows toward the bottom. A solid-matter removal machine 628 is installed in the first reservoir (preceding-stage reservoir) 621. The solid-matter removal machine 628 strains solid matter contained in a waste liquid, for example, food refuse. The solid-matter removal machine 628 may be formed from a gold net having a mesh. The mesh has a size which allows, for example, solid matter floating in the waste liquid to be filtered.

Such a solid-matter removal machine 628 is provided so as to be attachable to the first reservoir 621. When the predetermined amount or more of the solid matter is accumulated, the solid-matter removal machine 628 is extracted from the first reservoir 621, and thus deposited solid matter is disposed. The solid matter is removed in a waste liquid which passes through the solid-matter removal machine 628. Thus, this waste liquid as a liquid mixture in which water and oil are mixed flows from the bottom of the first reservoir (preceding-stage reservoir) 621 toward the second reservoir (subsequent-stage reservoir) 622.

The second reservoir (subsequent-stage reservoir) 622 is an oil separation and collection reservoir that separates oil from a liquid in which water and oil are mixed, and collects the separated oil. A partition is formed on an upstream side of the second reservoir 622. The partition guides a liquid mixture which flows in from the bottom of the first reservoir 621 to the upper portion and causes the liquid mixture to overflow. The oil-water separation and collection unit 616 in the above-described embodiment is installed in the second reservoir (subsequent-stage reservoir) 622, so as to be attachable and detachable.

Figure 19:
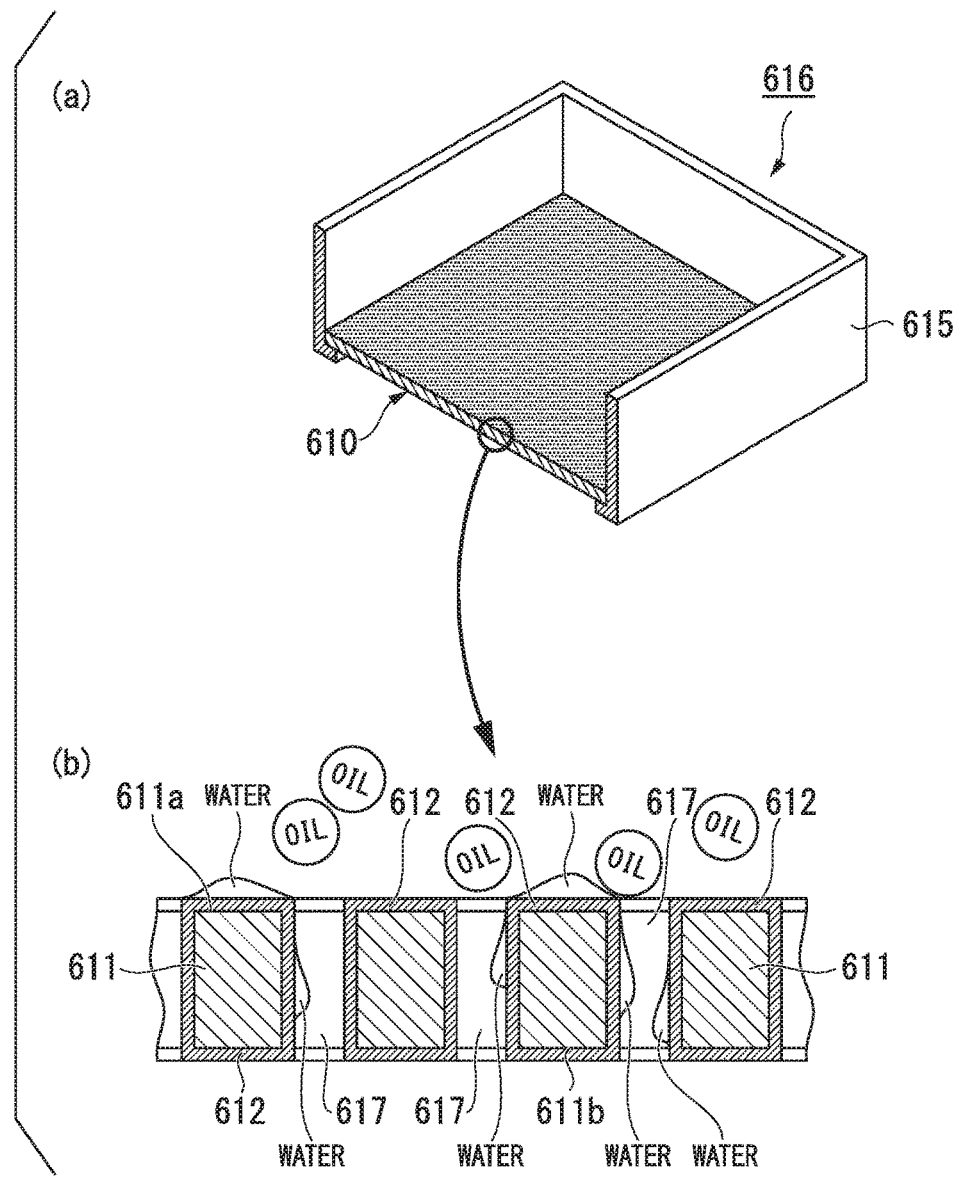
FIG. 19 is a perspective view and a diagram illustrating a 17th embodiment of the oil-water separation apparatus according to the present invention.

As illustrated in FIG. 19, the oil-water separation and collection unit 616 installed in the second reservoir (subsequent-stage reservoir) 622 is formed from an oil-water separation and collection tool (oil-water separation apparatus) 610 and a basket-like support member 615. The oil-water separation and collection tool (oil-water separation apparatus) 610 includes an oil-water separation filter medium formed from a base 611 and an oil-water-separating member 612. A channel 617 is formed in the base 611. The oil-water-separating member 612 covers the entirety of the surface of the base 611, which includes the channel 617. The basket-like support member 615 supports the oil-water separation and collection tool 610. The oil-water separation and collection tool 610 is disposed at the bottom of the support member 615. A knob 644 is formed in the support member 615. The knob 644 causes the entirety of the oil-water separation and collection unit 616 to be attachable and detachable to and from the second reservoir (subsequent-stage reservoir) 622.

In the second reservoir (subsequent-stage reservoir) 622, a liquid mixture flows in from the one surface 611a side (upper portion side) of the base 611 constituting the oil-water separation and collection tool 610, and flows out from the other surface 611b side (lower portion side). That is, if the liquid mixture is brought into contact with the oil-water separation and collection tool 610, only oil is aggregated by the hydrophilic and oil-repellent properties of the oil-water-separating member 612, and is separated on the one surface 611a side of the base 611. Moisture passes through the channel 617 of the base 611 by the hydrophilicity of the oil-water-separating member 612, and flows out from the other surface 611b side (lower portion side).

As described above, the liquid mixture flowing into the second reservoir (subsequent-stage reservoir) 622 is separated into oil and moisture by the oil-water separation and collection tool 610. The oil is collected by the oil-water separation and collection tool 610. The oil separated by the oil-water separation and collection tool 610 is stored on the surface of the oil-water separation and collection tool 610 or on a liquid surface of the second reservoir (subsequent-stage reservoir) 622. The oil-water separation and collection unit 616 is extracted from the second reservoir (subsequent-stage reservoir) 622, and thus, it is possible to extract the separated oil.

Moisture which is separated along with oil by the oil-water separation and collection tool 610 of the second reservoir (subsequent-stage reservoir) 622 flows from the bottom of the second reservoir (subsequent-stage reservoir) 622 toward the third reservoir.

The third reservoir 623 is a drainage reservoir for discharging moisture. Only moisture is discharged to the outside of the gathering machine 620 through a drain pipe. Regarding such drainage, the gathering machine 620 separates and collects oil or solid matter, and thus it is possible to directly perform discharging to the sewerage.

As described above, according to the gathering machine 620 in this embodiment, a liquid mixture in which water and oil are mixed is just brought into contact with the oil-water separation and collection tool (oil-water separation apparatus) 610, and thus it is possible to easily separate the liquid mixture into moisture and oil by the hydrophilic and oil-repellent properties of the oil-water-separating member 612, and to selectively collect only oil. The oil-water separation and collection tool (oil-water separation apparatus) 610 is provided in the gathering machine 620, and thus it is possible to easily separate and collect only oil from a liquid mixture in which water and oil are mixed, at low cost with a simple configuration.

<19th Embodiment>

FIG. 21(a) is a sectional view illustrating an oil-water separation apparatus according to a 19th embodiment. FIG. 21(b) is a diagram of an enlarged main portion illustrating an oil-water separation filter.

An oil-water separation apparatus 720 in this embodiment includes a housing (outer shell) 721 and a plurality of oil-water separation filters (oil-water separation filter media) 710 which are arranged in the housing 721.

In this embodiment, the plurality of oil-water separation filters (oil-water separation filter media) 710 are arranged at multi-stages at an interval along in a horizontal direction. Each of the oil-water separation filters 710 corresponds to a fiber assembly 711 having a channel through which oil is allowed to pass. Fine water droplets in a liquid mixture in which oil and moisture are mixed forms a liquid film on the surface of the oil-water-separating member 714 having hydrophilic and oil-repellent properties during a period when the liquid mixture passes through the multi-stage oil-water separation filter 710. The surface of the oil-water separation filter 710 flows down along a vertical direction by the specific gravity difference.

The fiber assembly (base) 711 constituting such an oil-water separation filter (oil-water separation filter medium) 710 may use cloth such as knit, texture, and nonwoven fabric, twist yarn, long fibers, and the like. For example, the peripheral edge of each oil-water separation filter 710 is fixed to the frame body, and the frame body is fixed at an upper portion, a lower portion, or both portions of the inside of the housing 721. A guide groove and the like of the frame body is disposed on the side surface of the housing 721, and thus the frame body can be inserted and fixed to the guide. In addition, a hole is provided in the frame body and a bar medium is caused to pass through this hole. Thus, a configuration in which the plurality of oil-water separation filters 710 are arranged at multi-stages in the housing 721 may be provided.

In a case where the fiber assembly (base) 711 is configured by twist yarn (sting-shaped medium), the fiber assembly 711 may be hung along the vertical direction of the frame body, so as to have a blind shape. In a case where the fiber assembly 711 is configured by long fibers, a configuration of being directly suspended in the housing 721 may be provided, or a configuration in which the long fibers are suspended to the frame body may be provided.

Oil in a liquid mixture is flipped by oil-repellent properties of the oil-water-separating member 714 formed in the fiber assembly 711. Fine water droplets are trapped by the hydrophilicity of the oil-water-separating member 714, and are formed to be a liquid film. The fine water droplets move toward a lower part of the vertical direction by combination of the capillary phenomenon and gravity.

In this embodiment, the oil-water separation filter (oil-water separation filter medium) 710 including the fiber assembly 711 is provided at multi-stages in a direction in which the liquid mixture flows. Thus, efficiency of removing water droplets is improved. A liquid-passing rate for the fiber assembly 711 is increased in comparison to, for example, the fiber assembly 711 configured by simple hydrophilic fibers.

In this embodiment, as the liquid mixture, a liquid in which oil is the main component, and moisture as fine water droplets is suspended in this oil is used.

The housing 721 has, for example, an exterior shape which forms a hollow. A plurality of oil-water separation filters 710 are accommodated in the housing 721. An inflow port 721a for a liquid mixture is formed on the side surface of the housing 721. Further, a water drain port 721b is formed on the bottom of the side surface of the housing 721. An oil drain port 721c is formed at the upper portion of the side surface.

The inflow port 721a of the housing 721 causes a liquid mixture formed from oil in which fine water droplets are mixed to flow out from a columnar side surface of the oil-water separation filter 710. The water drain port 721b causes moisture which is separated by the oil-water separation filter 710 and remains in the bottom of the housing 721 by the specific gravity difference from the oil to be discharged to the outside of the housing 721. The oil drain port 721c causes oil after moisture is separated by the oil-water separation filter 710 to be discharged from the upper portion of the housing 721 to the outside of the housing 721 by overflow.

The oil-water separation filter 710 includes the fiber assembly 711 and the oil-water-separating member 714 which is formed in the fiber assembly 711 and has hydrophilic and oil-repellent properties. In this embodiment, the oil-water-separating member 714 is formed in the entirety of the surface of the fiber assembly 711 in a predetermined thickness range.

The oil-water-separating member 714 imparts the hydrophilic and oil-repellent properties to the fiber assembly 711 by the fluorine compound which has an oil-repellency-imparting group and a hydrophilicity-imparting group.

The oil-water-separating member 714 may be formed such that the oil-water-separating member 714 forms a film on the surface of the fiber assembly 711. Further, the oil-water-separating member 714 may be impregnated to the inner side in a depth direction of the fiber assembly 711.

If, for example, a solution mixture in which oil is the main component and fine water droplets are mixed is caused to pass through such an oil-water separation filter (oil-water separation filter medium) 710 having hydrophilic and oil-repellent properties, by pressure feeding, oil which is brought into contact with the surface of the oil-water separation filter 710 is aggregated as an oil droplet having a large contact angle, by the oil-repellent properties. Thus, the oil droplet is flipped. The fine water droplet exhibits wettability having a small contact angle by the hydrophilicity. Thus, the fine water droplets wet the fiber surface and are permeated to the fiber surface. The water droplets move down under the fiber assembly 711 by an increase of the amount of adhering water droplets and by the capillary phenomenon. Moisture obtained by exceeding the water-retained amount is detached from the fiber assembly 711. With such an action, in the oil-water separation filter 710 having the hydrophilic and oil-repellent properties, even in a state where the fine water droplets are diffused in oil, the water droplets are caused to form a liquid film and the water droplets are collected. Thus, the oil and the moisture are immediately and reliably separated.

As illustrated in FIG. 21(b), a channel 717 for a liquid is formed in the fiber assembly (base) 711 formed from a porous medium. Such a channel 717 is formed from pores (fine hole, hollow, and communication hole) of a porous medium constituting the fiber assembly 711.

The oil-water-separating member 714 is configured from a material containing a fluorine compound which has an oil-repellency-imparting group and a hydrophilicity-imparting group. The oil-repellency-imparting group is a functional group for forming an oil droplet on the surface of the oil-water-separating member 714 at a contact angle of, for example, 40° or more. The hydrophilicity-imparting group is a functional group for imparting wettability to moisture at a contact angle of, for example, 20° or less to the surface of the oil-water-separating member 714.

The oil-water-separating member 714 imparts the hydrophilic and oil-repellent properties to the fiber assembly 711 by the existence of such an oil-repellency-imparting group and a hydrophilicity-imparting group. If a liquid mixture (may be simply referred to as a liquid below) containing water and oil is brought into contact with the fiber assembly 711 in which the oil-water-separating member 714 is formed, oil is flipped on the fiber assembly 711, and is aggregated to form an oil droplet having a large contact angle. Moisture holds wettability in which the contact angle is small, and moves along the oil-water-separating member 714 in a gravity direction. Thus, oil and moisture are separated. With such an action, the oil-water-separating member 714 can selectively separate and pass only moisture from a liquid, and can increase a water-permeating rate.

Figure 21:
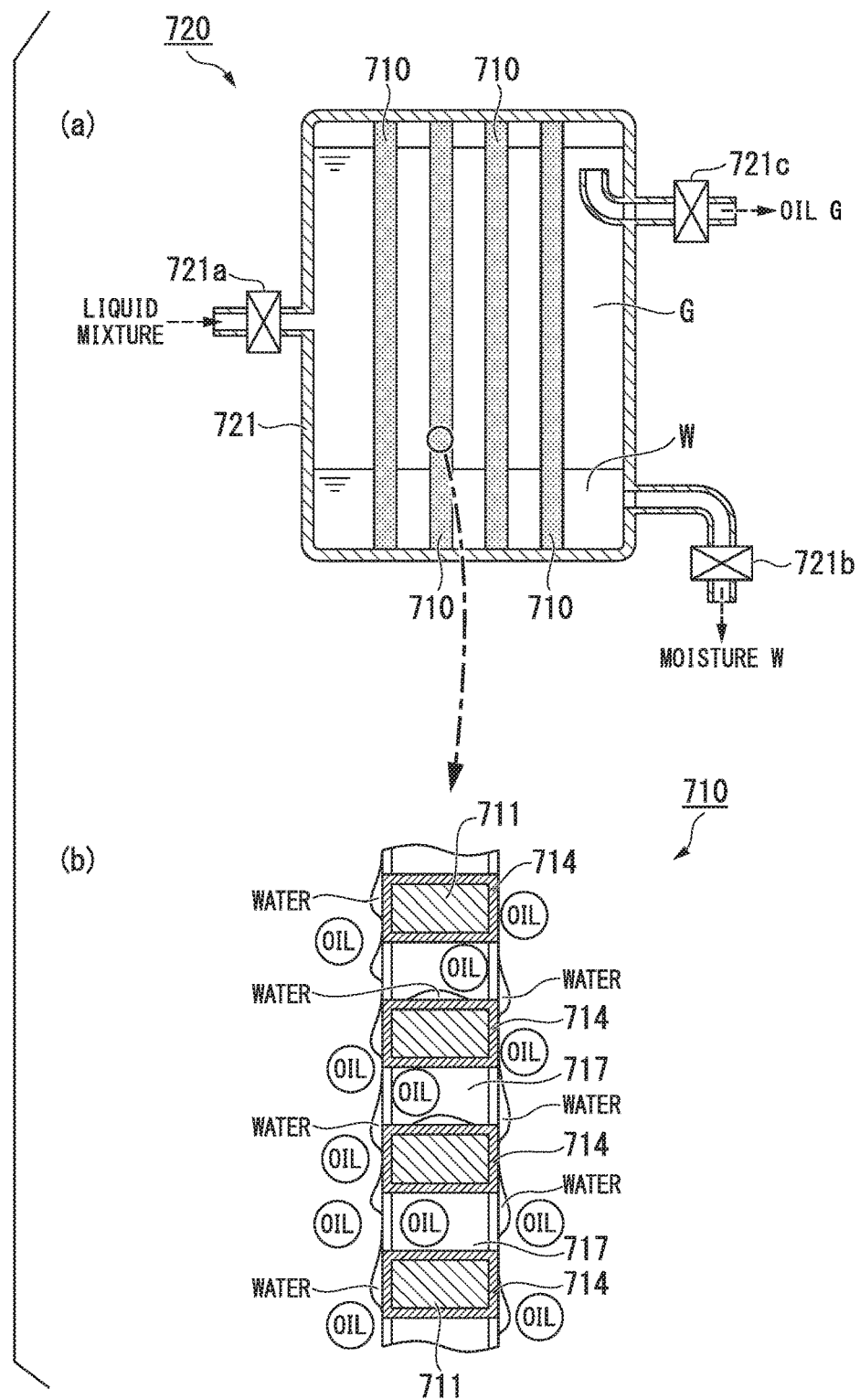
FIG. 21 is a sectional view illustrating a 19th embodiment of the oil-water separation apparatus according to the present invention.

If the diameter of the channel 717 in the fiber assembly 711 is set to have a size which exceeds the surface tension of oil, aggregated oil can also pass through the fiber assembly 711 by an influence of pressure. However, if the oil-water-separating member 714 is formed to have multi-stages as illustrated in FIG. 21, it is possible to remove only moisture from the liquid mixture.

In the configuration described in this embodiment, it is possible to increase a passing rate of a liquid mixture and to perform oil-water separation with high efficiency. The opening diameter of the fiber assembly 711 is appropriately changed in accordance with a composition ratio of oil and moisture in a liquid mixture. In a case where a large amount of moisture is contained in a liquid mixture, oil is blocked by the oil-water-separating member 714. In a case where a small amount of moisture is contained in the liquid mixture, the moisture is intended to be absorbed and removed by the oil-water-separating member 714. The opening diameter of the fiber assembly 711 is preferably set to pass oil.

According to the oil-water separation apparatus 720 having a configuration as described above, for example, if a solution mixture in which oil is the main component and fine water droplets are mixed is press-fed to the oil-water separation filter (oil-water separation filter medium) 710 from the inflow port 721a of the housing 721, oil in the solution mixture brought into contact with the oil-water separation filter 710 forms an oil droplet having a large contact angle, by the oil-repellent properties of the oil-water separation filter 710. The oil droplet is flipped. The fine water droplet holds wettability having a small contact angle by hydrophilicity, and moves along the oil-water-separating member in the gravity direction. Thus, oil and moisture are separated. Moisture separated from oil which is coarsened in this manner stays in the bottom of the housing 721 by the specific gravity difference from the oil.

Oil after moisture is separated by the oil-water separation filter 710 can be discharged from the upper portion of the housing 721 to the outside of the housing 721 by overflow. The moisture which stays in the bottom of the housing 721 by the specific gravity difference from the oil can be discharged from the water drain port 721b to the outside of the housing 721.

As described above, the oil-water separation filter (oil-water separation filter medium) 710 having hydrophilic and oil-repellent properties as in the present invention is used, and thus, for example, if a solution mixture in which oil is the main component and fine water droplets are mixed is caused to pass through the oil-water separation filter 710, oil brought into contact with the surface of the oil-water separation filter 710 forms an oil droplet having a large contact angle, by the oil-repellent properties. The oil droplet is flipped. The fine water droplet exhibits wettability having a small contact angle by hydrophilicity. Thus, the fine water droplets wet the fiber surface and are permeated to the fiber surface. The water droplets move down under the fiber assembly 711 by an increase of the amount of adhering water droplets and by the capillary phenomenon. Moisture obtained by exceeding the water-retained amount is detached from the fiber assembly 11.

The oil-water separation filter 710 having the hydrophilic and oil-repellent properties, and thus it is possible to reduce time to perform oil-water separation, and to perform oil-water separation for a short period with high efficiency.

If the oil-water separation filter 710 formed from the fiber assembly is configured from a compressible material, for example, an oil-water mixed liquid in the housing is pressed by air pressure and the like, so as to compress the fiber assembly. Thus, it is possible to efficiently discharge moisture occluded in the fiber assembly, and to further reduce time to perform oil-water separation. As a compressible material as described above, a long fiber filtration medium may be appropriately used.

In the oil-water separation filter 710, in a case of containing only the fluorine compounds represented by the formulas (1) to (4), it is possible to apply excellent hydrophilic and oil-repellent properties while a perfluoroalkyl group having 8 or more carbon atoms which are continuously bonded to each other is not contained, and a chemical structure which does not have a concern of generating PFOS or PFOA, which becomes a problem from the viewpoint of bioaccumulation or environmental adaptability, is provided.

Figure 27:
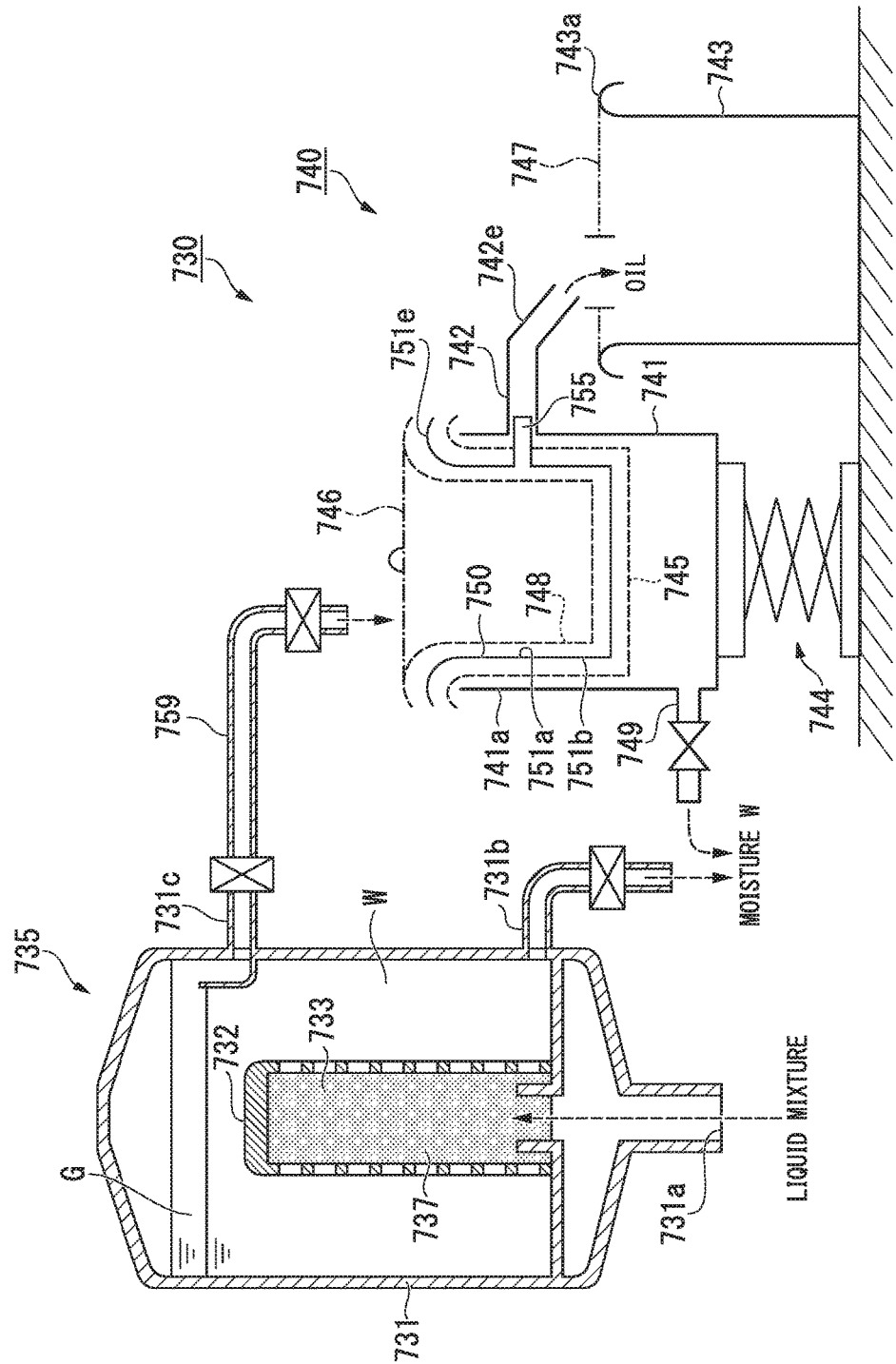
FIG. 27 is a sectional view illustrating a modification example of the 19th embodiment of the oil-water separation apparatus according to the present invention.

FIG. 27 is a sectional view illustrating an oil-water separation apparatus according to a modification example of a 19th embodiment.

An oil-water separation apparatus 730 in this embodiment includes a coarsening unit 735 and an oil-water separation filter (oil-water separation filter medium) 750. The coarsening unit 735 is disposed in the housing 731 and includes a coarsening filter 733 accommodated in the filter case 732. The oil-water separation apparatus 730 further includes an oil-water separation unit 740 and a transportation unit 759. The oil-water separation unit 740 is disposed on the subsequent stage side (downstream side) of the coarsening unit 735. The transportation unit 759 transports a liquid to a space between the coarsening unit 735 and the oil-water separation unit 740.

The coarsening filter 733 has, for example, an exterior shape formed to be columnar, and a liquid mixture passes through the coarsening filter 733. In this embodiment, as the liquid mixture, a liquid in which moisture is the main component, and oil as fine oil droplets is suspended in this moisture is used.

The housing 731 constituting the coarsening unit 735 has, for example, an exterior shape which forms a hollow columnar shape, and thus can hold the filter case 732 in which the coarsening filter 733 is accommodated. An inflow port 731a for a liquid mixture is formed on one opening end side of the housing 731. Further, a water drain port 731b is formed in the bottom of the side surface of the housing 731, and an oil drain port 731c is formed at the upper portion of the side surface.

The inflow port 731a of the housing 731 causes a liquid mixture formed from water in which fine oil droplets are mixed to flow in from the column bottom of the coarsening filter 733. The water drain port 731b discharges moisture separated by the coarsening filter 733 from the lower portion of the housing 731 to the outside of the housing 731 by using the specific gravity difference from oil and by underflow. The oil drain port 731c discharges oil from the upper portion of the housing 731 to the outside of the housing 731 by overflow, while causing oil to float on the higher layer of the moisture by the coarsening filter 733.

The filter case 732 is a columnar case that accommodates the coarsening filter 733. Multiple through-holes are formed in the circumferential surface of the filter case 732. Such a filter case 732 prevents deformation or spilling-out of the coarsening filter 733. As the filter case 732, a net-like cylinder and the like may be used.

The coarsening filter 733 is formed from a coarsening member 737 in which coarsening properties are imparted to a base formed from a porous material. As such a member, generally, a fiber assembly having lipophilicity is used. The coarsening member 737 is brought into contact with a liquid mixture in which water and oil are suspended, and aggregates fine oil droplets. Thus, the size of the oil droplet becomes large. Specifically, coarsening means that minute liquid droplets having a diameter (liquid droplet diameter) of, for example, about 0.1 to 50 μm form a coarse liquid droplet of, for example, 0.1 mm.

The oil-water separation unit 740 holds the oil-water separation filter (oil-water separation filter medium) 750 formed to have, for example, a bottomed columnar shape, in the oil-water separation unit 740. The oil-water separation unit 740 includes a liquid reservoir 741 at a lower portion. In the liquid reservoir 741, a liquid-discharging port 749 is formed. In the liquid reservoir 741, an upper portion forms an open surface, and an oil discharge channel 742 which is extended to the outside of the liquid reservoir 741 is formed in the vicinity of the open surface, so as to be integrated with the liquid reservoir 741. The oil discharge channel 742 guides oil separated by the oil-water separation filter 750 to the outside of the liquid reservoir 741. The oil discharge channel 742 may be formed, for example, in a manner such that a portion of an upper edge of the liquid reservoir 741 is cut out and developed outwardly.

An oil drain port 755 is formed in the vicinity of the open end 751e of the oil-water separation filter (oil-water separation filter medium) 750, that is, at a portion being in contact with the oil discharge channel 742. The oil drain port 755 causes the separated oil to flow toward the oil discharge channel 742. Such an oil drain port 755 is formed from, for example, an opening which is formed on a circumferential surface of the oil-water separation filter 750 and a cylindrical member which is connected to the opening. The cylindrical member may be bonded to the circumferential surface of the oil-water separation filter 750, for example, by sewing the member and the circumferential surface together or by heat welding.

A dispersion plate 748 as with, for example, a mesh member is further provided on the inner surface 751a of the oil-water separation filter 750. The dispersion plate 748 has, for example, a columnar shape having a bottom. An upper edge of the dispersion plate 748 is bent outwardly, and thus the upper edge of the dispersion plate 748 is separated over the oil-water separation filter 750, and the dispersion plate 748 is hooked and engaged on an edge on an open surface 741a side of the liquid reservoir 741. Regarding such a dispersion plate 748, when a liquid mixture containing water and oil is input to the liquid reservoir 741, the dispersion plate 748 receives the liquid mixture temporarily. Thus, the liquid mixture has a passing rate which is significantly lowered when the liquid mixture passes through the dispersion plate 748, and it is possible to largely relieve collision of the liquid mixture added to the oil-water separation filter 750. It is possible to suppress trapping of air. In addition, even though solid matter such as a trash, which has a relatively large size, is put and mixed in a liquid mixture flowing into the oil-water separation unit 740, it is possible to remove this solid matter in advance, and thus to prevent blockage of the oil-water separation filter 750 occurring by the trash.

A support member 745 is disposed on the outer surface 751b side of the oil-water separation filter 750 so as to be overlapped. The support member 745 has, for example, a columnar shape having a bottom. An upper edge of the support member 745 is bent outwardly, and thus the upper edge of the support member 745 overlaps the oil-water separation filter 750, and the support member 745 is hooked and engaged on an edge on an open surface 741a side of the liquid reservoir 741. The support member 745 is configured from a hard member through which at least moisture is allowed to pass, for example, from a metal material (a punching plate) in which multiple openings are formed. Such a support member 745 supports the flexible oil-water separation filter 750 from the outer surface 751b side.

Such a support member 745 is formed to overlap the outer surface 751b side of the oil-water separation filter 750. Thus, for example, even though a large amount of liquid flows into the oil-water separation filter 750 at one time, it is possible to prevent modification of the oil-water separation filter 750 or breaking of the bottom occurring by the weight of a liquid, and to efficiently perform oil-water separation filtration of a liquid. Such a support member 745 may use a ceramics material which has a relatively large pore, a hard plastic material in which an opening is formed, and the like.

An oil tank 743 is disposed at an outflow end 742e of the oil discharge channel 742. The oil tank 743 is used for receiving oil which flows out through the oil discharge channel 742. Further, the oil-water separation unit 740 includes liquid reservoir-moving means 744 for moving the liquid reservoir 741 up and down. It is preferable that a lid member 746 for covering an open surface 741a of the liquid reservoir 741 or a lid member 747 for covering an open surface 743a of the oil tank 743 be further provided.

The oil-water separation apparatus 730 in this embodiment causes the coarsening unit 735 on the previous stage side to coarsen an oil droplet of a liquid mixture in which fine oil droplets are mixed, causes the coarsened oil droplet to float on a water layer, and then discharges the oil droplet. In addition, in the oil-water separation unit 740 on the subsequent stage side, oil-water separation into moisture and oil which are mixed in the discharged oil is completely performed.

Firstly, in the coarsening unit 735, if a solution mixture in which moisture is the main component and fine oil droplets are mixed is press-fed to the coarsening filter 733 from the inflow port 731a of the housing 731, oil in the solution mixture brought into contact with the coarsening filter 733 is aggregated by coarsening properties of the coarsening filter 733, and forms an oil droplet having a large contact angle. The oil droplet is separated from the moisture. In this manner, oil which is coarsened and separated from moisture floats on the upper portion of the housing 731 by the specific gravity difference from the moisture.

The oil separated from the moisture by the coarsening filter 733 may be discharged from the upper portion of the housing 731 to the outside of the housing 731 by overflow. The moisture accumulated at the lower portion of the housing 731 by the specific gravity difference from the oil may be discharged from the water drain port 731b to the outside of the housing 731.

The oil after moisture is separated by the coarsening filter 733 is discharged from the oil drain port 731c by overflow. Thus, some moisture is mixed. A liquid mixture formed from oil which contains moisture in this manner is transported to the oil-water separation unit 740 through the transportation unit 759 formed from a tube and the like.

In the liquid mixture flowing into the oil-water separation unit 740, only moisture which remains in the oil passes through the oil-water separation filter 750 by the hydrophilic and oil-repellent properties of the oil-water separation filter 750, and the moisture is stored in the lower portion of the liquid reservoir 741. Oil in which moisture is completely removed is collected through the oil discharge channel 742 by the oil tank 743. Moisture removed from the oil may be easily discharged from the water drain port 749 to the outside of the liquid reservoir 741. It is possible to set the height of the liquid reservoir 741 to be at an optimum position in accordance with the height of the oil tank 743, by using the liquid reservoir-moving means 744.

In this embodiment, the coarsening filter 733 that coarsens minute oil droplets in a liquid mixture containing water and oil, and separates water and oil by the specific gravity difference, and the oil-water separation filter 750 that removes moisture contained in oil floating on a water surface are independently provided. Thus, it is possible to improve oil-water separation capability for a liquid mixture, and to separate the liquid mixture into oil and moisture with high efficiency.

Figure 28:
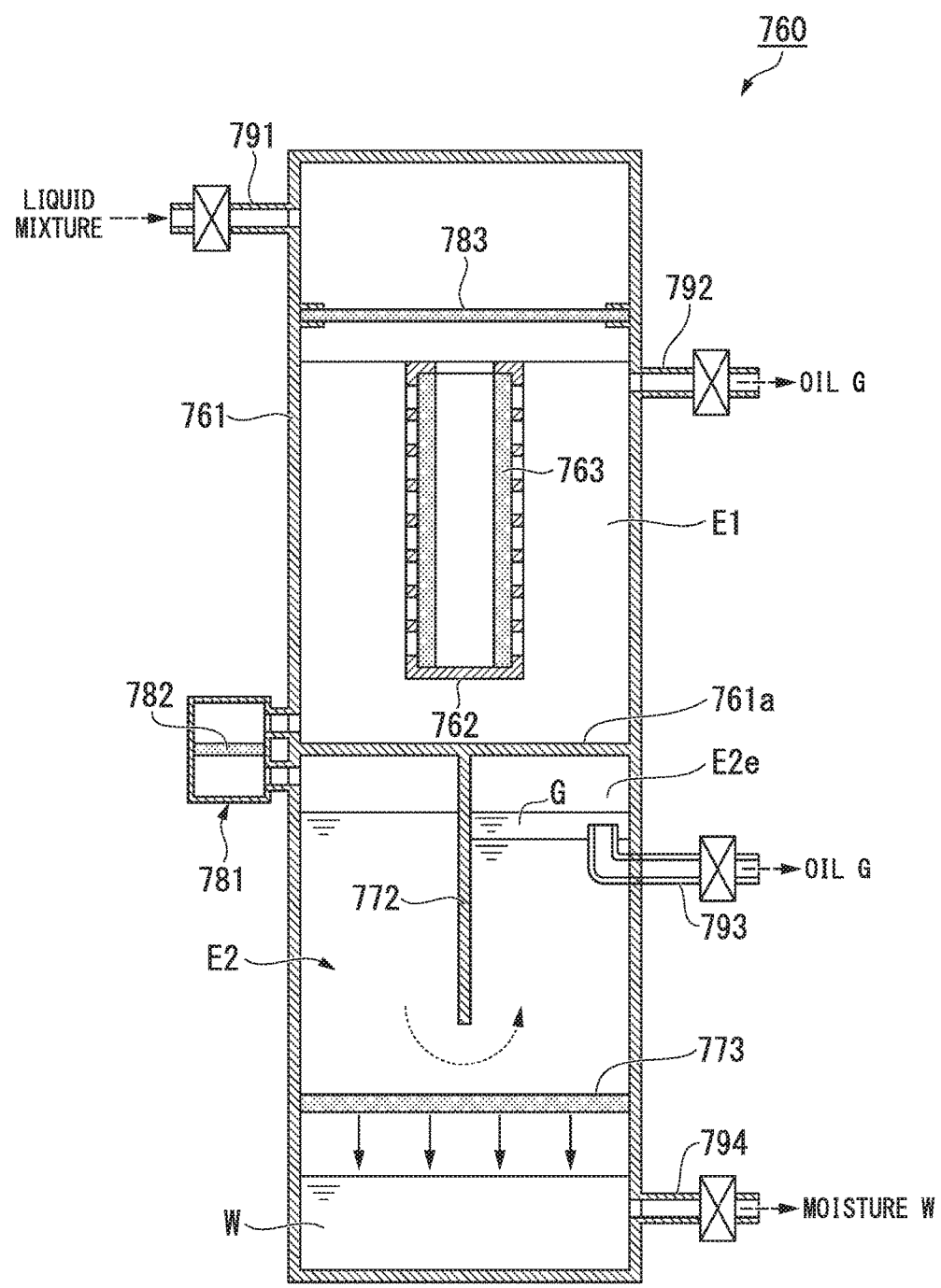
FIG. 28 is a sectional view illustrating another modification example of the 19th embodiment of the oil-water separation apparatus according to the present invention.

FIG. 28 is a sectional view illustrating an oil-water separation apparatus according to another modification example of the 19th embodiment.

An oil-water separation apparatus 760 in this embodiment includes a coarsening filter 763, an oil-water separation filter (oil-water separation filter medium) 773, and a solid-matter removal filter unit 781. The coarsening filter 763 is disposed in an upper portion region E1 of a housing 761 and is accommodated in a filter case 762. The upper portion region E1 is subdivided at the center by a partition plate 761a. The oil-water separation filter (oil-water separation filter medium) 773 is disposed in a lower portion region E2 of the housing 761. The solid-matter removal filter unit 781 links the upper portion region E1 and the lower portion region E2 of the housing 761 to each other. Such a solid-matter removal filter unit 781 has a function as a transportation unit for connecting the coarsening filter 763 and the oil-water separation filter 773.

Further, a pre-filter 783 is formed on the preceding stage side of the coarsening filter 763 in the upper portion region E1. An inflow port 791 for a liquid mixture of water and oil is formed at the upper portion of the upper portion region E1 of the housing 761. Oil drain ports 792 and 793 are formed in the upper portion region E1 and the lower portion region E2 of the housing 761, respectively. Further, a water drain port 794 is formed at the lower portion of the lower portion region E2.

In the oil-water separation apparatus 760 having such a configuration, for example, if a liquid mixture of water and oil flows from the inflow port 791, firstly, the pre-filter 783 removes solid matter and the like which are relatively large.

Water droplets or oil droplets in the liquid mixture are coarsened by the coarsening filter 763 disposed in the upper portion region E1 of the housing 761, and separation into oil and moisture is performed. Oil may float on the upper portion of the separated moisture, and may be discharged from the oil drain port 792 to the outside of the housing 761. Only in the coarsening filter 763 is completely separating oil and moisture difficult. Thus, some oil droplets remain in the separated moisture.

Most of oil is removed by the coarsening filter 763, and a liquid mixture in which some oil remains in moisture flows into the solid-matter removal filter unit 781 from the upper portion region E1. Here, fine solid matter and the like contained in the liquid mixture are removed by the solid-matter removal filter 782 formed in the solid-matter removal filter unit 781. As such a solid-matter removal filter 782, various solid matter filtration filter such as a nonwoven fabric filter or a ceramics filter may be used.

The liquid mixture passing through the solid-matter removal filter unit 781 flows into the lower portion region E2 of the housing 761. Moisture and oil are completely separated from the liquid mixture by the hydrophilic and oil-repellent properties of the oil-water separation filter (oil-water separation filter medium) 773 disposed in the lower portion region E2 of the housing 761. That is, the moisture passes through the oil-water separation filter 773 and is accumulated in the bottom of the housing 761.

Oil is flipped by oil-repellent properties of the oil-water separation filter 773, flows toward a section E2e on a downstream side of the lower portion region E2 subdivided by a partition 772, and then floats on a liquid surface in the section E2e by the specific gravity difference. Oil which is separated in this manner can be discharged from the oil drain port 793 to the outside of the housing 761. Moisture in which oil is completely removed may be discharged from the water drain port 794 at the lower portion of the housing 761.

In this embodiment, the coarsening filter 763 which coarsens minute water droplets in a liquid mixture containing water and oil and separates water and oil by the specific gravity difference is disposed on the preceding stage side. In addition, the oil-water separation filter 773 which removes oil remaining in the moisture is disposed on the subsequent stage side. Thus, it is possible to improve oil-water separation capability for a liquid mixture and to separate the liquid mixture into oil and moisture with high efficiency.

The coarsening filter 763 is disposed on the preceding stage side, or filters 782 and 783 for solid matter filtration are formed between the coarsening filter 763 and the oil-water separation filter 773. Thus, it is possible to perform oil-water separation and to remove solid matter contained in the liquid mixture.

<20th Embodiment>

Figure 22:
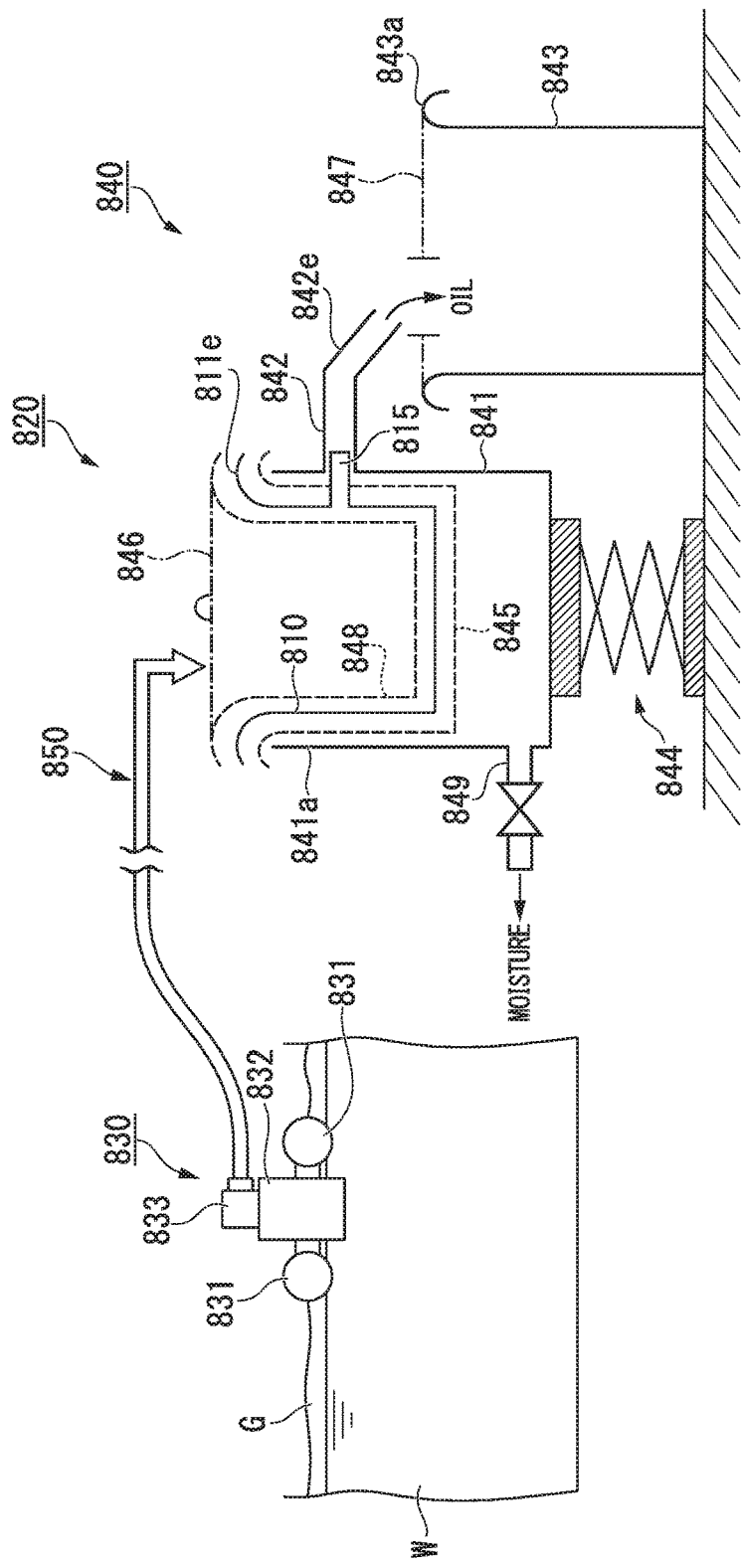
FIG. 22 is a schematic configuration diagram illustrating a 20th embodiment of the oil-water separation apparatus according to the present invention.

FIG. 22 is a schematic configuration diagram illustrating an oil-water separation apparatus according to a 20th embodiment.

An oil-water separation apparatus 820 in this embodiment includes an intake unit 830, an oil-water separation unit 840, and a joint unit 850. The intake unit 830 takes in a liquid mixture containing water and oil. The oil-water separation unit 840 separates the in-taken liquid mixture into moisture and oil. The joint unit 850 connects the intake unit 830 and the oil-water separation unit 840.

In this embodiment, the intake unit 830 is configured from a float type oil-water collection device. For example, such a float type oil-water collection device (intake unit) causes oil to float on the surface of the sea or a river in which the oil flows out and collects oil G which floats in the vicinity of a liquid surface, along with water W. The intake unit 830 is formed from a float 831, an absorbing mechanism 832, a connection portion 833, and the like. The absorbing mechanism 832 is formed from, for example, a suction port of a liquid, a submersible pump, or the like. Such an absorbing mechanism 832 may float in the vicinity of a water surface by the float 831. The connection portion 833 causes the absorbed liquid mixture to be discharged toward the joint unit 850.

Such an intake unit 830 sucks up oil G which floats on a water surface, for example, on the surface of the sea, along with water (see water) W by the absorbing mechanism 832 which floats in the vicinity of the water surface by the float 831. Then, the intake unit 830 sends the liquid mixture to the joint unit 850 from the connection portion 833.

The connection portion 833 is formed from a transfusion tube, for example. The connection portion 833 sends the liquid mixture taken by the intake unit 830 to the oil-water separation unit 840. For example, in a case where the intake unit 380 and the oil-water separation unit 840 are separated from each other, it is also preferable that an auxiliary pump and the like for increasing liquid pressure, if necessary, be further formed in the connection portion 833.

The oil-water separation unit 840 includes a liquid reservoir 841. In the liquid reservoir 841, an oil-water separation filtration filter (oil-water separation filter medium) 810 formed to have, for example, a bottomed columnar shape is held, and a liquid-discharging port 849 is formed at the lower portion. In the liquid reservoir 841, an upper portion forms an open surface, and an oil discharge channel 842 which is extended to the outside of the liquid reservoir 841 is formed in the vicinity of the open surface so as to be integrated with the liquid reservoir 841. The oil discharge channel 842 guides oil separated by the oil-water separation filtration filter 810 to the outside of the liquid reservoir 841. The oil discharge channel 842 may be formed, for example, in a manner such that a portion of an upper edge of the liquid reservoir 841 is cut out and developed outwardly.

An oil drain port 815 is formed in the vicinity of the open end 811a of the oil-water separation filtration filter (oil-water separation filter medium) 810, that is, at a portion being in contact with the oil discharge channel 842. The oil drain port 815 causes the separated oil to flow toward the oil discharge channel 842. Such an oil drain port 815 is formed from, for example, an opening which is formed on a circumferential surface of the oil-water separation filtration filter 810, and a cylindrical member which is connected to the opening. The cylindrical member may be bonded to the circumferential surface of the oil-water separation filtration filter 810, for example, by sewing the member and the circumferential surface together or by heat welding.

A dispersion plate 848 as with, for example, a mesh member is further provided on the inner surface side of the oil-water separation filtration filter 810. The dispersion plate 848 has, for example, a columnar shape having a bottom. An upper edge of the dispersion plate 848 is bent outwardly, and thus the upper edge of the dispersion plate 848 is separated over the oil-water separation filtration filter 810, and the dispersion plate 848 is hooked and engaged on an edge on an open surface 841a side of the liquid reservoir 841. Regarding such a dispersion plate 848, when a liquid mixture containing water and oil is input to the liquid reservoir 841, the dispersion plate 848 receives the liquid mixture temporarily. Thus, the liquid mixture has a passing rate which is significantly lowered when the liquid mixture passes through the dispersion plate 848, and it is possible to largely relieve collision of the liquid mixture added to the oil-water separation filtration filter 810. It is possible to suppress trapping of air. In addition, even though solid matter such as a trash, which has a relatively large size, is put and mixed in a liquid mixture flowing into the oil-water separation unit 840, it is possible to remove this solid matter in advance, and thus to prevent blockage of the oil-water separation filtration filter 810 occurring by the trash.

A support member 845 is disposed on the outer surface side of the oil-water separation filtration filter 810 so as to be overlapped.

The support member 845 has, for example, a columnar shape having a bottom. An upper edge of the support member 845 is bent outwardly, and thus the upper edge of the support member 845 overlaps the oil-water separation filtration filter 810, and the support member 845 is hooked and engaged on an edge on an open surface 841a side of the liquid reservoir 841. The support member 845 is configured from a hard member through which at least moisture is allowed to pass, for example, from a metal material (a punching plate) in which multiple openings are formed. Such a support member 845 supports the flexible oil-water separation filtration filter 810 from the outer surface (for example, outer surface 11b illustrated in FIG. 1(b)) side.

Such a support member 845 is formed to overlap the outer surface side of the oil-water separation filtration filter 810. Thus, for example, even though a large amount of liquid flows into the oil-water separation filtration filter 810 at one time, it is possible to prevent modification of the oil-water separation filtration filter 810 or breaking of the bottom occurring by the weight of a liquid, and to efficiently perform oil-water separation filtration of a liquid. Such a support member 845 may use a ceramics material which has a relatively large pore, a hard plastic material in which an opening is formed, and the like.

An oil tank 843 is disposed at an outflow end 842e of the oil discharge channel 842. The oil tank 843 is used for receiving oil which flows out through the oil discharge channel 842. Further, the oil-water separation unit 840 includes liquid reservoir-moving means 844 for moving the liquid reservoir 841 up and down. It is preferable that a lid member 846 for covering an open surface 841a of the liquid reservoir 841 or a lid member 847 for covering an open surface 843a of the oil tank 843 be further provided.

As illustrated in FIG. 1(b), the oil-water separation filtration filter 810 includes a base 11 and an oil-water-separating member 14 formed in the base 11. As the base 11, a baglike object having an upper portion which forms an open end, for example, in this embodiment, an object formed to be a bottomed columnar shape is appropriately used. In this embodiment, such a base 11 is configured from a flexible porous fiber. The porous fiber is a fiber assembly, and has a gap between fibers or between pieces of twist yarn. Woven fabric, knitted fabric, nonwoven fabric, or the like is appropriate.

As illustrated in FIG. 1(b), a channel 17 for a liquid is formed in the base 11. Such a channel 17 is formed from pores (fine hole, hollow, and communication hole) of a porous fiber constituting the base 11.

The channel 17 causes the inner surface 11a and the outer surface 11b of the baglike base 11 to communicate with each other, and passes moisture through the channel 17.

An oil-water-separating member 14 is formed on the surface (surface layer) of at least the inner surface 11a of the base 11. In this embodiment, the oil-water-separating member 14 is formed in the entirety of the inner surface 11a and the outer surface 11b of the base 11, which includes the surface of the inner wall of the channel 17.

The oil-water-separating member 14 may be formed such that the oil-water-separating member 14 forms a film on the surface of the base 11. Further, the oil-water-separating member 14 may be impregnated to the inner side in a depth direction of the base 11.

The oil-water-separating member 14 is configured of a material containing a fluorine compound which has an oil-repellency-imparting group and a hydrophilicity-imparting group. The oil-repellency-imparting group is a functional group for forming an oil droplet at a contact angle of, for example, 40° or more to the surface of the oil-water-separating member 14. The hydrophilicity-imparting group is a functional group for imparting wettability to moisture at a contact angle of, for example, 20° or less to the surface of the oil-water-separating member 14.

The oil-water-separating member 14 imparts the hydrophilic and oil-repellent properties to the base 11 by the existence of such an oil-repellency-imparting group and a hydrophilicity-imparting group. If a liquid mixture (may be simply referred to as a liquid below) containing water and oil is brought into contact with the base 11 in which the oil-water-separating member 14 is formed, the oil is aggregated as an oil droplet having a large contact angle, and moisture holds wettability in which the contact angle is small. Accordingly, oil which is aggregated and forms a large oil droplet passing through the channel 17 is not allowed. The moisture which holds the wettability can pass through the channel 17 in a state of being in contact with the oil-water-separating member 14. With such an action, the oil-water-separating member 14 can selectively separate and pass only oil from a liquid, and can increase a water-permeating rate.

According to the oil-water separation apparatus 820 having a configuration as described above, for example, it is possible to easily collect oil spilled to a water surface and to reliably separate a liquid mixture in which water and oil are mixed during collection into oil and moisture. For example, if the intake unit 830 including the float 831 is caused to float on the surface of the sea or a river in which the oil flows out, and the absorbing mechanism 832 is operated, it is possible to suck oil floating in the vicinity of a water surface, along with water. At this time, the vicinity of a water surface is sucked, and thus it is possible to selectively suck oil, and to reduce the amount of sucked water.

A liquid mixture taken by the intake unit 830 flows into the liquid reservoir 841 constituting the oil-water separation unit 840 through the joint unit 850 such as a transfusion tube. The liquid mixture flowing into the liquid reservoir 841 is brought into contact with the oil-water separation filtration filter 810, and is separated into oil and moisture by the hydrophilic and oil-repellent properties of the oil-water-separating member 14.

The separated oil floats in the vicinity of the liquid level of the oil-water separation filtration filter 810 by the specific gravity difference. The oil flows out from an oil drain port 815 formed in the vicinity of an upper edge of the oil-water separation filtration filter 810 through the oil discharge channel 842. The outflowing oil is stored in the oil tank 843.

Moisture obtained by removing and filtering oil in the oil-water separation filtration filter 810 so as to perform filtration is stored at the lower portion of the liquid reservoir 841. Moisture obtained in this manner does not contain oil, and can be easily discharged from the liquid-discharging port 849 to the outside of the liquid reservoir 841. It is possible to set the height of the liquid reservoir 841 to be at an optimum position in accordance with the height of the oil tank 843 by using the liquid reservoir-moving means 844.

As described above, according to the oil-water separation apparatus 820 in this embodiment, the intake unit 830 is installed in the surface of the sea or a river in which the oil flows out. Thus, the spilled oil is easily collected, and moisture contained in the collected oil is reliably separated. Accordingly, the oil is easily reused. Since oil is not contained in the separated water, the water can be discharged without performing oil removal treatment and the like in other processes.

The oil remaining on the surface of the inner side of the oil-water separation filtration filter 810 is removed, and thus it is possible to repeatedly use the oil-water separation filtration filter 810. A method in which replacement with a new oil-water separation filtration filter 810 is performed without removing the separated oil whenever the oil-water separation filtration filter 810 is used once or several times, and the oil-water separation filtration filter 810 used for collecting oil is discarded may be performed.

In the oil-water separation filtration filter 810, the hydrophilic and oil-repellent properties are applied to the base 11. Thus, adhering of an organic molecule, or soil and mud is difficult, and accordingly, excellent anti-fouling properties are obtained. Attached dirt is easily removed by physical treatment of, for example, turning over and washing, and ease of washability is also excellent.

In the oil-water separation filtration filter 810, in a case of containing only the fluorine compounds represented by the formulas (1) to (4), it is possible to apply excellent hydrophilic and oil-repellent properties while a perfluoroalkyl group having 8 or more carbon atoms which are continuously bonded to each other is not contained, and a chemical structure which does not have a concern of generating PFOS or PFOA, which becomes a problem from the viewpoint of bioaccumulation or environmental adaptability, is provided.

As the oil-water separation apparatus having another configuration, for example, an oil-water separation apparatus for a form of being installed in a drainage reservoir of a factory is exemplified. Such an oil-water collection and separation device includes an intake unit that takes in a liquid mixture containing water and oil, an oil-water separation unit that separates the in-taken liquid mixture into moisture and oil, and a joint unit that connects the intake unit and the oil-water separation unit.

The intake unit is configured from a stationary-installation type oil-water collection device. Such a stationary-installation type oil-water collection device (intake unit) is installed, for example, in a drainage reservoir of a factory, and collects oil mixed in discharged water. The intake unit is formed from an oil-attraction mechanism, a connection portion, and the like. The oil-attraction mechanism rotates, for example, a belt (intake medium) so as to be brought into contact with oil. Oil contained in water adhering to the belt is dropped off by a wiper, and thus the oil-attraction mechanism collects oil (liquid mixture) containing water. Such a mechanism is known as a belt-type oil collection device.

A well-known oil collection device such as a disk type oil collection device obtained by being replaced with a disk for rotating the intake medium, and a screw-type oil collection device obtained by replacing the intake medium with a spiral screw may be used as the intake unit.

Oil (liquid mixture) which contains water and is taken in by the intake unit formed from such a belt-type oil collection device and the like flows into the liquid reservoir constituting an oil-water separation unit through the joint unit. The liquid mixture flowing into the liquid reservoir is brought into contact with the oil-water separation filtration filter (oil-water separation filter medium), and is separated into oil and moisture by the hydrophilic and oil-repellent properties of the oil-water-separating member. The separated oil floats in the vicinity of the liquid level of the oil-water separation filtration filter by the specific gravity difference. The oil flows out from an oil drain port formed in the vicinity of an upper edge of the oil-water separation filtration filter, through the oil discharge channel. The outflowing oil is stored in the oil tank. Since moisture is removed in oil which is separated in this manner, the moisture can be caused to flow back to a lubricating oil tank and be reused.

Moisture obtained by removing and filtering oil in the oil-water separation filtration filter so as to perform filtration is stored at the lower portion of the liquid reservoir. Moisture obtained in this manner does not contain oil, and can be easily discharged from the liquid-discharging port to the outside of the liquid reservoir.

According to the oil-water separation apparatus having such a configuration, for example, it is possible to reliably remove moisture contained in oil such as lubricating oil only by stationarily installing a lubricating oil tank. In addition, it is possible to cause the separated oil to flow back to a lubricating oil tank 65 again, and to reuse the oil.

As the oil-water separation apparatus having another configuration, for example, an oil-water separation apparatus which is stationarily installed in a drainage reservoir of a factory and the like, and collects oil from the drainage reservoir in a case where oil is spilled out and flows into the drainage reservoir is exemplified. Such an oil-water collection and separation device include an intake unit that takes in a liquid mixture containing water and oil, an oil-water separation unit that separates the in-taken liquid mixture into moisture and oil, and a joint unit that connects the intake unit and the oil-water separation unit. An intermediate reservoir is formed in the joint unit.

The intake unit is configured from a stationary-installation type oil-water collection device. Such a stationary-installation type oil-water collection device (intake unit) is stationarily installed, for example, in a drainage reservoir of a factory and the like, and collects oil. When the oil is collected, water is also mixed. The intake unit is formed from an oil-attraction mechanism, a connection portion, and the like. The oil-attraction mechanism rotates, for example, a belt (intake medium) so as to be brought into contact with oil. Oil contained in water adhering to the belt is dropped off by a wiper, and thus the oil-attraction mechanism collects oil (liquid mixture) containing water. Such a mechanism is known as a belt-type oil collection device.

A well-known oil collection device such as a disk type oil collection device obtained by being replaced with a disk for rotating the intake medium, and a screw-type oil collection device obtained by replacing the intake medium with a spiral screw may be used as the intake unit.

A liquid mixture which contains water and oil and is taken in by the intake unit formed from such a belt-type oil collection device and the like is stored in the intermediate reservoir constituting the joint unit. In such an intermediate reservoir, a liquid mixture taken from the drainage reservoir is caused to be in a standstill state, and moisture at the lower portion is discharged, and thus the proportion of the oil in the liquid mixture is increased. The liquid mixture in which the proportion of the oil is increased in the intermediate reservoir flows into the liquid reservoir constituting the oil-water separation unit. The liquid mixture flowing into the liquid reservoir is brought into contact with the oil-water separation filtration filter, and is separated into oil and moisture by the hydrophilic and oil-repellent properties of the oil-water-separating member. The separated oil floats in the vicinity of the liquid level of the oil-water separation filtration filter by the specific gravity difference. The oil flows out from an oil drain port formed in the vicinity of an upper edge of the oil-water separation filtration filter through the oil discharge channel. The outflowing oil is stored in the oil tank.

Moisture obtained by removing and filtering oil in the oil-water separation filtration filter (oil-water separation filter medium) so as to perform filtration is stored at the lower portion of the liquid reservoir. Moisture obtained in this manner does not contain oil, and can be easily discharged from the liquid-discharging port to the outside of the liquid reservoir.

According to the oil-water separation apparatus having such a configuration, it is possible to easily collect oil flowing into the drainage reservoir, and to remove moisture. However, the proportion of the oil in the liquid mixture taken from the drainage reservoir is increased by the intermediate reservoir, and thus it is possible to reduce a load of the oil-water separation filtration filter (oil-water separation filter medium), to lengthen the span of life of the oil-water separation filtration filter, and to reduce running cost relating to oil-water separation.

The oil-water separation apparatus can be also used in oil-water collection and separation, for example, in a groundwater area in which oil is infiltrated. As an example, installation is performed by using a belt-type oil collection device as the intake unit so as to cause a circulation belt of the belt-type oil collection device to reach a groundwater area including oil. Groundwater (liquid mixture) containing oil which has been collected by the belt is separated into oil and moisture by the oil-water separation unit, and thus it is possible to collect oil infiltrated to a groundwater area.

<21st Embodiment>

Figure 23:
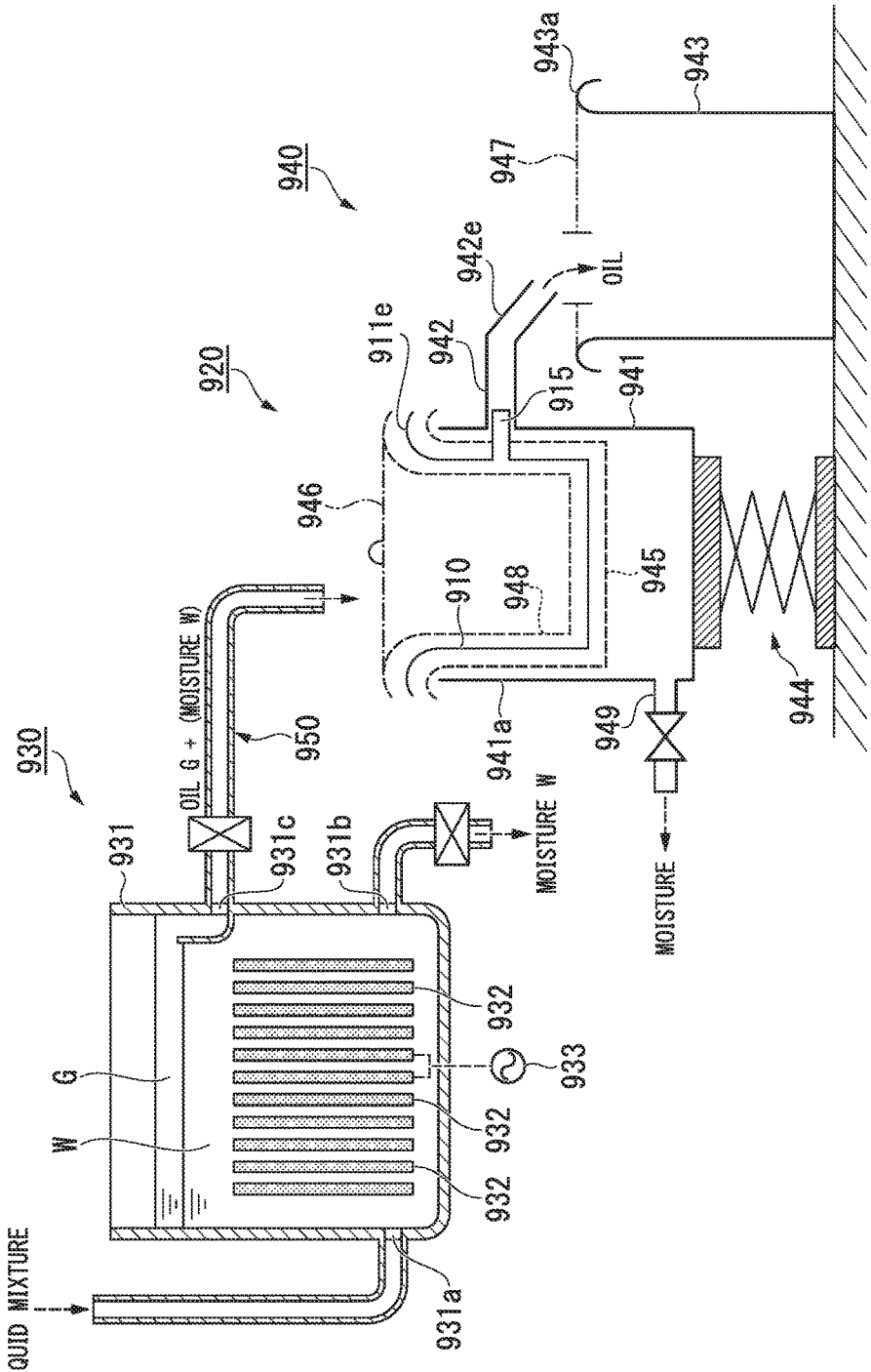
FIG. 23 is a sectional view illustrating a 21th embodiment of the oil-water separation apparatus according to the present invention.

FIG. 23 is a sectional view illustrating an oil-water separation apparatus according to a 21st embodiment.

An oil-water separation apparatus 920 in this embodiment includes a demulsification unit 930, an oil-water separation unit 940, and a transportation unit 950. The transportation unit 950 transports a liquid between the demulsification unit 930 and the oil-water separation unit 940.

The demulsification unit 930 coarsens fine oil droplets dispersed in an oil-water mixed liquid in which moisture and oil are suspended, and cause the oil to float on a higher layer of the moisture. The oil-water separation unit 940 separates a solution mixture containing oil which has coarsened by the demulsification unit 930 into oil and moisture by the oil-water separation filter (oil-water separation filter medium) 910 which forms the oil-water-separating member 14 (see FIG. 1(b)).

In this embodiment, the demulsification unit 930 is an electric-field application type demulsification device that coarsens fine oil droplets obtained by emulsifying an oil-water mixed liquid by using a high-frequency AC voltage. The demulsification unit 930 includes a liquid reservoir 931, an electrode 932, and a high-frequency power source device 933. The liquid reservoir 931 introduces an oil-water mixed liquid. The electrode 932 is disposed in the liquid reservoir 931. The high-frequency power source device 933 cause a high-frequency AC voltage to flow into the electrode 932.

The liquid reservoir 931 has, for example, an exterior shape which forms a rectangular shape, and can hold the electrode 932 provided therein. An inflow port 931a for a liquid mixture is formed in the vicinity of the bottom of the liquid reservoir 931. In addition, a water drain port 931b is formed in the bottom of the side surface of liquid reservoir 931, and an oil drain port 931c is formed at the upper portion of the side surface thereof. The oil drain port 931c causes oil to flow out to the outside of the liquid reservoir 931 by overflow.

For example, a pair of strip-shape electrode plates are disposed to face each other, and the electrode 932 is configured from a resultant obtained by arranging a plurality of electrode plate pairs. The electrode 932 is configured from metal having excellent conductivity, for example, a stainless steel plate, a nickel plate, a titanium plate, and the like. A carbon electrode and the like may be also appropriately used. The high-frequency power source device 933 generates a high-frequency AC voltage, and applies a voltage of, for example, about 1 V to 50 V/cm (per 1 cm as an interval between electrodes) to the electrode 932. In this embodiment, the electrode plate pair constituting the electrode 932 faces the inflow port 931a for a liquid mixture. However, the electrode plate pair may be disposed to be parallel to the inflow port 931a.

The oil-water separation unit 940 includes a liquid reservoir 941. In the liquid reservoir 941, the oil-water separation filter (oil-water separation filter medium) 910 formed to have, for example, a bottomed columnar shape is held, and a water drain port 949 is formed at a lower portion. In the liquid reservoir 941, an upper portion forms an open surface, and an oil discharge channel 942 which is extended to the outside of the liquid reservoir 941 is formed in the vicinity of the open surface so as to be integrated with the liquid reservoir 941. The oil discharge channel 942 guides oil separated by the oil-water separation filter 910 to the outside of the liquid reservoir 941. The oil discharge channel 942 may be formed, for example, in a manner such that a portion of an upper edge of the liquid reservoir 941 is cut out and developed outwardly.

An oil drain port 915 is formed in the vicinity of the open end 911e of the oil-water separation filter (oil-water separation filter medium) 910, that is, at a portion being in contact with the oil discharge channel 942. The oil drain port 915 causes the separated oil to flow toward the oil discharge channel 942. Such an oil drain port 915 is formed from, for example, an opening which is formed on a circumferential surface of the oil-water separation filter 910, and a cylindrical member which is connected to the opening. The cylindrical member may be bonded to the circumferential surface of the oil-water separation filter 910, for example, by sewing the member and the circumferential surface together or by heat welding.

A dispersion plate 948 as with, for example, a mesh member is further provided on the inner surface side of the oil-water separation filter 910. The dispersion plate 948 has, for example, a columnar shape having a bottom. An upper edge of the dispersion plate 948 is bent outwardly, and thus the upper edge of the dispersion plate 948 is separated over the oil-water separation filter 910, and the dispersion plate 948 is hooked and engaged on an edge on an open surface 941*a* side of the liquid reservoir 941. Regarding such a dispersion plate 948, when a liquid mixture containing water and oil is input to the liquid reservoir 941, the dispersion plate 948 receives the liquid mixture temporarily. Thus, the liquid mixture has a passing rate which is significantly lowered when the liquid mixture passes through the dispersion plate 948, and it is possible to largely relieve collision of the liquid mixture added to the oil-water separation filter 910. It is possible to suppress trapping of air. In addition, even though solid matter such as a trash, which has a relatively large size, is put and mixed in a liquid mixture flowing into the oil-water separation unit 940, it is possible to remove this solid matter in advance, and thus to prevent blockage of the oil-water separation filter 910 occurring by the trash.

A support member 945 is disposed on the outer surface side of the oil-water separation filter 910 so as to be overlapped. The support member 945 has, for example, a columnar shape having a bottom. An upper edge of the support member 945 is bent outwardly, and thus the upper edge of the support member 945 overlaps the oil-water separation filter 910, and the support member 945 is hooked and engaged on an edge on an open surface 941*a* side of the liquid reservoir 941. The support member 945 is configured from a hard member through which at least moisture is allowed to pass, for example, from a metal material (a punching plate) in which multiple openings are formed. Such a support member 945 supports the flexible oil-water separation filter 910 from the outer surface side thereof.

Such a support member 945 is formed to overlap the outer surface side of the oil-water separation filter 910. Thus, for example, even though a large amount of liquid flows into the oil-water separation filter 910 at one time, it is possible to prevent modification of the oil-water separation filter 910 or breaking of the bottom occurring by the weight of a liquid, and to efficiently perform oil-water separation filtration of a liquid. Such a support member 945 may use a ceramics material which has a relatively large pore, a hard plastic material in which an opening is formed, and the like.

An oil tank 943 is disposed at an outflow end 942*e* of the oil discharge channel 942. The oil tank 943 is used for receiving oil which flows out through the oil discharge channel 942. Further, the oil-water separation unit 940 includes liquid reservoir-moving means 944 for moving the liquid reservoir 941 up and down. It is preferable that a lid member 946 for covering an open surface 941*a* of the liquid reservoir 941 or a lid member 947 for covering an open surface 943*a* of the oil tank 943 be further provided.

The oil-water separation filtration filter (oil-water separation filter medium) 910 includes a base 11, and an oil-water-separating member 14 (see FIG. 1(*b*)) formed in the base 11.

As the base 11, a baglike object having an upper portion which forms an open end 911*e*, for example, in this embodiment, an object formed to be a bottomed columnar shape is appropriately used. In this embodiment, such a base 11 is configured from a flexible porous fiber. The porous fiber is a fiber assembly, and has a gap between fibers or between pieces of twist yarn. Woven fabric, knitted fabric, nonwoven fabric, or the like is appropriate.

A channel 17 (see FIG. 1(*b*)) for a liquid is formed in the base 11. Such a channel 17 is formed from pores (fine hole, hollow, and communication hole) of a porous fiber constituting the base 11. The channel 17 causes the inner surface 11*a* and the outer surface 11*b* of the baglike base 11 to communicate with each other, and passes moisture through the channel 17.

An oil-water-separating member 14 is formed on the surface (surface layer) of at least the inner surface 11*a* of the base 11. In this embodiment, the oil-water-separating member 14 is formed in the entirety of the inner surface 11*a* and the outer surface 11*b* of the base 11, which includes the surface of the inner wall of the channel 17.

The oil-water-separating member 14 may be formed such that the oil-water-separating member 14 forms a film on the surface of the base 11. Further, the oil-water-separating member 14 may be impregnated to the inner side in a depth direction of the base 11.

The oil-water-separating member 14 is configured of a material containing a fluorine compound which has an oil-repellency-imparting group and a hydrophilicity-imparting group. The oil-repellency-imparting group is a functional group for forming an oil droplet at a contact angle of, for example, 40° or more to the surface of the oil-water-separating member 14. The hydrophilicity-imparting group is a functional group for imparting wettability to moisture at a contact angle of, for example, 20° or less to the surface of the oil-water-separating member 14.

The oil-water-separating member 14 imparts the hydrophilic and oil-repellent properties to the base 11 by the existence of such an oil-repellency-imparting group and a hydrophilicity-imparting group. If a liquid mixture (may be simply referred to as a liquid below) containing water and oil is brought into contact with the base 11 in which the oil-water-separating member 14 is formed, the oil is aggregated as an oil droplet having a large contact angle, and moisture holds wettability in which the contact angle is small. Accordingly, oil which is aggregated and forms a large oil droplet passing through the channel 17 is not allowed. The moisture which holds the wettability can pass through the channel 17 in a state of being in contact with the oil-water-separating member 14. With such an action, the oil-water-separating member 14 can selectively separate and pass only oil from a liquid, and can increase a water-permeating rate.

In the oil-water separation apparatus 920 having a configuration as described above, the demulsification unit 930 on the preceding stage side coarsens oil droplets in an oil-water mixed liquid and causes the coarsened oil droplets to float up on a water layer and to be discharged. In the oil-water separation unit 940 on the subsequent stage side, oil-water separation into moisture and oil which is mixed in the discharged oil is completely performed.

Firstly, in the demulsification unit 930, an oil-water suspension liquid is introduced into the liquid reservoir 931 from the inflow port 931*a*. In the liquid reservoir 931, a high-frequency AC voltage is applied to the oil-water suspension liquid by the electrode 932. The oil-water suspension liquid receives an action of an electric field generated by the high-frequency AC voltage which has been applied to the electrode 932. The electric field causes an interfacial electrokinetic potential (zeta potential) of oil in the liquid to be neutralized, and aggregation and coarsening of fine oil droplets is accelerated. As a result, the separated oil droplets float in the liquid reservoir 931 by the specific gravity difference from moisture, and a surface layer (oil-rich layer) is generated at the surface layer portion of the liquid reservoir 931. The lower layer portion almost maintains a state of water.

The oil floating at the surface layer portion is discharged from the oil drain port 931*c* by overflow, and is transported to the oil-water separation unit 930 through the transportation unit 950. At this time, oil G discharged from the oil drain port 931*c* corresponds to a liquid mixture in which moisture W is mixed. This is because excluding moisture is not possible when a liquid in the vicinity of an interface between oil and moisture flows out.

In the liquid mixture flowing into the oil-water separation unit 940, only moisture which remains in the oil passes through the oil-water separation filter 910 by the hydrophilic and oil-repellent properties of the oil-water separation filter (oil-water separation filter medium) 910, and the moisture is stored in the lower portion of the liquid reservoir 941. Oil in which moisture is completely removed is collected through the oil discharge channel 942 by the oil tank 943. Moisture removed from the oil may be easily discharged from the water drain port 949 to the outside of the liquid reservoir 941. It is possible to set the height of the liquid reservoir 941 to be at an optimum position in accordance with the height of the oil tank 943 by using the liquid reservoir-moving means 944.

In this embodiment, regarding an oil-water mixed liquid in which water and oil are suspended, firstly, oil droplets are coarsened by the demulsification unit 930 on the preceding stage side, and are caused to float on the higher layer. A solution mixture in which oil is the main component and moisture is mixed is subjected to oil-water separation by the oil-water separation filter 910 of the oil-water separation unit 940 on the subsequent stage side. Thus, it is possible to improve oil-water separation capability for an oil-water mixed liquid, and to separate the oil-water suspension liquid into oil and moisture with high efficiency.

In the oil-water separation filter 910, the hydrophilic and oil-repellent properties are applied to the base 11 (see FIG. 1(*b*)). Thus, adhering of an organic molecule, or soil and mud which are contaminated by oil is difficult, and accordingly, excellent anti-fouling properties are obtained. Attached dirt is easily removed by physical treatment of, for example, turning over and washing, and ease of washability is also excellent.

In the oil-water separation filter 910, in a case of containing only the fluorine compounds represented by the formulas (1) to (4), it is possible to apply excellent hydrophilic and oil-repellent properties while a perfluoroalkyl group having 8 or more carbon atoms which are continuously bonded to each other is not contained, and a chemical structure which does not have a concern of generating PFOS or PFOA, which becomes a problem from the viewpoint of bioaccumulation or environmental adaptability, is provided.

As the oil-water separation apparatus having another configuration, for example, the following oil-water separation apparatus is exemplified. The oil-water separation apparatus includes a demulsification unit, an oil-water separation unit, and a transportation unit that transports a liquid between the demulsification unit and the oil-water separation unit. The oil-water separation apparatus includes an air-bubble jet type demulsification device as the demulsification unit. The demulsification device coarsens fine oil droplets (emulsion) obtained by emulsifying an oil-water mixed liquid.

The demulsification unit is an air-bubble jet type demulsification device that coarsens fine oil droplets (emulsion) obtained by emulsifying an oil-water mixed liquid, by fine air bubbles (microbubble). The demulsification unit includes a liquid reservoir that introduces an oil-water mixed liquid, an air-bubble generation device which is disposed in the vicinity of the bottom of the liquid reservoir, and a gas supply device that supplies a high-pressure gas to the air-bubble generation device.

The liquid reservoir has, for example, an exterior shape which forms a rectangular shape. An inflow tube for a liquid mixture, which is extended from an open surface at an upper portion thereof toward the bottom, is formed in the liquid reservoir. In addition, a water drain port is formed in the bottom of the side surface of liquid reservoir, and an oil drain port is formed at the upper portion of the side surface thereof. The oil drain port causes oil to flow out to the outside of the liquid reservoir by overflow.

The air-bubble generation device includes an air diffusion plate for making the input high-pressure gas to be microbubbles. In the air diffusion plate, multiple micropores are provided. For example, a gas is ejected from the micropores having a diameter of about 1 μm to 10 μm, and thus fine air bubbles (microbubbles) for an oil-water suspension liquid in the liquid reservoir are generated. The gas supply device is formed from, for example, a compressor, and supplies high-pressure air, nitrogen gas, and the like to the air-bubble generation device.

In the oil-water separation apparatus having a configuration as described above, the demulsification unit on the preceding stage side coarsens oil droplets in an oil-water mixed liquid and causes the coarsened oil droplets to float up on a water layer and to be discharged. In the oil-water separation unit on the subsequent stage side, oil-water separation into moisture and oil which is mixed in the discharged oil is completely performed.

Firstly, in the demulsification unit, an oil-water suspension liquid is introduced into the liquid reservoir from the inflow tube. In the liquid reservoir, fine air bubbles (microbubbles) for the oil-water suspension liquid are ejected from the air-bubble generation device. In the oil-water suspension liquid, emulsion is broken by the fine air bubbles. Then, the separated oil droplets are adhered to the fine air bubbles, and thus the oil droplets are rapidly lifted up to the liquid level. The fine oil droplets are broken, and thus aggregation and coarsening is accelerated. As a result, the separated oil droplets float in the liquid reservoir by the specific gravity difference from moisture, and a surface layer (oil-rich layer) is generated at the surface layer portion of the liquid reservoir. The lower layer portion almost maintains a state of water.

The oil floating at the surface layer portion is discharged from the oil drain port by overflow, and is transported to the oil-water separation unit through the transportation unit. At this time, oil discharged from the oil drain port corresponds to a liquid mixture in which moisture is mixed. This is because excluding moisture is not possible when a liquid in the vicinity of an interface between oil and moisture flows out.

In the liquid mixture flowing into the oil-water separation unit, only moisture which remains in the oil passes through the oil-water separation filter by the hydrophilic and oil-repellent properties of the oil-water separation filter (oil-water separation filter medium), and the moisture is stored in the lower portion of the liquid reservoir. Oil in which moisture is completely removed is collected through the oil discharge channel by the oil tank. Moisture removed from the oil may be easily discharged from the water drain port to the outside of the liquid reservoir.

In this embodiment, regarding an oil-water mixed liquid in which water and oil are suspended, oil droplets are coarsened by fine air bubbles, and are caused to float on the higher layer. A solution mixture in which oil is the main component and moisture is mixed is subjected to oil-water separation by the oil-water separation filter of the oil-water separation unit on the subsequent stage side. Thus, it is possible to improve oil-water separation capability for an oil-water mixed liquid, and to separate the oil-water suspension liquid into oil and moisture with high efficiency.

A filter for solid matter filtration is formed in the transportation unit, and thus it is possible to perform oil-water separation and to remove solid matter contained in the liquid mixture.

<22nd Embodiment>

Figure 24:
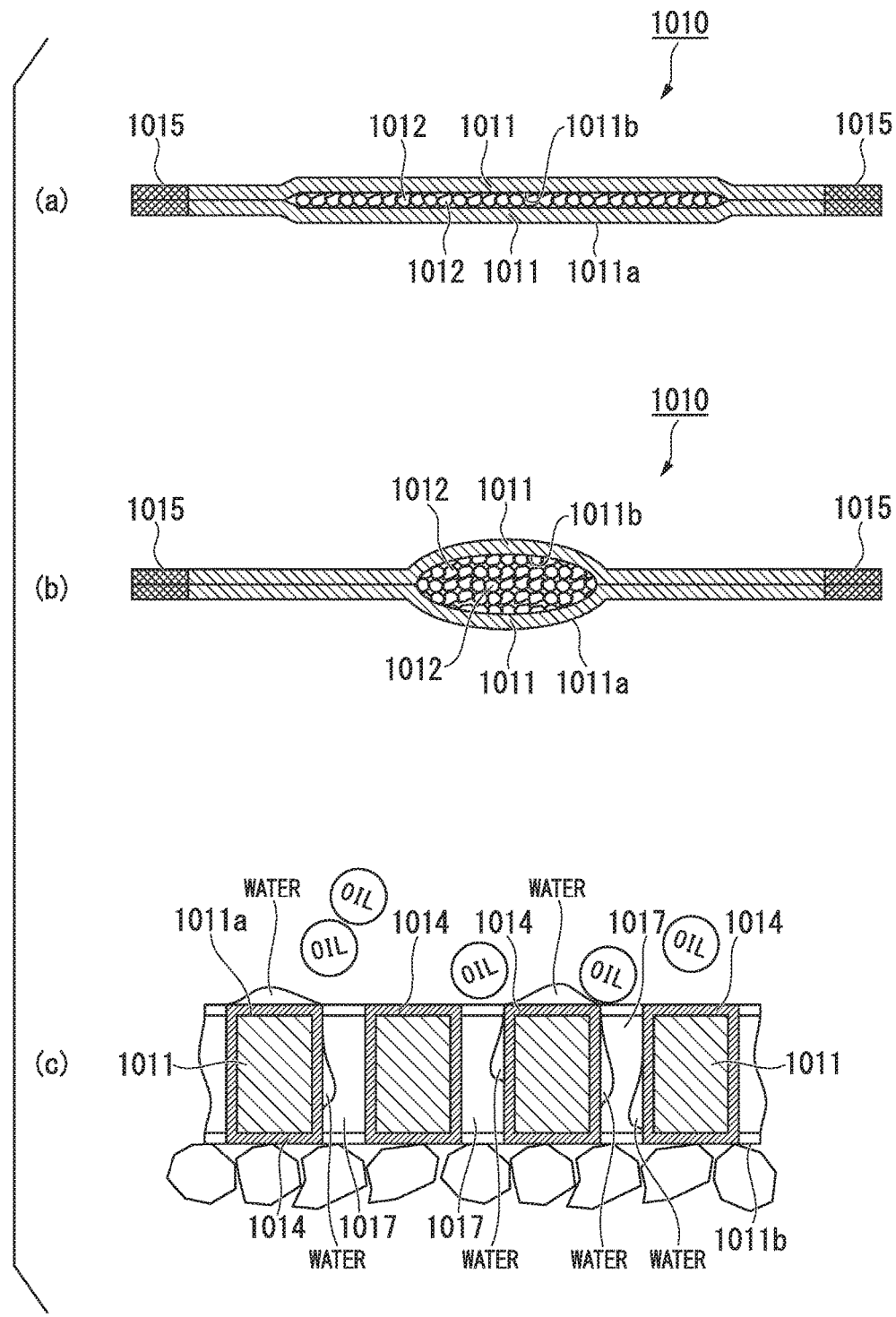
FIG. 24 is a sectional view illustrating a 22th embodiment of the oil-water separation apparatus according to the present invention.

FIG. 24(a) is a sectional view illustrating a configuration of a water-absorbent oil-repellent tool (oil-water separation apparatus) in this embodiment. FIG. 24(b) is a sectional view illustrating another configuration of the water-absorbent oil-repellent tool (oil-water separation apparatus) in this embodiment. FIG. 24(c) is a diagram of an enlarged main portion illustrating an exterior medium constituting a water-absorbent oil-repellent tool (oil-water separation apparatus).

A water-absorbent oil-repellent tool (oil-water separation apparatus) 1010 in this embodiment includes an exterior medium (base) 1011 formed to have a bag shape, and a water-absorbent material 1012 accommodated in the exterior medium 1011. An oil-water-separating member 1014 is formed on at least an outer surface 1011a of the exterior medium (base) 1011. The oil-water-separating member 1014 constitutes an oil-water separation filter medium along with the exterior medium (base) 1011.

The water-absorbent oil-repellent tool 1010 illustrated in FIG. 24(a) is an example in which a water-absorbent material 1012 is sealed in the exterior medium 1011 at normal pressure. The water-absorbent oil-repellent tool 1010 illustrated in FIG. 24(b) is an example in which water-absorbent material 1012 is decompressed to be sealed in the exterior medium 1011. In the following descriptions, the water-absorbent oil-repellent tool 1010 illustrated in FIG. 24(b) will be described as an example.

The exterior medium (base) 1011 is a baglike object obtained, for example, in a manner such that a rectangular sheet medium is bent and overlapped, and peripheral regions of three sides except for the bending side are bonded to each other. In addition, a baglike object obtained in a manner such that two rectangular sheet media having the same shape are overlapped with each other, and peripheral regions of four sides are bonded to each other may be provided.

A bonding portion 1015 formed in the peripheral regions of such an exterior medium 1011 forms a portion for bonding sheet media which constitute the exterior medium 1011 to each other by sewing using a thread, by adhering with an adhesive having oil resistance, or by heat welding. When the water-absorbent oil-repellent tool 1010 is manufactured, a bonding portion on only one side among such bonding portions 1015 remains without being bonded. After the inside of the exterior medium 1011 is filled with the water-absorbent material 1012, the bonding portion 1015 is formed. Thus, it is possible to obtain the water-absorbent oil-repellent tool 1010.

In the exterior medium 1011, an inner space on a side inner than the bonding portion 1015 formed at the peripheral edge is formed to be allowed to be expanded in order to correspond to volumetric expansion occurring by the water-absorbent material 1012 absorbing water.

The exterior medium 1011 is formed from a sheet-like fibrous base such as woven fabric, knitted fabric, or non-woven fabric or from a polymeric porous base. As a specific example, a natural fiber, organic polymer, a glass fiber, and the like are exemplified. In this embodiment, a nonwoven fabric sheet formed from a polypropylene porous medium is used as the exterior medium 1011. A more-detailed specific example of the exterior medium 1011 will be described later.

The water-absorbent material 1012 may be a material which can absorb moisture and hold a state of absorbing the moisture. As the water-absorbent material 1012, various water-absorbent materials as follows may be used: a chemical water-absorbent material such as a substance which chemically reacts with water, or a substance having deliquescence; and a physical water-absorbent material using properties in which a porous surface easily attracts water molecules. The shape of the water-absorbent material 1012 may be a particulate body, powder, a gel-like substance, and the like which have a particle diameter to an extent of not being left outwardly from the exterior medium 1011. In this embodiment, a particulate body of crosslinked sodium polyacrylate is used as the water-absorbent material 1012. A more-detailed specific example of the water-absorbent material 1012 will be described later.

As illustrated in FIG. 24(c), for example, a channel 1017 through which moisture is allowed to pass is formed in the exterior medium (base) 1011. Such a channel 1017 is formed from pores (fine hole, hollow, and communication hole) of a sheet-like fibrous base or a polymeric porous base constituting the exterior medium 1011. The channel 1017 causes the outer surface 1011a and the inner surface 1011b of the baglike exterior medium 1011 to communicate with each other, and passes moisture through the channel 1017. Moisture which reaches the inner surface 1011b side of the exterior medium 1011 is absorbed by the water-absorbent material 1012.

An oil-water-separating member 1014 is formed on the surface (surface layer) of at least the outer surface 1011a of the exterior medium 1011. In this embodiment, the oil-water-separating member 1014 is formed in the entirety of the outer surface 1011a and the inner surface 1011b of the exterior medium 1011, which includes the surface of the inner wall of the channel 1017.

In the oil-water-separating member 1014, particles of the oil-water-separating member 1014 may be dispersed (diffused) on the surface of the exterior medium 1011 so as to form a film shape. Further, the particles of the oil-water-separating member 1014 may be dispersed to an inner side in a thickness direction of the exterior medium 1011.

The oil-water-separating member 1014 is configured from a material containing a fluorine compound which has an oil-repellency-imparting group and a hydrophilicity-imparting group. The oil-repellency-imparting group is a functional group for forming an oil droplet on the surface of the oil-water-separating member 1014 at a contact angle of, for example, 40° or more. The hydrophilicity-imparting group is a functional group for imparting wettability to moisture at a contact angle of, for example, 20° or less to the surface of the oil-water-separating member 1014.

The oil-water-separating member 1014 imparts the hydrophilic and oil-repellent properties to the exterior medium 1011 by the existence of such an oil-repellency-imparting group and a hydrophilicity-imparting group. If oil containing moisture is brought into contact with the exterior medium 1011 in which the oil-water-separating member 1014 is formed, the oil forms an oil droplet having a large contact angle, and moisture holds wettability in which the contact angle is small. Thus, the moisture which holds the wettability can pass through the channel 1017 in a state of being in contact with the oil-water-separating member 1014. With such an action, the oil-water-separating member 1014 can selectively separate and pass only moisture in oil, and can increase a water-permeating rate.

(Water-absorbent Material)

The water-absorbent material 1012 constituting the water-absorbent oil-repellent tool 1010 in this embodiment may use water-absorptive polymer or an inorganic water-absorbent material.

As the water-absorptive polymer medium, for example, a polyacrylate salt, a crosslinking type of isobutylene-maleic anhydride, a polysulfonate salt, a maleic anhydride salt, polyacrylamide, polyvinyl alcohol, polyethylene oxide, and polysaccharides such as starch or cellulose may be used. In particular, from a viewpoint of water-absorptive properties, crosslinked sodium polyacrylate is preferable. As a preferable specific example of the water-absorptive polymer, AQUALIC CA (product name: manufactured by NIPPON SHOKUBAI CO., LTD.), AQUALIC CS" (product name: manufactured by NIPPON SHOKUBAI CO., LTD.) having salt resistance, and the like are exemplified.

As the inorganic water-absorbent material, silica gel, a molecular sieve, and the like are exemplified.

The shape of the absorbent material 1012 may have a particulate shape forming a spherical shape or a polygonal shape, or have a fibrous shape. The diameter may be about 50 to 1500 μm, and more preferably about 100 to 850 μm.

As the water-absorbent material 1012, a material in which the total specific gravity in a state of absorbing water is set to be 1.0 to 1.5, and preferably set to be 1.0 to 1.2 is preferably used. Thus, it is possible to prevent floating of the water-absorbent oil-repellent tool 1010 on an oil surface, for example, when the water-absorbent oil-repellent tool 1010 is disposed in oil having specific gravity of 1 or less. If the specific gravity of a water-absorbent material is more than 1.5, the load is excessive, and thus handling properties may be degraded.

<23rd Embodiment>

Figure 29A:
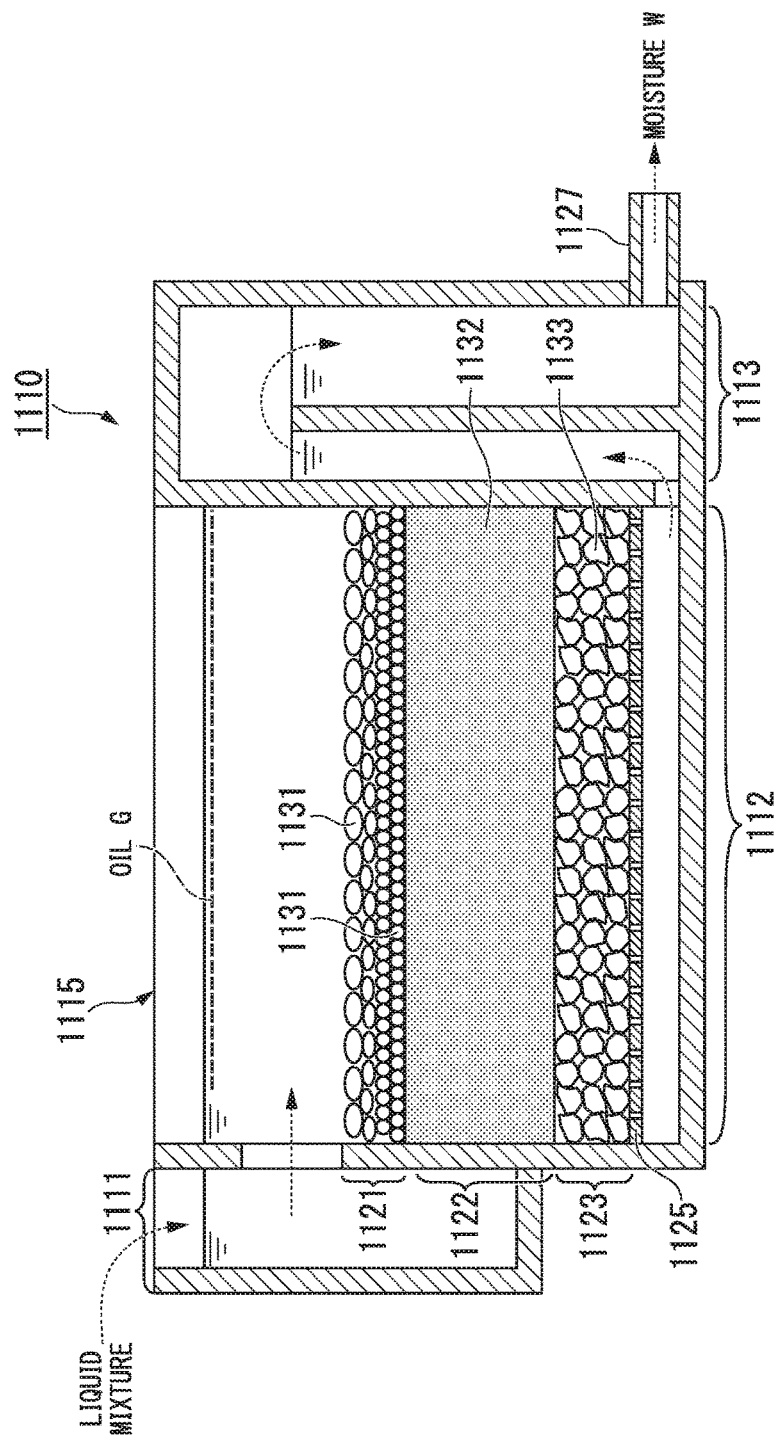
FIG. 29A is a sectional view illustrating a 23rd embodiment of the oil-water separation apparatus according to the present invention.

FIG. 29A is a sectional view illustrating a configuration of an oil-water separation apparatus in this embodiment.

An oil-water separation filtration device (oil-water separation apparatus) 1110 in this embodiment includes a liquid reservoir 1115 formed from an oil-water separation filtration reservoir 1112, an introduction reservoir 1111, and a discharge reservoir 1113. The introduction reservoir 1111 is provided on the preceding stage side of the oil-water separation filtration reservoir 1112. The discharge reservoir 1113 is provided on the subsequent stage side of the oil-water separation filtration reservoir 1112.

The introduction reservoir 1111 is a buffer tank for introducing a liquid mixture (sewage) containing, for example, water and oil to the liquid reservoir 1115. In the oil-water separation filtration reservoir 1112, the liquid mixture flowing from the introduction reservoir 1111 is separated into oil and moisture, and solid matter, organic matter, or the like contained in the moisture is removed. The discharge reservoir 1113 is a buffer tank for maintaining the liquid level position of the oil-water separation filtration reservoir 1112 to be constant. A water drain port 1127 is formed in the discharge reservoir 1113.

An oil-water separation layer (oil-water separation filter medium) 1121, a first filter layer 1122, and a second filter layer 1123 are formed in the oil-water separation filtration reservoir 1112 in order from the upper side. The layers 1121, 1122, and 1123 are formed to overlap each other. A water-collecting medium 1125 is provided at a lower portion of the second filter layer 1123.

The oil-water separation layer (oil-water separation filter medium) 1121 is formed from a medium in which multiple oil-water separation media 1131 which will be described later are laid to have a layer shape. The oil-water separation layer 1121 separates a liquid mixture into oil and moisture, and causes moisture to flow toward the first filter layer 1122, which is the lower layer, by gravity.

The first filter layer (filter layer) 1122 is formed from a medium in which a filtering medium 1132 is laid to have a layer shape. The second filter layer (filter layer) 1123 is formed from a medium in which a filtering medium 1133 is laid to have a layer shape. As the filtering medium 1132 constituting the first filter layer 1122, for example, sand is preferably used. As the filtering medium 1133 constituting the second filter layer 1123, for example, gravel is preferably used. The first filter layer 1122 is, for example, a sand layer. The first filter layer 1122 removes fine solid matter, dissolved water-soluble impurities, and organic matter such as various germs, which are dispersed in moisture which has passed through the oil-water separation layer 1121. The removal is performed by a physical reaction and a biochemical interaction. The physical reaction means, for example, blocking or attraction of floating matter occurring by sand.

As the sand used in such a first filter layer 1122, sand having a large amount of quartz and high hardness is preferable. For example, sand having properties and shape which are described in the standards (JWWA-A103:2006) of Japan Water Works Association may be used. For example, in a case where slow filtration (about 5 to 10 m/day) is performed by using the oil-water separation filtration device 1110 in this embodiment, sand in which an effective diameter is about 0.30 to 0.45 mm and a uniformity coefficient is equal to or less than 2.0 is preferably used. In a case where fast filtration (about 100 to 200 m/day) is performed by using the oil-water separation filtration device 10 in this embodiment, sand in which an effective diameter is about 0.5 to 0.8 mm and a uniformity coefficient is equal to or less than 1.5 is preferably used.

For example, a test sieve determined in JIS Z 8801 is selected, and a particle diameter accumulation curve is created based on the percentage of the weight of sand passing through the sieve. The effective diameter and the uniformity coefficient of sand used in the first filter layer 1122 are calculated based on the created particle diameter accumulation curve. If the effective diameter is small, particles of sand are small. If the particle diameter is aligned well, the value of the uniformity coefficient is small.

The second filter layer 1123 is, for example, a gravel layer. The second filter layer 1123 also has a filtration action of moisture, but functions as a support layer of the sand layer, that is, prevents sand constituting the first filter layer 1122 to be inserted into the water-collecting medium 1125, as the main purpose. In a case where reverse flow washing is performed on the oil-water separation filtration device 1110, washing water is uniformly dispersed. As gravel used in such a second filter layer 1123, a substance having high hardness, and having a round shape having a small edge is preferably used.

A support formed from a sheet-like member such as woven fabric or nonwoven fabric, through which water is allowed to pass may be further provided between the oil-water separation layer 1121 and the first filter layer 1122.

The water-collecting medium (water-collecting device) 1125 provided at a lower portion of the second filter layer 1123 supports a gravel layer constituting the second filter layer 1123 and causes the filtered moisture to pass. Such a water-collecting medium 1125 is disposed to be separated from the bottom plate of the liquid reservoir 1115. Moisture filtered by gravity flows out toward the discharge reservoir 1113 from a gap between the water-collecting medium 1125 and the bottom plate of the liquid reservoir 1115.

Figure 29B:
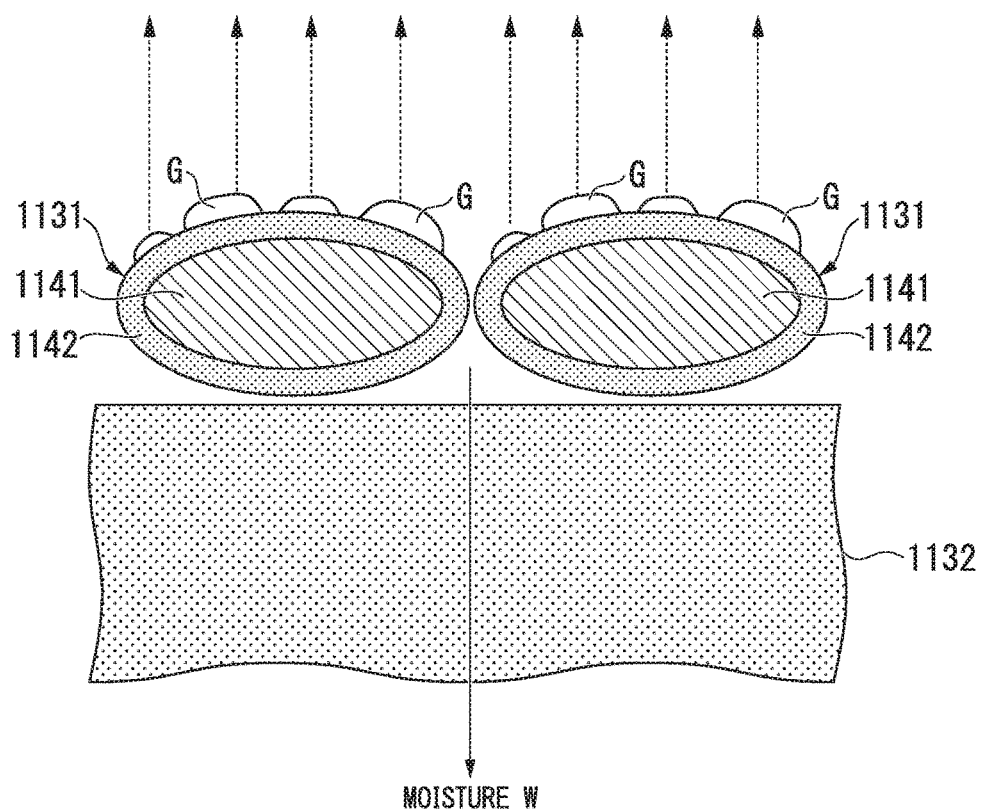
FIG. 29B is a sectional view of an enlarged main portion illustrating a portion of an oil-water separation layer in the 23rd embodiment of the oil-water separation apparatus according to the present invention.

FIG. 29B is a sectional view of an enlarged main portion illustrating a portion of the oil-water separation layer.

The oil-water separation medium 1131 is a lump or particulate matter having a sectional shape which is oval, circular, or amorphous. Each oil-water separation medium 1131 is formed from a base 1141 and an oil-water-separating member 1142 formed in the base 1141. The oil-water-separating member 1142 may be formed to cover the entirety of the surface of the base 1141. In addition, the oil-water-separating member 1142 may be scattered in the base so as to cause the oil-water-separating member 1142 to be exposed on the surface of the base 1141. In this embodiment, the oil-water-separating member 1142 is formed to cover the entirety of the surface of the base 1141.

As the oil-water separation medium 1131, a substance in which an average diameter of lumps or particles is, for example, about 0.04 mm to 3 mm may be used. The oil-water separation layer 1121 may be configured by using only the oil-water separation medium 1131 having a single size, or may be configured by using the oil-water separation medium 1131 having a plurality of sizes. In a case where the oil-water separation medium 1131 having a plurality of sizes is used, a medium in which the size becomes larger toward the oil-water separation medium 1131 at the higher layer, and the size becomes smaller toward the oil-water separation medium 1131 at the lower layer is preferably laid. According to such a laying method, the oil-water separation medium 1131 may be effectively used up to a lower layer in the oil-water separation layer 1121 in which oil-water separation medium 1131 is stacked. Thus, such a laying method is preferable. Further, the channel for a liquid, which is configured by gaps between particles of the oil-water separation medium 1131, gradually becomes narrower from the higher layer toward the lower layer. Thus, the number of chances that oil droplets flipped by an oil-repellent effect of the oil-water separation medium 1131 are brought into contact with each other is also gradually increased. Aggregation and coarsening of the oil droplets is accelerated from the higher layer toward the lower layer, and a floating and separation effect by the specific gravity difference is more easily obtained for minute oil droplets.

The oil-water separation layer (oil-water separation filter medium) 1121 in which such an oil-water separation medium 1131 is laid to have a layer shape separates a liquid mixture containing water and oil into moisture and oil by hydrophilicity and oil-repellent properties (hydrophilic and oil-repellent properties) of the oil-water-separating member 1142. For example, if a liquid mixture flows from the introduction reservoir 1111 toward the oil-water separation filtration reservoir 1112, the liquid mixture is separated into moisture and oil by the hydrophilic and oil-repellent properties of the oil-water separation medium 1131 constituting the oil-water separation layer 1121. Moisture (W in FIG. 29A) passes through the oil-water separation layer 1121 by gravity and then reaches the first filter layer 1122. Oil (G in FIG. 29A) separated in the oil-water separation layer 1121 is aggregated and accumulated in the oil-water separation layer 1121. A portion of the oil floats in the vicinity of the liquid level of the oil-water separation filtration reservoir 1112. With such an action of the oil-water separation layer 1121, only the separated moisture reaches the first filter layer 1122, which is a lower layer.

According to the oil-water separation filtration device (oil-water separation apparatus) 1110 in this embodiment, the oil-water separation layer (oil-water separation filter medium) 1121 is formed by using the oil-water separation medium 1131 in which the oil-water-separating member 1142 is formed in the base 1141. Thus, it is possible to separate a liquid mixture into water and oil only by gravity, and to perform separation into moisture and oil at low cost with a simple configuration. Such an oil-water separation layer (oil-water separation filter medium) 1121 is formed in the higher layer of the first filter layer (filter layer) 1122, for example, a sand layer. Thus, filtration capability of the first filter layer (filter layer) 1122 is degraded by adhering of oil, and water in which oil remains does not flow out from the oil-water separation filtration device 1110.

In this embodiment, for example, the base 1141 is configured from a material containing a ferromagnetic substance, and thus it is also possible to easily perform maintenance of the oil-water separation layer (oil-water separation filter medium) 1121. That is, if oil or impurities are fixed to the oil-water separation medium 1131 by performing oil-water separation for a long term, it is difficult that such fixed matter is removed by reverse flow washing. Thus, it is necessary that the oil-water separation medium 1131 be periodically extracted from the liquid reservoir 1115 and be separately washed, or replacement with a not-used oil-water separation medium 1131 be performed.

The base 1141 is configured from a material containing a ferromagnetic substance, and thus, when the oil-water separation medium 1131 is extracted from the liquid reservoir 1115, the oil-water separation medium 1131 is attracted by a magnetic force. Accordingly, it is possible to easily extract the oil-water separation medium 1131 from the liquid reservoir 1115, and to improve maintenance properties.

<Drainage System>

Figure 25:
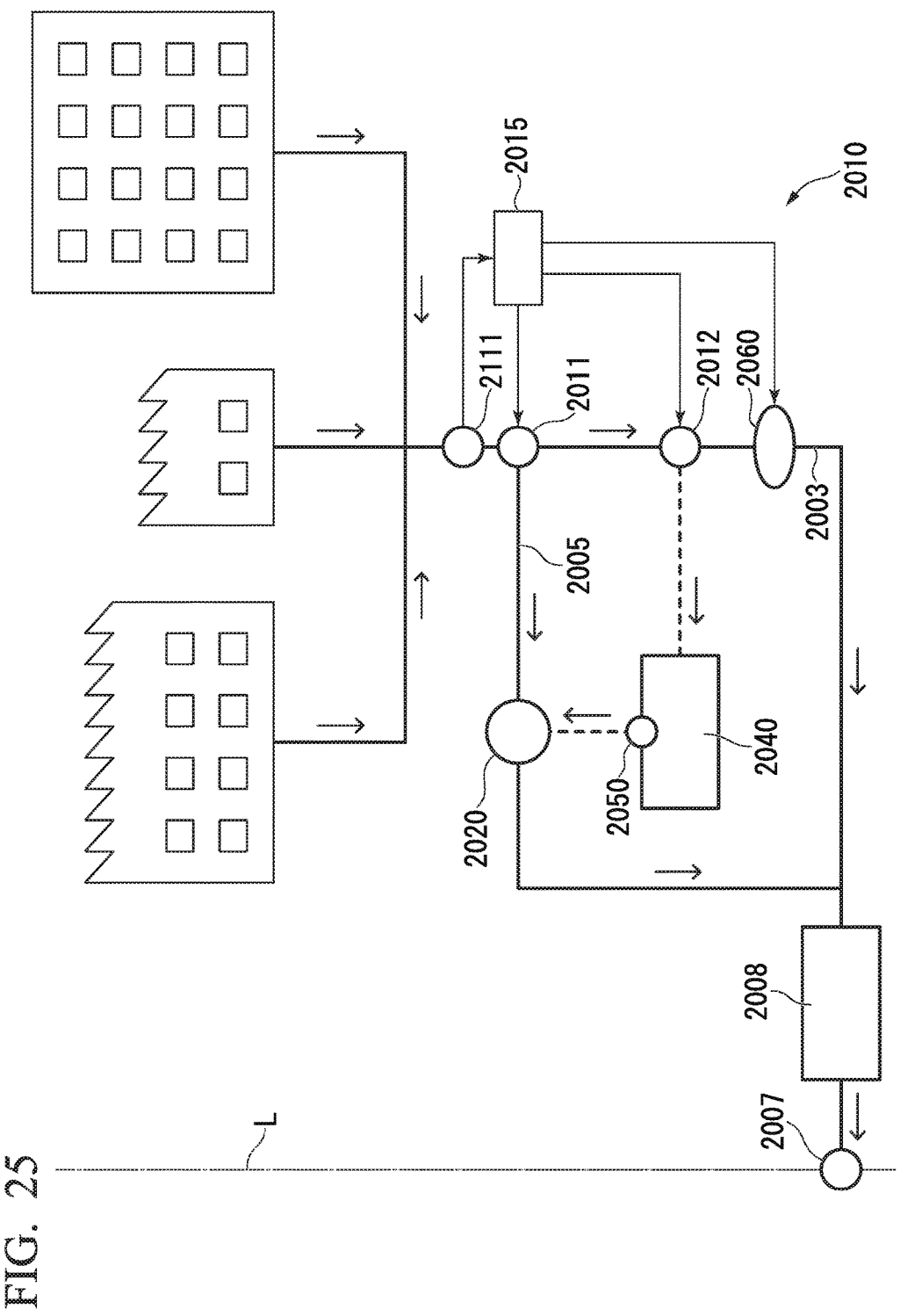
FIG. 25 is a schematic configuration diagram illustrating a drainage system according to the present invention.

FIG. 25 is a diagram illustrating an example of a drainage system to which the oil-water separation apparatus is applied.

A drainage system 2010 in this embodiment includes an oil leakage detector 2111, an oil fence 2060, an oil-water separation apparatus 2020, a water storage tank 2040, a floating oil collection device 2050, and a control unit 2015. The oil leakage detector 2111 detects leakage of oil to water in the process of being drained. The oil fence 2060 is provided so as to be attachable and detachable to and from a drainage channel 2003. The oil-water separation apparatus 2020 is arranged in a bypass path 2005 which is branched and provided from the drainage channel 2003. The water storage tank 2040 is branched and provided from the drainage channel 2003, and stores drained water which contains oil. The floating oil collection device 2050 collects floating oil on a water surface of the drained water which has been stored in the water storage tank 2040. The control unit 2015 applies commands to a first channel switch valve 2011 and a second channel switch valve 2012 which are arranged in the drainage channel 2003, and changes a channel for drained water.

In this embodiment, a water drain port 2007 is provided on a site boundary line L, and a drainage treatment facility 2008 is provided on an upstream side of the water drain port 2007. The oil leakage detector 2111 and the oil fence 2060 are arranged on an upstream side of the drainage treatment facility 2008.

In this embodiment, an oil film detector that detects an oil film spreading on the water surface of the drained water is used as the oil leakage detector 2111. The oil film detector is operated by, for example, a semiconductor laser scanning method. The oil film detector has a configuration in which a laser beam is applied onto the water surface of the drained water, reflectivity is measured, and the presence or absence of an oil film is detected based on a difference between reflectivity of water and reflectivity of oil.

As such an oil leakage detector 2111, for example, the oil film detector LO-300 manufactured by HORIBA Ltd, the oil film detectors OF-1600 and ODL-1600A manufactured by DKK-TOA Corporation, the oil film detector LMD-3000 manufactured by Asahi Kasei Technosystem Co., Ltd, OFM Series which are spillage oil monitoring devices manufactured by Nippon Sokki Co., Ltd. are exemplified. The commercial products may be appropriately selected and used.

The oil-water separation apparatus 2020 may apply the oil-water separation apparatus (180) itself, which has a configuration illustrated in FIG. 11, for example. Thus, detailed descriptions thereof will be omitted.

The floating oil collection device 2050 provided in the water storage tank 2040 may apply the float type oil-water collection device itself, which forms the intake unit (830) illustrated in FIG. 22, and thus detailed descriptions thereof will be omitted.

The oil fence 2060 may apply the oil-water separation and collection tool itself in the 12th embodiment, for example. Thus, detailed descriptions thereof will be omitted.

In the drainage system 2010, which is this embodiment, if the oil leakage detector 2111 detects leakage of oil, a detection signal is transmitted to the control unit 2015. If the oil leakage detector 2111 detects leakage of oil, firstly, the control unit 2015 outputs a command to arrange the oil fence 2060 in the drainage channel 2003. Then, if the treated amount of drained water containing oil exceeds a predetermined amount, the control unit 2015 transmits a command to the first channel switch valve 2011 provided in the drainage channel 2003 so as to introduce the drained water which contains oil to the oil-water separation apparatus 2020. Further, in a case where the control unit 2015 determines that the treated amount of the drained water containing oil exceeds treatment capability of the oil-water separation apparatus 2020, the control unit 2015 transmits commands to the first channel switch valve 2011 and the second channel switch valve 2012 which are provided in the drainage channel 2003. The control unit 2015 changes a channel for the drained water from a channel toward the bypass path 2005 to a channel toward the water storage tank 2040, and thus the drained water is temporarily stored in the water storage tank 2040. Separation and collection of oil is performed in a manner such that floating oil on the water surface of the drained water which has been stored in the water storage tank 2040 is collected along with water by the floating oil collection device 2050, and then is introduced to the oil-water separation apparatus 2020.

According to the drainage system 2010, which is this embodiment and has a configuration as described above, firstly, the oil fence 2060 is rapidly arranged in the drainage channel 2003 at a time point when the leakage of oil is detected. Thus, it is possible to restrict spillage of oil to the upstream side of the oil fence 2060. In a case where the treated amount of the drained water exceeds a predetermined amount, and thus preventing spillage of oil is difficult only by using the oil fence 2060, the drained water is introduced to the oil-water separation apparatus 2020, and thus it is possible to separate oil. In a case where the treated amount of the drained water is increased and exceeds the treatment capability of the oil-water separation apparatus 2020, the drained water is temporarily stored in the water storage tank 2040, and oil floating on the water surface is introduced to the oil-water separation apparatus 2020. Thus, it is possible to appropriately separate oil from the drained water by the oil-water separation apparatus 2020. Accordingly, it is possible to reliably prevent the oil spilling out of a site boundary line L.

Hitherto, the embodiments of the present invention have been described. However, the embodiments are proposed as examples, and are not limited to the range of the present invention. Regarding the embodiments, other various embodiments may be conducted. Various omissions, substitutions, and changes may be performed in a range without departing from the gist of the invention. The embodiments and modifications are included in the inventions described in claims and the equivalent range, similarly to being included in the range or the gist of the invention.

EXAMPLES

Advantages of the oil-water separation apparatus according to the present invention were verified.

Verification Example 1 of First Embodiment

When verification was performed, an oil-water separation filtration device having a configuration illustrated in FIG. 1, which included an oil-water-separating member, was produced. The oil-water-separating member was obtained by coating nonwoven fabric with a fluorine compound in which an oil-repellency-imparting group and a hydrophilicity-imparting group were provided in a molecule.

Specifically, polypropylene nonwoven fabric (basis weight: 40 g/m$^2$, thickness: 0.09 mm) having an area of 314 cm$^2$ was immersion-treated in a liquid (surface-coating material). Then, natural drying was performed (increased amount after drying: 0.5 g), and thus an oil-water-separating member having a configuration illustrated in FIG. 1 was produced. The liquid (surface-coating material) was prepared in a manner such that 2 mass % of a nitrogen-containing fluorine compound synthesized as an oil-repellent hydrophilic agent in Synthetic Example 1, and 4 mass % of polyvinyl butyral (S-LEC BL-1 manufactured by SEKISUI CHEMICAL CO., LTD.) were dissolved in 94 mass % of ethanol.

A simulation liquid in which 5 L of water and 1 L of n-hexadecane were mixed was supplied to an oil-water separation filtration device including the oil-water-separating member, at room temperature under normal pressure while stirring well. An elapse period was measured every time 1 L of water passed through the oil-water-separating member, and permeation flux (unit: cm$^3$/cm$^2$·min) was calculated.

A supply of the simulation liquid was stopped at a time point when the integrated quantity of water passing through the oil-water-separating member reached 3 L. 3 L of the passing water was accumulated, and quantitative analysis was performed for the concentration of n-hexadecane in water by a hexan extraction and gas chromatography method. Table 1 shows results of this measurement.

TABLE 1

| Integration quantity of passing water | L | 1 | 2 | 3 |
|---|---|---|---|---|
| Permeation flux of water | cm$^3$/cm$^2$ · min | 1.8 | 2.0 | 1.9 |
| Concentration of n-hexadecane in water | mg/L | | <5 | |

It can be confirmed that, if the oil-water separation filtration device in the present invention is used, it is possible to separate a solution mixture in which water and oil are mixed into moisture and oil with high accuracy, based on the results in Table 1. For example, the separated moisture may contain non-aqueous oil which is less than 5 mg/L (allowable limit of mineral oils in drained water, which is determined in the water pollution control law and sewerage act).

Experiment examples and advantages in a case of changing the type of the fluorine compound of an oil-water separation layer formed in the oil-water separation filtration device described in the present invention will be described in detail. The present invention is not limited to the experiment examples.

Synthetic Example 1

Synthesis of 2-[3-[[perfluoro(2-methyl-3-dibutyl aminopropanoyl)]amino]propyl-dimethyl-ammonium]acetate 120 g of perfluoro(2-methyl-3-dibutylaminopropionic acid)fluoride obtained by electrolytic fluorination of 2-methyl-3-dibutyl amiopropionate methyl were dropped in a solution in which 39 g of dimethyl aminopropylamine was dissolved in 500 ml of an IPE solvent, in an ice bath. Stirring was performed at room temperature for two hours, and then filtration was performed. An IPE layer in a filtrate was subjected to washing treatment by a NaHCO$_3$ aqueous solution and a NaCl aqueous solution. Liquid separation was performed, and then water washing was performed. Then, IPE was distilled, and thus 64 g of $(C_4F_9)_2NCF_2CF(CF_3)CONHC_3H_6N(CH_3)_2$ was obtained as a crude product (yield of 47%).

Then, 8 g of obtained $(C_4F_9)_2NCF_2CF(CF_3)CONHC_3H_6N(CH_3)_2$ was flowed back along with sodium monochloroacetate for one night, while stirring in ethanol. After filtration and concentration, 9 g of a dimethyl betaine substance represented by the formula (5) was obtained (yield of 99%).

Synthetic Example 2

Synthesis of 2-[3-[[perfluoro(3-dibutylaminopropanoyl)]amino]propyl-dimethyl-ammonium]acetate 20 g of perfluoro(3-dibutyl aminopropionic acid)fluoride obtained by electrolytic fluorination of 3-dibutyl amiopropionate methyl was dropped in a solution in which 4 g of dimethyl aminopropylamine was dissolved in 50 ml of an IPE solvent, in an ice bath. Stirring was performed at room temperature for two hours, and then filtration was performed. An IPE layer in a filtrate was subjected to washing treatment by a NaHCO$_3$ aqueous solution and a NaCl aqueous solution. Liquid separation was performed, and then water washing was performed. Then, IPE was distilled, and thus 14 g of $(C_4F_9)_2NC_2F_4CONHC_3H_6N(CH_3)_2$ was obtained as a crude product (yield of 60%).

Then, 3 g of obtained $(C_4F_9)_2NC_2F_4CONHC_3H_6N(CH_3)_2$ was flowed back along with sodium monochloroacetate for one night, while stirring in ethanol. Thus, 3 g of a dimethyl betaine substance represented by the formula (6) was obtained (yield of 92%).

[Chemical Formula 10]

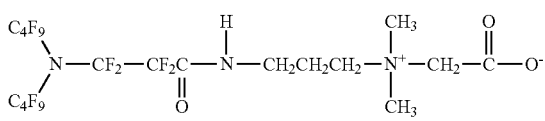

(6)

Synthetic Example 3

Synthesis of 2-[3-[[perfluoro(2-methyl-3-piperidino propanoyl)]amino]propyl-dimethyl-ammonium]acetate 20 g of perfluoro(2-methyl-3-piperidinopropionic acid) fluoride obtained by electrolytic fluorination was dropped in a solution in which 9 g of dimethyl aminopropylamine were dissolved in 110 ml of an IPE solvent, in an ice bath. Stirring was performed at room temperature for two hours, and then filtration was performed. An IPE layer in a filtrate was subjected to washing treatment by a NaHCO$_3$ aqueous solution and a NaCl aqueous solution. Liquid separation was performed, and then water washing was performed. Then, IPE was distilled, and thus 18 g of $CF_2(CF_2CF_2)_2NCF_2CF(CF_3)CONHC_3H_6N(CH_3)_2$ was obtained as a crude product (crude yield of 76%).

Then, 10 g of the obtained crude product of $CF_2(CF_2CF_2)_2NCF_2CF(CF_3)CONHC_3H_6N(CH_3)_2$ was flowed back along with 3 g of sodium monochloroacetate for one night, while stirring in ethanol. Thus, 11 g of a dimethyl betaine substance represented by the formula (7) was obtained (yield of 99%).

[Chemical Formula 9]

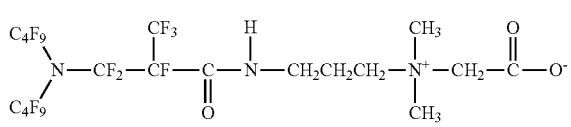

(5)

[Chemical Formula 11]

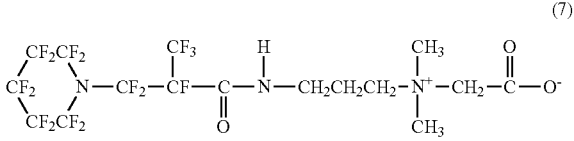

(7)

Synthetic Example 4

Synthesis of 2-[3-[[perfluoro(2-methyl-3-morpholinopropanoyl)]amino]propyl-dimethyl-ammonium]acetate 21 g of perfluoro(3-methyl-3-morpholinopropionic acid) fluoride obtained by electrolytic fluorination was dropped in a solution in which 10 g of dimethyl aminopropylamine were dissolved in 100 ml of an IPE solvent, in an ice bath. Then, stirring was performed at room temperature for two hours, and then filtration was performed. An IPE layer in a filtrate was subjected to washing treatment by a $NaHCO_3$ aqueous solution and a NaCl aqueous solution. Liquid separation was performed, and then water washing was performed. Then, IPE was distilled, and thus 22 g of $O(CF_2CF_2)_2NCF_2CF(CF_3)CONHC_3H_6N(CH_3)_2$ was obtained as a crude product (crude yield of 88%).

Then, 10 g of the obtained crude product of $O(CF_2CF_2)_2NCF_2CF(CF_3)CONHC_3H_6N(CH_3)_2$ was flowed back along with 3 g of sodium monochloroacetate for one night, while stirring in ethanol. Thus, 11 g of a dimethyl betaine substance represented by the formula (8) was obtained (yield of 99%).

[Chemical Formula 12]

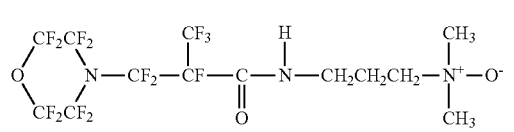

(8)

Synthetic Example 5

Synthesis of perfluoro(3-dibutylaminopropionic acid)calcium 352 g of a 12.5% sodium hydroxide aqueous solution was put into a 2 L glass flask, and 837 g of perfluoro(3-dibutylaminopropionic acid)fluoride obtained by electrolytic fluorination of methyl 3-dibutylaminopropionate was dropped so as to cause a reaction. After dropping, 500 ml of ethyl acetate was added, and then sodium perfluoro(3-dibutylaminopropionic acid) was extracted. After an ethyl acetate layer was separated from water, ethyl acetate was distilled in a rotary evaporator. 488 g of sodium perfluoro(3-dibutylaminopropionic acid) of a light-yellow solid body was obtained.

Then, 488 g of sodium perfluoro(3-dibutylaminopropionic acid) and 280 g of 95% sulfuric acid were put into a 1 L of glass flask, and were mixed. Reduced-pressure distillation was performed, and thus 436 g of perfluoro (3-dibutylaminopropionic acid) of a solid body was obtained at normal temperature (yield of 93% from a sodium salt).

23.5 g of perfluoro (3-dibutylaminopropionic acid) was neutralized in a methanol/water liquid mixture by 1.5 g of calcium hydroxide. Crystals obtained by precipitation were separated by filtration. Drying was performed at 100° C., and thus 23.5 g of perfluoro(3-dibutylaminopropionic acid) calcium represented by the formula (9) was obtained (yield of 97%). The solubility of the compound to water at room temperature was 0.02 mass %.

[Chemical Formula 13]

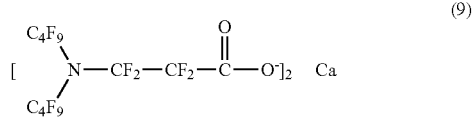

(9)

Synthetic Example 6

Synthesis of 3-[3-[[perfluoro(2-methyl-3-morpholinopropanoyl)]amino]propyl-dimethyl-ammonium]propanesulfonate 21 g of perfluoro(3-methyl-3-morpholinopropionic acid) fluoride obtained by electrolytic fluorination of 2-methyl-3-morpholinopropionate methyl was dropped in a solution in which 10 g of dimethyl aminopropylamine was dissolved in 100 ml of an IPE solvent, in an ice bath. Then, stirring was performed at room temperature for two hours, and then filtration was performed. An IPE layer in a filtrate was subjected to washing treatment by a $NaHCO_3$ aqueous solution and a NaCl aqueous solution. Liquid separation was performed, and then water washing was performed. Then, IPE was distilled, and thus 22 g of $O(CF_2CF_2)_2NCF_2CF(CF_3)CONHC_3H_6N(CH_3)_2$ was obtained as a crude product (crude yield of 88%).

Then, 5 g of obtained $O(CF_2CF_2)_2NCF_2CF(CF_3)CONHC_3H_6N(CH_3)_2$ was flowed back along with 1,3-propane sultone for one night, while stirring in methylene chloride. Then, reprecipitation in a fluorinated solvent AK225 and an IPE mixture solvent was performed, and thus 5.5 g of a sulfobetaine substance represented by the following formula (10) was obtained (yield of 98%).

[Chemical Formula 14]

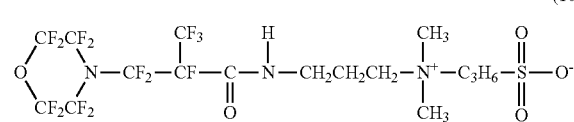

(10)

Synthetic Example 7

Synthesis of 3-[3-[[perfluoro(2-methyl-3-dibutylaminopropanoyl)]amino]propyl-dimethyl-ammonium] propanesulfonate 120 g of perfluoro(2-methyl-3-dibutylaminopropionic acid)fluoride obtained by electrolytic fluorination of 2-methyl-3-dibutyl amiopropionate methyl was dropped in a solution in which 39 g of dimethyl aminopropylamine was dissolved in 500 ml of an IPE solvent, in an ice bath. Stirring was performed at room temperature for two hours, and then filtration was performed. An IPE layer in a filtrate was subjected to washing treatment by a $NaHCO_3$ aqueous solution and a NaCl aqueous solution. Liquid separation was performed, and then water washing was performed. Then, IPE was distilled, and thus 64 g of $(C_4F_9)_2NCF_2CF(CF_3)CONHC_3H_6N(CH_3)_2$ was obtained as a crude product (yield of 47%).

Then, 15 g of obtained $(C_4F_9)_2NCF_2CF(CF_3)$ $CONHC_3H_6N(CH_3)_2$ was flowed back along with 1,3-propane sultone for 23 hours, while stirring in acetonitrile. Then, reprecipitation in a fluorinated solvent AK225 and an IPE mixture solvent was performed, and thus 13 g of a sulfobetaine substance represented by the formula (11) was obtained (yield of 75%).

[Chemical Formula 15]

(11)

$$\begin{array}{c} C_4F_9 \\ \diagdown \\ \diagup \\ C_4F_9 \end{array} N-CF_2-\underset{\underset{O}{\|}}{CF}-\underset{\underset{}{|}}{\overset{\overset{CF_3}{|}}{C}}-\underset{\underset{}{|}}{\overset{\overset{H}{|}}{N}}-CH_2CH_2CH_2-\underset{\underset{}{|}}{\overset{\overset{CH_3}{|}}{N^+}}-C_3H_6-\underset{\underset{O}{\|}}{\overset{\overset{O}{\|}}{S}}-O^-$$

(Binder)

As a binder, polyvinyl butyral (S-LEC B, BL-1, S-LEC BL-S, S-LEC BM-2, S-LEC K KS-10 manufactured by SEKISUI CHEMICAL CO., LTD.), acrylic resin (ARUFON UC-3000 manufactured by TOAGOSEI CO., LTD.), and terpene phenolic resin (YS POLYSTER N125 manufactured by YASUHARA CHEMICAL CO., LTD.) were used.

<Manufacturing of Oil-water-Separating Member>

Firstly, an oil-repellent hydrophilic agent, a binder, and methanol or ethanol which is a solvent were mixed with each other at predetermined proportions, thereby a surface-coating material was manufactured.

Then, the base was dipped into the surface-coating material so as to sufficiently impregnate with the solution. The base was removed, and then natural drying was performed. Thus, the solvent was removed. In this manner, an oil-water-separating member for a permeation test was manufactured.

<Evaluation by Oil-water-Separating Member Permeation Test>

Water and n-hexadecane were each dropped in the produced oil-water-separating member for a permeation test. Permeability was visually determined based on the following definitions, and thus the hydrophilic and oil-repellent properties were evaluated.

For a dropping method of water and n-hexadecane, the following conditions were used.

Dropped quantity: (40 to 45) μL/droplet (water)
Dropped quantity: (20 to 25) μL/droplet (n-hexadecane)
Dropping height: 5 cm from the surface of the oil-water-separating member
Dropping tool: polyfiller
Measurement temperature: room temperature (22±1° C.)

In an oil-water-separating member permeation test, the definitions of evaluation results are as follows.

Immediate permeation: permeation occurs within 30 seconds after liquid droplets are dropped in the oil-water-separating member for a permeation test Gradual permeation: permeation occurs for a period which is longer than 30 seconds and within five minutes after liquid droplets are dropped No permeation: permeation does not occur for 30 minutes after liquid droplets are dropped <Evaluation of Durability by Ultrasonic Washing>

The oil-water-separating member for a permeation test was immersed in 50 ml of pure water, and ultrasonic washing was performed at room temperature by using an ultrasonic washer USK-5R (240 W, 40 kHz) manufactured by AS ONE Corporation.

Replacement with pure water was performed each of 90 minutes during a period from ultrasonic wave irradiation start to six hours, and was performed for each of 60 minutes during a period after six hours.

After three hours from ultrasonic wave irradiation, after six hours, and after eight hours, the oil-water-separating member was extracted, and the hydrophilic and oil-repellent properties were evaluated by a method similar to that for the oil-water-separating member permeation test.

Experiment Example 1

2 mass % of a nitrogen-containing fluorine compound synthesized as an oil-repellent hydrophilic agent in Synthetic Example 1, and 4 mass % of S-LEC B BL-S as a binder were mixed and dissolved in 94 mass % of methanol as a solvent, at the above proportions, thereby a surface-coating material was manufactured.

Then, polypropylene nonwoven fabric having a basis weight of 72 g/m² and a thickness of 0.26 mm was used as a base, and the base was coated with the manufactured surface-coating material by using the above-described method. Thus, an oil-water-separating member for a permeation test in Experiment Example 1 was manufactured. The following Table 2 shows manufacturing conditions.

Water and n-hexadecane were each dropped in the oil-water-separating member for a permeation test of Experiment Example 1, and initial performance and permeability after ultrasonic washing were evaluated. The following Table 3 shows evaluation results.

Experiment Example 2

An oil-water-separating member for a permeation test in Experiment Example 2 was manufactured similarly to that in Experiment Example 1 except that S-LEC B BL-1 was used as the binder, and ethanol was used as the solvent. Then, initial performance and permeability after ultrasonic washing were evaluated by using a method similar to that in Experiment Example 1. The following Table 2 shows manufacturing conditions. The following Table 3 shows evaluation results.

Experiment Example 3

2 mass % of a nitrogen-containing fluorine compound synthesized as an oil-repellent hydrophilic agent in Synthetic Example 1, and 20 mass % of S-LEC B BL-1 as a binder were mixed and dissolved in 78 mass % of ethanol, at the above proportions, thereby a surface-coating material was manufactured.

Then, in a manner similar to that in Experiment Example 1, an oil-water-separating member for a permeation test in Experiment Example 2 was manufactured. Then, initial performance and permeability after ultrasonic washing were evaluated by using a method similar to that in Experiment Example 1. The following Table 2 shows manufacturing conditions. The following Table 3 shows evaluation results.

Experiment Example 4

An oil-water-separating member for a permeation test in Experiment Example 4 was manufactured in a manner similar to that in Experiment Example 1 except that S-LEC B BM-2 was used as the binder. Then, initial performance and permeability after ultrasonic washing were evaluated by using a method similar to that in Experiment Example 1. The following Table 2 shows manufacturing conditions. The following Table 3 shows evaluation results.

Experiment Example 5

An oil-water-separating member for a permeation test in Experiment Example 5 was manufactured in a manner similar to that in Experiment Example 1 except that S-LEC K KS-10 was used as the binder. Then, initial performance and permeability after ultrasonic washing were evaluated by using a method similar to that in Experiment Example 1. The following Table 2 shows manufacturing conditions. The following Table 3 shows evaluation results.

Experiment Example 6

An oil-water-separating member for a permeation test in Experiment Example 2 was manufactured in a manner similar to that in Experiment Example 1 except that ARU-FON UC-3000 was used as the binder, and ethanol was used as the solvent. Then, initial performance and permeability after ultrasonic washing were evaluated by using a method similar to that in Experiment Example 1. The following Table 2 shows manufacturing conditions. The following Table 3 shows evaluation results.

Experiment Example 7

An oil-water-separating member for a permeation test in Experiment Example 7 was manufactured in a manner similar to that in Experiment Example 1 except that YS POLYSTER N125 was used as the binder, and ethanol was used as the solvent. Then, initial performance and permeability after ultrasonic washing were evaluated by using a method similar to that in Experiment Example 1. The following Table 2 shows manufacturing conditions. The following Table 3 shows evaluation results.

Experiment Example 8

2 mass % of a nitrogen-containing fluorine compound synthesized as an oil-repellent hydrophilic agent in Synthetic Example 1, and 4 mass % of S-LEC B BL-1 as a binder were mixed and dissolved in 94 mass % of methanol as a solvent, at the above proportions, thereby a surface-coating material was manufactured.

Then, polyethylene/polypropylene composite nonwoven fabric having a basis weight of 60 g/m$^2$ and a thickness of 0.40 mm was used as a base, and the base was coated with the manufactured surface-coating material by using the above-described method. Thus, an oil-water-separating member for a permeation test in Experiment Example 8 was manufactured, and then initial performance and permeability after ultrasonic washing were evaluated by using a method similar to that in Experiment Example 1. The following Table 2 shows manufacturing conditions. The following Table 3 shows evaluation results.

Experiment Example 9

2 mass % of a nitrogen-containing fluorine compound synthesized as an oil-repellent hydrophilic agent in Synthetic Example 2, and 4 mass % of S-LEC B BL-1 as a binder were mixed and dissolved in 94 mass % of methanol as a solvent, at the above proportions, thereby a surface-coating material was manufactured.

Then, polypropylene nonwoven fabric having a basis weight of 72 g/m$^2$ and a thickness of 0.26 mm was used as a base, and the base was coated with the manufactured surface-coating material by using the above-described method. Thus, an oil-water-separating member for a permeation test in Experiment Example 9 was manufactured. Then, initial performance and permeability after ultrasonic washing were evaluated by using a method similar to that in Experiment Example 1. The following Table 2 shows manufacturing conditions. The following Table 3 shows evaluation results.

Experiment Example 10

An oil-water-separating member for a permeation test in Experiment Example 10 was manufactured in a manner similar to that in Experiment Example 9 except that a nitrogen-containing fluorine compound synthesized in Synthetic Example 3 was used as an oil-repellent hydrophilic agent. Then, initial performance and permeability after ultrasonic washing were evaluated by using a method similar to that in Experiment Example 1. The following Table 2 shows manufacturing conditions. The following Table 3 shows evaluation results.

Experiment Example 11

An oil-water-separating member for a permeation test in Experiment Example 11 was manufactured in a manner similar to that in Experiment Example 9 except that a nitrogen-containing fluorine compound synthesized in Synthetic Example 4 was used as an oil-repellent hydrophilic agent. Then, initial performance and permeability after ultrasonic washing were evaluated by using a method similar to that in Experiment Example 1. The following Table 2 shows manufacturing conditions. The following Table 3 shows evaluation results.

Experiment Example 12

An oil-water-separating member for a permeation test in Experiment Example 12 was manufactured in a manner similar to that in Experiment Example 9 except that a nitrogen-containing fluorine compound synthesized in Synthetic Example 5 was used as an oil-repellent hydrophilic agent. Then, initial performance and permeability after ultrasonic washing were evaluated by using a method similar to that in Experiment Example 1. The following Table 2 shows manufacturing conditions. The following Table 3 shows evaluation results.

Comparative Experiment Example 1

A compound which has a straight-chain nitrogen-containing perfluoroalkyl group in a molecule, and a polyoxyalkylene group as a hydrophilic group, and is represented by the formula (12) was dissolved in methanol, thereby 2.0 mass % of a methanol solution was manufactured.

The manufactured methanol solution was set as a surface-coating material of Comparative Example 1. Polypropylene nonwoven fabric having a basis weight of 72 g/m$^2$ and a thickness of 0.26 mm was coated with the solution, thereby an oil-water-separating member for a permeation test in Comparative Example 1 was manufactured. Then, initial performance and permeability after ultrasonic washing were evaluated by using a method similar to that in Experiment Example 1. The following Table 2 shows manufacturing conditions. The following Table 3 shows evaluation results.

[Chemical Formula 16]

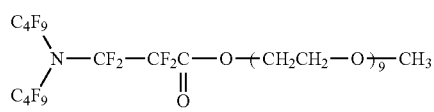

(12)

Comparative Experiment Example 2

A compound which has a cyclic nitrogen-containing perfluoroalkyl group in a molecule, and a polyoxyalkylene group as a hydrophilic group, and is represented by the formula (13) was dissolved in methanol, thereby 2.0 mass % of a methanol solution was manufactured. The manufactured methanol solution was set as a surface-coating material of Comparative Example 2. Polypropylene nonwoven fabric having a basis weight of 72 g/m² and a thickness of 0.26 mm was coated with the solution, thereby an oil-water-separating member for a permeation test in Comparative Example 2 was manufactured. Then, initial performance and permeability after ultrasonic washing were evaluated by using a method similar to that in Experiment Example 1. The following Table 2 shows manufacturing conditions. The following Table 3 shows evaluation results.

[Chemical Formula 17]

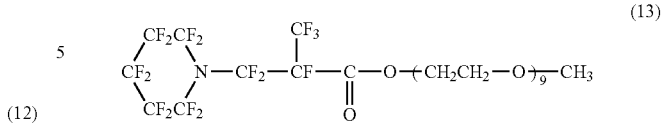

(13)

Comparative Experiment Example 3

A solution in which 98 mass % of methanol as a solvent was added and dissolved in 2 mass % of commercial calcium perfluorohexanoate represented by the formula (14) was set as a surface-coating material in Comparative Example 3.

Then, a commercial PTFE membrane filter having a diameter of 47 mm (ADVANTEC T100A-:hole diameter of 1 μm, porosity of 79%, thickness of 75 μm) was used as the base. The base was coated with the manufactured surface-coating material by using the above-described method. Thus, an oil-water-separating member for a permeation test in Comparative Example 3 was manufactured. Then, initial performance and permeability after ultrasonic washing were evaluated by using a method similar to that in Experiment Example 1. The following Table 2 shows manufacturing conditions. The following Table 3 shows evaluation results.

[Chemical Formula 18]

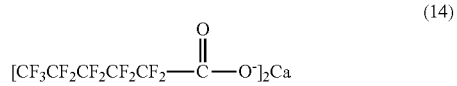

(14)

TABLE 2A

| Treatment Compound | [wt %] | Binder [wt %] | Solvent [wt %] | Base | Basis weight [g/m²] | Surface-coating material adhering amount (solid matter) [g/m²] |
|---|---|---|---|---|---|---|
| Experiment Example 1 (structure shown) | 2 | BL-S 4 | methanol 94 | polypropylene nonwoven fabric | 72 | 10.7 |
| Experiment Example 2 | 2 | BL-1 4 | ethanol 94 | polypropylene nonwoven fabric | 72 | 9.2 |
| Experiment Example 3 | 2 | BL-1 20 | ethanol 78 | polypropylene nonwoven fabric | 72 | 51.6 |
| Experiment Example 4 | 2 | BM-2 4 | methanol 94 | polypropylene nonwoven fabric | 72 | 8.4 |
| Experiment Exam- | 2 | KS-10 4 | methanol 94 | polypropylene | 72 | 10.2 |

TABLE 2A-continued

| | Treatment Compound | Binder [wt %] | Solvent [wt %] | Base | Basis weight [g/m²] | Surface-coating material adhering amount (solid matter) [g/m²] |
|---|---|---|---|---|---|---|
| Experiment Example 5 (ple 5) | | | | non-woven fabric | | |
| Experiment Example 6 | | 2 | UC-3000 4 | ethanol 94 | polypropylene non-woven fabric | 72 | 8.5 |
| Experiment Example 7 | | 2 | N125 4 | ethanol 94 | polypropylene non-woven fabric | 72 | 8.8 |
| Experiment Example 8 | | 2 | BL-1 4 | methanol 94 | polyethylene/polypropylene composite non-woven fabric | 60 | 8.6 |
| Experiment Example 9 | (C$_4$F$_9$)$_2$N—CF$_2$—CF$_2$C(=O)—N(H)—CH$_2$CH$_2$CH$_2$—N$^+$(CH$_3$)$_2$—CH$_2$—C(=O)—O$^-$ | 2 | BL-1 4 | methanol 94 | polypropylene non-woven fabric | 72 | 10.2 |
| Experiment Example 10 | [cyclic (CF$_2$CF$_2$)$_2$(CF$_2$)N]—CF$_2$—CF(CF$_3$)—C(=O)—N(H)—CH$_2$CH$_2$CH$_2$—N$^+$(CH$_3$)$_2$—CH$_2$—C(=O)—O$^-$ | 2 | BL-1 4 | methanol 94 | polypropylene non-woven fabric | 72 | 14.0 |
| Experiment Example 11 | [cyclic O(CF$_2$CF$_2$)$_2$N]—CF$_2$—CF(CF$_3$)—C(=O)—N(H)—CH$_2$CH$_2$CH$_2$—N$^+$(CH$_3$)$_2$—CH$_2$—C(=O)—O$^-$ | 2 | BL-1 4 | methanol 94 | polypropylene non-woven fabric | 72 | 17.4 |
| Experiment Example 12 | [(C$_4$F$_9$)$_2$N—CF$_2$—CF$_2$—C(=O)—O$^-$]$_2$ Ca | 2 | BL-1 4 | methanol 94 | polypropylene non-woven fabric | 72 | 15.7 |
| Comparative Experiment Example 1 | (C$_4$F$_9$)$_2$N—CF$_2$—CF$_2$C(=O)—O—(CH$_2$CH$_2$—O)$_a$—CH$_3$ | 2 | — | methanol 98 | polypropylene non-woven fabric | 72 | — |

TABLE 2A-continued

| | Treatment Compound | Binder [wt %] | Solvent [wt %] | Base | Basis weight [g/m²] | Surface-coating material adhering amount (solid matter) [g/m²] |
|---|---|---|---|---|---|---|
| Comparative Experiment Example 2 | 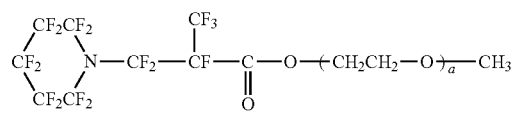 | 2 | methanol 98 | polypropylene nonwoven fabric | 72 | — |
| Comparative Experiment Example 3 |  | 2 | methanol 98 | PTFE membrane filter | — | — |

TABLE 3

| | Filter permeation test result | | | | | | | |
|---|---|---|---|---|---|---|---|---|
| | Initial performance | | After 3 hours from ultrasonic washing | | After 6 hours from ultrasonic washing | | After 8 hours from ultrasonic washing | |
| | water | n-hexadecane | water | n-hexadecane | water | n-hexadecane | water | n-hexadecane |
| Experiment Example 1 | Immediate permeation Hydrophilicity | No permeation Oil repellency | Immediate permeation Hydrophilicity | No permeation Oil repellency | Immediate permeation Hydrophilicity | No permeation Oil repellency | Immediate permeation Hydrophilicity | No permeation Oil repellency |
| Experiment Example 2 | Immediate permeation Hydrophilicity | No permeation Oil repellency | Immediate permeation Hydrophilicity | No permeation Oil repellency | Immediate permeation Hydrophilicity | No permeation Oil repellency | Gradual permeation Hydrophilicity | Immediate permeation Lipophilicity |
| Experiment Example 3 | Immediate permeation Hydrophilicity | No permeation Oil repellency | Immediate permeation Hydrophilicity | No permeation Oil repellency | Immediate permeation Hydrophilicity | No permeation Oil repellency | Immediate permeation Hydrophilicity | No permeation Oil repellency |
| Experiment Example 4 | Immediate permeation Hydrophilicity | No permeation Oil repellency | Immediate permeation Hydrophilicity | No permeation Oil repellency | Immediate permeation Hydrophilicity | No permeation Oil repellency | Immediate permeation Hydrophilicity | Immediate permeation Lipophilicity |
| Experiment Example 5 | Immediate permeation Hydrophilicity | No permeation Oil repellency | Immediate permeation Hydrophilicity | No permeation Oil repellency | Immediate permeation Hydrophilicity | No permeation Oil repellency | Immediate permeation Hydrophilicity | Immediate permeation Lipophilicity |
| Experiment Example 6 | Immediate permeation Hydrophilicity | No permeation Oil repellency | Immediate permeation Hydrophilicity | No permeation Oil repellency | No permeation Water repellency | Gradual permeation Lipophilicity | — | — |
| Experiment Example 7 | Immediate permeation Hydrophilicity | No permeation Oil repellency | Immediate permeation Hydrophilicity | Immediate permeation Lipophilicity | — | — | — | — |
| Experiment Example 8 | Immediate permeation Hydrophilicity | No permeation Oil repellency | Immediate permeation Hydrophilicity | No permeation Oil repellency | Immediate permeation Hydrophilicity | Immediate permeation Lipophilicity | — | — |
| Experiment Example 9 | Immediate permeation Hydrophilicity | No permeation Oil repellency | Immediate permeation Hydrophilicity | No permeation Oil repellency | Immediate permeation Hydrophilicity | Immediate permeation Lipophilicity | — | — |
| Experiment Example 10 | Immediate permeation Hydrophilicity | No permeation Oil repellency | Gradual permeation Hydrophilicity | Immediate permeation Lipophilicity | — | — | — | — |
| Experiment Example 11 | Immediate permeation Hydrophilicity | No permeation Oil repellency | Gradual permeation Hydrophilicity | Immediate permeation Lipophilicity | — | — | — | — |
| Experiment Example 12 | Gradual permeation Hydrophilicity | No permeation Oil repellency | Gradual permeation Hydrophilicity | Immediate permeation Lipophilicity | — | — | — | — |
| Comparative Experiment Example 1 | Immediate permeation Hydrophilicity | Immediate permeation Lipophilicity | — | — | — | — | — | — |
| Comparative Experiment Example 2 | Immediate permeation Hydrophilicity | Immediate permeation Lipophilicity | — | — | — | — | — | — |

TABLE 3-continued

| | Filter permeation test result | | | | | | | |
|---|---|---|---|---|---|---|---|---|
| | Initial performance | | After 3 hours from ultrasonic washing | | After 6 hours from ultrasonic washing | | After 8 hours from ultrasonic washing | |
| | water | n-hexadecane | water | n-hexadecane | water | n-hexadecane | water | n-hexadecane |
| Comparative Experiment Example 3 | No permeation Water repellency | Gradual permeation Lipophilicity | — | — | — | — | — | — |

As shown in Table 3, in the oil-water-separating members for a permeation test in Experiment Examples 1 and 3, initial performance of permeability was hydrophilic and oil-repellent properties, and the hydrophilic and oil-repellent properties were also maintained after eight hours from when the ultrasonic washing was performed.

In the oil-water-separating members for a permeation test in Experiment Examples 2, 4, and 5, initial performance of permeability was hydrophilic and oil-repellent properties, and the hydrophilic and oil-repellent properties were also maintained after six hours from when the ultrasonic washing was performed.

In the oil-water-separating members for a permeation test in Experiment Examples 6, 8, and 9, initial performance of permeability was hydrophilic and oil-repellent properties, and the hydrophilic and oil-repellent properties were also maintained after three hours from when the ultrasonic washing was performed.

In the oil-water-separating members for a permeation test in Experiment Examples 7, 10, 11, and 12, initial performance of permeability was hydrophilic and oil-repellent properties, but hydrophilic and lipophilic properties were exhibited after three hours from when the ultrasonic washing was performed.

On the contrary, in the oil-water-separating members for a permeation test in Comparative Examples 1 and 2, a permeation result of water was "immediate permeation", a permeation result of n-hexadecane was "immediate permeation", and thus it was confirmed that the oil-water-separating members had hydrophilic and lipophilic properties.

In the oil-water-separating member for a permeation test in Comparative Example 3, a permeation result of water was "no permeation", a permeation result of n-hexadecane was "gradual permeation", and thus it was confirmed that the oil-water-separating member had water-repellent and lipophilic properties.

If water and n-hexadecane were each dropped in a nonwoven fabric filter which was subjected to surface treatment with an oil-repellent hydrophilic agent, and was the oil-water-separating member constituting the oil-water separation filtration device according to the present invention, water was spread, and was permeated into the nonwoven fabric filter. On the contrary, n-hexadecane was held to have an oil droplet shape.

Similarly, if water and n-hexadecane were each dropped in a not-treated nonwoven fabric, water was held to have a water droplet shape, and n-hexadecane was spread, and was permeated into the nonwoven fabric filter.

<Evaluation by Oil-water Separation Test>

Experiment Example 13

Polypropylene nonwoven fabric (basis weight: 15 g/m$^2$, thickness: 0.16 mm, average pore diameter: 7 μm, and maximum pore diameter: 14 μm) was cut off so as to have a circular filter shape having a diameter of 60 mm. The polypropylene nonwoven fabric was immersion-treated in a liquid (surface-coating material). Then, natural drying was performed (increased amount after drying: 0.0141 g), and an oil-water separation test was performed at room temperature in a normal-pressure filtration device. In the liquid (surface-coating material), 2 g of a nitrogen-containing fluorine compound synthesized as an oil-repellent hydrophilic agent in Synthetic Example 1, and 4 g of polyvinyl butyral (S-LEC BL-1 manufactured by SEKISUI CHEMICAL CO., LTD.) were dissolved in 94 g of methanol.

A liquid mixture of 30 ml of water and 10 ml of n-hexadecane was used as a test liquid.

When the test liquid was supplied to a normal-pressure filtration device, while stirring well, water passed through the nonwoven fabric (permeation flux: 1.2 cm$^3$/cm$^2$·min), but n-hexadecane could not pass through the nonwoven fabric. Thus, oil was completely separated.

Experiment Example 14

Polypropylene nonwoven fabric (basis weight: 20 g/m$^2$, thickness: 0.21 mm, average pore diameter: 14 μm, and maximum pore diameter: 23 μm) was cut off so as to have a circular filter shape having a diameter of 60 mm. The polypropylene nonwoven fabric was immersion-treated in a surface-coating material having the same composition as that in Experiment Example 13. Then, natural drying was performed (increased amount after drying: 0.0298 g), and the oil-water separation test was performed at room temperature in a normal-pressure filtration device.

A liquid mixture of 30 ml of water and 10 ml of n-hexadecane was used as a test liquid.

When the test liquid was supplied to a normal-pressure filtration device, while stirring well, water passed through the nonwoven fabric (permeation flux: 2.4 cm$^3$/cm$^2$·min), but n-hexadecane could not pass through the nonwoven fabric. Thus, oil was completely separated.

Experiment Example 15

Polypropylene nonwoven fabric (basis weight: 20 g/m$^2$, thickness: 0.24 mm, average pore diameter: 21 μm, and maximum pore diameter: 37 μm) was cut off so as to have a circular filter shape having a diameter of 60 mm. The polypropylene nonwoven fabric was immersion-treated in a surface-coating material having the same composition as that in Experiment Example 13. Then, natural drying was performed (increased amount after drying: 0.0216 g), and the oil-water separation test was performed at room temperature in a normal-pressure filtration device.

A liquid mixture of 30 ml of water and 10 ml of n-hexadecane was used as a test liquid.

When the test liquid was supplied to a normal-pressure filtration device, while stirring well, water passed through the nonwoven fabric (permeation flux: 6.3 cm³/cm²·min), but n-hexadecane could not pass through the nonwoven fabric. Thus, oil was completely separated.

Verification Example of Modification Example of First Embodiment

Advantages of the oil-water separation filtration device according to the present invention were verified.

Example 21

Columnar polypropylene nonwoven fabric (basis weight: 40 g/m², and thickness: 0.09 mm) had an open end at an upper portion, and a bottom which had a diameter of 22 cm, and a height of 25 cm. The columnar polypropylene nonwoven fabric was immersion-treated in a liquid (surface-coating material). Then, natural drying was performed (increased amount after drying: 0.281 g), and thus an oil-water separation filtration filter having a configuration illustrated in FIG. 7 was produced. The liquid was prepared by using 0.5 mass % of a nitrogen-containing fluorine compound synthesized as an oil-repellent hydrophilic agent in Synthetic Example 1, 0.5 mass % of polyvinyl butyral (S-LEC BL-1 manufactured by SEKISUI CHEMICAL CO., LTD.), 0.5 mass % of AEROSIL 300 (manufactured by JAPAN AEROSIL corporation), and 98.5 mass % of ethanol.

The oil-water separation filtration filter was inserted into a cylindrical type resin container which has an outer diameter of 21.6 cm, an inner diameter of 20.2 cm, and a height of 60 cm, and includes a discharge valve on a side surface of a lower portion. An upper end portion of the filter was bent along an outer circumference of the container, and was fixed by rolling a rubber band. A liquid mixture of water and n-hexadecane at an amount ratio of 5:1 was supplied at room temperature and normal pressure, while stirring well, so as to maintain a height from the bottom of the filter to a liquid level of the simulation liquid of 9 cm. A water-passing rate (unit: cm³/min) per one minute was measured for each of five minutes, during a period until 20 minutes elapsed from when water passed through the filter.

When the passed water was visually observed, an oil film derived from n-hexadecane was not recognized. Table 4 shows measurement results.

Verification Example 2 of First Embodiment

Example 22

Polypropylene nonwoven fabric (basis weight: 40 g/m², and thickness: 0.09 mm) having a diameter of 24 cm was immersion-treated in a liquid (surface-coating material) which had the same composition as that in Example 21. Then, natural drying was performed (increased amount after drying: 0.060 g), and thus an oil-water separation filtration filter was produced. The filter was stuck to the bottom surface of a resin pipe having an inner diameter of 20.2 cm, thereby an oil-water separation filtration unit was produced.

Then, the oil-water separation filtration unit was attached to a cylindrical type resin container which has an outer diameter of 26.7 cm, an inner diameter of 25.0 cm, and a height of 60 cm, and includes a discharge valve on a side surface of a lower portion. Then, the water-passing rate was measured in a manner similar to that in Example 21. When the passed water was visually observed, an oil film derived from n-hexadecane was not recognized. Table 4 shows measurement results.

TABLE 4

| | | Elapse time min | 5 | 10 | 15 | 20 |
|---|---|---|---|---|---|---|
| Example 21 | Water-passing rate | cm³/min | 1,860 | 1,610 | 1,620 | 1,610 |
| Example 22 | Water-passing rate | cm³/min | 850 | 730 | 740 | 730 |

It was confirmed that, if the oil-water separation apparatus according to the present invention was used, it was possible to separate a solution mixture in which water and oil are mixed into moisture and oil with high accuracy, based on results shown in Table 4.

Verification Example 1 of 11th Embodiment

Advantages of the oil-water separation and collection tool according to the present invention were verified.

Example 31

Columnar polypropylene nonwoven fabric (basis weight: 20 g/m², thickness: 0.21 mm, average pore diameter: 14 μm, and maximum pore diameter: 23 μm) had an open end at an upper portion, and a bottom which had a diameter of 18 cm, and a height of 11 cm. The columnar polypropylene nonwoven fabric was immersion-treated in a liquid (surface-coating material). Then, natural drying was performed (increased amount after drying: 0.016 g), and thus an oil-water separation filtration filter was produced. The liquid was prepared in a manner such that 0.5 mass % of a nitrogen-containing fluorine compound synthesized as an oil-repellent hydrophilic agent in Synthetic Example 1, 0.5 mass % of polyvinyl butyral (S-LEC BL-1 manufactured by SEKISUI CHEMICAL CO., LTD.), and 0.5 mass % of AEROSIL 300 (manufactured by JAPAN AEROSIL corporation) were dissolved in 98.5 mass % of ethanol.

The oil-water separation filtration filter was inserted into a holding portion (stainless steel boiling basket having a diameter of 18 cm, a height of 9 cm, a length of a handle of 14.5 cm, and 16 meshes) of an operation member. An upper end portion of the filter was bent along an outer circumferential edge of the holding portion, and was fixed by rolling a rubber band. Thus, an oil-water separation and collection tool in Example 1 was obtained. A liquid mixture of water and n-hexadecane at an amount ratio of 6:1 was put at room temperature and normal pressure for about five seconds, while stirring well, until a height from the bottom of the filter to a liquid level of the simulation liquid was 6 cm. The total amount of water was discharged for 60 seconds from when water started to pass through the filter, and n-hexadecane remained in a collection tool. When the passed water was visually observed, an oil film derived from n-hexadecane was not recognized.

Verification Example 2 of 11th Embodiment

Example 32

Except that polypropylene nonwoven fabric having a basis weight of 20 g/m², a thickness of 0.24 mm, an average pore diameter of 21 μm, and the maximum pore diameter of 37 μm was used, the fabric was immersion-treated in a liquid (surface-coating material) having the same composition as that in Example 31. Then, natural drying was performed (increased amount after drying: 0.015 g), and thus an oil-water separation filtration filter was produced.

When a liquid mixture of water and n-hexadecane at an amount ratio of 6:1 was put into the oil-water separation filtration filter in a manner similar to that in Example 31, the total amount of water was discharged for 50 seconds, and n-hexadecane remained in the collection tool. When the passed water was visually observed, an oil film derived from n-hexadecane was not recognized.

Comparative Example 31

When a liquid mixture of water and n-hexadecane at an amount ratio of 6:1 was put into polypropylene nonwoven fabric of Example 31, which was not subjected to the hydrophilic and oil-repellent treatment, in a manner similar to that in Example 31, n-hexadecane passed through the nonwoven fabric. Thus, collecting n-hexadecane was not possible.

Comparative Example 32

When a liquid mixture of water and n-hexadecane at an amount ratio of 6:1 was put into polypropylene woven fabric of Example 32, which was not subjected to the hydrophilic and oil-repellent treatment, in a manner similar to that in Example 31, n-hexadecane passed through the nonwoven fabric. Thus, collecting n-hexadecane was not possible.

It was confirmed that, if the oil-water separation and collection tool according to the present invention was used, it was possible to separate a solution mixture in which water and oil are mixed into moisture and oil with high accuracy, and to collect oil, based on Examples and Comparative Examples.

Verification Example of 14th Embodiment

Advantages of the sandbag according to the present invention were verified.

Experiment Example 41

Polypropylene nonwoven fabric (basis weight: 20 g/m$^2$, thickness: 0.24 mm, average pore diameter: 21 µm, and maximum pore diameter: 37 µm) was cut off so as to have a rectangular shape of 70 cm×50 cm. The polypropylene nonwoven fabric was immersion-treated in a liquid (surface-coating material). Then, natural drying was performed (increased amount after drying: 0.061 g). The liquid (surface-coating material) was prepared by using 0.5 mass % of a nitrogen-containing fluorine compound synthesized as an oil-repellent hydrophilic agent in Synthetic Example 1, 0.5 mass % of polyvinyl butyral (S-LEC BL-1 manufactured by SEKISUI CHEMICAL CO., LTD.), 0.5 mass % of AEROSIL 300 (manufactured by JAPAN AEROSIL corporation), and 98.5 mass % of ethanol.

A wooden frame having inner dimensions of 60 cm×40 cm was installed on a resin bat. A sheet subjected to the hydrophilic and oil-repellent treatment was fixed to the wooden frame, so as to cause the looseness of the center portion to be 5 cm.

5 L of a liquid mixture of water and n-hexadecane at an amount ratio of 6:1 was poured on a sheet which was subjected to the hydrophilic and oil-repellent treatment, while stirring well, and thus the sheet was saturated with the liquid mixture. The pouring was performed at room temperature and normal pressure for about ten seconds.

The total amount of water was discharged for 80 seconds from when water started to pass through the filter, and n-hexadecane remained on a sheet. When the passed water was visually observed, an oil film derived from n-hexadecane was not recognized.

Comparative Example 41

When a liquid mixture of water and n-hexadecane at an amount ratio of 6:1 was poured on polypropylene nonwoven fabric of Example 41, which was not subjected to the hydrophilic and oil-repellent treatment, in a manner similar to that in Example 41, n-hexadecane passed through the nonwoven fabric.

It was confirmed that polypropylene nonwoven fabric which was usable in any of a bag body of a sandbag and a drainage net was subjected to the hydrophilic and oil-repellent treatment, and thus the polypropylene nonwoven fabric could be used as the material of the bag body of a sandbag and the drainage net for preventing diffusion of oil, based on Experiment Example 41 and Comparative Example 41.

Verification Example of 15th Embodiment

Advantages of the oil fence according to the present invention were verified.

Experiment Example 51

Polypropylene nonwoven fabric (basis weight: 20 g/m$^2$, thickness: 0.21 mm, average pore diameter: 14 µm, and maximum pore diameter: 23 µm) was wound around an outer side surface of a stainless steel round basket having a diameter of 150 mm, a height of 150 mm, and an opening dimension of 5.5 mm angle. A joint of the nonwoven fabric was subjected to heat welding, and thus processing to be columnar was performed.

The polypropylene nonwoven fabric was immersion-treated in a liquid (surface-coating material). Then, natural drying was performed (adhered amount after drying: 0.177 g/m$^2$), thereby polypropylene nonwoven fabric subjected to hydrophilic and oil-repellent treatment was obtained. The liquid (surface-coating material) was prepared in a manner such that 0.5 mass % of a nitrogen-containing fluorine compound synthesized as an oil-repellent hydrophilic agent in Synthetic Example 1, 0.5 mass % of polyvinyl butyral (S-LEC BL-1 manufactured by SEKISUI CHEMICAL CO., LTD.), and 0.5 mass % of AEROSIL 300 (manufactured by JAPAN AEROSIL corporation) were dissolved in 98.5 mass % of ethanol.

The stainless steel round basket was covered by polypropylene nonwoven fabric subjected to the hydrophilic and oil-repellent treatment, and thus an outer side surface was covered by the polypropylene nonwoven fabric subjected to the hydrophilic and oil-repellent treatment. The resultant of the covering was used as a columnar oil prevention fence.

A columnar oil prevention fence formed from polypropylene nonwoven fabric which had been subjected hydrophilic and oil-repellent treatment was loaded in a constant-temperature shaking water tank, and water was put into the constant-temperature shaking water tank, so as to cause the oil prevention fence to be immersed in water having a depth of 100 mm.

Then, 250 ml of n-hexadecane was put into the oil prevention fence. Setting to 25±0.1° C. was performed, and then shaking and stirring were performed. The oil prevention fence was moved back and forth, and thus the liquid surface moved up and down.

When the oil prevention fence was observed after six hours elapsed, the height of the liquid surface in the oil prevention fence was not changed, and an oil film of n-hexadecane was not recognized on an outer side of the oil prevention fence.

Comparative Example 51

Polypropylene nonwoven fabric of Example 51, which was not subjected to the hydrophilic and oil-repellent treatment had water-repellent and lipophilic properties. Thus, water was flipped and oil passed through the nonwoven fabric. A resultant obtained by covering an outer side of the stainless steel round basket with the polypropylene nonwoven fabric in a manner similar to that in Example 51 was loaded in the constant-temperature shaking water tank. Then, a shaking and stirring test was performed. If the oil prevention fence was observed after six hours, n-hexadecane had leaked out of the oil prevention fence, and a water level in the oil prevention fence had lowered.

As a result of Example 51 and Comparative Example 51, water did not pass through polypropylene nonwoven fabric which was not subjected to the hydrophilic and oil-repellent treatment. Thus, when shaking and stirring were performed, resistance of water applied to the nonwoven fabric was increased, and vibration amplitude in up and down movement of water was increased. Thus, n-hexadecane and water climbed over the upper edge of the oil fence. On the contrary, since water passed through the polypropylene nonwoven subjected to the hydrophilic and oil-repellent treatment, resistance of water was relieved, and simultaneously, n-hexadecane was flipped. Thus, it was understood that water or n-hexadecane did not climb over the upper edge of the fence, and this polypropylene nonwoven could be appropriately used as an oil prevention fence.

Verification Example 1 of 17th Embodiment

Advantages of the oil-water separation porous medium according to the present invention were verified.

Experiment Example 61

A commercial glass filter (SIBATA glass filter, capacitance of 30 ml, pore size of 100 to 160 μm) was used as a porous medium. The glass filter was immersion-treated in a liquid (surface-coating material), and drying was performed at 60° C. for two hours. The liquid was prepared by using 2 mass % of a fluorine compound synthesized in Synthetic Example 1, 4 mass % of polyvinyl butyral (S-LEC BL-1 manufactured by SEKISUI CHEMICAL CO., LTD.), and 94 mass % of ethanol.

Then, a liquid mixture of 20 ml of water and 5 ml of n-hexadecane was poured on a surface-treated glass filter at room temperature, while stirring the liquid mixture. Filtration at normal pressure was performed, and the oil-water separation test was performed.

As a result, water passed through the glass filter, but n-hexadecane could not pass through the glass filter. Thus, oil was completely separated.

Verification Example 2 of 17th Embodiment

Experiment Example 62

A commercial glass filter (SIBATA glass filter, capacitance of 30 ml, pore size of 16 to 40 μm) was used as a porous medium. The glass filter was immersion-treated in a liquid (surface-coating material), and drying was performed at 60° C. for two hours. The liquid was prepared by using 2 mass % of a fluorine compound synthesized in Synthetic Example 1, 4 mass % of polyvinyl butyral (S-LEC BL-1 manufactured by SEKISUI CHEMICAL CO., LTD.), and 94 mass % of ethanol.

Then, the oil-water separation test was performed in a manner similar to that in Experiment Example 61, by using a liquid mixture of 20 ml of water and 5 ml of n-hexadecane.

As a result, water passed through the glass filter, but n-hexadecane could not pass through the glass filter. Thus, oil was completely separated.

Verification Example 1 of Modification Example of 16th Embodiment

Experiment Example 63

A commercial polypropylene cartridge filter (ADVANTEC compact cartridge MCP-7-C10E: length of 48 mm, effective filtration area of 500 $cm^2$, nominal pore diameter of 7 μm) (see diagram illustrated in FIG. 2) was used as a porous medium. The glass filter was immersed in a liquid (surface-coating material), and thus the cartridge filter was subjected to surface treatment. The liquid was prepared by using 2 mass % of a fluorine compound synthesized in Synthetic Example 1, 4 mass % of polyvinyl butyral (S-LEC BL-1 manufactured by SEKISUI CHEMICAL CO., LTD.), and 94 mass % of ethanol. The cartridge filter was dried at 60° C. for two hours, and then, was combined with a housing (ADVANTEC: MTA type, and inner capacity of about 250 ml).

Then, 1 L of a liquid mixture of water and n-hexadecane at an amount ratio of 6:1 was put into a liquid separation funnel with a cock. An inflow port of the housing and the foot of the liquid separation funnel were connected to each other by a tube. While the liquid mixture was shaken and mixed well, the liquid mixture was caused to pass through the cartridge filter at room temperature, at water head pressure corresponding to a water column of 50 to 40 cm. 500 ml of water was discharged for 10 seconds from when water started to be discharged from the cartridge filter. At this time, if liquid passing was suspended, and the passed water was visually observed, an oil film derived from n-hexadecane was not recognized.

Verification Example 2 of Modification Example of 16th Embodiment

Experiment Example 64

A polypropylene cartridge filter (ADVANTEC compact cartridge MCP-010AM-C10E: length of 48 mm, effective filtration area of 190 $cm^2$, and nominal pore diameter of 1 μm) was used as a porous medium. The polypropylene cartridge filter was a six-layer (six-stage) pleat-type in which a hole diameter becomes smaller from an outer layer toward an inner layer. The cartridge filter was immersed in a liquid (surface-coating material), and thus the cartridge filter was subjected to surface treatment. The liquid was prepared by using 2 mass % of a fluorine compound synthesized in Synthetic Example 6, 4 mass % of polyvinyl butyral (S-LEC BL-1 manufactured by SEKISUI CHEMICAL CO., LTD.), and 94 mass % of ethanol. The cartridge filter was dried at 60° C. for two hours, and then, was combined with a housing (ADVANTEC: MTA type, and inner capacity of about 250 ml).

Then, similarly to Experiment Example 63, a liquid mixture of water and n-hexadecane was passed through the cartridge filter. 500 ml of water was discharged for 20 seconds from when water started to be discharged from the cartridge filter. At this time, if liquid passing was suspended, and the passed water was visually observed, an oil film derived from n-hexadecane was not recognized.

Verification Example 3 of Modification Example of 16th Embodiment

Experiment Example 65

A polyester wire-wound cartridge filter (ADVANTEC cartridge TCW-10-EPS: length of 250 mm, and nominal pore diameter of 10 μm) was used as a porous medium. The polyester wire-wound cartridge filter has an inclined hole-diameter type in which density gradient of fibers is provided from an outside to the center and a hole diameter is continuously reduced. The cartridge filter was immersed in a liquid (surface-coating material), and thus the cartridge filter was subjected to surface treatment. The liquid was prepared by using 2 mass % of a fluorine compound synthesized in Synthetic Example 1, 4 mass % of polyvinyl butyral (S-LEC BL-1 manufactured by SEKISUI CHEMICAL CO., LTD.), and 94 mass % of ethanol. The cartridge filter was dried at 60° C. for two hours, and then, was combined with a housing (ADVANTEC: plastic housing 1PA).

Then, a liquid separation funnel with cock and a water tank including a stirring machine were prepared. A tube was attached to the foot of the liquid separation funnel, and was connected to an inflow port of the housing. 10 L of a liquid mixture of water and n-hexadecane at an amount ratio of 6:1 was put into a water tank. While stirring the liquid mixture, the liquid mixture was put into a liquid separation funnel by a pump. While water head pressure corresponding to a water column of 50 to 40 cm was maintained, the liquid mixture was caused to pass through the cartridge filter from the liquid separation funnel, at room temperature. 3 L of water was discharged for 20 seconds from when water started to be discharged from the cartridge filter. At this time, if liquid passing was suspended, and the passed water was visually observed, an oil film derived from n-hexadecane was not recognized.

Comparative Example 61

When a liquid mixture of 20 ml of water and 5 ml of n-hexadecane was poured on a glass filter of Example 61, which was not subjected to the hydrophilic and oil-repellent treatment, n-hexadecane passed through the nonwoven fabric. Thus, oil and water were not separated.

<Evaluation by Measuring Contact Angle>

Regarding a coating film which was the oil-water-separating member in the present invention, and was obtained by a fluorine compound, a contact angle was measured.

Specifically, firstly, fluorine compounds obtained in Synthetic Example 1 and Synthetic Example 6 described above were dissolved in ethanol, thereby 0.2 mass % of an ethanol solution was prepared. A glass plate was dipped into the liquid. The glass plate was removed, and then natural drying was performed. Thus, ethanol was removed. Thus, a coating film was formed on the glass plate.

Water and n-hexadecane (referred to as oil below) was dropped onto the obtained coating film. An angle (unit: degree) at a contact portion between the glass substrate and a liquid droplet was measured by an automatic contact angle meter (manufactured by Kyowa Interface Science Co., Ltd, "Drop Master 701").

For a dropping method of water and n-hexadecane, the following conditions were used.

Dropped quantity: 2 μL/droplet (water)
Dropped quantity: 2 μL/droplet (n-hexadecane)
Measurement temperature: room temperature (22±1° C.)

As a result of the measurement, a contact angle of the coating film obtained by the fluorine compound in each of Synthetic Example 1 and Synthetic Example 2 to water was 17°. A contact angle to oil was 66°.

Verification Example of 19th Embodiment

Experiment Example 71

Polypropylene nonwoven fabric having nominal filtration precision of 200 μm was immersion-treated in a liquid (surface-coating material), and natural drying was performed (increased amount after drying: 21.7 $g/m^2$). The liquid was prepared by using 0.5 parts by mass of a nitrogen-containing fluorine compound which was synthesized as an oil-repellent hydrophilic agent in Synthetic Example 1, and was represented by the formula (5), 0.5 parts by mass of polyvinyl butyral (S-LEC BL-1 manufactured by SEKISUI CHEMICAL CO., LTD.) as the binder, 0.5 parts by mass (as $SiO2$) of silica sol (ORGANOSILICASOL IPA-ST manufactured by NISSAN CHEMICAL INDUSTRIES. LTD.) as an inorganic compound, and 97.1 parts by mass of a solvent (55.5 parts by mass of hexafluoroxylene, 37.0 parts by mass of ethanol, and 4.6 parts by mass of n-butanol).

Measuring the contact angle of the nonwoven fabric to water was impossible because water was immediately absorbed in the nonwoven fabric. Apparently, the contact angle was 0 degree. The contact angle of n-hexadecane was 110 degrees.

Then, an oil-water mixed liquid in which 5 ml of water and n-hexadecane were put into a 50 ml graduated cylinder so as to cause the total amount to be set to 40 ml was prepared. The oil-water mixed liquid was separated into two layers, and the liquid depth thereof was 115 mm. When a test piece of polyester nonwoven fabric which was cut off so as to have a width of 15 mm and a length of 150 mm, and was subjected to the hydrophilic and oil-repellent treatment was immersed in the oil-water mixed liquid, the test piece absorbed water immediately after immersion started. After 15 minutes, water in the graduated cylinder was reduced to be 4.5 ml. When the test piece was extracted from the oil-water mixed liquid, a form was observed in which the height of water absorbed to the test piece increased up to 98 mm, and water which exceeded the holding amount of water of the test piece was propagated and dropped down along the test piece. n-hexadecane did not adhere to the test piece.

Comparative Example 71

When a contact angle of water and n-hexadecane of polypropylene nonwoven fabric which had not been subjected to the hydrophilic and oil-repellent treatment, and had nominal filtration precision of 200 μm was measured, water and n-hexadecane were also permeated to the nonwoven fabric, and the contact angle was apparently 0 degrees.

A test piece obtained by cutting the polyester nonwoven fabric off so as to have a width of 15 mm, and the length of 150 mm, which were the same as those in Example 1, was put into an oil-water mixed liquid in which 5 ml of water and n-hexadecane were put by using a 50 ml graduated cylinder similar to Example 1 so as to cause the total amount to be set to 40 ml. The test piece absorbed n-hexadecane immediately after immersion started. After 15 minutes, the liquid level of n-hexadecane in the graduated cylinder was reduced to be 38.5 ml. The liquid level of water was not changed from 5 ml. When the test piece was extracted after 15 minutes, the height of n-hexadecane absorbed to the test piece was increased up to 150 mm.

The following were confirmed based on the above results. If a fiber assembly such as polyester nonwoven fabric subjected to the hydrophilic and oil-repellent treatment was provided in a liquid in which oil and water were provided together, the polyester nonwoven fabric subjected to the hydrophilic and oil-repellent treatment can flip oil and absorb water. Water which exceeded the holding amount of water was propagated and dropped down along the polyester nonwoven fabric. Thus, it was verified that oil and moisture in a liquid mixture could be reliably separated.

Verification Example of 21th Embodiment

Experiment Example 81

Polypropylene nonwoven fabric (basis weight: 20 g/m$^2$, thickness: 0.24 mm, average pore diameter: 21 μm, and maximum pore diameter: 37 μm) was cut off so as to have a rectangular shape of 70 cm×50 cm. The polypropylene nonwoven fabric was immersion-treated in a liquid (surface-coating material). Then, natural drying was performed (increased amount after drying: 0.061 g). The liquid (surface-coating material) was prepared by using 0.5 mass % of a nitrogen-containing fluorine compound which had been synthesized as an oil-repellent hydrophilic agent in the above-described Synthetic Example 1, and was represented by the formula (5), 0.5 mass % of polyvinyl butyral (S-LEC BL-1 manufactured by SEKISUI CHEMICAL CO., LTD.), 0.5 mass % of AEROSIL 300 (manufactured by JAPAN AEROSIL corporation), and 98.5 mass % of ethanol.

A wooden frame having inner dimensions of 60 cm×40 cm was installed on a resin bat. A sheet subjected to the hydrophilic and oil-repellent treatment was fixed to the wooden frame, so as to cause the looseness of the center portion to be 5 cm.

Then, 5 L of a floating oil layer (liquid mixture of water and n-hexadecane at amount ratio of about 1:1) after a high-frequency AC voltage was applied by using a high-frequency power source device so as to perform demulsification was poured onto a sheet subjected to the hydrophilic and oil-repellent treatment at room temperature at normal pressure for about 10 seconds. Thus, the sheet was saturated with the liquid mixture. The total amount of water was discharged for 50 seconds from when water started to pass through the filter, and n-hexadecane remained on a sheet. When the passed water was visually observed, an oil film derived from n-hexadecane was not recognized. Oil and water were completely separated.

Verification Example of Other Configuration of 21th Embodiment

Experiment Example 82

Polypropylene nonwoven fabric (basis weight: 20 g/m$^2$, thickness: 0.24 mm, average pore diameter: 21 μm, and maximum pore diameter: 37 μm) was cut off so as to have a rectangular shape of 70 cm×50 cm. The polypropylene nonwoven fabric was immersion-treated in a liquid (surface-coating material). Then, natural drying was performed (increased amount after drying: 0.061 g). The liquid (surface-coating material) was prepared by using 0.5 mass % of a nitrogen-containing fluorine compound which had been synthesized as an oil-repellent hydrophilic agent in the above-described Synthetic Example 1, and was represented by the formula (5), 0.5 mass % of polyvinyl butyral (S-LEC BL-1 manufactured by SEKISUI CHEMICAL CO., LTD.), 0.5 mass % of AEROSIL 300 (manufactured by JAPAN AEROSIL corporation), and 98.5 mass % of ethanol.

A wooden frame having inner dimensions of 60 cm×40 cm was installed on a resin bat. A sheet subjected to the hydrophilic and oil-repellent treatment was fixed to the wooden frame, so as to cause the looseness of the center portion to be 5 cm.

Then, 5 L of a floating oil layer (liquid mixture of water and n-hexadecane at amount ratio of about 1:1) after emulsified fine oil droplets of an oil-water mixed liquid were coarsened by fine bubbles (microbubbles) and by using an air-bubble jet type demulsification device was poured onto a sheet subjected to the hydrophilic and oil-repellent treatment at room temperature at normal pressure for about 10 seconds. Thus, the sheet was saturated with the liquid mixture. The total amount of water was discharged for 50 seconds from when water started to pass through the filter, and n-hexadecane remained on a sheet. When the passed water was visually observed, an oil film derived from n-hexadecane was not recognized. Oil and water were completely separated.

Comparative Example 81

When a liquid mixture of water and n-hexadecane at an amount ratio of 6:1 was poured on polypropylene nonwoven fabric which was not subjected to the hydrophilic and oil-repellent treatment, in a manner similar to that in Example 81, n-hexadecane passed through the nonwoven fabric. Thus, oil and water were not separated.

Verification Example 1 of 22th Embodiment

Advantages of the water-absorbent oil-repellent tool according to the present invention were verified.

Experiment Example 91

An external bag (material: polyester) of a commercial water-absorbent polymer sandbag (merchandise name: water pita N type NAKAMURA CONSTRUCTION, Inc.) was cut off so as to have a square of about 6 cm. The resultant obtained by the cutoff was immersion-treated in a liquid (surface-coating material), and then natural drying was performed. In the liquid, 2 g of a nitrogen-containing fluorine compound synthesized in Synthetic Example 1, and 4 g of polyvinyl butyral (S-LEC BL-1 manufactured by SEKISUI CHEMICAL CO., LTD.) was dissolved in 94 g of ethanol.

The polyester sheet which had been obtained and subjected to hydrophilic and oil-repellent treatment processing was attached to a Kiriyama separation funnel (manufactured by Kiriyama glass Co.) for filter paper of 60 mmφ. 30 ml of n-hexadecane was poured onto the polyester sheet at 22° C. at normal pressure. However, even though two hours elapsed, n-hexadecane did not pass through the polyester sheet. When 30 ml of water was poured onto the polyester sheet, the total amount of water passed within about 30 seconds.

Comparative Experiment Example 91

When 30 ml of n-hexadecane was poured similarly to Experiment Example 101 without performing the hydrophilic and oil-repellent treatment on the external bag of a water-absorbent polymer sandbag in Experiment Example 91, the total amount passed within about two minutes. When 30 ml of water was poured onto the polyester sheet, the total amount of water passed within about 30 seconds.

Verification Example 2 of 22th Embodiment

Example 91

Polypropylene nonwoven fabric (basis weight: 15 g/m$^2$, thickness: 0.16 mm, average pore diameter: 7 μm, and maximum pore diameter of 14 μm) was folded up, and a side surface was subjected to heat welding by heat sealing. Then, processing was performed so as to obtain an envelope having the bottom of about 20 mm. The cylinder was immersion-treated in a liquid (surface-coating material), and natural drying was performed. In the liquid, 2 g of a nitrogen-containing fluorine compound synthesized in Synthetic Example 1 and 4 g of polyvinyl butyral (S-LEC BL-1 manufactured by SEKISUI CHEMICAL CO LTD.) was dissolved in 94 g of ethanol.

A polyvinyl alcohol aqueous film (aqueous film Hi-Selon C-200 (manufactured by Nippon Synthetic Chemical Industry Co., Ltd.) was folded up, and the side surface was subjected to heat welding by heat sealing. Then, processing was performed so as to obtain an envelope having the bottom of about 10 mm. 0.1 g of commercial super absorptive polymer "sodium salt cross-linkage in the acrylic acid polymerization" (manufactured by Wako Pure Chemical Industries, Ltd.) as a water absorbent was put into the cylinder. The entirety was compressed evenly, and then an entrance portion was closed by heat sealing.

An inner bag which was formed of polyvinyl alcohol aqueous film and in which a water absorbent was stored was inserted into the polypropylene nonwoven fabric cylinder. 1.0 g of manganese sand was input. The entirety was compressed evenly, and then an entrance portion was closed by heat sealing. Thus, a water-absorbent and oil-repellent medium having a height of about 50 mm was produced.

Then, a colorimetric tube which had an inner diameter of about 21 mm and capacity of 50 ml, and had a sliding plug attached thereto was prepared. The water-absorbent and oil-repellent medium was inserted into the colorimetric tube in a state where the entrance portion of the tube was directed upwardly.

A liquid mixture of 19 ml of n-hexadecane and 1 ml of water had been warmed to be 25° C. in advance. The liquid mixture was poured into the colorimetric tube while being shaken and mixed well, and was covered with a stopper. The resultant of the covering was loaded in a constant-temperature shaking water tank of 25.0±0.1° C. Then, shaking and stirring were performed. When the inside of the colorimetric tube was visually observed after three minutes, water was completely attracted to the inside of the water-absorbent and oil-repellent medium.

Comparative Example 91

0.1 g of sodium salt cross-linkage in the acrylic acid polymerization (manufactured by Wako Pure Chemical Industries, Ltd.) was put into a polypropylene nonwoven fabric cylinder similar to that in Example 91, without performing the hydrophilic and oil-repellent treatment. The entrance portion was closed by heat sealing.

Then, the resultant of the closing was inserted into a colorimetric tube similar to that in Example 91. A liquid mixture of 19 ml of n-hexadecane and 1 ml of water was put into the colorimetric tube, and then shaking and stirring were performed in a constant-temperature shaking water tank of 25.0±0.1° C.

When the colorimetric tube was visually confirmed after 24 hours, water remained in the bottom of the colorimetric tube.

It could be confirmed that an external bag of a commercial water-absorbent polymer sandbag was subjected to the hydrophilic and oil-repellent treatment, and thus it was possible to use the external bag as a water-absorbent oil-repellent tool, based on Experiment Example 91 and Example 91.

From the above experimental results, according to the present invention, it was confirmed that, even in a case where oil was leaked during drainage, it was possible to efficiently separate and collect oil from drained water.

Verification Example of 23th Embodiment

Experiment Example 101

85 g of 2.5 mass % of an ethanol solution of polyvinyl butyral (S-LEC BL-1 manufactured by SEKISUI CHEMICAL CO., LTD.) was added to a mixture in which commercial magnetite (manufactured by KANTO Chemical Co., Inc.: triiron tetroxide) and nylon beads (Fuji Manufacturing Co., Ltd.: density of 1.14 g/cm$^3$, and granularity of 0.2 mm×0.2 mm) were mixed at a mass ratio of 10:90. Stirring and mixing was performed at 600 rpm for one minute, thereby grains were manufactured. Then, drying was performed at 85° C. for one night, thus magnetite-nylon mixed powder having a specific gravity of 1.54 g/cm$^3$ was obtained. Then, the granulated powder substance was crushed by a crushing machine, and was classified into particles having a particle diameter of 0.2 to 0.5 mm, by sieving. The magnetite and the commercial polyethylene power (density of 0.95 g/cm$^3$, and granularity of 0.08 to 0.15 mm) were mixed at a mass ratio of 10:90 so as to manufacture grains. Thus, magnetite-nylon mixed powder having a specific gravity of 1.38 was obtained.

Then, the granulated powder substance was crushed by a crushing machine, and was classified into particles having a particle diameter of 0.5 to 1 mm, by sieving. The magnetite and the polyethylene power were mixed at a mass ratio of 5:95 so as to manufacture grains. Thus, magnetite-nylon mixed powder having specific gravity of 1.16 g/cm$^3$ was obtained. Then, the granulated powder substance was crushed by a crushing machine, and was classified into particles having a particle diameter of 1 to 2 mm, by sieving.

The powder substances were spray-coated with an ethanol solution of 2 mass % of a nitrogen-containing fluorine compound synthesized as the oil-repellent hydrophilic agent in Synthetic Example 7, and 4 mass % of polyvinyl butyral (S-LEC BL-1 manufactured by SEKISUI CHEMICAL CO., LTD.). Then, natural drying was performed, thereby oil-water separation magnetic particles were obtained.

A glass filter holder (ADVANTEC Toyo Roshi Ltd.) was prepared. The glass filter holder had an inner diameter of 37 mm and a length of 118 mm, had an upper end which was opened, and had a support screen which had 100 meshes and was formed of SUS316, at the bottom. The lower portion of the filter holder became narrower, and a discharge tube having an outer diameter of 16 mm was bonded to the lower portion. Filter paper of No. 5A was loaded on the support screen. A rubber tube was attached to the discharge tube, and the tube was pressed by a pinch cock.

For the first time, the filter holder was saturated with water, and a small amount of filtration sand (manufactured by Tohkemy Corporation, particle diameter of 0.30 to 0.45 mm, and density of 2.57 to 2.67 g/cm$^3$) was slowly put into the filter holder. Thus, the filter holder was filled with the filtration sand so as to cause the layer height of filtration sand to be 10 mm. Then, a small amount of oil-water separation magnetic particles having a particle diameter of 0.2 to 0.5 mm were slowly put into the filter holder. Thus, the filter holder was filled with the filtration sand on filter paper, so as to cause the layer height of filtration sand to be 10 mm. The filter holder was filled with oil-water separation magnetic particles having a particle diameter of 0.5 to 1 mm on the filtration sand so as to cause the layer height of filtration sand to be 10 mm. Further, the filter holder was filled with oil-water separation magnetic particles having a particle diameter of 1 to 2 mm on the magnetic particles so as to cause the layer height of filtration sand to be 10 mm. Finally, a water level was adjusted so as to cause a portion of 10 mm higher than the oil-water separation magnetic particle layer to be set as a water surface.

50 ml of a liquid mixture of water and n-hexadecane at an amount ratio of 3:1 was shaken and mixed well. Then, the liquid mixture was poured into the tube along the inner wall of the filter holder by using a funnel, so as not to disturb the upper portion of the filled layer. The pouring was performed at room temperature (22° C.). When the pinch cock was loosened, and a liquid flowed out from the filter holder, only water was discharged from the filter holder, and n-hexadecane remained in the oil-water separation magnetic particle layer. Then, the pinch cock was closed. Water was put into the filter holder up to the oil-water separation magnetic particle layer, and then the filter holder was left in place. After 16 hours elapsed, n-hexadecane floated on the oil-water separation magnetic particle layer.

Finally, the oil-water separation magnetic particle in the filter holder was transported to a stainless steel butt, and the oil-water separation magnetic particle was collected by a magnet.

REFERENCE SIGNS LIST

10 OIL-WATER SEPARATION APPARATUS
11 OIL-WATER SEPARATION FILTER MEDIUM
13 BASE
14 OIL-WATER-SEPARATING MEMBER
17 CHANNEL

The invention claimed is:
1. An oil-water separation apparatus, comprising:
an oil-water separation filter medium which includes a base and an oil-water-separating member which is formed on the base and is configured to separate a liquid mixture containing water and oil into moisture and oil,
wherein
the oil-water-separating member contains a fluorine compound which has an oil-repellency-imparting group and a hydrophilicity-imparting group, and
a form of the base is fibrous organic matter, particulate organic matter, fibrous inorganic matter, particulate inorganic matter, a porous medium of organic matter, or a porous medium of inorganic matter,
and wherein
the fluorine compound contains one or more compounds having a structure represented by the following formulas (1) to (4),

[Chemical Formula 1]

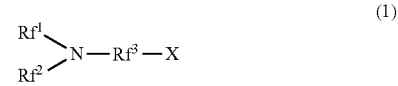

[Chemical Formula 2]

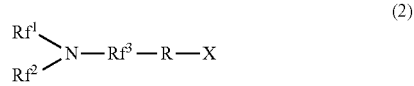

[Chemical Formula 3]

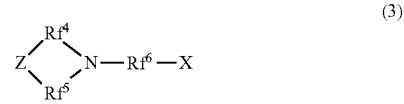

[Chemical Formula 4]

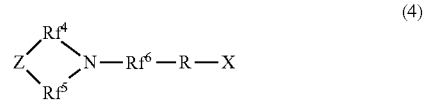

in the formulas (1) and (2), a nitrogen-containing perfluoroalkyl group formed from $Rf^1$ and $Rf^2$ and a nitrogen-containing perfluoroalkylene group formed from $Rf^3$ constitute the oil-repellency-imparting group,
each of $Rf^1$ and $Rf^2$ in the formulas (1) and (2) is a straight-chain or branched perfluoroalkyl group which is the same as or different from each other, and has 1 to 6 carbon atoms, and $Rf^3$ is a straight-chain or branched perfluoroalkylene group which has 1 to 6 carbon atoms,
in the formulas (3) and (4), a nitrogen-containing perfluoroalkylene group formed from $Rf^4$, $Rf^5$, and $Rf^6$, further, Z constitutes the oil-repellency-imparting group,
each of $Rf^4$, $Rf^5$, and $Rf^6$ in the formulas (3) and (4) is a straight-chain or branched perfluoroalkylene group which is the same as or different from each other, and has 1 to 6 carbon atoms, and Z includes any of an oxygen atom, a nitrogen atom, a $CF_2$ group, and a CF group,
in the formulas (2) and (4), R is a linking group which is a bivalent organic group, and
in the formulas (1) to (4), X is any one hydrophilicity-imparting group selected from the group consisting of an anion type, a cation type, and an amphoteric type,
in a case where the hydrophilicity imparting group X is the anion type, the X has "—$CO_2M^1$", "—$SO_3M^1$", "—$OSO_2M^1$", "—$OP(OH)O_2M^1$", "—$OPO_3M^1{}_2$", "=$O_2PO_2M^1$", or "$PO(OH)_y(OM^1)_{2-y}$"(wherein $M^1$ indicates alkali metal, alkaline-earth metal, Mg, and Al, and $R^1R^2R^3R^4N^+$; $R^1$ to $R^4$ indicate straight chain or branched alkyl groups which are independent from each other, and have hydrogen atoms or 1 to 20 carbon atoms), in a case where the hydrophilicity-imparting group X is the cation type, the X has "—$N^+R^5R^6R^7Cl^{31}$", "—$N^+R^5R^6R^7Br^{31}$", "—$N^+R^5R^6R^7I^{-}$", "—$N^+R^5R^6R^7.CH_3SO_3^{31}$", "—$N^+R^5R^6R^7SO_4^{31}$", "—$N^+R^5R^6R^7NO_3^{-}$", "(—$N^+R^5R^6R^7)_2CO_3^{2-}$", or "(—$N^+R^5R^6R^7)_2SO_4^{2-}$" at the termination ($R^5$ to $R^7$ are straight chain or branched alkyl groups which are independent from each other, and have hydrogen atoms or 1 to 20 carbon atoms), and in a case where the hydrophilicity-imparting group X is the amphoteric type, the X has a carboxy betaine type of "—$N^+R^8R^9(CH_2)_nCO_2^{-}$", a sulfobetaine type of "—$N^+R^8R^9(CH_2)_nSO_3^{-}$", an amine oxide type of "—$N^+R^8R^9O^{-}$", or a phosphobetaine type of "—$OPO_3^{-}(CH_2)_nN^+R^8R^9R^{10}$" at the termination (n is an integer of 1 to 5, $R^8$ and $R^9$ indicates an alkyl group having a hydrogen atom or 1 to 10 carbon atoms, and $R^{10}$ indicates an alkyl group having a hydrogen atom or 1 to 10 carbon atoms or an alkylene group having 1 to 10 carbon atoms).

2. The oil-water separation apparatus according to claim 1, wherein the oil-water-separating member is bound to the base by an organic binder or an inorganic binder.

3. The oil-water separation apparatus according to claim 1, further comprising:
a liquid reservoir which is subdivided into an upper region and a lower region by the oil-water-separating member,
wherein a water drain port for discharging the moisture is formed in the lower region of the liquid reservoir, and filtering the liquid mixture is performed by gravity.

4. The oil-water separation apparatus according to claim 3, wherein an oil drain port for discharging the oil is formed in the upper region of the liquid reservoir.

5. The oil-water separation apparatus according to claim 1, wherein
the base has a bag shape of which one end side is opened, and is formed from a porous medium which includes at least a channel through which the moisture is allowed to pass.

6. The oil-water separation apparatus according to claim 5, wherein
a support member through which at least the moisture is allowed to pass is disposed on an outer surface side of the oil-water separation filter medium so as to overlap the outer surface side of the oil-water separation filter medium, and
the support member supports the oil-water separation filter medium from the outer surface side.

7. The oil-water separation apparatus according to claim 1, further comprising:
a holding portion for holding the oil-water separation filter medium,
wherein the base is formed from a material including a channel through which at least the moisture passes.

8. The oil-water separation apparatus according to claim 7, wherein
an edge of the base is attachable and detachable to and from the holding portion.

9. The oil-water separation apparatus according to claim 1, wherein,
the base is a bag body, and
the bag body is formed from a material including a channel through which at least the moisture is allowed to pass, and is filled with weights.

10. The oil-water separation apparatus according to claim 9, further comprising:
a drainage net which is extended from one end portion of the bag body, and includes the oil-water-separating member,
wherein the drainage net is formed from a material including a channel through which at least moisture is allowed to pass.

11. The oil-water separation apparatus according to claim 1, wherein,
the base forms a curtain, and has a float for floating the base on a surface of water,
the curtain is attached to a lower portion of the float, and
the curtain is formed from a material including a channel through which at least the moisture is allowed to pass.

12. The oil-water separation apparatus according to claim 1, wherein,
the base is formed from a porous base including multiple pores which penetrate a space between one surface into which the liquid mixture flows, and another surface which faces the one surface,
an opening diameter of the pore is from 0.1 μm to 180 μm, and
the oil-water-separating member is formed on a surface of the pore.

13. The oil-water separation apparatus according to claim 12, wherein,
the pore is directed from the one surface toward the other surface, and
the opening diameter of the pores is reduced by stages or continuously.

14. The oil-water separation apparatus according to claim 1, wherein
the oil-water separation apparatus constitutes a gathering machine,
at least a preceding-stage reservoir and a subsequent-stage reservoir are arranged in series from an inflow side into which the liquid mixture flows, toward an outflow side by which the moisture obtained by oil-water separation flows out, and
the oil-water separation filter medium is provided so as to be attachable and detachable to and from at least one of the preceding-stage reservoir or the subsequent-stage reservoir.

15. The oil-water separation apparatus according to claim 1, wherein
the base is formed from a fiber assembly,
the oil-water-separating member is formed in the fiber assembly, and
the oil-water separation filter medium is brought into contact with the liquid mixture, so as to cause water droplets to form a liquid film and to flip oil.

16. The oil-water separation apparatus according to claim 15, further comprising:
a coarsening filter which includes a coarsening member configured to be brought into contact with the liquid mixture and to coarsen a water droplet or an oil droplet,
wherein the oil-water separation filter medium is disposed on the subsequent stage side of the coarsening filter.

17. The oil-water separation apparatus according to claim 1, further comprising:
    an intake unit configured to take the liquid mixture in;
    an oil-water separation unit which includes the oil-water separation filter medium and is configured to separate the liquid mixture into moisture and oil; and
    a joint unit configured to connect the intake unit and the oil-water separation unit.

18. The oil-water separation apparatus according to claim 1, further comprising:
    a demulsification unit configured to coarsen minute oil droplets dispersed in an oil-water mixed liquid obtained by mixing moisture and oil, and to cause the oil to float on a higher layer of the moisture;
    an oil-water separation unit configured to perform oil-water separation of a solution mixture containing oil which is coarsened by the demulsification unit, by using the oil-water separation filter medium; and
    a transportation unit configured to transport the solution mixture from the demulsification unit toward the oil-water separation unit.

19. The oil-water separation apparatus according to claim 1, wherein
    the oil-water separation filter medium is formed on a surface of the base,
    the base is formed from a baglike exterior medium through which the moisture passes, and the oil does not pass, and
    a water-absorbent material is accommodated in the exterior medium.

20. The oil-water separation apparatus according to claim 1, further comprising:
    a filter layer in which a filtering medium is formed;
    the oil-water separation filter medium formed so as to overlap the filter layer; and
    a liquid reservoir which accommodates the filter layer and the oil-water separation filter medium,
    wherein
    the oil-water separation filter medium is formed in a manner such that multiple layers of an oil-water separation medium formed from the base and the oil-water-separating member which is formed around the base are disposed, and
    the oil-water separation filter medium filters the liquid mixture by gravity.

21. A drainage system which includes the oil-water separation apparatus according to claim 1, the system comprising:
    an oil leakage detector configured to detect leakage of oil into a drainage;
    an oil-water separation mechanism configured to separate oil from a liquid mixture in which the oil is contained in the drainage; and
    a control unit configured to operate the oil-water separation mechanism, when the oil leakage detector detects leakage of oil into the drainage,
    wherein the oil-water separation mechanism includes the oil-water separation apparatus.

* * * * *